US011192872B2

(12) United States Patent
Den Ouden et al.

(10) Patent No.: US 11,192,872 B2
(45) Date of Patent: Dec. 7, 2021

(54) PURIFIED 2,5-FURANDICARBOXYLIC ACID PATHWAY PRODUCTS

(71) Applicant: Stora Enso Oyj, Helsinki (FI)

(72) Inventors: Henricus Johannes Cornelis Den Ouden, Helsinki (FI); Valery Sokolovskii, Helsinki (FI); Thomas R. Boussie, Helsinki (FI); Gary M. Diamond, Helsinki (FI); Eric L. Dias, Helsinki (FI); Guang Zhu, Helsinki (FI); Staffan Torssell, Helsinki (FI); Vincent J. Murphy, Helsinki (FI)

(73) Assignee: Stora Enso Oyj, Helsinki (FI)

( * ) Notice: Subject to any disclaimer, the term of this patent is extended or adjusted under 35 U.S.C. 154(b) by 145 days.

(21) Appl. No.: 16/628,816

(22) PCT Filed: Jul. 11, 2018

(86) PCT No.: PCT/US2018/041694
§ 371 (c)(1),
(2) Date: Jan. 6, 2020

(87) PCT Pub. No.: WO2019/014382
PCT Pub. Date: Jan. 17, 2019

(65) Prior Publication Data
US 2020/0223812 A1 Jul. 16, 2020

Related U.S. Application Data

(60) Provisional application No. 62/531,569, filed on Jul. 12, 2017, provisional application No. 62/614,852, filed on Jan. 8, 2018, provisional application No. 62/626,549, filed on Feb. 5, 2018.

(51) Int. Cl.
C07D 307/68 (2006.01)
(52) U.S. Cl.
CPC .................. C07D 307/68 (2013.01)
(58) Field of Classification Search
CPC ........................ C07D 307/68; A61K 31/341
USPC .......................................... 549/485; 514/461
See application file for complete search history.

(56) References Cited

U.S. PATENT DOCUMENTS

| | | |
|---|---|---|
| 2,673,860 A | 3/1954 | Kuhn et al. |
| 2,750,394 A | 6/1956 | Peniston |
| 2,754,330 A | 7/1956 | Schreyer |
| 2,829,823 A | 4/1958 | Fedder |
| 2,917,529 A | 12/1959 | Drysdale |
| 2,929,823 A | 3/1960 | Garber et al. |
| 3,118,912 A | 1/1964 | Smith |
| 3,184,479 A | 5/1965 | Matter et al. |
| 3,290,263 A | 12/1966 | Smythe et al. |
| 3,326,944 A | 6/1967 | Lew |
| 3,329,626 A | 7/1967 | Teter et al. |
| 3,483,228 A | 12/1969 | Garber et al. |
| 4,005,178 A | 1/1977 | Bennett et al. |
| 4,339,387 A | 7/1982 | Fleche et al. |
| 4,400,468 A | 8/1983 | Faber |
| 4,438,082 A | 3/1984 | Dettling et al. |
| 4,533,743 A | 8/1985 | Medeiros et al. |
| 4,590,283 A | 5/1986 | Gaset et al. |
| 4,740,605 A | 4/1988 | Rapp et al. |
| 4,912,237 A | 3/1990 | Zeitsch et al. |
| 4,971,657 A | 11/1990 | Avignon et al. |
| 4,977,283 A | 12/1990 | Leupold et al. |
| 5,296,639 A | 3/1994 | Klug et al. |
| 5,312,967 A | 5/1994 | Kiely et al. |
| 5,472,648 A | 12/1995 | Alisch et al. |
| 5,474,965 A | 12/1995 | Nakatsuji et al. |
| 5,639,929 A | 6/1997 | Bharadwaj et al. |
| 6,337,302 B1 | 1/2002 | Teng et al. |
| 6,500,969 B1 | 12/2002 | Zhou et al. |
| 6,518,440 B2 | 2/2003 | Lightner et al. |
| 6,534,680 B1 | 3/2003 | Rauls et al. |
| 6,599,723 B1 | 7/2003 | Hembre et al. |
| 6,743,928 B1 | 6/2004 | Hanna |
| 6,861,387 B2 | 3/2005 | Ruth et al. |
| 7,109,145 B2 | 9/2006 | Ruth et al. |
| 7,208,439 B2 | 4/2007 | Zhong et al. |
| 7,317,116 B2 | 1/2008 | Sanborn |
| 7,385,081 B1 | 6/2008 | Gong |
| 7,411,078 B2 | 8/2008 | Miura et al. |
| 7,566,681 B2 | 7/2009 | Bock et al. |
| 7,572,925 B2 | 8/2009 | Dumesic et al. |
| 7,579,490 B2 | 8/2009 | Sanborn et al. |
| 7,700,788 B2 | 4/2010 | Lilga et al. |

(Continued)

FOREIGN PATENT DOCUMENTS

| | | |
|---|---|---|
| AU | 2011205116 A1 | 8/2011 |
| BR | PI1106661 | 8/2013 |
| CA | 2097821 | 1/1997 |
| CN | 102190785 | 9/2001 |
| CN | 101899145 | 12/2010 |
| CN | 102827361 | 12/2012 |
| CN | 103570926 | 2/2014 |

(Continued)

OTHER PUBLICATIONS

Deng et al., 2012, Conversion of Carbohydrates into 5-Hydroxymethylfurfural Catalyzed by ZnCl2 in Water. Chemical Communications 48(44): 5494-5496.
Abbadi et al., 1995, Effect of pH in the Pt-catalyzed oxidation of D-glucose to D-gluconic acid, J Mol Catalysis A: Chem 97:111-118.
Aiken et al., 2012, Molecular Mapping of the Acid Catalysed Dehydration of Fructose Chem. Commun., 48:5850-5852 and Supplemental Information.

(Continued)

Primary Examiner — Jeffrey H Murray
(74) Attorney, Agent, or Firm — Knobbe Martens Olson & Bear LLP

(57) ABSTRACT

The present disclosure provides processes for the purification of 2,5-furandicarboxylic acid (FDCA). The present disclosure further provides crystalline preparations of purified FDCA, as well as processes for making the same. In addition, the present disclosure provides mixtures used in processes for the purification of FDCA.

24 Claims, 68 Drawing Sheets

(56) References Cited

U.S. PATENT DOCUMENTS

| | | |
|---|---|---|
| 7,939,681 B2 | 5/2011 | Zhao et al. |
| 8,038,763 B2 | 10/2011 | Eichhorn et al. |
| 8,058,458 B2 | 11/2011 | Sanborn |
| 8,071,504 B2 | 12/2011 | Ragle et al. |
| 8,133,289 B2 | 3/2012 | Gruter et al. |
| 8,183,020 B2 | 5/2012 | Hanke |
| 8,193,381 B2 | 6/2012 | Lilga et al. |
| 8,193,382 B2 | 6/2012 | Lilga et al. |
| 8,231,693 B2 | 7/2012 | Gruter |
| 8,236,261 B2 | 8/2012 | Ragle et al. |
| 8,242,292 B2 | 8/2012 | Yutaka et al. |
| 8,242,293 B2 | 8/2012 | Gruter et al. |
| 8,273,504 B2 | 9/2012 | Goia et al. |
| 8,277,521 B2 | 10/2012 | Gruier |
| 8,314,260 B2 | 11/2012 | Gruter et al. |
| 8,314,267 B2 | 11/2012 | Brandvold |
| 8,324,409 B2 | 12/2012 | Rauchfuss et al. |
| 8,338,626 B2 | 12/2012 | Gruter et al. |
| 8,455,668 B2 | 6/2013 | Fu et al. |
| 8,501,989 B2 | 8/2013 | Boussie et al. |
| 8,519,167 B2 | 8/2013 | Muñoz de diego et al. |
| 8,524,923 B2 | 9/2013 | Grushin et al. |
| 8,546,288 B2 | 10/2013 | Pulskamp et al. |
| 8,558,018 B2 | 10/2013 | Sanborn |
| 8,568,680 B2 | 10/2013 | Hui et al. |
| 8,604,225 B2 | 12/2013 | Pedersen et al. |
| 8,658,810 B2 | 2/2014 | Partin et al. |
| 8,669,383 B2 | 3/2014 | Howard et al. |
| 8,669,397 B2 | 3/2014 | Boussie et al. |
| 8,709,286 B2 | 4/2014 | Bloom et al. |
| 8,729,256 B2 | 5/2014 | Moliner-marin et al. |
| 8,748,479 B2 | 6/2014 | Shaikh et al. |
| 8,754,000 B2 | 6/2014 | Chan et al. |
| 8,772,513 B2 | 7/2014 | Janka et al. |
| 8,772,515 B2 | 7/2014 | Dumesic et al. |
| 8,785,667 B2 | 7/2014 | Grushin et al. |
| 8,785,668 B2 | 7/2014 | Du et al. |
| 8,791,277 B2 | 7/2014 | Janka et al. |
| 8,791,278 B2 | 7/2014 | Shaikh et al. |
| 8,796,477 B2 | 8/2014 | Janka et al. |
| 8,809,556 B2 | 8/2014 | Janka et al. |
| 8,846,960 B2 | 9/2014 | Janka et al. |
| 8,846,984 B2 | 9/2014 | Allgeier et al. |
| 8,846,985 B2 | 9/2014 | Allgeier et al. |
| 8,859,788 B2 | 10/2014 | Partin et al. |
| 8,859,826 B2 | 10/2014 | Allgeier et al. |
| 8,865,921 B2 | 10/2014 | Muñoz de diego et al. |
| 8,877,950 B2 | 11/2014 | Gruter et al. |
| 8,901,326 B2 | 12/2014 | Howard et al. |
| 8,912,349 B2 | 12/2014 | Shaikh et al. |
| 8,916,719 B2 | 12/2014 | Shaikh et al. |
| 8,916,720 B2 | 12/2014 | Shaikh et al. |
| 8,927,768 B2 | 1/2015 | Boussie et al. |
| 8,969,404 B2 | 3/2015 | Janka et al. |
| 9,006,470 B2 | 4/2015 | Janka et al. |
| 9,018,423 B2 | 4/2015 | Allgeier et al. |
| 9,023,751 B2 | 5/2015 | Mizutani |
| 9,028,580 B1 | 5/2015 | Andrews |
| 9,029,579 B2 | 5/2015 | Janka et al. |
| 9,029,580 B2 | 5/2015 | Janka et al. |
| 9,029,581 B2 | 5/2015 | Partin et al. |
| 9,032,355 B2 | 5/2015 | Bantas et al. |
| 9,035,094 B2 | 5/2015 | Dias et al. |
| 9,035,109 B2 | 5/2015 | Dias et al. |
| 9,045,787 B2 | 6/2015 | Ruijssenaars et al. |
| 9,090,550 B2 | 7/2015 | Howard et al. |
| 9,090,581 B2 | 7/2015 | De Sousa Dias et al. |
| 9,108,979 B2 | 8/2015 | Davis et al. |
| 9,145,805 B2 | 9/2015 | Sato et al. |
| 9,156,766 B2 | 10/2015 | Boussie et al. |
| 9,156,805 B2 | 10/2015 | Shaikh et al. |
| 9,156,806 B2 | 10/2015 | Shaikh et al. |
| 9,162,998 B2 | 10/2015 | Backes et al. |
| 9,169,229 B2 | 10/2015 | Parker et al. |
| 9,181,157 B2 | 11/2015 | Allgeier et al. |
| 9,199,957 B2 | 12/2015 | Siqueira et al. |
| 9,199,958 B2 | 12/2015 | Janka et al. |
| 9,206,148 B2 | 12/2015 | Cho et al. |
| 9,206,149 B2 | 12/2015 | Janka et al. |
| 9,227,904 B1 | 1/2016 | Hong et al. |
| 9,228,051 B2 | 1/2016 | Carman, Jr. et al. |
| 9,238,635 B2 | 1/2016 | Essayem et al. |
| 9,249,118 B2 | 2/2016 | Janka et al. |
| 9,260,403 B2 | 2/2016 | Yoshikuni et al. |
| 9,266,850 B2 | 2/2016 | Janka et al. |
| 9,309,181 B2 | 4/2016 | Chwae et al. |
| 9,321,744 B1 | 4/2016 | Hsu et al. |
| 9,376,414 B2 | 6/2016 | Van haveren et al. |
| 9,388,116 B2 | 7/2016 | Stensrud et al. |
| 9,388,152 B2 | 7/2016 | Ibert et al. |
| 9,416,119 B2 | 8/2016 | Bloom et al. |
| 9,422,258 B2 | 8/2016 | Bloom et al. |
| 9,428,480 B2 | 8/2016 | Janka et al. |
| 9,458,122 B2 | 10/2016 | Shaikh et al. |
| 9,464,026 B2 | 10/2016 | Stensrud et al. |
| 9,468,908 B2 | 10/2016 | Salem et al. |
| 9,475,787 B2 | 10/2016 | Mihovilovic et al. |
| 9,499,506 B2 | 11/2016 | Besson et al. |
| 9,506,060 B2 | 11/2016 | Bandaru et al. |
| 9,506,090 B2 | 11/2016 | Kambourakis et al. |
| 9,528,133 B2 | 12/2016 | Kambourakis et al. |
| 9,586,923 B2 | 3/2017 | Subramaniam et al. |
| 9,611,241 B2 | 4/2017 | Boussie et al. |
| 9,617,234 B1 | 4/2017 | Dumesic et al. |
| 9,643,945 B2 | 5/2017 | Mazoyer et al. |
| 9,670,118 B2 | 6/2017 | Allgeier et al. |
| 9,682,368 B2 | 6/2017 | Dias et al. |
| 9,701,652 B2 | 7/2017 | Miller et al. |
| 9,765,045 B2 | 9/2017 | Stensrud et al. |
| 9,783,516 B2 | 10/2017 | Bloom et al. |
| 10,017,486 B2 | 7/2018 | Boussie et al. |
| 10,093,638 B2 | 10/2018 | Masuno et al. |
| 10,208,006 B2 | 2/2019 | Sokolovskii et al. |
| 10,351,544 B2 | 7/2019 | Almeida et al. |
| 10,385,033 B2 | 8/2019 | Gordillo et al. |
| 10,442,780 B2 | 10/2019 | Sokolovskii et al. |
| 10,457,657 B2 | 10/2019 | Metkar et al. |
| 10,464,913 B2 | 11/2019 | Almeida et al. |
| 10,538,499 B2 | 1/2020 | Howard et al. |
| 10,654,819 B2 | 5/2020 | Sokolovskii et al. |
| 10,851,074 B2 | 12/2020 | Sokolovskii et al. |
| 2006/0084800 A1 | 4/2006 | Chenault |
| 2007/0027341 A1 | 2/2007 | Rossi et al. |
| 2007/0179312 A1 | 8/2007 | O'Meadhra et al. |
| 2008/0081883 A1 | 4/2008 | King et al. |
| 2009/0030215 A1 | 1/2009 | Dignan et al. |
| 2009/0131690 A1 | 5/2009 | Gruter et al. |
| 2009/0156841 A1 | 6/2009 | Sanborn et al. |
| 2009/0306415 A1 | 12/2009 | Gruter et al. |
| 2009/0311568 A1 | 12/2009 | Yamada |
| 2010/0004437 A1 | 1/2010 | Binder et al. |
| 2010/0052469 A1 | 3/2010 | Naruse et al. |
| 2010/0058650 A1 | 3/2010 | Gruter et al. |
| 2010/0081833 A1 | 4/2010 | Gruter et al. |
| 2010/0083565 A1 | 4/2010 | Gruter et al. |
| 2010/0178584 A1 | 7/2010 | Hibino et al. |
| 2010/0196802 A1 | 8/2010 | Tabata et al. |
| 2010/0212217 A1 | 8/2010 | Gruter et al. |
| 2010/0212218 A1 | 8/2010 | Gruter |
| 2010/0218415 A1 | 9/2010 | Gruter et al. |
| 2010/0218416 A1 | 9/2010 | Gruter |
| 2010/0299991 A1 | 12/2010 | Gruter |
| 2010/0317822 A1 | 12/2010 | Boussie et al. |
| 2010/0317879 A1 | 12/2010 | Zhao et al. |
| 2011/0082304 A1 | 4/2011 | Gruter et al. |
| 2011/0282020 A1 | 11/2011 | Sipos |
| 2011/0302826 A1 | 12/2011 | Gruter |
| 2011/0306790 A1 | 12/2011 | Murphy et al. |
| 2012/0083610 A1 | 4/2012 | Gruter et al. |
| 2012/0237855 A1 | 9/2012 | Hucul et al. |
| 2012/0271060 A1 | 10/2012 | Muñoz de diego et al. |
| 2012/0282352 A1 | 11/2012 | Lewis et al. |
| 2012/0302768 A1 | 11/2012 | Janka et al. |
| 2012/0302773 A1 | 11/2012 | Janka et al. |

(56) References Cited

U.S. PATENT DOCUMENTS

| | | |
|---|---|---|
| 2013/0095263 A1 | 4/2013 | Carman, Jr. et al. |
| 2013/0137882 A1 | 5/2013 | Borsotti et al. |
| 2013/0171397 A1 | 7/2013 | Ghosh et al. |
| 2013/0184495 A1 | 7/2013 | Dias et al. |
| 2013/0295485 A1 | 11/2013 | Gottesfeld et al. |
| 2013/0324708 A1 | 12/2013 | De Sousa Dias et al. |
| 2014/0024844 A1 | 1/2014 | Janka et al. |
| 2014/0073805 A1 | 3/2014 | Franke et al. |
| 2014/0121389 A1 | 5/2014 | Essayem et al. |
| 2014/0142328 A1 | 5/2014 | Shaikh et al. |
| 2014/0205786 A1 | 7/2014 | Nederberg et al. |
| 2014/0235880 A1 | 8/2014 | Shaikh et al. |
| 2014/0271446 A1 | 9/2014 | Desmedt et al. |
| 2014/0295508 A1 | 10/2014 | Yoshikuni et al. |
| 2014/0302982 A1 | 10/2014 | Liu et al. |
| 2014/0315262 A1 | 10/2014 | Sanborn et al. |
| 2014/0343305 A1 | 11/2014 | Subramaniam et al. |
| 2014/0349351 A1 | 11/2014 | Jensen et al. |
| 2014/0364631 A1 | 12/2014 | Davis et al. |
| 2014/0371413 A1 | 12/2014 | Miura et al. |
| 2015/0010965 A1 | 1/2015 | Ertl et al. |
| 2015/0031904 A1 | 1/2015 | Cho et al. |
| 2015/0045576 A1 | 2/2015 | Benecke et al. |
| 2015/0048274 A1 | 2/2015 | Eyal et al. |
| 2015/0051412 A1 | 2/2015 | Janka et al. |
| 2015/0087848 A1 | 3/2015 | Oyola et al. |
| 2015/0110983 A1 | 4/2015 | Kriegel et al. |
| 2015/0119588 A1 | 4/2015 | van Haveren et al. |
| 2015/0126731 A1 | 5/2015 | Essayem et al. |
| 2015/0141584 A1 | 5/2015 | Saywell et al. |
| 2015/0183755 A1 | 7/2015 | Subramaniam et al. |
| 2015/0218118 A1 | 8/2015 | Mihovilovic et al. |
| 2015/0232498 A1 | 8/2015 | Riisager et al. |
| 2015/0274687 A1 | 10/2015 | Ibert et al. |
| 2015/0299095 A1 | 10/2015 | Stensrud et al. |
| 2015/0321119 A1 | 11/2015 | Parker et al. |
| 2015/0321180 A1 | 11/2015 | Parker et al. |
| 2015/0322028 A1 | 11/2015 | Janka et al. |
| 2015/0322029 A1 | 11/2015 | Janka et al. |
| 2015/0329927 A1 | 11/2015 | Parekh |
| 2015/0336090 A1 | 11/2015 | Kanna et al. |
| 2015/0193364 A1 | 12/2015 | Blocksome et al. |
| 2015/0376154 A1 | 12/2015 | Besson et al. |
| 2016/0009015 A1 | 1/2016 | Bouffand et al. |
| 2016/0016926 A1 | 1/2016 | Sanborn |
| 2016/0024039 A1 | 1/2016 | Mazoyer et al. |
| 2016/0028093 A1 | 1/2016 | Pietrasz et al. |
| 2016/0053289 A1 | 2/2016 | Ertl |
| 2016/0075672 A1 | 3/2016 | Van Haveren et al. |
| 2016/0130244 A1 | 5/2016 | Janka et al. |
| 2016/0145662 A1 | 5/2016 | Van Spronsen et al. |
| 2016/0207898 A1 | 7/2016 | Singh et al. |
| 2016/0207899 A1 | 7/2016 | Yi et al. |
| 2016/0221979 A1 | 8/2016 | Yashiro et al. |
| 2016/0221980 A1 | 8/2016 | Parker et al. |
| 2016/0289161 A1 | 10/2016 | Stensrud et al. |
| 2016/0311790 A1 | 10/2016 | Janka et al. |
| 2016/0332979 A1 | 11/2016 | Fontenot et al. |
| 2017/0015643 A1 | 1/2017 | Venkitasubramanian et al. |
| 2017/0050119 A1 | 2/2017 | Roa Engel et al. |
| 2017/0050944 A1 | 2/2017 | Kambourakis et al. |
| 2017/0088865 A1 | 3/2017 | Kambourakis et al. |
| 2017/0137363 A1 | 5/2017 | Asikainen et al. |
| 2017/0144982 A1 | 5/2017 | Miller et al. |
| 2017/0157530 A1 | 6/2017 | Parker et al. |
| 2017/0197930 A1 | 7/2017 | Sokolovskii et al. |
| 2017/0226144 A1 | 8/2017 | Kuo et al. |
| 2017/0260154 A1 | 9/2017 | Janka et al. |
| 2017/0305873 A1 | 10/2017 | Miller et al. |
| 2017/0313670 A1 | 11/2017 | De Sousa Dias et al. |
| 2018/0093894 A1 | 4/2018 | Smith et al. |
| 2018/0222877 A1 | 8/2018 | Metkar et al. |
| 2019/0016658 A1 | 1/2019 | Mullen et al. |
| 2019/0031797 A1 | 1/2019 | Dyson et al. |
| 2019/0083960 A1 | 3/2019 | Kim et al. |
| 2019/0119238 A1 | 4/2019 | Metkar et al. |
| 2019/0233386 A1 | 8/2019 | Sokolovskii et al. |
| 2019/0270717 A1 | 9/2019 | Masuno et al. |
| 2019/0300494 A1 | 10/2019 | Metkar et al. |
| 2019/0389826 A1 | 12/2019 | Metkar et al. |
| 2020/0002300 A1 | 1/2020 | Kunz et al. |
| 2020/0010441 A1 | 1/2020 | Sokolovskii et al. |
| 2021/0078964 A1 | 3/2021 | Sokolovskii et al. |

FOREIGN PATENT DOCUMENTS

| | | |
|---|---|---|
| CN | 103965146 | 8/2014 |
| EP | 1834950 A1 | 9/2007 |
| EP | 2053047 A1 | 4/2009 |
| EP | 2103606 A1 | 9/2009 |
| EP | 2105438 A1 | 9/2009 |
| EP | 2050742 B1 | 7/2010 |
| EP | 2105439 B1 | 10/2011 |
| EP | 2390247 A1 | 11/2011 |
| EP | 2455373 A1 | 5/2012 |
| EP | 2487170 A1 | 8/2012 |
| EP | 2565189 A1 | 3/2013 |
| EP | 2703395 A1 | 3/2014 |
| EP | 2864302 B1 | 4/2015 |
| EP | 2864304 | 4/2015 |
| EP | 2864305 | 4/2015 |
| EP | 2864306 | 4/2015 |
| EP | 3015463 A1 | 5/2016 |
| EP | 2784069 B1 | 7/2016 |
| EP | 2714671 B1 | 9/2016 |
| EP | 2423205 B1 | 10/2016 |
| EP | 3137184 | 3/2017 |
| EP | 2953937 | 9/2017 |
| FR | 2663933 A1 | 1/1992 |
| FR | 2664273 A1 | 1/1992 |
| FR | 2669634 | 5/1992 |
| FR | 2669635 B1 | 6/1994 |
| FR | 2723946 | 3/1996 |
| GB | 591858 A1 | 9/1947 |
| GB | 600871 A1 | 4/1948 |
| GB | 876463 A1 | 9/1961 |
| JP | H0288569 A | 3/1990 |
| JP | 2006-328374 | 12/2006 |
| JP | 2012-144744 | 8/2012 |
| JP | 5120944 B2 | 1/2013 |
| JP | 2013-155388 | 8/2013 |
| JP | 5311778 B2 | 10/2013 |
| JP | 5446121 B2 | 3/2014 |
| KR | 2012107573 | 10/2012 |
| WO | WO 1992/10486 | 6/1992 |
| WO | WO 2007/104514 | 9/2007 |
| WO | WO 2007/104515 | 9/2007 |
| WO | WO 2008/054804 | 5/2008 |
| WO | WO 2009/030504 | 3/2009 |
| WO | WO 2009/030506 | 3/2009 |
| WO | WO 2009/030507 | 3/2009 |
| WO | WO 2009/030508 | 3/2009 |
| WO | WO 2009/030509 | 3/2009 |
| WO | WO 2009/030511 | 3/2009 |
| WO | WO 2009/141166 | 11/2009 |
| WO | WO 2010/077133 | 7/2010 |
| WO | WO 2010/132740 | 11/2010 |
| WO | WO 2011/043660 | 4/2011 |
| WO | WO 2011/043661 | 4/2011 |
| WO | WO 2011/149339 | 12/2011 |
| WO | WO 2011/155964 | 12/2011 |
| WO | WO 2012/015616 | 2/2012 |
| WO | WO 2012/091570 | 7/2012 |
| WO | WO 2012/091573 | 7/2012 |
| WO | WO 2012/156479 | 11/2012 |
| WO | WO 2012/161967 | 11/2012 |
| WO | WO 2012/161970 | 11/2012 |
| WO | WO 2013/034763 | 3/2013 |
| WO | WO 2013/048248 | 4/2013 |
| WO | WO 2013/053816 | 4/2013 |
| WO | WO 2013/062408 | 5/2013 |
| WO | WO 2013/095263 | 6/2013 |
| WO | WO 2013/100768 | 7/2013 |
| WO | WO 2013/103574 | 7/2013 |

(56) References Cited

FOREIGN PATENT DOCUMENTS

| | | |
|---|---|---|
| WO | WO 2013/106136 | 7/2013 |
| WO | WO 2013/117585 | 8/2013 |
| WO | WO 2013/120989 | 8/2013 |
| WO | WO 2013/133489 | 9/2013 |
| WO | WO 2013/144525 | 10/2013 |
| WO | WO 2013/191944 A1 | 12/2013 |
| WO | WO 2014/032731 | 3/2014 |
| WO | WO 2014/033289 | 3/2014 |
| WO | WO 2014/037560 | 3/2014 |
| WO | WO 2014/058859 | 4/2014 |
| WO | WO 2014/074482 A1 | 5/2014 |
| WO | WO 2014/100254 | 6/2014 |
| WO | WO 2014/100256 | 6/2014 |
| WO | WO 2014/100257 | 6/2014 |
| WO | WO 2014/100265 | 6/2014 |
| WO | WO 2014/102413 | 7/2014 |
| WO | WO 2014/122319 | 8/2014 |
| WO | WO 2014/152366 | 9/2014 |
| WO | WO 2014/154676 | 10/2014 |
| WO | WO 2014/158838 | 10/2014 |
| WO | WO 2014/163500 | 10/2014 |
| WO | WO 2014/173973 | 10/2014 |
| WO | WO 2014/182171 | 11/2014 |
| WO | WO 2014/204296 | 12/2014 |
| WO | WO 2014/204313 | 12/2014 |
| WO | WO 2014/209112 | 12/2014 |
| WO | WO 2015/015243 | 2/2015 |
| WO | WO 2015/030590 | 3/2015 |
| WO | WO 2015/031910 | 3/2015 |
| WO | WO 2015/041601 | 3/2015 |
| WO | WO 2015/056270 | 4/2015 |
| WO | WO 2015/066570 | 5/2015 |
| WO | WO 2015/088341 | 6/2015 |
| WO | WO 2015/113060 | 7/2015 |
| WO | WO 2015/168327 | 11/2015 |
| WO | WO 2015/171704 | 11/2015 |
| WO | WO 2015/189481 | 12/2015 |
| WO | WO 2015/197699 | 12/2015 |
| WO | WO 2016/053186 | 4/2016 |
| WO | WO 2016/057628 | 4/2016 |
| WO | WO 2016/057673 | 4/2016 |
| WO | WO 2016/057676 | 4/2016 |
| WO | WO 2016/057682 | 4/2016 |
| WO | WO 2016/057687 | 4/2016 |
| WO | WO 2016/059205 | 4/2016 |
| WO | WO 2016/068712 | 5/2016 |
| WO | WO 2016/076710 | 5/2016 |
| WO | WO 2016/076711 | 5/2016 |
| WO | WO 2016/133384 | 8/2016 |
| WO | WO 2016/141148 | 9/2016 |
| WO | WO 2016/146752 | 9/2016 |
| WO | WO 2016/146753 | 9/2016 |
| WO | WO 2016/166421 | 10/2016 |
| WO | WO 2016/168233 | 10/2016 |
| WO | WO 2016/186278 | 11/2016 |
| WO | WO 2016/195499 | 12/2016 |
| WO | WO 2016/195500 A1 | 12/2016 |
| WO | WO 2016/196499 | 12/2016 |
| WO | WO 2017/019431 | 2/2017 |
| WO | WO 2017/019441 | 2/2017 |
| WO | WO 2017/019444 | 2/2017 |
| WO | WO 2017/019445 | 2/2017 |
| WO | WO 2017/019447 | 2/2017 |
| WO | WO 2017/030668 | 2/2017 |
| WO | WO 2017/034985 | 3/2017 |
| WO | WO 2017/050815 | 3/2017 |
| WO | WO 2017/075391 | 5/2017 |
| WO | WO 2017/075425 | 5/2017 |
| WO | WO 2017/083297 | 5/2017 |
| WO | WO 2017/097843 | 6/2017 |
| WO | WO 2017/123763 | 7/2017 |
| WO | WO 2017/155286 | 9/2017 |
| WO | WO 2019/014382 | 1/2019 |
| WO | WO 2019/058270 | 3/2019 |
| WO | WO 2019/072920 | 4/2019 |
| WO | WO 2019/089448 | 5/2019 |
| WO | WO 2019/185646 | 10/2019 |
| WO | WO 2019/229077 | 12/2019 |
| WO | WO 2019/229080 | 12/2019 |
| WO | WO 2020/011996 | 1/2020 |

OTHER PUBLICATIONS

Amarasekara et al., 2013, Synthesis and Characterization of All Renewable Resources Based Branched Polyester: Poly(2,5-furandicarboxylic acid-co-glycerol) ISRN Polymer Science, vol. 2013, Article ID 645169.

Artz et al., 2015, Selective Aerobic Oxidation of HMF to 2,5-Diformylfuran on Covalent Triazine Frameworks-Supported Ru Catalysts, ChemSusChem. 8(4):672-679.

Bari, Mar. 15-18, 2016, The 100% Bio-Based Replacement for PET! Presented at the 31st Annual World Petrochemical Conference, Houston, TX, in 28 pages.

Barrett et al., 1951, The determination of pore volume and area distributions in porous substances. I. Computations from nitrogen isotherms, J. Am. Chem. Soc. 73:373-380.

Besson et al., 2000, Selective oxidation of alcohols and aldehydes on metal catalysts, 57:127-141.

Bratuescu, 2000, Cyclisation under the Action of the Microwaves of the D-Saccaric acid to 2,5-Furandicarboxylic acid. Revue Roumaine de Chimie, 45(9):883-885 (Article in French).

Brunauer et al., 1938, Adsorption of bases in multimolecular layers, J Am Chem Soc. 60:309-311.

Caes et al., 2011, Conversion of fructose into 5-(hydroxymethyl)furfural in sulfolane, ChemSusChem, 4:353-356.

Casanova et al., 2009, Biomass into Chemicals: Aerobic Oxidation of 5-Hydroxymethyl-2-furfural into 2,5-Furandicarboxylic Acid with Gold Nanoparticle Catalysts, ChemSusChem, 2(12):1138-1144; Abstract Only.

Casanova et al., 2009, Biomass into Chemicals: One pot-base free oxidative esterification of 5-hydroxymethyl-2-furfural into 2,5-dimethylfuroate with gold on nanoparticulated ceria, J Catalysis, 265(1):109-116.

Cope et al., Jan. 1956, Benzofuran from saccharic acid, Notes, p. 141.

Corma et al., 2007, Chemical routes for the Transformation of Biomass into Chemicals, Chem Rev., 107:2411-2502.

Davis et al., 2011, Oxidation of 5-hydroxymethylfurfural over supported Pt, Pd and Au catalysts, Catalysis Today 160(1):55-66; Abstract Only.

Davis S.E., 2012, 5-Hydroxymethylfurfural Oxidation on Supported Metal Catalysts, Dissertation, University of Virginia, 130 pp.

De Jong et al., 2012, Furandicarboxylic Acid (FDCA), A Versatile Building Block for a Very Interesting Class of Polyesters In Biobased Monomers, Polymers, and Materials, Smith et al. [Eds.], Chapter 1; ACS Symposium Series; American Chemical Society, Washington, D.C. in 13 pages.

Diamond et al., 2013, Application of high trhoughput experimentation to the production fo commodity chemicals from renewable feedstocks, in Modern Applications of High Throughput R&D in Heterogeneous Catalysis, Hagemeyer et al., [Eds.], Bentham Science Publishers, Chapter 8, pp. 299-309.

Gattinger et al., Nov. 16, 2016, Presentation #466868: Cyclization and Dehydration of Aldaric Acids to 2,5-Furandicarboxylic Acid, at the Annual Meeting of AiChE, San Francisco, CA—Abstract Only.

Gorbanev et al., 2011, Selective Aerobic Oxidation of 5-Hydroxymethylfurfural in Water Over Solid Ruthenium Hydroxide Catalysts with Magnesium-based Supports, Catal Lett. 141:1752-1760; Abstract Only.

Gruter et al., 2012, Accelerating research into bio-based FDCA-polyesters by using small scale parallel film reactors, Comb. Chem. High Throughput Screening,15:180-188.

Gupta et al., 2011, Hydrotalcite-supported gold-nanoparticle-catalysted highly efficient base-free aqueous oxidation of 5-hydroxymethylfurfural into 2,5-furandicarboxylic acid under atmospheric oxygen pressure Green Chem., 13:824-827 and Supplementary Material in 11 pages.

(56) References Cited

OTHER PUBLICATIONS

Han et al., 2016, Base-free aerobic oxidation of 5-hydroxymethylfurfural to 2,5-furandicarboxylic acid over a Pt/C—O—Mg catalyst, Green Chem. 18(6):1597-1604.
Kazi et al., 2011, Techno-economic Analysis of Dimethylfuran (DMF) and Hydroxymethylfurfural (HMF) Production from Pure Fructose in Catalytic Processes, Chem Eng J., 169:329-338.
Kimura et al., 1993, Selective oxidation of glycerol on a platinum-bismuth catalyst, Applied Catalysis A: General 96(2):217-228.
Koopman et al., Apr. 2010, Efficient whole-cell biotransformation of 5-(hydroxymethyl)furfural into FDCA, 2,5-furandicarboxylic acid, Bioresource Technology, 101:6291-6296.
Kröger et al., 2000, A new approach for the production of 2,5-furandicarboxylic acid by in situ oxidation of 5-hydroxymethylfurfural starting from fructose, Topics in Catalysis, 13:237-242.
Lu et al., 2013, Aerobic oxidation of primary aliphatic alcohols over bismuth oxide supported platinum catalysts in water, Green Chem., 15:2215-2221.
MacFarlane et al., 2007, Ionic liquids-Progress on the Fundamental Issues, Aust J Chem., 60:3-5.
Mallat et al., 1994, Partial Oxidation of cinnamyl alcohol on bimetallic catalysts of improved resistance to self-poisoning, in Studies in Surface Science and Catalysis, Corberan et al. [Eds.], Elsevier; 82:561-570.
Mallat et al., 1994, Platinum-catalyzed oxidation of alcohols in aqueous solutions. The role of Bi-promotion in suppression of catalyst deactivation, in Catalyst Deactivation—Studies in Surface Science & Catalysis; Delmon et al. [Eds.], vol. 88, pp. 385-389.
Mallat et al., 1998, Aerobic Oxidation of alpha-substituted alcohols over promoted plantinum metal catalysts, in Supported Reagents and Catalysts in Chemistry, Hodnett [Ed.]; pp. 66-71.
March's Advanced Organic Chemistry, M. B. Smith et al., [Eds.]; 7th Edition, Wiley (2013); TOC.
Modern Polyesters: Chemistry and Technology of Polyesters and Copolyesters, J. Scheirs et al., [Eds.]; Wiley (2003); TOC.
Pavone, Jun. 2016, Bio-Based Furan Dicarboxylic Acid (FDCA) and Its Polymer Polyethylene Furanoate (PEF), HIS Chemical, PEP Report 294, in 409 pages.
Payne et al., 2010, Solubility of bio-sources feedstocks in 'green' solvents, Green Chem, 12:1648-1653.
Ragauskas et al., 2006, The Path Forward for Biofuels and Biomaterials, Science 311:484-489.
Rasrendra et al., 2013, Experimental studies on the pyrolysis of humins from the acid-catalysed dehydration of C6-sugars, J Analyt Appl Pyrolysis. 104:299-307. (2013) 104:299-307.
Rass et al., 2013, Selective aqueous phase oxidation of 5-hydroxymethylfurfural to 2,5-furandicarboxylic acid over Pt/C catalysts: influence of the base and effect of bismuth promotion, Green Chem, 15:2240-2251.
Rass et al., 2015, Selective aerobic oxidation of 5-HMF into 2,5-furandicarboxylic acide with Pt catalysts supported on TiO2- and ZrO2-based supports, ChemSusChem, 8:1206-1217.
Rogers et al., 2007, Ionic Liquids, Accounts of Chemical Research 40(11):1077-1078.
Shiramizu et al., 2013, Expanding the Scope of Biomass-Derived Chemicals through Tandem Reactions based on Oxorhenium-catalyzed Deoxydehydration, Angew Chem Int Ed. 52(49):12905-12909.
Sigma-Aldrich®, Jun. 22, 2010, 2,5-Furandicarboxylic acid—97%, Product Specification, 1 p.

Sixta H., Jun. 19-22, 2017, Advances in Biorefinery: 7-Furan Biorefinery; Aalto University School of Chemical Technology, Finland; PPPresentation for Course/CHEM-L2020 in 89 pages.
Sousa et al., Sep. 2015, Biobased polyesters and other polymers from 2,5-furandicarboxylic acid: a tribute to furan excellency, Polym Chem., 6(33):5961-5983.
Szmant et al., 1981, The Preparation of 5-Hydroxymethylfurfuraidehyde from High Fructose Corn Syrup and Other Carbohydrates, J Chem Tech Biotech. 31(1):135-145, Abstract only.
Teong et al., 2014, Poly-benzylic ammonium chloride resins as solid catalysts for fructose dehydration, ChemSusChem, 7:2120-2126.
Tong et al., 2011, Defunctionalization of fructose and sucrose: iron-catalyzed production of 5-hydroxymethylfurfural from fructose and sucrose, Catalysis Today, 175:524-527.
Trieble, Aug. 2012, Simulation and Economic Analysis of 5-Hydroxymethylfurfural Conversion to 2,5-Furandicarboxylic Acid, Dipl. Ing. Thesis (Leoben University of Mining) in 143 pages.
Tucker et al., 2012, Acid-Functionalized SBA-15-Type Periodic Mesoporous Organosilicas and Their Use in the Continuous Production of 5-Hydroxymethylfurfural, ACS Catalysis, 2:1865-1876 and Supporting Documentation in 15 pages.
U.S. EPA, Office of Water, Nov. 2005, Membrane Filtration Guidance Manual, EPA 815-R-06-009, 332 pp.
Van Putten et al., 2013, Hydroxymethylfurfural, A Versatile Platform Chemical Made from Renewable Resources Chem. Rev., 113:1499-1597.
Verdeguer, et al., 1993, Oxydation catalytique du HMF en acide 2,5-furane dicarboxylique, Journal of Molecular Catalysis, 85:327-344.
Villa et al., 2013, Pd-modified Au on Carbon as an Effective and Durable Catalyst for the Direct Oxidation of HMF to 2,5-Furandicarboxylic Acid, Chem. Sus. Chem., 6:609-612.
Vinke et al., 1990, Platinum catalyzed oxidation of 5-hydroxymethylfurfural, Studies in Surface Science & Catalysis, 55:147-158.
Wan et al., 2014, Base-Free Aerobic Oxidation of 5-Hydroxymethylfurfural to 2,5-Furandicarboxylic Acid in Water Catalyzed by Functionalized Carbon Nanotube-Supported Au—Pd Alloy Nanoparticles ACS Catal., 4(7):2175-2185 and Supporting Information in 17 pages.
Werpy et al. (Eds.), 2004, Top Value Added Chemicals from Biomass vol. 1: Results of Screening for Potential Candidates from Sugars and Synthesis Gas, U.S. Dept. of Energy, Office of Scientific Information: Oak Ridge, Tenn. DOE/GO-102004-1992, 76 pp.
Wilkes, 2002, A short history of ionic liquides-from molten salts to neoteric solvents, Green Chemistry, 4:73-80.
Xie et al., 2016, Influence of Dioxygen on the Promotional Effect of Bi during Pt-Catalyzed Oxidation of 1,6-Hexnediol, ACS Catal. 6:4206-4217.
Yang et al. 2015, Effect of organic solvent and Brønsted acid on 5-hydroxymethylfurfural preparation from glucose over CrCl3. RSC Adv. 5:27805-27813.
Zhang et al., 2015, Advances in catalytic production of bio-based polyester monomer 2,5-furandicarboxylic acid derived from ilgnocellulosic biomass, Carbohyd Polymers 130:420-428.
International Search Report for PCT/US2018/041694 dated Jan. 10, 2018.
Morozov, Andrey A., "Synthesis and study of the properties of derivatives of 5-hydroxymethylfurfural". Doctoral Dissertation for the degree of chemical sciences, (2014) Krasnoyarsk (23 pages).
Russian Office Action dated Oct. 15, 2021 for Application No. 2019143853, filed Dec. 25, 2019. (17 pages).

PURIFIED 2,5-FURANDICARBOXYLIC ACID PATHWAY PRODUCTS

CROSS REFERENCE TO RELATED APPLICATIONS

This application is a U.S. National Phase Application of PCT International Application Number PCT/US2018/041694, filed on Jul. 11, 2018, designating the United States of America and published in the English language, which is an International Application of and claims the benefit of priority to U.S. Provisional Application No. 62/531,569, filed on Jul. 12, 2017, U.S. Provisional Application No. 62/614,852, filed on Jan. 8, 2018, and U.S. Provisional Application No. 62/626,549, filed on Feb. 5, 2018. The disclosures of the above-referenced applications are hereby expressly incorporated by reference in their entireties.

PARTIES OF JOINT RESEARCH AGREEMENT

The subject matter disclosed and the claimed invention was made by, or on behalf of, and/or in connection with a joint research agreement between Rennovia, Inc. and Stora Enso Oyj that was in effect on and before the date the claimed invention was made, and the claimed invention was made as a result of activities undertaken within the scope of the agreement.

FIELD

The present disclosure relates to processes and mixtures for the removal of impurities from 2,5-furandicarboxylic acid pathway products to produce purified 2,5-furandicarboxylic acid pathway products. In some embodiments, the process includes the reduction and removal of 5-formylfuran-2-carboxylic acid. In some embodiments, the process includes the removal of hydroxymethylfurancarboxylic acid. In some embodiments, the mixture includes 5-formylfurancarboxylic acid. In some embodiments the mixture includes hydroxymethylfurancarboxylic acid.

BACKGROUND

Furan-2,5-dicarboxylic acid (FDCA) is compound with industrial importance. For example, FDCA can be polymerized to industrial quality polyesters. However, methods used to produce FDCA often result in an FDCA product containing impurities. Such impurities include 5-formylfuran-2-carboxylic acid (FFCA). Impurities can be difficult to remove from FDCA. FDCA products containing impurities can lead to the formation of undesirable color bodies. Color bodies include colored substances and also precursors to colored substances (e.g. precursors can be converted to colored substances during a polymerization reaction). Color bodies are known to form from reaction intermediates or side products from the oxidation of 5-hydroxymethylfurfural (HMF) during the production of FDCA. A known color body forming impurity is 5-formylfuran-2-carboxylic acid (FFCA), an intermediate structure formed during the oxidation of HMF to FDCA. There exists a need for processes that remove impurities from FDCA.

SUMMARY

In one aspect, the present disclosure is directed to a process for producing a purified 2,5-furandicarboxylic acid (FDCA) pathway product comprising: contacting an FDCA pathway product comprising FDCA and 5-formylfurancarboxylic acid (FFCA) with hydrogen in the presence of a heterogeneous reduction catalyst and a solvent under conditions sufficient to form a reaction mixture for reducing the FFCA to hydroxymethylfurancarboxylic acid (HMFCA), and producing a purified FDCA pathway product; wherein the purified FDCA pathway product comprises FDCA, HMFCA, less than 10% molar impurities of FFCA, less than 10% molar impurities of 5-methyl-2-furoic acid (MFA), and less than 10% molar impurities of tetrahydrofuran-2,5-dicarboxylic acid (THFDCA); wherein the solvent is a multi-component solvent comprising water and a water-miscible aprotic organic solvent; and wherein the heterogeneous reduction catalyst comprises a solid support and a metal selected from the group consisting of Cu, Ni, Co, Pd, Pt, Ru, Ag, Au, Rh, Os, Ir, and any combination thereof.

The purified FDCA pathway product can comprise greater than 90% of FDCA by molar purity. The purified FDCA pathway product can comprise greater than 95% of FDCA by molar purity. The purified FDCA pathway product can comprise greater than 99% of FDCA by molar purity. The purified FDCA pathway product can comprise a molar purity of FFCA in the range of from or any number in between 0.1 and 5%.

The purified FDCA pathway product can comprise less than 5% of FFCA by molar purity. The purified FDCA pathway product can comprise less than 1% of FFCA by molar purity. The purified FDCA pathway product can comprise less than 0.5% of FFCA by molar purity. The purified FDCA pathway product can comprise less than 0.1% of FFCA by molar purity. The purified FDCA pathway product can comprise less than 0.05% of FFCA by molar purity.

The purified FDCA pathway product can comprise a molar purity of MFA in the range of from or any number in between 0.1 and 5%. The purified FDCA pathway product can comprise less than 5% of MFA by molar purity. The purified FDCA pathway product can comprise less than 1% of MFA by molar purity. The purified FDCA pathway product can comprise less than 0.1% of MFA by molar purity.

The purified FDCA pathway product can comprise a molar purity of THFDCA in the range of from or any number in between 0.1% and 0.9%. The purified FDCA pathway product can comprise less than 0.9% of THFDCA by molar purity. The purified FDCA pathway product can comprise less than 0.5% of THFDCA by molar purity. The purified FDCA pathway product can comprise less than 0.1% of THFDCA by molar purity.

The yield of HMFCA reduced from FFCA can be greater than 25%. The yield of HMFCA reduced from FFCA can be greater than 40%. The yield of HMFCA reduced from FFCA can be greater than 75%. The yield of HMFCA reduced from FFCA can be greater than 90%. The yield of HMFCA reduced from FFCA can be greater than 95%. The yield of HMFCA reduced from FFCA can be greater than 99%.

The solid support can be selected from the group consisting of carbon, zirconium dioxide, titanium dioxide, silicon carbide, silicon dioxide, $Al_2O_3$, and any combination thereof. The heterogeneous reduction catalyst further can comprise a promoter. The promoter can be selected from the group consisting of Ti, Zr, Cr, Mo, W, Mn, Ru, Cu, Zn, Sb, Bi, Sn, Au, Ag, Pb, Te, and any combination thereof. The solid support can be a shaped porous carbon support. The solid support can be a shaped porous carbon support. The solid support can be zirconium dioxide. The solid support can be titanium dioxide. The solid support can be silicon carbide. The solid support can be a combination of zirconium dioxide and titanium dioxide. The solid support can have a surface area of less than 200 $m^2/g$ but not zero.

The water-miscible aprotic organic solvent can be selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. The water-miscible aprotic organic solvent can be an ether. The water-miscible aprotic organic solvent can be selected from the group consisting of a light water-miscible organic solvent and a heavy water-miscible organic solvent.

The water and the water-miscible aprotic organic solvent can be present in a ratio of from or any number in between 1:6 to 6:1 v/v water:water-miscible organic solvent. The water and the water-miscible aprotic organic solvent can be present in a ratio within a range defined by 1:6 to 6:1 v/v water:water-miscible aprotic organic solvent. The water-miscible aprotic organic solvent can comprise at least 10 vol % of the multi-component solvent. The water-miscible aprotic organic solvent and the water can be present in a weight % ratio of 3:2 water-miscible aprotic organic solvent:water. The water-miscible aprotic organic solvent and the water can be present in a weight % ratio of 4:1 water-miscible aprotic organic solvent:water.

The solvent can be a multi-component solvent comprising water and two different water-miscible organic solvents. The water-miscible organic solvents can be both water-miscible aprotic organic solvents. Each of the water-miscible aprotic organic solvents can be independently selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone.

The process can be performed at a temperature of less than or equal to 150° C. The process can be performed at a temperature in the range of from or any number in between 50° C. to 130° C. The process can be performed at a temperature in the range of from or any number in between 80° C. to 120° C. The process can be performed at a temperature in the range of from or any number in between 70° C. to 125° C.

The process can be performed at a hydrogen pressure in the range of from or any number in between 50 psi to 1000 psi. The process can be performed at a hydrogen pressure of 100 psi to 500 psi. The process can be performed at a hydrogen pressure in the range of from or any number in between 200 psi to 525 psi. The process can be performed for greater than or equal to 30 minutes. The process can be performed in the range of from or any number in between 30 minutes to 300 minutes.

The heterogeneous reduction catalyst and FFCA can be present in the FDCA pathway product in a weight % ratio range of 1:0.001 to 1:1 of heterogeneous reduction catalyst: FFCA. The process can be performed in a continuous flow reactor.

The process can further comprise producing the FDCA pathway product by:

(a) contacting an oxidation feedstock comprising a furanic oxidation substrate and an oxidation solvent with oxygen in the presence of a heterogeneous oxidation catalyst under conditions sufficient to form a reaction mixture for oxidizing the furanic oxidation substrate to an FDCA pathway product, and producing the FDCA pathway product;

wherein the FDCA pathway product comprises FDCA and FFCA; wherein the reaction mixture is substantially free of added base; wherein the heterogeneous oxidation catalyst comprises a solid support and a noble metal; wherein the heterogeneous oxidation catalyst comprises a plurality of pores and a specific surface area in the range of from or any number in between 20 $m^2/g$ to 500 $m^2/g$; and wherein the solvent and the oxidation solvent are the same.

The furanic oxidation substrate can be selected from the group consisting of 5-(hydroxymethyl)furfural (HMF), diformylfuran (DFF), hydroxymethylfurancarboxylic acid (HMFCA), and formylfurancarboxylic acid (FFCA). The oxidation feedstock can comprise the furanic oxidation substrate at a concentration of at least 5% by weight. The furanic oxidation substrate can be present in the oxidation feedstock at a concentration of at least 10% by weight. The heterogeneous oxidation catalyst can comprise the metal at a loading in the range of from or any number in between 0.3% to 5% by weight of the heterogeneous oxidation catalyst. The heterogeneous oxidation catalyst can further comprise a promoter. The promoter can be selected from the group consisting of Ti, Zr, Cr, Mo, W, Mn, Ru, Cu, Zn, Sb, Bi, Sn, Au, Ag, Pb, Te, and any combination thereof. The solid support can be a shaped porous carbon support. The solid support can be zirconium dioxide. The solid support can be titanium dioxide. The solid support can be silicon carbide. The solid support can be a combination of zirconium dioxide and titanium dioxide. The solid support can have a surface area of less than 200 $m^2/g$ but not zero.

The process can further comprise a second oxidation step, wherein the second oxidation step comprises:

(b) contacting a second oxidation feedstock comprising a second furanic oxidation substrate and a second oxidation solvent with oxygen in the presence of a second heterogeneous oxidation catalyst under conditions sufficient to form a second reaction mixture for oxidizing the second furanic oxidation substrate to produce a second FDCA pathway product, and producing the second FDCA pathway product;

wherein the second FDCA pathway product comprises FDCA and FFCA; wherein (the first) contacting step (a) produces a first FDCA pathway product that is an FDCA pathway intermediate compound, either alone or together with FDCA; wherein the second furanic oxidation substrate is the first FDCA pathway product; wherein the second reaction mixture is substantially free of added base; wherein the second heterogeneous oxidation catalyst comprises a second solid support and a second noble metal, that may be the same or different from the (first) noble metal in step (a); and wherein the second heterogeneous oxidation catalyst comprises a plurality of pores and a specific surface area in the range of from or any number in between 20 $m^2/g$ to 500 $m^2/g$.

The process can further comprise crystallizing the purified FDCA product to produce FDCA having a molar purity of greater than 99%. The process can further comprise crystallizing the purified FDCA product to produce FDCA having a molar purity of greater than 99.5%. The process can further comprise crystallizing the purified FDCA product to produce FDCA having a molar purity of greater than 99.8%. The process can further comprise crystallizing the purified FDCA product to produce FDCA having a molar purity of greater than 99.9%.

Crystallizing the purified FDCA product can comprise dissolving the purified FDCA product in a first crystallization solution, wherein the first crystallization solution comprises a crystallization solvent, wherein the crystallization solvent comprises water and a crystallization water-miscible aprotic organic solvent. The crystallization water-miscible aprotic organic solvent can be selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. The crystallization water-miscible aprotic organic solvent can be an ether. The crystallization water-miscible aprotic organic solvent and the water can be present in a weight % ratio of 3:2 crystallization water-miscible aprotic organic solvent:water. The crystallization water-miscible aprotic organic solvent and the water can be present in a weight % ratio of 4:1 water-miscible aprotic organic solvent:water. The purified FDCA product can be dissolved in the first crystallization solution at a temperature of 110-120° C. (e.g., 110, 111, 112, 113, 114, 115, 116, 117, 118, 119, or 120° C. or at a temperature within a range defined by any two of the aforementioned temperatures). The purified FDCA product can be dissolved in the first crystallization solution at a temperature of 110-115° C. The purified FDCA product can be dissolved in the first crystallization solution at a temperature of 120° C. Crystallizing the purified FDCA product can further comprise dissolving the purified FDCA product in a second crystallization solution, wherein the second crystallization solution comprises a crystallization solvent, wherein the crystallization solvent comprises water and a crystallization water-miscible aprotic organic solvent. Crystallizing the purified FDCA product can further comprise dissolving the purified FDCA product in any subsequent number of crystallization solution, (e.g. a third, fourth, fifth or sixth crystallization solution) wherein the second crystallization solution comprises a crystallization solvent, wherein the crystallization solvent comprises water and a crystallization water-miscible aprotic organic solvent.

In another aspect, the present disclosure is directed to a mixture comprising: a purified 2,5-furandicarboxylic acid (FDCA) pathway product comprising FDCA, HMFCA, less than 10% molar impurities of FFCA, less than 10% molar impurities of 5-methyl-2-furoic acid (MFA), and less than 10% molar impurities of tetrahydrofuran-2,5-dicarboxylic acid (THFDCA); a heterogeneous reduction catalyst comprising a solid support and a metal selected from the group consisting of Cu, Ni, Pd, Pt, Ru, Ag, Au, Rh, Os, Ir, and any combination thereof; and a multi-component solvent comprising water and a water-miscible aprotic organic solvent.

The mixture can further comprise hydrogen. The purified FDCA pathway product can comprise less than 10% molar impurities of 2,5-diformylfuran (DFF). The solid support can be selected from the group consisting of carbon, zirconium dioxide, silicon carbide, silicon dioxide, and $Al_2O_3$, any combination thereof. The heterogeneous reduction catalyst can be selected from the group consisting of $Cu/SiO_2$, $Cu/Mn/Al_2O_3$, $Ni/Al_2O_3$, Pd/C, Ru/C, and any combination thereof. The solid support can be a shaped porous carbon support. The solid support can have a surface area of less than 200 $m^2/g$ but not zero.

The FFCA and FDCA can be at least partially dissolved in the multi-component solvent. The water-miscible aprotic organic solvent can be selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. The water-miscible aprotic organic solvent can be selected from the group consisting of a light water-miscible organic solvent and a heavy water-miscible organic solvent. The water and the water-miscible aprotic organic solvent can be present in a ratio of from or any number in between 1:6 to 6:1 v/v water:water-miscible organic solvent. The water and the water-miscible aprotic organic solvent can be present in a ratio within a range defined by 1:6 to 6:1 v/v water:water-miscible aprotic organic solvent. The water and the water-miscible aprotic organic solvent can be present in a ratio of 1:1 v/v water:water-miscible aprotic organic solvent. The water-miscible aprotic organic solvent can comprise at least 10 vol % of the multi-component solvent. The water-miscible aprotic organic solvent and the water can be present in a weight % ratio of 3:2 water-miscible aprotic organic solvent:water. The water-miscible aprotic organic solvent and the water can be present in a weight % ratio of 4:1 water-miscible aprotic organic solvent:water.

The multi-component solvent can comprise water and two different water-miscible organic solvents. Each of the water-miscible aprotic organic solvents can be independently selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone.

DETAILED DESCRIPTION

Figure 1:
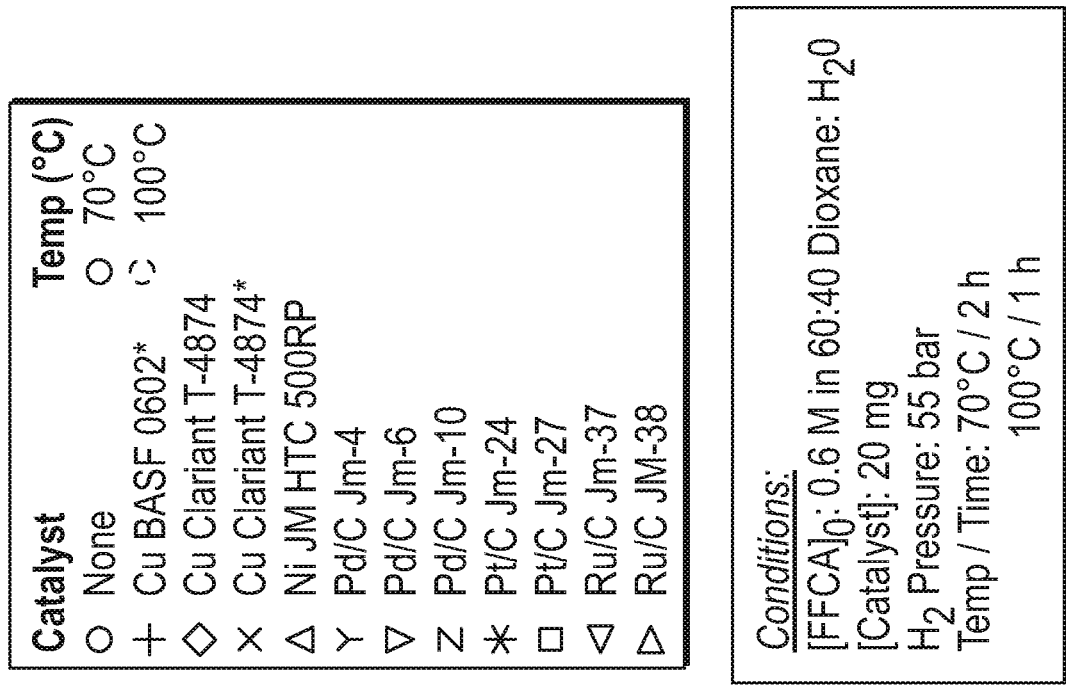
FIG. 1 depicts the selectivity of reduction of FFCA to HMFCA using several catalysts, different temperatures and different reaction times.
Figure 1:
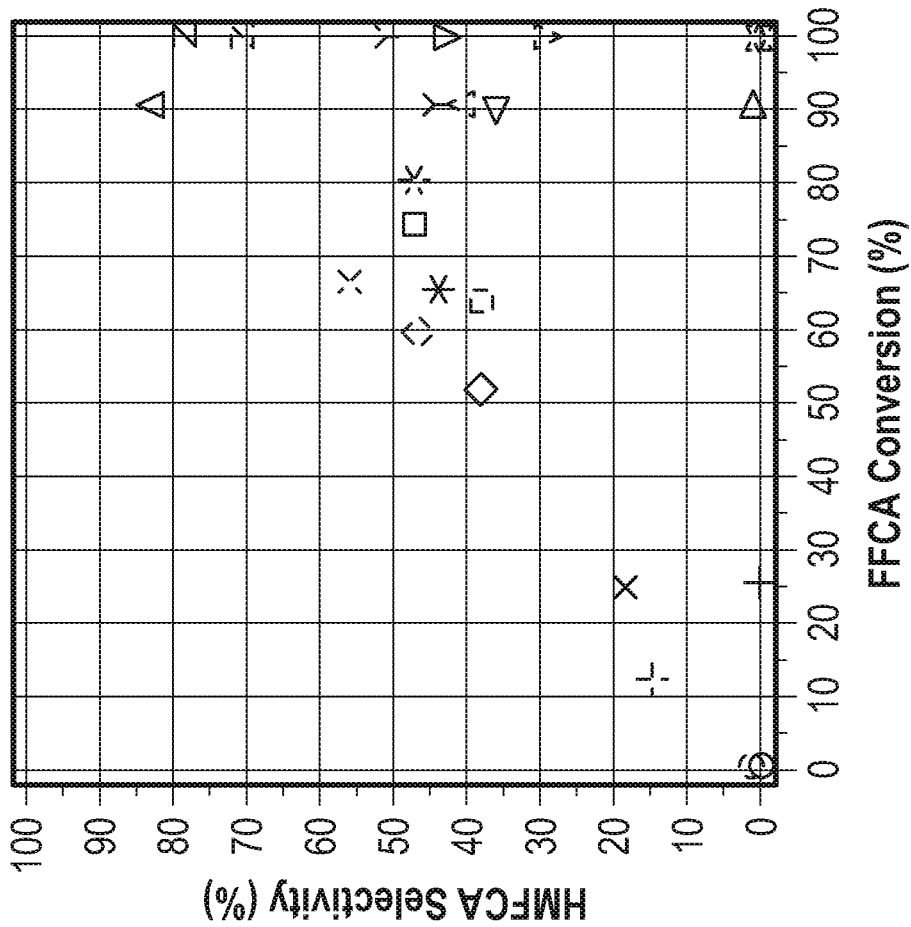

I. Processes for Producing an FDCA Pathway Product

Processes for producing an FDCA pathway product are described by Rennovia and Stora Enso in International Application No. PCT/US17/13197 to Sokolovskii et al., which is hereby expressly incorporated by reference in its entirety.

In one embodiment, the present disclosure provides processes for producing furandicarboxylic acid (FDCA) pathway products from the oxidation of a furanic oxidation substrate. As used herein, the terms "furandicarboxylic acid pathway product" and "FDCA pathway product" are used interchangeably to refer to 2,5-furandicarboxylic acid (FDCA) or a 2,5-furandicarboxylic acid pathway intermediate compound. The term "furandicarboxylic acid pathway" is used herein to refer to the pathway depicted in Scheme 1, which shows the conversion of HMF (compound I) to FDCA (compound V). As used herein, the terms "2,5-furandicarboxylic acid pathway intermediate compound" and "FDCA pathway intermediate compound" are used interchangeably to refer to any one of diformylfuran (DFF), hydroxymethylfurancarboxylic acid (HMFCA), and 5-formylfurancarboxylic acid (FFCA), which correspond to Compounds II, III, and IV in Scheme 1, respectively.

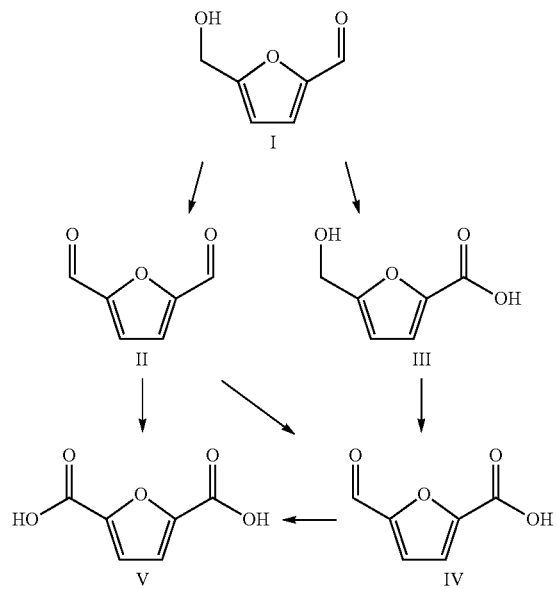

Scheme 1
Furandicarboxylic Acid Pathway

The present disclosure includes a process for producing an FDCA pathway product from a furanic oxidation substrate, the process comprising:

(a) contacting an oxidation feedstock comprising a furanic oxidation substrate and an oxidation solvent with oxygen in the presence of a heterogeneous oxidation catalyst under conditions sufficient to form a reaction mixture for oxidizing the furanic oxidation substrate to an FDCA pathway product, and producing the FDCA pathway product, wherein the oxidation solvent is a solvent selected from the group consisting of an organic solvent and a multicomponent solvent, wherein the reaction mixture is substantially free of added base, and wherein the heterogeneous oxidation catalyst comprises a solid support and a noble metal, and wherein the heterogeneous oxidation catalyst comprises a plurality of pores and a specific surface area in the range of from or any number in between 20 $m^2/g$ to 500 $m^2/g$, such as e.g., 20, 30, 40, 50, 60, 70, 80, 90, 100, 120, 140, 160, 180, 200, 225, 250, 275, 300, 325, 350, 375, 400, 425, 450, 475, or 500 $m^2/g$ or is within a range defined by any two of the aforementioned surface areas.

The term "substantially free of added base" is used herein to refer to the lack of any base added to the reaction mixture (i.e., no added base), or the addition of a de minimis quantity of base. The term "de minimis quantity of base" refers herein to an amount of base which, when added to a reaction mixture employed in the practice of the present disclosure, does not alter the oxidation reaction by more than 1% with respect to product yield or product selectivity, as compared to the same oxidation reaction performed under the same conditions with the exception that no base is added to the reaction mixture. Typically, the processes of the present disclosure are carried out under base-free conditions, e.g., no base is added to the reaction mixture during the contacting (i.e., oxidation) step.

Oxidation processes of the present disclosure may result in the production of the desired FDCA pathway product at a yield that is typically at least 80% and a selectivity that is typically at least 90% (both on a molar basis). In some embodiments, the yield is at least 85%, and in other embodiments, it is at least 90%, at least 95%, and often, at least 98% or at least 99%. In some embodiments, the yield ranges from between 85-90%, 87-92%, 90-95%, 92-97%, 95-98%, or 97-99%, or is within a range defined by any of two of the aforementioned percentages. The selectivity with respect to production of the desired FDCA pathway product is more typically at least 91% or at least 92% or at least 93% or at least 94% or at least 95% or at least 96% or at least 97% or at least 98% or at least 99%. In some embodiments, the selectivity with respect to the desired FDCA pathway product ranges from between 91-93%, 92-94%, 93-95%, 94-96%, 95-97%, 96-98%, 97-99%, or is within a range defined by any of two of the aforementioned percentages. The desired FDCA pathway product is usually FDCA. The term "oxidation feedstock" refers herein to a source material for the furanic oxidation substrate. As used herein, the term "furanic oxidation substrate" refers to a compound that is HMF or an FDCA intermediate compound (e.g., DFF, HMFCA, or FFCA, or combination thereof) or a combination thereof. Oxidation feedstocks employed in the practice of the processes described herein may be employed in any of a variety of forms, including, for example, a solution, a suspension, a dispersion, an emulsion, and the like. Typically, the oxidation feedstock comprises the furanic oxidation substrate in solution with the oxidation solvent.

In the oxidation processes described herein, the FDCA pathway product typically comprises FDCA. In certain embodiments, the furanic oxidation substrate typically comprises HMF. However, it may be desirable to use a furanic oxidation substrate that is an FDCA pathway intermediate compound or mixture of FDCA pathway intermediate compounds, e.g., DFF, HMFCA, or FFCA, or a mixture of any two or more thereof. This may be an attractive option in situations where HMF has been previously oxidized to an FDCA pathway intermediate compound or mixture of intermediate compounds, and the intermediate compound(s) is (are) available for use as a raw material. When such intermediates are used as furanic oxidation substrates in the oxidative processes of the present disclosure, the resulting FDCA pathway product typically comprises FDCA, but it may also comprise a different FDCA pathway intermediate compound that is "downstream" (from an oxidation standpoint) in the FDCA pathway, of the FDCA pathway intermediate employed as the furanic oxidation substrate.

The oxidation feedstock may contain other agents or residual components that are soluble or insoluble in the oxidation feedstock. For example, the oxidation feedstock may be a crude oxidation feedstock of HMF, or other furanic oxidation substrate, and the oxidation solvent. The term "crude feedstock" refers herein to a feedstock that, in addition to comprising the desired furanic oxidation substrate, also comprises impurities and/or by-products related to the production, isolation, and/or purification of the desired furanic oxidation substrate. For example, the oxidation feedstock, may, in addition, comprise certain biomass-related components that originate from biomass or are by-products, which are generated in the conversion of biomass to a sugar (by, for example, thermal, chemical, mechanical, and/or enzymatic degradative means), where such sugar is subsequently converted to HMF. Thus, the oxidation feedstock may also comprise a component selected from a variety of polysaccharides and/or polysaccharide-containing mixtures (e.g., substances or mixtures comprising or consisting of cellulose, lignocellulose, hemicellulose, starch, oligosaccharides e.g., a raffinose, a maltodextrin, a cellodextrin, monosaccharides e.g., glucose, fructose, galactose, mannose, xylose, rabbinose, disaccharides e.g., sucrose, lactose, maltose, cellobiose, furanic substrates such as furfural, oligomeric or polymeric humin by-products (humins) and/or residual mineral acids or any mixture thereof. Similarly, the oxidation feedstock may be a crude feedstock of HMF oxidation products comprising HMF and/or FDCA pathway intermediate compounds.

In addition to the high yields and high selectivity observed, oxidation processes provided in the present disclosure produce FDCA pathway products, such as, for example, FDCA at relatively high concentrations in a resulting product solution. The high productivity levels obtained from the processes described herein are believed to be due to the combined use of the heterogeneous oxidation catalysts employed and the properties of the oxidation solvent.

As used herein, the term, "oxidation solvent" refers to a solvent that is an organic solvent or a multi-component solvent in which the furanic oxidation substrate and the desired FDCA pathway product are each separately soluble at a minimum level of at least 2% by weight at the temperature at which the contacting (oxidation) step is conducted. Typically, the oxidation solvent is one in which the FDCA pathway product has a solubility of at least 3 wt %, at least 4 wt %, and more typically, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt % or is within a range defined by any two of the aforementioned solubilities, as measured at the temperature at which the contacting step is carried out. In some embodiments, the FDCA pathway product has a solubility that ranges from between 2-4 wt %, 3-5 wt %, 4-6 wt %, 5-7 wt %, 6-8 wt %, 7-9 wt %, 8-10 wt %, 9-11 wt %, 10-12 wt %, 11-13 wt %, 12-14 wt %, or 13-15% or is within a range defined by any of two of the aforementioned solubilities. The solubility of the FDCA pathway product in a candidate organic solvent or candidate multi-component solvent can be readily determined using known methods.

Without wishing to be bound by theory, the oxidation solvents employed in the present disclosure are believed to facilitate the efficient conversion of furanic oxidation substrate to FDCA pathway product (catalyzed by the high performing catalysts of the present disclosure) by, among other things, eliminating product precipitation that may lead to reactor/catalyst fouling. Moreover, the relatively high concentrations of FDCA and FDCA intermediate compounds that may be achieved in the processes of the present disclosure results in high process productivity and less costly solvent removal, in contrast to processes that employ poor solvents such as, for example water or the acetic acid-water mixtures described in U.S. Pat. No. 7,700,788. Thus, the present disclosure provides processes that are particularly attractive for the commercial scale production of FDCA, and related intermediates.

When carrying out the oxidation processes of the present disclosure, the furanic oxidation substrate may be present in the oxidation feedstock at any concentration up to its solubility limit, in circumstances where the feedstock is a solution. In some embodiments, the concentration of furanic oxidation substrate in the oxidation feedstock is at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt % or is within a range defined by any two of the aforementioned concentrations, by weight of the oxidation feedstock. In some embodiments, the concentration of furanic oxidation substrate in the oxidation feedstock ranges from 1-3 wt %, 2-4 wt %, 3-5 wt %, 4-6 wt %, 5-7 wt %, 6-8 wt %, 7-9 wt %, 8-10 wt %, 9-11 wt %, 10-12 wt %, 11-13 wt %, 12-14 wt %, or 13-15% or is within a range defined by any two of the aforementioned weight percentages. Typically, the furanic oxidation substrate is present in the oxidation feedstock at a concentration of at least 5 wt %. More typically, the furanic oxidation substrate is present in the oxidation feedstock at a concentration of at least 6 wt %, or at least 7 wt %, or at least 8 wt %, or at least 9 wt %, or at least 10 wt %, or at least 11 wt %, or at least 12 wt %, or at least 13 wt %, or at least 14 wt %, or at least 15 wt % or is within a range defined by any two of the aforementioned concentrations, at the temperature at which the contacting (oxidation) step is conducted. In some embodiments, the furanic oxidation substrate is present in the oxidation feedstock at the temperature at which the contacting (oxidation) step is conducted in a concentration that ranges from between 6-8 wt %, 7-9 wt %, 8-10 wt %, 9-11 wt %, 10-12 wt %, 11-13 wt %, 12-14 wt %, or 13-15% or is within a range defined by any of two of the aforementioned weight percentages.

Organic solvents that exhibit the requisite minimal solvating requirements for the furanic oxidation substrate and FDCA are suitable for use in the practice of the present disclosure, either alone or as a component of a multi-component solvent. In particular, the use of aprotic organic solvents, in combination with the catalysts and conditions described herein, appear to facilitate the high productivities observed with respect to the processes of the present disclosure. Therefore, in some embodiments, the oxidation solvent comprises an aprotic organic solvent (e.g., an ether, an ester, or a ketone) either alone (e.g., as a single-component solvent) or as a component of a multi-component solvent. When used in a multi-component solvent, the aprotic organic solvent is typically miscible with the other component(s) of the multi-component solvent. The term "multi-component solvent" refers herein to a mixture of two, three, or more solvent species. Multi-component solvents employed in the practice of the present disclosure may comprise two or more solvent species selected from a first organic solvent species, a second organic solvent species, or water. When the multi-component solvent comprises water and an organic solvent, the organic solvent is a water-miscible organic solvent. Typically, the water-miscible organic solvent is a water-miscible aprotic organic solvent.

Illustrative multi-component solvents that exhibit this effect include those that comprise water and a water-miscible aprotic organic solvent. Exemplary water-miscible aprotic solvents suitable for use in the practice of the present disclosure include: tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and/or gamma-valerolactone. Preferably, the water-miscible aprotic organic solvent is an ether, such as, for example, a glyme, dioxane (1,4-dioxane), a dioxolane (e.g., 1,3-dioxolane), or a tetrahydrofuran. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, and/or a highly ethoxylated diether of a high molecular weight alcohol ("higlyme"). Often, the oxidation solvent is a multi-component solvent comprising water and a water-miscible aprotic organic solvent that is glyme, diglyme, or dioxane.

Organic solvents and multi-component solvents suitable for use as an oxidation solvent in the practice of the present disclosure are described and can be readily identified as described by Rennovia and Stora Enso in PCT Application No. PCT/US17/13197, which, as previously mentioned, is hereby expressly incorporated by reference in its entirety.

In some embodiments, the composition of the oxidation solvent may take into consideration the requirements of further downstream processes (e.g., to facilitate product recovery, purification, and the like, such as the downstream processes for producing a purified FDCA pathway product described in this application), or upstream processes (e.g., the conversion of a sugar to the furanic oxidation substrate).

In some embodiments it may be desirable to employ an oxidation solvent that is a multi-component solvent comprising a light solvent and a heavy solvent. The term "light solvent" refers to a solvent having a boiling point at a certain pressure that occurs at a temperature that is less than the boiling point (temperature) of the heavy solvent at the same pressure. Conversely, the term "heavy solvent" refers to a solvent having a boiling point at a certain pressure that occurs at a temperature that is higher than the boiling point (temperature) of the light solvent at the same pressure. When the multi-component solvent comprises water and a water-miscible organic solvent, the water-miscible organic solvent may be a light water-miscible organic solvent (e.g., a water-miscible organic solvent having a boiling point that occurs at a temperature less than the boiling point of water) or it may be a heavy water-miscible organic solvent (e.g., a water-miscible organic solvent having a boiling point that occurs at a temperature higher than the boiling point of water). Typically, the light and heavy water-miscible organic solvents are a light and heavy aprotic organic solvent, respectively. Exemplary light water-miscible (and aprotic) organic solvents employed with water in a multi-component solvent include, for example, glyme, a dioxolane (e.g., 1,3-dioxolane), or tetrahydrofuran. Exemplary heavy water-miscible (and aprotic) organic solvents employed with water in a multi-component solvent include, for example, dioxane, ethyl glyme, diglyme (diethylene glycol dimethyl ether), ethyl diglyme, triglyme, butyl diglyme, tetraglyme, or a polyglyme. In some embodiments (e.g., continuous reactor systems), all or a portion of the oxidation solvent or component thereof may be removed from the production solution (e.g., via distillation) and recycled to the reaction mixture. In such embodiments, it may be desirable to employ a multi-component solvent having a composition that corresponds to an azeotrope or which is capable of forming an azeotrope (e.g., an "azeotropic composition") at a temperature employed during the oxidation step (e.g., contacting step), or at a temperature employed during a process that is upstream or downstream of the oxidation step. Use of such multi-component solvents having an azeotropic composition may facilitate the recycling of the oxidation solvent (as part of the azeotropic composition) to the oxidation step, or to processes that occur upstream and/or downstream of the oxidation step.

In some embodiments, the water-miscible organic solvent species is at least 5 volume % (vol %), at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % or is within a range defined by any two of the aforementioned volume %s of the multi-component solvent; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol % (but not zero) or within a range defined by any two of the aforementioned volume %s (bout not zero), respectively, of the multi-component system.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

In some embodiments, the volume ratio of water to water-miscible organic solvent is in the range from or any number in between 1:6 to 6:1. In certain embodiments, the volume ratio is from or any number in between 1:4 to 4:1 water:water-miscible organic solvent. In other embodiments, the volume ratio is from or any number in between 1:4 to 3:1 water:water miscible organic solvent. In other embodiments, the volume ratio is from or any number in between 1:3 to 3:1 water:water miscible organic solvent. In certain embodiments, the volume ratio is 1:1 water:water-miscible organic solvent.

In some embodiments, the multi-component solvent comprises water and two different water-miscible organic solvents. Typically, both of the water-miscible organic solvents are water-miscible aprotic organic solvents. Each of the two water-miscible aprotic solvents can be independently selected from tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), and/or gamma-valerolactone. One or both of the water-miscible aprotic organic solvent can be an ether, such as, for example, a glyme, dioxane (for example 1,4-dioxane), dioxolane (e.g., 1,3-dioxolane), tetrahydrofuran, and the like. Glymes include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, and/or a highly ethoxylated diether of a high molecular weight alcohol ("higlyme").

In some embodiments, the volume ratio of water to the first and second water-miscible organic solvent is approximately 1:1:1 (v:v:v). In some embodiments, the volume ratio of water to the first and second water-miscible organic solvent is approximately 1:2:1 (v:v:v). In some embodiments, the volume ratio of water to the first and second water-miscible organic solvent is approximately 1:2:2 (v:v: v). In some embodiments, the volume ratio of water to the first and second water-miscible organic solvent is approximately 2:1:1 (v:v:v).

In some embodiments, the multi-component solvent comprises water and two different water-miscible organic solvents with the relative amounts of water to the first and second water-miscible organic solvents. Suitable multi-component solvents comprising water and two different water-miscible organic solvents are described by Rennovia and Stora Enso in PCT Application No. PCT/US17/13197, which, as previously mentioned, is hereby expressly incorporated by reference in its entirety.

The contacting step is often carried out for a time sufficient to produce a product solution comprising (soluble) FDCA pathway product at a concentration of at least 2 wt %, at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt % or at a concentration that is within a range defined by any two of the aforementioned values. Correspondingly, when a product solution is produced that comprises the (soluble) FDCA pathway product it is produced at a concentration of at least 2 wt %, at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt %) or at concentration that is within a range defined by any two of the aforementioned values. The term "product solution" refers herein to a solution of soluble FDCA pathway product and other soluble components of the reaction mixture in the oxidation solvent. The phrase "a time sufficient to produce a product solution comprising the FDCA pathway product at a concentration of" is used herein to refer to a minimum amount of time required to produce the specified concentration of the FDCA pathway product in the product solution.

Heterogeneous oxidation catalysts employed in the practice of the present disclosure typically have the noble metal dispersed on the internal and/or external surfaces of the support. The term "noble metal" refers herein to ruthenium, rhodium, palladium, silver, osmium, iridium, platinum or gold or mixtures thereof. In certain preferred embodiments, the metal is platinum, or gold, or a combination thereof. In some embodiments, the metal is platinum. In some embodiments, the metal is gold. The heterogeneous oxidation catalyst may further include a promoter to enhance the performance of the heterogeneous oxidation catalyst. Suitable promoters may include Ti, Zr, Cr, Mo, W, Mn, Ru, Cu, Zn, Sb, Bi, Sn, Au, Ag, Pb, or Te, or mixtures thereof. When the metal is platinum, or gold, or combination thereof, suitable promoters include, for example, Bi, Te, Sn, Pd, Ir, Mo, or W, or mixtures thereof. In some embodiments, the promoter is Bi. In some embodiments, the promoter is Te. In some embodiments, the promoter is Sn.

The heterogeneous oxidation catalyst typically comprises the noble metal at a total metal loading in the range of from or any number in between 0.3% to 5% by weight. In some embodiments, the metal loading is in the range of from or any number in between 0.5% to 4% by weight. In some embodiments, the metal loading ranges from or any number in between 2-4 wt %. In some embodiments, the metal loading is 2 wt %. In some embodiments, the metal loading is 3 wt %. In some embodiments, the metal loading is 4 wt %. When two or more metals are employed, the heterogeneous oxidation catalyst may comprise a plurality of heterogeneous oxidation catalyst particles, each comprising the two or more metals, or the heterogeneous oxidation catalyst may comprise a mixture of heterogeneous oxidation catalyst metal-particle species, e.g., a first plurality of heterogeneous oxidation catalyst particles comprising a first metal species and a second plurality of heterogeneous oxidation catalyst particles comprising a second metal species. Methods for preparing the heterogeneous oxidation catalysts employed in the practice of the present disclosure are described by Rennovia and Stora Enso in PCT Application No. PCT/US17/13197, which, as previously mentioned, is hereby expressly incorporated herein by reference in its entirety.

The solid support component of the heterogeneous oxidation catalyst may comprise any type of material known by those having ordinary skill in the art as being suitable for use as a catalytic support that also has the specific surface area requirement described herein. Suitable materials include, for example, a metal oxide, a carbonaceous material, a polymer, a metal silicate, a metal carbide, or any composite material prepared therefrom. Exemplary metal oxides include silicon oxide (silica), zirconium oxide (zirconia), titanium oxide (titania), titanium dioxide, or aluminum oxide (alumina). As used herein, the term "carbonaceous" refers to graphite and carbon black, which may or may not be in an activated form. Exemplary metal silicates include, for example, an orthosilicate, a borosilicate, or an aluminosilicate (e.g., a zeolite). Exemplary metal carbides include, for example, silicon carbide. Suitable polymeric solid support materials include polystyrene, polystyrene-co-divinyl benzene, polyamides, or polyacrylamides.

Suitable solid support materials also include a composite material prepared from, or comprising a binder and a material selected a metal oxide, a carbonaceous material, a polymer, a metal silicate, and/or a metal carbide. In some embodiments, the binder is a resin. In other embodiments, the composite material comprises a carbonized binder and a material selected from a metal oxide, a carbonaceous material, a metal silicate, and/or a metal carbide. In one embodiment, the composite material comprises a carbonized binder and carbon black, which may or may not be or comprise an activated carbon. Methods for making such carbon-based composite materials are described by Rennovia in PCT Application No. PCT/US15/28358 to Dias et al., which is hereby expressly incorporated herein by reference in its entirety.

In some embodiments, the solid support comprises a carbon black material selected from Aditya Birla CDX-KU, Aditya Birla CSCUB, Aditya Birla R2000B, Aditya Birla R2500UB, Aditya Birla R3500B, Aditya Birla R5000U2, Arosperse 5-183A, Asbury 5302, Asbury 5303, Asbury 5345, Asbury 5348R, Asbury 5358R, Asbury 5365R, Asbury 5368, Asbury 5375R, Asbury 5379, Asbury A99, Cabot Monarch 120, Cabot Monarch 280, Cabot Monarch 570, Cabot Monarch 700, Cabot Norit Darco 12x20L1, Cabot Vulcan XC72, Continental N120, Continental N234, Continental N330, Continental N330-C, Continental N550, Norit ROX 0.8, Orion Arosperse 138, Orion Arosperse 15, Orion Color Black FW 2, Orion Color Black FW 255, Orion HiBlack 40B2, Orion Hi-Black 50 L, Orion Hi-Black 50 LB, Orion Hi-Black 600 L, Orion HP-160, Orion Lamp Black 101, Orion N330, Orion Printex L6, Sid Richardson Ground N115, Sid Richardson Ground SR155, Sid Richardson SC159, Sid Richardson SC419, Timcal Ensaco 150G, Timcal Ensaco 250G, Timcal Ensaco 260G, and/or Timcal Ensaco 350G or any combination thereof.

Metal impregnation of the solid support typically results in a negligible change in the specific surface, pore diameters, and specific volume of the solid support. Heterogeneous oxidation catalysts that are suitable for use in the present disclosure are typically prepared using a solid support that comprises a plurality of pores and a specific surface area in the range of from e.g., 20 m$^2$/g to 500 m$^2$/g, such as e.g., 20, 30, 40, 50, 60, 70, 80, 90, 100, 120, 140, 160, 180, 200, 225, 250, 275, 300, 325, 350, 375, 400, 425, 450, 475, or 500 m$^2$/g or within a range defined by any two of the aforementioned surface areas. Specific surface area can be determined using known methods, such as, for example, the method of Bruanauer, Emmett and Teller (J. Am. Chem. Soc. 1938, 60:309-311) and/or mercury porosimetry. See e.g., ASTM Test Methods D3663, D6556, and D4567, each of which is incorporated by reference in its entirety. Typically, heterogeneous oxidation catalysts (and solid supports) employed in the practice of the present disclosure have a specific surface area in the range of from or any number in between 25 m$^2$/g to 250 m$^2$/g, and sometimes in the range of from or any number in between 25 m$^2$/g to 225 m$^2$/g, or from or any number in between 25 m$^2$/g to 200 m$^2$/g, or from or any number in between 25 m$^2$/g to 175 m$^2$/g, or from or any number in between 25 m$^2$/g to 150 m$^2$/g, or from or any number in between 25 m$^2$/g to 125 m$^2$/g, or from or any number in between 25 m$^2$/g to 100 m$^2$/g. These specific surface areas are relatively low when compared to highly porous catalytic support materials that are more typically used in the art, such as, for example, activated carbon. The relatively low surface area of the heterogeneous oxidation catalysts employed in the oxidative processes of the present disclosure is believed to favorably contribute to the high selectivity and yields observed with respect to the conversion of the furanic oxidation substrates to FDCA and FDCA pathway intermediate compounds under substantially base-free conditions.

Commensurate with the relatively low specific surface areas, the heterogeneous oxidation catalysts (and solid support components thereof) employed in the practice of the present disclosure also typically have relatively moderate to low specific pore volumes when compared to other oxidation catalysts. Heterogeneous oxidation catalysts (and solid support components thereof) employed in the practice of the present disclosure typically have a specific pore volume (determined on the basis of pores having a diameter of 1.7 nm to 100 nm) that is, from or any number in between 0.1 cm$^3$/g to 1.5 cm$^3$/g, from or any number in between 0.1 cm$^3$/g to 0.8 cm$^3$/g, from or any number in between 0.1 cm$^3$/g to 0.7 cm$^3$/g, from or any number in between 0.1 cm$^3$/g to 0.6 cm$^3$/g, from or any number in between 0.1 cm$^3$/g to 0.5 cm$^3$/g, from or any number in between 0.2 cm$^3$/g to 0.8 cm$^3$/g, from or any number in between 0.2 cm$^3$/g to 0.7 cm$^3$/g, from or any number in between 0.2 cm$^3$/g to 0.6 cm$^3$/g, from or any number in between 0.2 cm$^3$/g to 0.5 cm$^3$/g, from or any number in between 0.3 cm$^3$/g to 1 cm$^3$/g, from or any number in between 0.3 cm$^3$/g to 0.9 cm$^3$/g, from or any number in between 0.3 cm$^3$/g to 0.8 cm$^3$/g, from or any number in between 0.3 cm$^3$/g to 0.7 cm$^3$/g, from or any number in between 0.3 cm$^3$/g to 0.6 cm$^3$/g, or from or any number in between 0.3 cm$^3$/g to 0.5 cm$^3$/g or within a range defined by any two of the aforementioned values, as measured by a method for determining pore diameters and specific pore volumes, such as that described in E. P. Barrett, L. G. Joyner, P. P. Halenda, *J. Am. Chem. Soc.* (1951) 73:373-380 and ASTM D4222-03 (2008) (the method referred to herein as the "BJH method"), both of which are hereby expressly incorporated herein by reference in their entireties, and by the method of mercury porosimetry (e.g., using a mercury porosimeter, such as, for example, the Micromeritics Autopore V 9605 Mercury Porosimeter (Micromeritics Instrument Corp., Norcross, Ga.) in accordance with the manufacturer's instructions). See e.g., ASTM 3663, ASTM D-4284-12 and D6761-07 (2012), all of which are hereby expressly incorporated herein by reference in their entireties.

Typically, the heterogeneous oxidation catalyst has a mean pore diameter in the range of from or any number in between 10 nm to 100 nm, as measured by the BJH method and/or mercury porosimetry. More typically, the heterogeneous oxidation catalyst has a mean pore diameter in the range of from or any number in between 10 nm to 90 nm, as measured by the BJH method and/or mercury porosimetry. In some embodiments, the mean pore diameter is in the range of from or any number in between 10 nm to 80 nm, or from or any number in between 10 nm to 70 nm, or from or any number in between 10 nm to 60 nm, and often from or any number in between 10 nm to 50 nm, as determined by the BJH method and/or mercury porosimetry. In some embodiments, the mean pore diameter is in the range of from or any number in between 20 nm to 100 nm, as measured by the BJH method and/or mercury porosimetry. In certain of these embodiments, the mean pore diameter is in the range from or any number in between 20 nm to 90 nm, or from or any number in between 20 nm to 80 nm, or from or any number in between 20 nm to 70 nm, or from or any number in between 20 nm to 60 nm, or from or any number in between 10 nm to 50 nm, as determined by the BJH method and/or mercury porosimetry. The catalysts employed in the practice of the present disclosure typically have a relatively high concentration of pores in the size ranges described above.

Suitable heterogeneous oxidation catalysts are described by Rennovia and Stora Enso in PCT Application No. PCT/US17/13197, which, as previously mentioned, is hereby expressly incorporated by reference in its entirety.

In some embodiments, the heterogeneous oxidation catalyst may be prepared on extruded supports. Catalysts with extruded supports are beneficial for use in many industrial applications, such as continuous industrial fixed bed reactors, which can be used in the production of an FDCA pathway product. Industrial fixed bed reactors must deploy suitably shaped and sized catalysts, such as extrudates, in order to avoid the excessive pressure drop associated with the use of powdered catalysts, which typically are difficult to deploy industrially in fixed bed reactor systems.

In further embodiments, the metal and/or the promoter may be selectively located in a shell covering the exterior surface area of the extruded support, thereby efficiently presenting the catalytically active surface to the reaction medium as metals and promoters deposited in the center of the support would not likely be accessible to the reaction medium. In some embodiments, the exterior surface area of the extruded support comprises the surface area of the outer layer surface of the extruded support. In some embodiments, the exterior surface area of the extruded support comprises the surface area of the pores of the extruded support.

In some embodiments, the extruded support comprises carbon, zirconium dioxide, titanium dioxide, silicon carbide, silicon dioxide, Al$_2$O$_3$, monmorillonite, or any combination thereof.

In carrying out the processes for producing an FDA pathway product, oxygen may be provided in neat form (i.e., O$_2$ only, with no other gases) or as a component of a mixture of gases (e.g., air, oxygen-enriched air, and the like). The molar ratio of oxygen to the furanic oxidation substrate during the contacting step is typically in the range of from 2:1 to 10:1. In some embodiments, the molar ratio of oxygen to the furanic oxidation substrate is from 2:1 to 10:1, or from 3:1 to 5:1. During the contacting step, oxygen is typically present at a partial pressure in the range of from or any number in between 50 psig to 1000 psig. More typically, oxygen is present at a partial pressure in the range of from or any number in between 50 psig to 200 psig. In some embodiments, oxygen is present at a partial pressure in the range from or any number in between 50-200 psig, 100-300 psig, 200-400 psig, 300-500 psig, 400-600 psig, 500-700 psig, 600-800 psig, 700-900 psig, or 800-1000 psig, or within a range defined by any two of the aforementioned partial pressures.

The contacting (oxidation) step is typically carried out at a temperature in the range of from or any number in between 50° C. to 200° C. In some embodiments, the contacting step is carried out at a temperature in the range of from or any number in between 80° C. to 180° C., and in other embodiments, the contacting step carried out at a temperature in the range from or any number in between 90° C. to 160° C. or from or any number in between 100° C. to 160° C. In certain preferred embodiments, the contacting step is carried out at a temperature in the range of from or any number in between 90° C. to 180° C., and sometimes it is carried out at a temperature in the range of from or any number in between 110° C. to 160° C.

In some embodiments, it may be desirable to carry out the oxidation of the furanic oxidation substrate to the desired FDCA pathway product in a series of two or more oxidation steps, where the first oxidation step is as described above, and where the second oxidation step comprises:

(b) contacting a second oxidation feedstock comprising a second furanic oxidation substrate and a second oxidation solvent with oxygen in the presence of a second heterogeneous oxidation catalyst under conditions sufficient to form a second reaction mixture for oxidizing the second furanic oxidation substrate to produce a second FDCA pathway product, wherein (the first) contacting step (a) produces a first FDCA pathway product that is an FDCA pathway intermediate compound, either alone or together with FDCA, wherein the second furanic oxidation substrate is the first FDCA pathway product, wherein the second reaction mixture is substantially free of added base, and wherein the second heterogeneous oxidation catalyst comprises a second solid support and a noble metal that may be the same or different from the (first) noble metal in step (a), and wherein the second heterogeneous oxidation catalyst comprises a plurality of pores and a specific surface area in the range of from or any number in between 20 m²/g to 500 m²/g, such as e.g., 20, 30, 40, 50, 60, 70, 80, 90, 100, 120, 140, 160, 180, 200, 225, 250, 275, 300, 325, 350, 375, 400, 425, 450, 475, or 500 m²/g or is within a range defined by any two of the aforementioned surface areas.

The second FDCA pathway product is a downstream oxidation product of the first FDCA pathway product, and typically comprises FFCA, or FDCA. Typically, the second FDCA pathway product comprises FDCA. Usually, the second oxidation step is free of added base.

Noble metals, catalyst metal loadings, solid support materials, and reaction conditions (e.g., reaction temperatures, oxygen (partial) pressure, molar ratio of oxygen to furanic oxidation substrate, and the like) that are suitable for using in the first oxidation process are also suitable for using in the second oxidation process. The second heterogeneous oxidation catalyst may be the same or different than that used in the first oxidation process (i.e., the "first" heterogeneous oxidation catalyst"). Oxidation solvents that are suitable for use in the second oxidation feedstock are the same as those that are suitable for use in the first oxidation process (i.e., the "first oxidation solvent"). The multi-stage oxidation process format may be desirable if optimal production of the desired FDCA pathway product requires a change in reaction conditions during the course of conversion from the furanic oxidation substrate to the desired FDCA pathway product. For example, it may be desirable to carry out the second oxidation reaction at a higher or lower temperature than the first oxidation reaction, or maintain the molar ratio of oxygen to feedstock component in the second oxidation reaction at a higher or lower ratio than in the first oxidation reaction, or maintain the partial pressure of oxygen in the second oxidation reaction at a higher or lower partial pressure than in the first oxidation reaction. The composition of the second oxidation solvent may be the same as the composition of the first oxidation solvent or it may be different. If it is different, it may still have in common one or more of the same solvent species component. The noble metal in the second heterogeneous oxidation catalyst is typically platinum, gold, or a combination thereof. Usually, the noble metal used in the second heterogeneous oxidation catalyst is platinum.

FDCA pathway product(s) produced by the oxidation processes described herein may be recovered from the reaction mixture by separating the heterogeneous oxidation catalyst from a product solution comprising the FDCA pathway product(s) and the oxidation solvent. The product solution includes the oxidation solvent and soluble components of the reaction mixture and excludes the heterogeneous oxidation catalyst. The product solution may be further concentrated with respect to the soluble components by removal of a portion of the oxidation solvent. Oxidation solvent removal may be accomplished by evaporation (e.g., by using an evaporator), distillation, and the like.

Alternatively, or further to the isolation step, the FDCA pathway product may be crystallized. Thus, in one embodiment, the present disclosure provides a process for producing a crystalline FDCA pathway product composition, the method comprising:

providing a crystallization solution comprising an FDCA pathway product and a crystallization solvent that is a solvent selected from the group consisting of an organic solvent and a multi-component solvent; initiating crystallization of the FDCA pathway product; and producing a plurality of FDCA pathway product crystals of different particle sizes.

As used herein, the term "crystallization solvent" refers to a solvent from which the FDCA pathway product can be crystallized when conditions are imposed that cause a reduction in solubility of the FDCA pathway product in the crystallization solvent (e.g., temperature reduction (cooling) or solvent removal). The crystallization solvent may be water, an organic solvent, or a multi-component solvent comprising water and a water-miscible organic solvent or two or more organic solvent species. The crystallization process may directly follow the oxidation process (e.g., either a single stage oxidation process or multi-stage oxidation process), or it may follow other unit operations downstream of the oxidation process.

When crystallization follows FDCA pathway product generation, the crystallization solution is typically a product solution comprising the FDCA pathway product and the oxidation solvent. In such embodiments, therefore, the crystallization solvent is the same as the oxidation solvent (e.g., the first oxidation solvent (single stage oxidation) or the second oxidation solvent (for two-stage oxidation)). Some solvents that are suitable for use in the oxidation solvent are also suitable for use as the crystallization solvent.

Industrial solution phase crystallizations are typically performed by introducing a saturated (or super-saturated) solution of the product into a crystallizer in which the solution is subjected to crystallization conditions, and crystallization is initiated by, for example, lowering the temperature or concentrating the solution by solvent evaporation (e.g., solvent removal), or a combination of both. Solvent evaporation may be used to concentrate the solution to initiate crystallization, and may also be used to adjust the solvent composition to lower the solubility of the FDCA pathway product. As used herein, the term "crystallization conditions" refers to an adjustment in temperature and/or adjustment in crystallization solution concentration and/or adjustment in crystallization solution composition that causes the initiation of crystallization of the FDCA pathway product.

In one embodiment where crystallization conditions include a temperature adjustment, the present disclosure provides a process for producing a crystalline FDCA preparation, the method comprising:

providing a crystallization solution comprising the FDCA pathway product and a crystallization solvent at a first temperature in the range of or any number in between 50° C. to 220° C., such as e.g., 50, 60, 70, 80, 90, 100, 110, 115, 120, 130, 140, 150, 160, 180, 190, 200, 210, or 220° C. or within a range defined by any two of the aforementioned temperatures; and cooling the crystallization solution to a second temperature that is lower than the first temperature to form a plurality of FDCA pathway product crystals of different particle sizes.

Cooling reduces the solubility of the FDCA pathway product in the crystallization solvent, causing crystals of FDCA pathway product to form in the solution. The first temperature is typically in the range of from or any number in between 60° C. to 180° C., such as e.g., 60, 70, 80, 90, 100, 110, 115, 120, 130, 140, 150, 160, or 180° C. or within a range defined by any two of the aforementioned temperatures. In some embodiments, the first temperature is in the range from or any number in between 70° C. to 150° C. such as e.g., 70, 80, 90, 100, 110, 115, 120, 130, 140, or 150° C. or within a range defined by any two of the aforementioned temperatures. When the crystallization solution is cooled, it is typically cooled to a temperature that is at or below 60° C., such as e.g., equal to or less than 60, 50, 40, 30, 20, 10, 5, or 0° C. or within a range defined by any two of the aforementioned temperatures. More typically, it is cooled to a temperature at or below 50° C. or at or below 40° C. such as, e.g., equal to or less than 50, 40, 30, 20, 10, 5, or 0° C. or within a range defined by any two of the aforementioned temperatures.

Suitable crystallization techniques are described by Rennovia and Stora Enso in PCT Application No. PCT/US17/13197, which, as previously mentioned, is hereby expressly incorporated by reference in its entirety.

The crystallization processes of the present disclosure may be carried out using known industrial crystallizer systems that are suitable for carrying out solution phase crystallizations. Suitable systems include for example, batch crystallizers, continuous crystallizers (e.g., forced circulation crystallizers, draft-tube crystallizers, draft-tube-baffled crystallizers, or Oslo-type crystallizers, and the like), and other such crystallizer systems.

Typically, the crystalline FDCA preparation comprises at least 98 wt % FDCA, and more typically, it comprises at least 99 wt % FDCA, and in some embodiments, it comprises greater than 99 wt % FDCA.

II. Pathway for Producing Purified FDCA Pathway Products

Described herein is a process for producing a purified FDCA pathway product that may involve contacting an FDCA pathway product comprising FDCA and 5-formylfurancarboxylic acid (FFCA) with hydrogen in the presence of a heterogeneous reduction catalyst and a solvent under conditions sufficient to form a reaction mixture for reducing the FFCA to hydroxymethylfurancarboxylic acid (HMFCA), and producing a purified FDCA pathway product. The terms "purified furandicarboxylic acid pathway product" and "purified FDCA pathway product" are used interchangeably herein to refer to the product of a process wherein an FDCA pathway product comprising FDCA and FFCA is contacted with hydrogen in the presence of a heterogeneous reduction catalyst and a solvent under conditions that form a reaction mixture that reduces FFCA to HMFCA. The purified FDCA pathway product comprises at least FDCA and HMFCA. In some embodiments, the processes for producing a purified FDCA pathway product described herein provide beneficial and advantageously high selectivity for reducing FFCA to HMFCA as compared with undesired reduction of FDCA. In some embodiments, the processes for producing a purified FDCA pathway product described herein can be conducted at a relatively low temperature, which can aid in the selective reduction of FFCA to HMFCA.

In some embodiments, the FDCA pathway product used in the process for producing a purified FDCA pathway product may be the same FDCA pathway product produced by a process described in Section I of this application. In some embodiments, the FDCA pathway product may comprise FDCA, FFCA, and one or more additional compounds selected from diformylfuran (DFF), hydroxymethylfurancarboxylic acid (HMFCA), 5-(hydroxymethyl)furfural (HMF), tetrahydrofuran dicarboxylic acid (THFDCA), and/or 5-methyl-2-furoic acid (MFA), or any combination thereof. In some embodiments, the FDCA pathway product may comprise FDCA, FFCA, and one or more additional FDCA pathway intermediate compound selected from diformylfuran (DFF), and/or hydroxymethylfurancarboxylic acid (HMFCA) or a mixture thereof. In some embodiments, the FDCA pathway product may comprise FDCA, FFCA, and one or more additional compounds selected from 5-(hydroxymethyl)furfural (HMF), tetrahydrofuran dicarboxylic acid (THFDCA), and/or 5-methyl-2-furoic acid (MFA), or any combination thereof.

Heterogeneous reduction catalysts employed in the process for producing a purified FDCA pathway product may comprise a metal dispersed on surfaces of a solid support. In some embodiments, the metal may be selected from cobalt, nickel, copper, silver, gold, ruthenium, rhodium, palladium, osmium, iridium and/or platinum, or combinations thereof. In some embodiments, the metal is selected from the group consisting of nickel, ruthenium, copper, silver, gold, platinum and iridium, or combinations thereof. In some embodiments, the metal is nickel. In some embodiments, the metal is ruthenium. In some embodiments, the metal is platinum. The heterogeneous reduction catalyst may further include a promoter to enhance the performance of the heterogeneous reduction catalyst. Suitable promoters may comprise Ti, Zr, Cr, Mo, W, Mn, Ru, Cu, Zn, Sb, Bi, Sn, Au, Ag, Pb or Te. When the metal is platinum or gold, or a combination thereof, suitable promoters include, for example, Bi, Te, Sn, Pd, Jr, Mo, and/or W. In some embodiments, the promoter is Bi. In some embodiments, the promoter is Te. In some embodiments, the promoter is Sn.

In some embodiments, the solid support comprises carbon, zirconium dioxide, silicon carbide, silicon dioxide, $Al_2O_3$, or any combination thereof. In some embodiments the support comprises carbon. In some embodiments, the solid support comprises carbon with a surface area of less than 200 $m^2/g$ (but not zero). In some embodiments, the solid support comprises a shaped porous carbon support described by Rennovia in WO 2017/075391 to Diamond et al., and WO 2017/075425 to Sokolovskii et al., both of which are hereby expressly incorporated herein in their entireties.

In some embodiments, the heterogeneous reduction catalysts may be $Cu/SiO_2$, $Cu/Mn/Al_2O_3$, $Ni/Al_2O_3$, Pd/C, Pt/C, or Ru/C. In some embodiments, the heterogeneous reduction catalysts may be obtained from a commercial source as a marketed product, such as but not limited to BASF Cu 0602, Clariant Cu T-4874, Johnson Matthey (JM) Ni HTC 500 RP, JM-4 Pd/C, JM-6 Pd/C, JM-10 Pd/C, JM-24 Pt/C, JM-27 Pt/C, JM-37 Ru/C, or JM-38 Ru/C.

In some embodiments, the heterogeneous reduction catalyst may be fabricated into a powder. In some embodiments, the heterogeneous reduction catalyst is reduced by subjecting it to forming gas. In some embodiments, the heterogeneous reduction catalyst is reduced by subjecting it to an elevated temperature (e.g., 150° C., 200° C., 250° C., 300° C., 350° C., 400° C., or more than 400° C.) in forming gas for several hours (e.g., 2, 3, 4, or more hours).

The heterogeneous reduction catalyst may comprise a metal that is loaded onto the solid support in the range of from or any number in between 0.3% to 5% by weight of the overall catalyst. In some embodiments, the metal loading is in the range of from or any number in between 0.5% to 4% by weight, 2% to 7% by weight, 4% to 10% by weight, 6% to 12% by weight, 8% to 15% by weight, 10% to 20% by weight, 15% to 25% by weight, 20% to 40% by weight, 30% to 50% by weight or 40% to 60% by weight or 50% to 70% by weight. In some embodiments, the metal loading ranges from or any number in between 2-4 wt %. In some embodiments, the metal loading is 2 wt %. In some embodiments, the metal loading is 3 wt %. In some embodiments, the metal loading is 4 wt %. In some embodiments, the metal loading ranges from or any number in between 20-70 wt %. In some embodiments, the metal loading is 20 wt %. In some embodiments, the metal loading is 30 wt %. In some embodiments, the metal loading is 40 wt %. In some embodiments, the metal loading is 50 wt %. In some embodiments, the metal loading is 60 wt %. In some embodiments, the metal loading is 70 wt %. When two or more metals are employed, the heterogeneous reduction catalyst may comprise a plurality of heterogeneous reduction catalyst particles, each comprising the two or more metals, or the heterogeneous reduction catalyst may comprise a mixture of heterogeneous reduction catalyst metal-particle species, e.g., a first plurality of heterogeneous reduction catalyst particles comprising a first metal species and a second plurality of heterogeneous reduction catalyst particles comprising a second metal species.

The solid support component of the heterogeneous reduction catalyst may comprise any type of material suitable for use as a catalytic support. Suitable materials include, for example, a metal oxide, a carbonaceous material, a polymer, a metal silicate, and/or a metal carbide, or any composite material prepared therefrom. In some embodiments, metal oxides include silicon oxide (silica), zirconium oxide (zirconia), titanium oxide (titania), titanium dioxide, and/or aluminum oxide (alumina). As used herein, the term "carbonaceous" refers to graphite and carbon black, which may or may not be in an activated form. In some embodiments, metal silicates include, for example, an orthosilicate, a borosilicate, or an aluminosilicate (e.g., a zeolite). In some embodiments, metal carbides include, for example, silicon carbide, and the like. In some embodiments, polymeric solid support materials include polystyrene, polystyrene-co-divinyl benzene, polyamides, or polyacrylamides.

Suitable solid support materials also include a composite material prepared from, or comprising a binder and a material selected from a metal oxide, a carbonaceous material, a polymer, a metal silicate, and/or a metal carbide or a mixture thereof. In some embodiments, the binder is a resin. In some embodiments, the composite material comprises a carbonized binder and a material selected from the group consisting of a metal oxide, a carbonaceous material, a metal silicate, and a metal carbide. In one embodiment, the composite material comprises a carbonized binder and carbon black, which may or may not be in an activated form.

In some embodiments, the solid support comprises a carbon black material selected from Aditya Birla CDX-KU, Aditya Birla CSCUB, Aditya Birla R2000B, Aditya Birla R2500UB, Aditya Birla R3500B, Aditya Birla R5000U2, Arosperse 5-183A, Asbury 5302, Asbury 5303, Asbury 5345, Asbury 5348R, Asbury 5358R, Asbury 5365R, Asbury 5368, Asbury 5375R, Asbury 5379, Asbury A99, Cabot Monarch 120, Cabot Monarch 280, Cabot Monarch 570, Cabot Monarch 700, Cabot Norit Darco 12x20L1, Cabot Vulcan XC72, Continental N120, Continental N234, Continental N330, Continental N330-C, Continental N550, Norit ROX 0.8, Orion Arosperse 138, Orion Arosperse 15, Orion Color Black FW 2, Orion Color Black FW 255, Orion HiBlack 40B2, Orion Hi-Black 50 L, Orion Hi-Black 50 LB, Orion Hi-Black 600 L, Orion HP-160, Orion Lamp Black 101, Orion N330, Orion Printex L6, Sid Richardson Ground N115, Sid Richardson Ground SR155, Sid Richardson SC159, Sid Richardson SC419, Timcal Ensaco 150G, Timcal Ensaco 250G, Timcal Ensaco 260G, and/or Timcal Ensaco 350G or any combination thereof.

Metal impregnation of the solid support typically results in a negligible change in the specific surface, pore diameters, and specific volume of the solid support. Heterogeneous reduction catalysts that are suitable for use in the present disclosure are typically prepared using a solid support that comprises a plurality of pores and a specific surface area in the range of from 20 $m^2/g$ to 500 $m^2/g$, such as e.g., 20, 30, 40, 50, 60, 70, 80, 90, 100, 120, 140, 160, 180, 200, 225, 250, 275, 300, 325, 350, 375, 400, 425, 450, 475, or 500 $m^2/g$ or is within a range defined by any two of the aforementioned surface areas. Specific surface area can be determined using known methods, such as, for example, the method of Bruanauer, Emmett and Teller (*J. Am. Chem. Soc.* 1938, 60:309-311) and/or mercury porosimetry. See e.g., ASTM Test Methods D3663, D6556, and D4567, each of which is hereby expressly incorporated by reference in its entirety. In some embodiments, the heterogeneous reduction catalyst (or solid support) employed in the process for producing a purified FDCA pathway product comprises a specific surface area in the range of from or any number in between 25 $m^2/g$ to 250 $m^2/g$, and sometimes in the range of from or any number in between 25 $m^2/g$ to 225 $m^2/g$, or from or any number in between 25 $m^2/g$ to 200 $m^2/g$, or from or any number in between 25 m$^2$/g to 175 m$^2$/g, or from or any number in between 25 m$^2$/g to 150 m$^2$/g, or from or any number in between 25 m$^2$/g to 125 m$^2$/g, or from or any number in between 25 m$^2$/g to 100 m$^2$/g.

Heterogeneous reduction catalysts (and solid support components thereof) employed in the practice of the present disclosure may comprise a specific pore volume (determined on the basis of pores having a diameter of 1.7 nm to 100 nm) that is, from or any number in between 0.1 cm$^3$/g to 1.5 cm$^3$/g, from or any number in between 0.1 cm$^3$/g to 0.8 cm$^3$/g, from or any number in between 0.1 cm$^3$/g to 0.7 cm$^3$/g, from or any number in between 0.1 cm$^3$/g to 0.6 cm$^3$/g, from or any number in between 0.1 cm$^3$/g to 0.5 cm$^3$/g, from or any number in between 0.2 cm$^3$/g to 0.8 cm$^3$/g, from or any number in between 0.2 cm$^3$/g to 0.7 cm$^3$/g, from or any number in between 0.2 cm$^3$/g to 0.6 cm$^3$/g, from or any number in between 0.2 cm$^3$/g to 0.5 cm$^3$/g, from or any number in between 0.3 cm$^3$/g to 1 cm$^3$/g, from or any number in between 0.3 cm$^3$/g to 0.9 cm$^3$/g, from or any number in between 0.3 cm$^3$/g to 0.8 cm$^3$/g, from or any number in between 0.3 cm$^3$/g to 0.7 cm$^3$/g, from or any number in between 0.3 cm$^3$/g to 0.6 cm$^3$/g, or from or any number in between 0.3 cm$^3$/g to 0.5 cm$^3$/g or within a range defined by any two of the aforementioned values, as measured by a method for determining pore diameters and specific pore volumes, such as that described in E. P. Barrett, L. G. Joyner, P. P. Halenda, *J. Am. Chem. Soc.* (1951) 73:373-380 and ASTM D4222-03 (2008) (the method referred to herein as the "BJH method"), both of which are hereby expressly incorporated herein by reference in their entireties, and by the method of mercury porosimetry (e.g., using a mercury porosimeter, such as, for example, the Micromeritics Autopore V 9605 Mercury Porosimeter (Micromeritics Instrument Corp., Norcross, Ga.) in accordance with the manufacturer's instructions). See e.g., ASTM 3663, ASTM D-4284-12 and D6761-07 (2012), all of which are hereby expressly incorporated by reference in their entireties.

The heterogeneous reduction catalyst may have a mean pore diameter in the range of from or any number in between 10 nm to 100 nm, as measured by the BJH method and/or mercury porosimetry. In some embodiments, the heterogeneous reduction catalyst has a mean pore diameter in the range of from or any number in between 10 nm to 90 nm, as measured by the BJH method and/or mercury porosimetry. In some embodiments, the mean pore diameter is in the range of from or any number in between 10 nm to 80 nm, or from or any number in between 10 nm to 70 nm, or from or any number in between 10 nm to 60 nm, and often from or any number in between 10 nm to 50 nm, as determined by the BJH method and/or mercury porosimetry. In some embodiments, the mean pore diameter is in the range of from or any number in between 20 nm to 100 nm, as measured by the BJH method and/or mercury porosimetry. In certain of these embodiments, the mean pore diameter is in the range from or any number in between 20 nm to 90 nm, or from or any number in between 20 nm to 80 nm, or from or any number in between 20 nm to 70 nm, or from or any number in between 20 nm to 60 nm, or from or any number in between 10 nm to 50 nm, as determined by the BJH method and/or mercury porosimetry.

In some embodiments, the heterogeneous reduction catalyst may be prepared on extruded supports. Catalysts with extruded supports are beneficial for use in many industrial applications, such as continuous industrial fixed bed reactors, which can be used in the production of a purified FDCA pathway product. Industrial fixed bed reactors must deploy suitably shaped and sized catalysts, such as extrudates, in order to avoid the excessive pressure drop associated with the use of powdered catalysts, which typically are difficult to deploy industrially in fixed bed reactor systems.

In further embodiments, the metal and/or the promoter may be selectively located in a shell covering the exterior surface area of the extruded support, thereby efficiently presenting the catalytically active surface to the reaction medium as metals and promoters deposited in the center of the support would not likely be accessible to the reaction medium. In some embodiments, the exterior surface area of the extruded support comprises the surface area of the outer layer surface of the extruded support. In some embodiments, the exterior surface area of the extruded support comprises the surface area of the pores of the extruded support.

In some embodiments, the extruded support comprises carbon, zirconium dioxide, titanium dioxide, silicon carbide, silicon dioxide, $Al_2O_3$, monmorillonite, or any combination thereof.

In some embodiments, the solvent employed in the process for producing a purified FDCA pathway product comprises an aprotic organic solvent (e.g., an ether, an ester, and/or a ketone, or a mixture thereof) either alone (e.g., as a single-component solvent) or as a component of a multi-component solvent. When used in a multi-component solvent, the aprotic organic solvent is typically miscible with the other component(s) of the multi-component solvent. In some embodiments, the multi-component solvent may comprise water and a water-miscible organic solvent. Typically, the water-miscible organic solvent is a water-miscible aprotic organic solvent.

Candidate component solvents for the multi-component solvent are not limited to solvents in which the FDCA pathway product and the purified FDCA pathway product are highly soluble. Multi-component solvents may exhibit a synergistic solvating effect with respect to FDCA, even when FDCA is poorly soluble in each component solvent. For example, FDCA has poor solubility in water. When paired with a water-miscible organic solvent having poor FDCA-solvating capabilities, the combination of water and the water-miscible organic solvent may exhibit enhanced FDCA-solvating capability. Furthermore, in some embodiments, the multi-component solvents disclosed herein are beneficial and advantageous because the multi-component solvent exhibits enhanced FDCA-solvating capability. In some embodiments, the multi-component solvents disclosed herein are beneficial because the same solvent can be used for producing the FDCA pathway product and the purified FDCA pathway product. In some embodiments, the processes for producing a purified FDCA pathway product described herein provides beneficial and advantageously high selectivity for reducing FFCA to HMFCA as compared with undesired reduction of FDCA. In some embodiments, the processes for producing a purified FDCA pathway product described herein can be conducted at a relatively low temperature, which can aid in the selective reduction of FFCA to HMFCA.

Illustrative multi-component solvents that exhibit this effect include those that comprise water and a water-miscible aprotic organic solvent. Exemplary water-miscible aprotic solvents suitable for use in the practice of the present disclosure include tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and/or gamma-valerolactone, or mixtures thereof. Preferably, the water-miscible aprotic organic solvent is an ether, such as, for example, a glyme, dioxane (1,4-dioxane), a dioxolane (e.g., 1,3-dioxolane), and/or tetrahydrofuran, or mixtures thereof. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, and/or a highly ethoxylated diether of a high molecular weight alcohol ("higlyme"), or mixtures thereof. Often, the organic solvent is a multi-component solvent comprising water and a water-miscible aprotic organic solvent that is glyme, diglyme, or dioxane or mixtures thereof.

In some embodiments, the multi-component solvent comprises water and dioxane. In some embodiments, the multi-component solvent comprises water and DME. In some embodiments, the multi-component solvent comprises water and diglyme. In some embodiments, the multi-component solvent comprises water and triglyme. In some embodiments, the multi-component solvent comprises water and tetraglyme. In some embodiments, the multi-component solvent comprises water and higlyme. In some embodiments, the multi-component solvent comprises water and NMP. In some embodiments, the multi-component solvent comprises water and MEK. In some embodiments, the multi-component solvent comprises water and gamma-valerolactone.

In some embodiments, the composition of the oxidation solvent used in the process for producing a purified FDCA pathway product may be the same as the solvent used in downstream processes (for example, to facilitate product recovery, additional purification, and the like), or upstream processes (for example, an FDCA pathway product process). In some embodiments it may be desirable to employ an organic solvent that is a multi-component solvent comprising a light solvent and a heavy solvent. When the multi-component solvent comprises water and a water-miscible organic solvent, the water-miscible organic solvent may be a light water-miscible organic solvent (e.g., a water-miscible organic solvent having a boiling point that occurs at a temperature less than the boiling point of water) or it may be a heavy water-miscible organic solvent (e.g., a water-miscible organic solvent having a boiling point that occurs at a temperature higher than the boiling point of water). Typically, the light and heavy water-miscible organic solvent are a light and heavy aprotic organic solvent, respectively. Exemplary light water-miscible (and aprotic) organic solvents employed with water in a multi-component solvent include, for example, glyme, a dioxolane (e.g., 1,3-dioxolane), and/or tetrahydrofuran, and the like. Exemplary heavy water-miscible (and aprotic) organic solvents employed with water in a multi-component solvent include, for example, dioxane, ethyl glyme, diglyme (diethylene glycol dimethyl ether), ethyl diglyme, triglyme, butyl diglyme, tetraglyme, and/or a polyglyme. In some embodiments (e.g., continuous reactor systems), all or a portion of the organic solvent or component thereof may be removed from the production solution (e.g., via distillation) and recycled to the reaction mixture. It such embodiments, it may be desirable to employ a multi-component solvent having a composition that corresponds to an azeotrope or which is capable of forming an azeotrope (e.g., an "azeotropic composition") at a temperature employed during the reduction step (e.g., contacting step), or at a temperature employed during a process that is upstream or downstream of the reduction step. Use of such multi-component solvents having an azeotropic composition may facilitate the recycling of the organic solvent (as part of the azeotropic composition) to the reduction step, or to processes that occur upstream and/or downstream of the reduction step.

In some embodiments, the water-miscible organic solvent species is at least 5 volume % (vol %), at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, respectively, of the multi-component system or is within a range defined by any two of the aforementioned volume %s.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

In some embodiments, the volume ratio of water to water-miscible organic solvent is in the range from, any number in between, or within 1:6 to 6:1. In certain embodiments, the volume ratio is from, any number in between, or within 1:4 to 4:1 water:water-miscible organic solvent. In some embodiments, the volume ratio is from, any number in between, or within 1:4 to 3:1 water:water miscible organic solvent. In some embodiments, the volume ratio is from, any number in between, or within 1:3 to 3:1 water:water miscible organic solvent. In certain embodiments, the volume ratio is 1:1 water:water-miscible organic solvent. In some embodiments, the volume ratio is 3:2 water:water-miscible organic solvent.

In some embodiments, the weight % ratio of water to water-miscible organic solvent is in the range from, any number in between, or within 1:6 to 6:1. In certain embodiments, the weight % ratio is from, any number in between, or within 1:4 to 4:1 water:water-miscible organic solvent. In some embodiments, the weight % ratio is from, any number in between, or within 1:4 to 3:1 water:water miscible organic solvent. In some embodiments, the weight % ratio is from, any number in between, or within 1:3 to 3:1 water:water miscible organic solvent. In certain embodiments, the weight % ratio is 1:1 water:water-miscible organic solvent. In some embodiments, the weight % ratio is 3:2 water:water-miscible organic solvent.

In some embodiments, the multi-component solvent comprises water and two different water-miscible organic solvents. Typically, both of the water-miscible organic solvents are water-miscible aprotic organic solvents. Each of the two water-miscible aprotic solvents can be independently selected from the group of tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), and/or gamma-valerolactone. One or both of the water-miscible aprotic organic solvent can be an ether, such as, for example, a glyme, dioxane (for example 1,4-dioxane), dioxolane (e.g., 1,3-dioxolane), tetrahydrofuran, and the like. Glymes include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, and/or a highly ethoxylated diether of a high molecular weight alcohol ("higlyme").

In some embodiments, the volume ratio of water to the first and second water-miscible organic solvent is approximately 1:1:1 (v:v:v). In some embodiments, the volume ratio of water to the first and second water-miscible organic solvent is approximately 1:2:1 (v:v:v). In some embodiments, the volume ratio of water to the first and second water-miscible organic solvent is approximately 1:2:2 (v:v:v). In some embodiments, the volume ratio of water to the first and second water-miscible organic solvent is approximately 2:1:1 (v:v:v).

In some embodiments, the amount of water included in the multi-component solvent may be e.g., at least 0.01 M, at least 0.02 M, at least 0.05 M, at least 0.10 M, at least 0.15 M, at least 0.25 M, at least 0.30 M, at least 0.35 M, at least 0.40 M, at least 0.45 M, at least 0.50 M, at least 0.60 M, at least 0.70 M, at least 0.80 M, at least 0.90 M, at least 1.0 M, at least 1.5 M, at least 2.0 M, at least 2.5 M, or at least 3.0 M or within a range defined by any two of the aforementioned concentrations. In some embodiments, the concentration of water in the multi-component solvent ranges from e.g., 0.01-3.0 M, 0.05-2.0 M, 0.10-1.0 M, or 0.20-0.50 M, or any concentration within the aforementioned ranges. The water may be present in the multi-component solvent at a concentration of at least 0.20 M. The water may be present in the multi-component solvent at a concentration of e.g., at least 0.2 M, or at least 0.3 M, or at least 0.4 M, or at least 0.5 M, or at least 0.6 M, or at least 0.8 M, or at least 1.0M, or at least 1.25 M, or at least 1.5 M or within a range defined by any two of the aforementioned concentrations. In some embodiments, the water may be present in the multi-component solvent at a concentration that ranges from e.g., between 0.2-2.0 M, 0.3-1.5 M, 0.4-1.25 M, 0.5-1.25 M, or 0.6-1.0 M, or any concentration within the aforementioned ranges.

In some embodiments, the FDCA pathway product may be present in the reaction mixture at any concentration up to its solubility limit. In some embodiments, the concentration of FDCA pathway product in the reaction mixture may be e.g., at least 0.01 M, at least 0.02 M, at least 0.05 M, at least 0.10 M, at least 0.15 M, at least 0.25 M, at least 0.30 M, at least 0.35 M, at least 0.40 M, at least 0.45 M, at least 0.50 M, at least 0.60 M, at least 0.70 M, at least 0.80 M, at least 0.90 M, at least 1.0 M, at least 1.5 M, at least 2.0 M, at least 2.5 M, or at least 3.0 M or within a range defined by any two of the aforementioned concentrations. In some embodiments, the concentration of FDCA pathway product in the reaction mixture ranges from e.g., 0.01-3.0 M, 0.05-2.0 M, 0.10-1.0 M, or 0.20-0.50 M, or any concentration within the aforementioned ranges. The FDCA pathway product may be present in the reaction mixture at a concentration of e.g., at least 0.20 M. The FDCA pathway product may be present in the reaction mixture at a concentration of e.g., at least 0.2 M, or at least 0.3 M, or at least 0.4 M, or at least 0.5 M, or at least 0.6 M, or at least 0.8 M, or at least 1.0M, or at least 1.25 M, or at least 1.5 M or within a range defined by any two of the aforementioned concentrations. In some embodiments, the FDCA pathway product may be present in the reaction mixture at a concentration that ranges from e.g., between 0.2-2.0 M, 0.3-1.5 M, 0.4-1.25 M, 0.5-1.25 M, or 0.6-1.0 M, or any concentration within the aforementioned ranges.

The process for producing a purified FDCA pathway product may include performing the process using a reaction mixture where the components of the reaction mixture are present at a designated concentration or ratio between components. In some embodiments, the heterogeneous reduction catalyst and FDCA pathway product are present in the reaction mixture in a weight % ratio of 1:0.04 of heterogeneous reduction catalyst:FDCA pathway product. In some embodiments, the heterogeneous reduction catalyst and FDCA pathway product are present in the reaction mixture in a weight % ratio of 1:0.12 of heterogeneous reduction catalyst:FDCA pathway product. In some embodiments, the heterogeneous reduction catalyst and FDCA pathway product are present in the reaction mixture in a weight % ratio of 1:0.3 of heterogeneous reduction catalyst:FDCA pathway product. In some embodiments, the heterogeneous reduction catalyst and FDCA pathway product are present in the reaction mixture in a weight % ratio of 1:0.5 of heterogeneous reduction catalyst:FDCA pathway product. In some embodiments, the heterogeneous reduction catalyst and FDCA pathway product are present in the reaction mixture in a weight % ratio of 1:1 of heterogeneous reduction catalyst:FDCA pathway product.

In some embodiments, the heterogeneous reduction catalyst and FDCA pathway product are present in the reaction mixture in a weight % ratio of 1:0.04 to 1:1 of heterogeneous reduction catalyst:FDCA pathway product, or any ratio between the aforementioned range. In some embodiments, the heterogeneous reduction catalyst and FDCA pathway product are present in the reaction mixture in a weight % ratio of 1:0.12 to 1:0.5 of heterogeneous reduction catalyst:FDCA pathway product, or any ratio between the aforementioned range. In some embodiments, the heterogeneous reduction catalyst and FDCA pathway product are present in the reaction mixture in a weight % ratio of 1:0.04 to 1:0.3 of heterogeneous reduction catalyst:FDCA pathway product, or any ratio between the aforementioned range. In some embodiments, the heterogeneous reduction catalyst and FDCA pathway product are present in the reaction mixture in a weight % ratio of 1:0.3 to 1:1 of heterogeneous reduction catalyst:FDCA pathway product, or any ratio between the aforementioned range. In some embodiments, the heterogeneous reduction catalyst and FDCA pathway product are present in the reaction mixture in a weight % ratio of 1:12 to 1:0.3 of heterogeneous reduction catalyst:FDCA pathway product, or any ratio between the aforementioned range.

In some embodiments, the heterogeneous reduction catalyst and FFCA are present in the reaction mixture in a weight % ratio of 1:0.001 of heterogeneous reduction catalyst:FFCA. In some embodiments, the heterogeneous reduction catalyst and FFCA are present in the reaction mixture in a weight % ratio of 1:0.04 of heterogeneous reduction catalyst:FFCA. In some embodiments, the heterogeneous reduction catalyst and FFCA are present in the reaction mixture in a weight % ratio of 1:0.12 of heterogeneous reduction catalyst:FFCA. In some embodiments, the heterogeneous reduction catalyst and FFCA are present in the reaction mixture in a weight % ratio of 1:0.3 of heterogeneous reduction catalyst:FFCA. In some embodiments, the heterogeneous reduction catalyst and FFCA are present in the reaction mixture in a weight % ratio of 1:0.5 of heterogeneous reduction catalyst:FFCA. In some embodiments, the heterogeneous reduction catalyst and FFCA are present in the reaction mixture in a weight % ratio of 1:1 of heterogeneous reduction catalyst:FFCA.

In some embodiments, the heterogeneous reduction catalyst and FFCA are present in the reaction mixture in a weight % ratio of 1:0.001 to 1:1 of heterogeneous reduction catalyst:FFCA, or any ratio between the aforementioned range. In some embodiments, the heterogeneous reduction catalyst and FFCA are present in the reaction mixture in a weight % ratio 1:0.04 to 1:1 of heterogeneous reduction catalyst:FFCA, or any ratio between the aforementioned range. In some embodiments, the heterogeneous reduction catalyst and FFCA are present in the reaction mixture in a weight % ratio of 1:0.001 to 1:0.04 of heterogeneous reduction catalyst:FFCA, or any ratio between the aforementioned range. In some embodiments, the heterogeneous reduction catalyst and FFCA are present in the reaction mixture in a weight % ratio of 1:0.12 to 1:0.5 of heterogeneous reduction catalyst:FFCA, or any ratio between the aforementioned range. In some embodiments, the heterogeneous reduction catalyst and FFCA are present in the reaction mixture in a weight % ratio of 1:0.04 to 1:0.3 of heterogeneous reduction catalyst:FFCA, or any ratio between the aforementioned range. In some embodiments, the heterogeneous reduction catalyst and FFCA are present in the reaction mixture in a weight % ratio of 1:0.3 to 1:1 of heterogeneous reduction catalyst:FFCA, or any ratio between the aforementioned range. In some embodiments, the heterogeneous reduction catalyst and FFCA are present in the reaction mixture in a weight % ratio of 1:12 to 1:0.3 of heterogeneous reduction catalyst:FFCA, or any ratio between the aforementioned range.

The process for producing a purified FDCA pathway product may include performing the process at a designated temperature. In some embodiments, the process is performed at a temperature of greater than 50° C. In some embodiments, the process is performed at a temperature of greater than 70° C. In some embodiments, the process is performed at a temperature of greater than 80° C. In some embodiments, the process is performed at a temperature of greater than 120° C. In some embodiments, the process is performed at a temperature of greater than 125° C. In some embodiments, the process is performed at a temperature of greater than 130° C. In some embodiments, the process is performed at a temperature of greater than 150° C.

In some embodiments, the process for producing a purified FDCA pathway product is performed at a temperature of 50° C. In some embodiments, the process is performed at a temperature of 70° C. In some embodiments, the process is performed at a temperature of 80° C. In some embodiments, the process is performed at a temperature of 120° C. In some embodiments, the process is performed at a temperature of 125° C. In some embodiments, the process is performed at a temperature of 130° C. In some embodiments, the process is performed at a temperature of 150° C.

In some embodiments the process for producing a purified FDCA pathway product is performed at a temperature of less than 50° C. (but not zero). In some embodiments, the process is performed at a temperature of less than 70° C. (but not zero). In some embodiments, the process is performed at a temperature of less than 80° C. (but not zero). In some embodiments, the process is performed at a temperature of less than 120° C. (but not zero). In some embodiments, the process is performed at a temperature of less than 125° C. (but not zero). In some embodiments, the process is performed at a temperature of less than 130° C. (but not zero). In some embodiments, the process is performed at a temperature of less than 150° C. (but not zero).

In some embodiments of the present disclosure, the process for producing a purified FDCA pathway product is performed at a temperature between 50° C. and 130° C., or any number in between the aforementioned range. In some embodiments, the process is performed at a temperature between 80° C. and 120° C., or any number in between the aforementioned range. In some embodiments, the process is performed at a temperature between 70° C. and 125° C., or any number in between the aforementioned range. In some embodiments, the process is performed at a temperature between 50° C. and 120° C., or any number in between the aforementioned range. In some embodiments, the process is performed at a temperature between 120° C. and 130° C., or any number in between the aforementioned range. In some embodiments, the process is performed at a temperature between 80° C. and 125° C., or any number in between the aforementioned range. In some embodiments, the process is performed at a temperature between 50° C. and 150° C., or any number in between the aforementioned range.

The process for producing a purified FDCA pathway product may include performing the process at a designated pressure. In some embodiments, pressurization is performed with hydrogen gas. In some embodiments, pressurization is performed with other suitable gasses, such inert gases, such as nitrogen, helium, or argon. In some embodiments, the process is performed at a pressure above 50 psi. In some embodiments, the process is performed at a pressure above 100 psi. In some embodiments, the process is performed at a pressure above 200 psi. In some embodiments, the process is performed at a pressure above 500 psi. In some embodiments, the process is performed at a pressure above 800 psi. In some embodiments, the process is performed at a pressure above 1000 psi.

In some embodiments, the process is performed at a pressure of 50 psi. In some embodiments, the process is performed at a pressure of 100 psi. In some embodiments, the process is performed at a pressure of 200 psi. In some embodiments, the process is performed at a pressure of 500 psi. In some embodiments, the process is performed at a pressure of 800 psi. In some embodiments, the process is performed at a pressure of 1000 psi. In some embodiments, the process is performed at a pressure of 14 bar. In some embodiments, the process is performed at a pressure of 35 bar. In some embodiments, the process is performed at a pressure of 55 bar.

In some embodiments, the process is performed at a pressure below 50 psi (but not zero). In some embodiments, the process is performed at a pressure below 100 psi (but not zero). In some embodiments, the process is performed at a pressure below 200 psi (but not zero). In some embodiments, the process is performed at a pressure below 500 psi (but not zero). In some embodiments, the process is performed at a pressure below 800 psi (but not zero). In some embodiments, the process is performed at a pressure below 1000 psi (but not zero).

In some embodiments of the present disclosure, the process is performed at a pressure between 50 psi to 1000 psi, or any number in between the aforementioned range. In some embodiments, the process is performed at a pressure between 100 psi to 500 psi, or any number in between the aforementioned range. In some embodiments, the process is performed at a pressure between 200 psi to 525 psi, or any number in between the aforementioned range. In some embodiments, the process is performed at a pressure between 500 psi to 1000 psi, or any number in between the aforementioned range. In some embodiments, the process is performed at a pressure between 150 psi to 600 psi, or any number in between the aforementioned range. In some embodiments, the process is performed at a pressure between 300 psi to 550 psi, or any number in between the aforementioned range.

The process for producing a purified FDCA pathway product may include performing the process for a designated amount of time. In some embodiments, the process is performed for greater than 30 minutes. In some embodiments, the process is performed for greater than 60 minutes. In some embodiments, the process is performed for greater than 120 minutes. In some embodiments, the process is performed for greater than 180 minutes. In some embodiments, the process is performed for greater than 240 minutes. In some embodiments, the process is performed for greater than 300 minutes.

In some embodiments, the process is performed for 30 minutes. In some embodiments, the process is performed for 60 minutes. In some embodiments, the process is performed for 120 minutes. In some embodiments, the process is performed for 180 minutes. In some embodiments, the process is performed for 240 minutes. In some embodiments, the process is performed for 300 minutes.

In some embodiments, the process is performed for less than 30 minutes (but not zero). In some embodiments, the process is performed for less than 60 minutes (but not zero). In some embodiments, the process is performed for less than 120 minutes (but not zero). In some embodiments, the process is performed for less than 180 minutes (but not zero). In some embodiments, the process is performed for less than 240 minutes (but not zero). In some embodiments, the process is performed for less than 300 minutes (but not zero).

In some embodiments, the process is performed between 30 minutes to 300 minutes, or any number in between the aforementioned range. In some embodiments, the process is performed between 60 minutes to 240 minutes, or any number in between the aforementioned range. In some embodiments, the process is performed between 60 minutes to 120 minutes, or any number in between the aforementioned range. In some embodiments, the process is performed between 120 minutes to 180 minutes, or any number in between the aforementioned range. In some embodiments, the process is performed between 60 minutes to 120 minutes, or any number in between the aforementioned range. In some embodiments, the process is performed between 180 minutes to 240 minutes, or any number in between the aforementioned range. In some embodiments, the process is performed between 2 to 4 hours, 2 to 6 hours, 3 to 8 hours, 5 to 10 hours, 8 to 12 hours, 10 to 15 hours, 12 to 20 hours, 15 to 24 hours, 1 to 2 days, 1 to 3 days, 2 to 4 days, or any number in between the aforementioned ranges.

In some embodiments, the process for producing a purified FDCA pathway product may comprise or consist of a reaction mixture comprising or consisting of an FDCA pathway product comprising or consisting of FDCA and FFCA; hydrogen at a pressure ranging from or any number in between 50-800 psi; a heterogeneous reduction catalyst comprising a solid support selected from the group of carbon, silicon dioxide, and/or $Al_2O_3$ or a mixture thereof, wherein the heterogeneous reduction catalyst further comprises a metal selected from Cu, Ni, Pd, Pt, and/or Ru or a mixture thereof; and a multicomponent solvent comprising water and a water-miscible aprotic organic solvent, wherein the water-miscible aprotic organic solvent comprises or consists of dioxane and/or sulfolane. In some embodiments, the temperature of the reaction mixture may range from or any number in between 60-140° C. In some embodiments, the reaction may proceed for a time ranging from or any number in between 1-24 h.

In some embodiments, the process for producing a purified FDCA pathway product may comprise or consist of a reaction mixture comprising or consisting of an FDCA pathway product at a molar concentration in the range from or any number in between 0.1-3.5 M and the FDCA pathway product comprises or consists of FDCA and FFCA; hydrogen at a pressure ranging from or any number in between 50-800 psi; a heterogeneous reduction catalyst at a weight ratio range of 1:0.04 to 1:1 of catalyst:FDCA pathway product; and wherein the heterogeneous reduction catalyst comprises a solid support selected from the group of carbon, silicon dioxide, and/or $Al_2O_3$ or a mixture thereof, wherein the heterogeneous reduction catalyst further comprises a metal selected from Cu, Ni, Pd, Pt, and/or Ru or a mixture thereof; and a multicomponent solvent comprising water and a water-miscible aprotic organic solvent, wherein the water-miscible aprotic organic solvent comprises or consists of dioxane and/or sulfolane. The multicomponent solvent may comprise water at a concentration ranging from or any number in between 0.1-2.5 M. In some embodiments, the temperature of the reaction mixture may range from or any number in between 60-140° C. In some embodiments, the reaction may proceed for a time ranging from or any number in between 1-24 h.

In some embodiments, the process for producing a purified FDCA pathway product may comprise or consist of a reaction mixture comprising or consisting of an FDCA pathway product comprising or consisting of FDCA and FFCA; hydrogen at a pressure ranging from or any number in between 50-800 psi; a heterogeneous reduction catalyst comprising or consisting of Pd/C, Pt/C, Ru/C, $Cu/Al_2O_3$, and/or $Ni/Al_2O_3$ or a mixture thereof, and a multicomponent solvent comprising water and a water-miscible aprotic organic solvent, wherein the water-miscible aprotic organic solvent comprises or consists of dioxane and/or sulfolane. In some embodiments, the temperature of the reaction mixture may range from or any number in between 60-140° C. In some embodiments, the reaction may proceed for a time ranging from or any number in between 1-24 h.

In some embodiments, the process for producing a purified FDCA pathway product may comprise or consist of a reaction mixture comprising or consisting of an FDCA pathway product at a molar concentration in the range from or any number in between 0.1-3.5 M and the FDCA pathway product comprises or consists of FDCA and FFCA; hydrogen at a pressure ranging from or any number in between 50-800 psi; a heterogeneous reduction catalyst at a weight ratio range of 1:0.04 to 1:1 of catalyst:FDCA pathway product; and wherein the heterogeneous reduction catalyst comprises or consists of Pd/C, Pt/C, Ru/C, $Cu/Al_2O_3$, and/or $Ni/Al_2O_3$ or a mixture thereof, and a multicomponent solvent comprising water and a water-miscible aprotic organic solvent, wherein the water-miscible aprotic organic solvent comprises or consists of dioxane and/or sulfolane. The multicomponent solvent may comprise water at a concentration ranging from or any number in between 0.1-2.5 M. In some embodiments, the temperature of the reaction mixture may range from or any number in between 60-140° C. In some embodiments, the reaction may proceed for a time ranging from or any number in between 1-24 h.

In some embodiments, the purified FDCA pathway product comprises FDCA, HMFCA, less than 10% molar impurities of MFA, and less than 10% molar impurities of THFDCA.

In some embodiments, the purified FDCA pathway product comprises greater than 90% of FDCA by molar purity. In some embodiments, the purified FDCA pathway product comprises greater than 95% of FDCA by molar purity. In some embodiments, the purified FDCA pathway product comprises greater than 99% of FDCA by molar purity.

In some embodiments, the purified FDCA pathway product comprises 90% to 99% of FDCA by molar purity, or any number in between the aforementioned range. In some embodiments, the purified FDCA pathway product comprises 95% to 99% of FDCA by molar purity, or any number in between the aforementioned range. In some embodiments, the purified FDCA pathway product comprises 90% to 95% of FDCA by molar purity, or any number in between the aforementioned range.

In some embodiments, the purified FDCA pathway product comprises less than 5% FFCA by molar purity. In some embodiments, the purified FDCA pathway product comprises less than 1% FFCA by molar purity. In some embodiments, the purified FDCA pathway product comprises less than 0.5% FFCA by molar purity. In some embodiments, the purified FDCA pathway product comprises less than 0.1% FFCA by molar purity. In some embodiments, the purified FDCA pathway product comprises less than 0.05% FFCA by molar purity.

In some embodiments, the purified FDCA pathway product comprises 0.05% to 5% FFCA by molar purity, or any number in between the aforementioned range. In some embodiments, the purified FDCA pathway product comprises 0.1% to 1% FFCA by molar purity, or any number in between the aforementioned range. In some embodiments, the purified FDCA pathway product comprises 0.05% to 0.5% FFCA by molar purity, or any number in between the aforementioned range. In some embodiments, the purified FDCA pathway product comprises 0.5% to 1% FFCA by molar purity, or any number in between the aforementioned range. In some embodiments, the purified FDCA pathway product comprises 1% to 5% FFCA by molar purity, or any number in between the aforementioned range.

In some embodiments, the purified FDCA pathway product comprises less than 5% MFA by molar purity. In some embodiments, the purified FDCA pathway product comprises less than 1% MFA by molar purity. In some embodiments, the purified FDCA pathway product comprises less than 0.5% MFA by molar purity. In some embodiments, the purified FDCA pathway product comprises less than 0.1% MFA by molar purity.

In some embodiments, the purified FDCA pathway product comprises 0.1% to 5% MFA by molar purity, or any number in between the aforementioned range. In some embodiments, the purified FDCA pathway product comprises 0.1% to 1% MFA by molar purity, or any number in between the aforementioned range. In some embodiments, the purified FDCA pathway product comprises 0.1% to 0.5% MFA by molar purity, or any number in between the aforementioned range. In some embodiments, the purified FDCA pathway product comprises 0.5% to 1% MFA by molar purity, or any number in between the aforementioned range. In some embodiments, the purified FDCA pathway product comprises 1% to 5% MFA by molar purity, or any number in between the aforementioned range.

In some embodiments, the purified FDCA pathway product comprises less than 1% THFDCA by molar purity. In some embodiments, the purified FDCA pathway product comprises less than 0.9% THFDCA by molar purity. In some embodiments, the purified FDCA pathway product comprises less than 0.5% THFDCA by molar purity. In some embodiments, the purified FDCA pathway product comprises less than 0.1% THFDCA by molar purity.

In some embodiments, the purified FDCA pathway product comprises 0.1% to 1% THFDCA by molar purity, or any number in between the aforementioned range. In some embodiments, the purified FDCA pathway product comprises 0.1% to 0.9% THFDCA by molar purity, or any number in between the aforementioned range. In some embodiments, the purified FDCA pathway product comprises 0.1% to 0.5% THFDCA by molar purity, or any number in between the aforementioned range. In some embodiments, the purified FDCA pathway product comprises 0.5% to 0.9% THFDCA by molar purity, or any number in between the aforementioned range. In some embodiments, the purified FDCA pathway product comprises 0.9% to 1% THFDCA by molar purity, or any number in between the aforementioned range.

In the processes described herein, the purified FDCA pathway product may further comprise HMFCA reduced from FFCA. In some embodiments, the yield of HMFCA reduced from FFCA is greater than 25%. In some embodiments, the yield of HMFCA reduced from FFCA is greater than 40%. In some embodiments, the yield of HMFCA reduced from FFCA is greater than 75%. In some embodiments, the yield of HMFCA reduced from FFCA is greater than 90%. In some embodiments, the yield of HMFCA reduced from FFCA is greater than 95%. In some embodiments, the yield of HMFCA reduced from FFCA is greater than 99%.

In some embodiments, the yield of HMFCA reduced from FFCA is 25% to 99%, or any number in between the aforementioned range. In some embodiments, the yield of HMFCA reduced from FFCA is 40% to 99%, or any number in between the aforementioned range. In some embodiments, the yield of HMFCA reduced from FFCA is 75% to 99%, or any number in between the aforementioned range. In some embodiments, the yield of HMFCA reduced from FFCA is 90% to 99%, or any number in between the aforementioned range. In some embodiments, the yield of HMFCA reduced from FFCA is 95% to 99%, or any number in between the aforementioned range. In some embodiments, the yield of HMFCA reduced from FFCA is 90% to 95%, or any number in between the aforementioned range.

In some embodiments, the purified FDCA pathway product comprises less than 10% DDF by molar purity. In some embodiments, the purified FDCA pathway product comprises less than 5% DDF by molar purity. In some embodiments, the purified FDCA pathway product comprises less than 1% DDF by molar purity. In some embodiments, the purified FDCA pathway product comprises less than 0.5% DDF by molar purity. In some embodiments, the purified FDCA pathway product comprises less than 0.1% DDF by molar purity.

In some embodiments, the purified FDCA pathway product comprises 0.1% to 10% DDF by molar purity, or any number in between the aforementioned range. In some embodiments, the purified FDCA pathway product comprises 0.1% to 5% DDF by molar purity, or any number in between the aforementioned range. In some embodiments, the purified FDCA pathway product comprises 0.1% to 1% DDF by molar purity, or any number in between the aforementioned range.

III. Crystallization of a Purified FDCA Pathway Product

The purified FDCA pathway product produced by the process described in Section II of this application may be further purified. In some embodiments, the purified FDCA pathway product is further purified by crystallization. Applicants have beneficially discovered that reduction of FFCA in an FDCA pathway product to HMFCA allows for easier removal of HMFCA from the purified FDCA pathway product through crystallization than attempting to remove FFCA from an FDCA pathway product via crystallization alone.

In some embodiments, the crystallization solution is the same multi-component solvent used in the process for producing a purified FDCA pathway product.

Solution phase crystallizations are typically performed by introducing a saturated (or super-saturated) solution of the purified PFCA pathway product into a crystallizer in which the solution is subjected to crystallization conditions, and crystallization is initiated by, for example, lowering the temperature or concentrating the solution by solvent evaporation (e.g., solvent removal), or a combination of both. Solvent evaporation may be used to concentrate the solution to initiate crystallization, and may also be used to adjust the solvent composition to lower the solubility of the purified FDCA pathway product.

In one embodiment where crystallization conditions include a temperature adjustment, the present disclosure provides a process for producing a crystalline FDCA preparation, the method comprising:

providing a crystallization solution comprising the purified FDCA pathway product and a crystallization solvent at a first temperature in the range of or any number in between 50° C. to 220° C., such as e.g., 50, 60, 70, 80, 90, 100, 110, 115, 120, 130, 140, 150, 160, 180, 190, 200, 210, or 220° C. or within a range defined by any two of the aforementioned temperatures; and cooling the crystallization solution to a second temperature that is lower than the first temperature to form a plurality of FDCA crystals of different particle sizes.

Cooling reduces the solubility of the FDCA in the crystallization solvent, causing crystals of FDCA to form in the solution. The first temperature is typically in the range of from or any number in between 60° C. to 180° C., such as e.g., 60, 70, 80, 90, 100, 110, 115, 120, 130, 140, 150, 160, or 180° C. or within a range defined by any two of the aforementioned temperatures. In some embodiments, the first temperature is in the range from or any number in between 70° C. to 150° C. such as e.g., 70, 80, 90, 100, 110, 115, 120, 130, 140, or 150° C. or within a range defined by any two of the aforementioned temperatures. When the crystallization solution is cooled, it is typically cooled to a temperature that is at or below 60° C., such as e.g., equal to or less than 60, 50, 40, 30, 20, 10, 5, or 0° C. or within a range defined by any two of the aforementioned temperatures. More typically, it is cooled to a temperature at or below 50° C. or at or below 40° C. such as, e.g., equal to or less than 50, 40, 30, 20, 10, 5, or 0° C. or within a range defined by any two of the aforementioned temperatures.

In an embodiment where solvent removal (evaporation) is used to initiate crystallization, the present disclosure provides a method for producing a crystalline FDCA preparation, the method comprising:

(a) providing a first crystallization solution comprising a purified FDCA pathway product and a first crystallization solvent selected from the group consisting of water, an organic solvent, and combinations thereof;

(b) removing a first portion of the first crystallization solvent from the first crystallization solution to produce a first purified FDCA pathway product slurry, wherein the first purified FDCA pathway product slurry comprises a first plurality of FDCA crystals and a second portion of the first crystallization solvent; and (c) separating the first plurality of FDCA crystals from the second portion of the first crystallization solvent.

In a further embodiment, the first plurality of FDCA crystals are recrystallized, by conducting the following additional steps:

(d) dissolving the first plurality of FDCA crystals in a second crystallization solvent to produce a second crystallization solution comprising FDCA and the second crystallization solvent; and (e) removing a first portion of the second crystallization solvent from the second crystallization solution to produce a second FDCA slurry, wherein the second FDCA slurry comprises a second plurality of FDCA crystals and a second portion of the second crystallization solvent; and (f) separating the second plurality of FDCA crystals from the second portion of the second crystallization solvent.

Removal of a portion of the crystallization solvent can be accomplished using known methods for removing solvents from a solution, such as, for example, evaporation, or distillation, and the like. Solvent removal may be facilitated by raising the temperature of the crystallization solution to effect vaporization of the crystallization solvent, or component thereof, resulting in one portion of the crystallization solvent being in a liquid phase and another portion being in a vapor phase, which is removed. Solvent removal results in an increase in concentration of the purified FDCA pathway product causing it to crystallize, thereby resulting in a slurry of FDCA crystals in a continuous liquid phase. Often, one or both of the first and second crystallization solvents is/are a multi-component solvent, where removing a first portion of the first and/or second crystallization solvents may involve removing all or part of one of the components of the multi-component solvent, and less or none of the other components. In these embodiments, the multi-component solvent may comprise one organic solvent species that is a light organic solvent and a second organic species that is a heavy organic solvent; or alternatively, it may comprise water and an organic solvent that is either a heavy or light, water-miscible organic solvent.

Separation of the first plurality of FDCA crystals and the second plurality of FDCA crystals from the second portion of the first crystallization solvent and the second portion of the second crystallization solvent, respectively, can be accomplished using known methods for separating solids from liquids, such as, for example, filtration, centrifugation, and the like.

The dissolving step (steps (a and d)) is typically carried out at an elevated temperature to facilitate the dissolution of the first FDCA crystals in the second crystallization solvent. The temperature will depend on the crystallization solvent employed, but can be readily determined by raising the temperature, and optionally adding more second crystallization solvent, until the first plurality of FDCA crystals has dissolved completely. Typically, the dissolving step is carried out at a temperature in the range from or any number in between 50° C. to 220° C., such as e.g., 50, 60, 70, 80, 90, 100, 110, 115, 120, 130, 140, 150, 160, 180, 190, 200, 210, or 220° C. or within a range defined by any two of the aforementioned temperatures. Often, the dissolving step is carried out at a temperature in the range from or any number in between 60° C. to 180° C., or in the range from or any number in between 70° C. to 150° C. such as e.g., 60, 70, 80, 90, 100, 110, 115, 120, 130, 140, 150, 160, 170, or 180° C. or within a range defined by any two of the aforementioned temperatures. In some embodiments, the dissolving step is carried out at the higher end of these ranges, such as, for example, in the range from or any number in between 100° C. to 220° C., or from or any number in between 150° C. to 220° C., such as e.g., 100, 110, 115, 120, 130, 140, 150, 160, 180, 190, 200, 210, or 220° C. or within a range defined by any two of the aforementioned temperatures.

The first and second crystallization solvent may be the same or different. In certain embodiments, at least one of the first and second crystallization solvents is a multi-component solvent that comprises a component solvent species common to both crystallization solvents. In some embodiments, the first crystallization solution comprising the purified FDCA pathway product is the multi-component solvent used in the process for producing the purified FDCA pathway product as described hereinabove. In some embodiments, the first crystallization solvent is not the same as the multi-component solvent used in the prior reduction step. In these embodiments, all or a portion of the multi-component solvent may be removed prior to the crystallization step, by, for example, evaporation, and the like. The resulting solids can be dissolved in a different solvent (e.g., water or a different organic solvent species) or different multi-component solvent (e.g., a solvent that does not have the same composition as the multi-component solvent from the process for producing the purified FDCA pathway product) to prepare the first crystallization solution.

Crystallizing the purified FDCA product can further comprise dissolving the purified FDCA product in any subsequent number of crystallization solvents, (e.g. a third, fourth, fifth or sixth crystallization solvents). In some embodiments, the subsequent crystallization solvents may be the same or different than those as described hereinabove for the first and/or second crystallization solvents. In some embodiments, the subsequent crystallization processes may be the same or different than those as described hereinabove for the first and/or second crystallization solvents.

In a specific embodiment, the crystallization solvent is a multi-component solvent comprising water and a water-miscible organic solvent. Thus, in a further embodiment, the present disclosure provides a process for producing a crystalline preparation of a purified FDCA pathway product, the process comprising:

providing a crystallization solution comprising a purified FDCA pathway product and a crystallization solvent that is a multi-component solvent comprising water and a water-miscible organic solvent;

initiating crystallization of the purified FDCA pathway product; and producing a plurality of purified FDCA pathway product crystals of different particle sizes.

In this embodiment, the water-miscible organic solvent is typically a water-miscible aprotic organic solvent. In an exemplary embodiment, the water-miscible aprotic organic solvent is an ether, such as, for example dioxane, dioxolane, and/or diglyme, or a mixture thereof. To illustrate the benefit of such solvent system, the FDCA solubility relationship in representative solvent compositions of the disclosure in comparison to water, dioxane, dioxolane (e.g., 1,3-dioxolane), and/or diglyme is discussed. The high solubility of FDCA in the solvent compositions of the disclosures enables the preparation of saturated solutions of FDCA in preparation for purification by crystallization. By adjusting the solvent composition by removing water or the organic solvent (or an azeotropic mixture of water and the organic solvent), it is possible to produce a solvent composition that is organic solvent rich (in the cases in which the chosen organic solvent is less volatile than water), or a solvent composition that is water rich (in the case that the chosen organic solvent is more volatile than water). FDCA is considerably less soluble in water or organic solvents than the solvent compositions of the disclosure. The saturated solutions of FDCA may be subjected to crystallization conditions by lowering the temperature or by solvent evaporation to adjust the solvent composition, or both.

Exemplary water-miscible aprotic solvents that are suitable for use in the crystallization processes of the present disclosure include tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), and/or gamma-valerolactone, or any mixture thereof. Preferably, the water-miscible aprotic organic solvent is an ether, such as, for example, a glyme, dioxane (for example 1,4-dioxane), dioxolane (e.g., 1,3-dioxolane), and/or tetrahydrofuran, or any mixture thereof. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, and/or a highly ethoxylated diether of a high molecular weight alcohol ("higlyme"), or any mixture thereof. Often, the water-miscible aprotic organic solvent is glyme, diglyme, or dioxane or any mixture thereof.

In some embodiments, the water-miscible organic solvent species is at least 5 vol %, at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent or within a range defined by any two of the aforementioned values; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, (but not zero) respectively, of the multi-component system or within a range defined by any two of the aforementioned values.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

More typically, the volume ratio of water to water-miscible organic solvent is typically in the range of from or any number in between 1:6 to 6:1 (v:v). In some embodiments, the volume ratio is from or any number in between 1:4 to 4:1 (v:v). In some embodiments, the volume ratio is from or any number in between 1:4 to 3:1 (v:v) water:water-miscible organic solvent. In some embodiments, the volume ratio is from or any number in between 1:4 to 1:3 (v:v) water:water miscible organic solvent. In certain embodiments, the volume ratio is 1:1 (v:v) water:water-miscible organic solvent.

Crystallization can be initiated using either temperature reduction (cooling) or solvent removal methods described above. When temperature reduction is used to initiate crystallization, the temperature of the crystallization solution is typically reduced from a first temperature that is typically in the range of from or any number in between 60° C. to 220° C., such as e.g., 60, 70, 80, 90, 100, 110, 115, 120, 130, 140, 150, 160, 180, 190, 200, 210, or 220° C. or within a range defined by any two of the aforementioned temperatures.

When water is a component of the crystallization solvent, the first temperature is often at the upper end of this range, e.g., in the range of from or any number in between 100° C. to 220° C. or in the range of from or any number in between 150° C. to 220° C. such as e.g., 100, 110, 115, 120, 130, 140, 150, 160, 180, 190, 200, 210, or 220° C. or within a range defined by any two of the aforementioned temperatures. In some embodiments, the first temperature is in the range of from or any number in between 60° C. to 180° C., such as e.g., 60, 70, 80, 90, 100, 110, 115, 120, 130, 140, 150, 160, or 180° C. or within a range defined by any two of the aforementioned temperatures to a second temperature that is lower than the first temperature. In some embodiments, the first temperature is in the range of from or any number in between 70° C. to 150° C., such as e.g., 70, 80, 90, 100, 110, 115, 120, 130, 140, or 150° C. or within a range defined by any two of the aforementioned temperatures. When the crystallization solution is cooled, it is typically cooled to a second temperature that is below 60° C., such as e.g., equal to or less than 60, 50, 40, 30, 20, 10, 5, or 0° C. or within a range defined by any two of the aforementioned temperatures. More typically, it is cooled to a second temperature below 50° C. or below 40° C. such as, e.g., equal to or less than 50, 40, 30, 20, 10, 5, or 0° C. or within a range defined by any two of the aforementioned temperatures.

Crystallization can also be initiated by removing a first portion of the crystallization solvent from the crystallization solution to produce a purified FDCA pathway product slurry, wherein the purified FDCA pathway product slurry comprises a first plurality of FDCA crystals of different particle sizes and a second portion of the crystallization solvent; and separating the plurality of FDCA crystals from the second portion of the first crystallization solvent. The first plurality of FDCA crystals may be optionally dissolved in the same or different crystallization solvent, and the process repeated to obtain a second plurality of FDCA crystals of different particle sizes.

Seed crystals of the purified FDCA pathway product may be added to further promote the initiation of crystallization. Other additives, such as anti-foaming agents or crystallization aids, may be added to the crystallization solution to promote the crystallization process, and enable the formation of a suspension containing FDCA crystals. Anti-foaming agents that are suitable for use in the practice of the present disclosure include, for example, silicones, surfactants, phosphates, alcohols, glycols, stearates and the like. Additives such as surfactants or electrolyte polymers may also influence the morphology and composition of the crystals formed. See, e.g., U.S. Pat. Nos. 5,296,639 and 6,534,680, which are hereby expressly incorporated herein by reference in their entireties. Other additives may function as a flow improver to prevent agglomeration of the crystalline product on storage (see for example U.S. Pat. No. 6,534,680).

FDCA crystals produced by the processes described herein can be separated from the solution (mother liquor) by centrifugation, filtration, or other suitable process for separating solids from liquids. The crystals can then be washed and dried using any suitable process known to those having ordinary skill in the art.

The crystallization processes described herein can be carried out as part of an integrated process for preparing FDCA crystals from a raw feed that comprises the purified FDCA pathway product. The set of process steps can be carried out in at least a first crystallization zone, a dissolution zone, and a second (refined) crystallization zone. The crystallization processes can also be carried out as part of an integrated process for preparing FDCA crystals from a purified FDCA pathway product feedstock comprising the FDCA pathway product and the multi-component solvent. In this process, the integrated crystallization process is further integrated with the reduction reaction processes described herein. In this integrated process, effluent from at least one reduction reaction zone is passed, as feedstock, into the integrated crystallization process. In the crystallization processes described herein, crystal separation operations (such as the use of a centrifuge) may optionally be deployed after each crystallization zone (for example between the crystallization zone and the next dissolution zone).

In some embodiments, the crystalline FDCA comprises at least 98 wt % FDCA, and more typically, it comprises at least 99 wt % FDCA, and in some embodiments, it comprises greater than 99 wt % FDCA.

In some embodiments, the crystalline FDCA comprises greater than 99% molar purity FDCA. In some embodiments, the crystalline FDCA preparation comprises greater than 99.5% molar purity FDCA. In some embodiments, the crystalline FDCA preparation comprises greater than 99.8% molar purity FDCA. In some embodiments, the crystalline FDCA preparation comprises greater than 99.9% molar purity FDCA. In some embodiments, the crystalline FDCA preparation comprises greater than 99.95% molar purity FDCA. In some embodiments, the crystalline FDCA preparation comprises greater than 99.99% molar purity FDCA. In some embodiments, the crystalline FDCA preparation contains no detectable levels of impurities.

The crystallization processes of the present disclosure may be carried out using known industrial crystallizer systems that are suitable for carrying out solution phase crystallizations. Suitable systems include for example, batch crystallizers, continuous crystallizers (e.g., forced circulation crystallizers, draft-tube crystallizers, draft-tube-baffled crystallizers, or Oslo-type crystallizers, and the like), and other such crystallizer systems.

The crystalline FDCA preparations of the present disclosure are typically dry, and comprise less than 1 wt % water. Often, they comprise less than 0.9 wt %, or less than 0.8 wt %, or less than 0.7 wt %, or less than 0.6 wt %, or less than 0.5 wt %, or less than 0.4 wt %, or less than 0.3 wt %, or less than 0.2 wt % water or an amount of water that is within a range defined by any two of the aforementioned amounts.

The processes disclosed may be performed at many scales. In some embodiments, the processes may be performed at small scales such that the amount compounds used are in the milligram to gram range. In some embodiments, the processes may be performed at industrial scales. In some embodiments, the industrial scale processes may be performed in multiple batches wherein multiple batches of the FDCA pathway product, purified FDCA pathway product and/or crystalized FDCA are obtained. In some embodiments, the industrial scale processes may be performed as a continuous process wherein the FDCA pathway product, purified FDCA pathway product and/or crystalized FDCA are continuously fluidly connected.

The processes of the present disclosure may be carried out in batch, semi-batch, or continuous flow reactor or format using reactors known in the art, such as, for example, fixed bed reactors, trickle bed reactors, slurry phase reactors, moving bed reactors, and the like.

IV. Reduction Catalyst Examples

Additional alternatives are disclosed in further detail in the following examples, which are not in any way intended to limit the scope of the claims.

Example 1

Catalyst testing was conducted within 1 ml glass vials housed in a 96-well insert situated in a high pressure high throughput reactor. See Diamond, G. M., Murphy, V., Boussie, T. R., in *Modern Applications of High Throughput R&D in Heterogeneous Catalysis*, (eds, Hagemeyer, A. and Volpe, A. Jr. Bentham Science Publishers 2014, Chapter 8, 299-309); see also U.S. Pat. No. 8,669,397, both of which are incorporated herein by reference. Up to 20 mg of each powder catalyst was placed into a reactor along with 0.25 ml of a solution prepared in a 3:2 (wt/wt) dioxane:$H_2O$ mixture with various amounts of 5-formyl-2-furoic acid (FFCA) and 2,5-furandicarboxylic acid (FDCA). The 1 ml reaction vials within the insert were each covered with a Teflon sheet, a silicon mat and a steel gas diffusion plate each containing pin-holes to enable gas entry. The insert was placed within a pressure vessel which was leak tested under nitrogen pressure. The atmosphere within the reactor was then replaced by hydrogen at target pressure (e.g., 500 psig) and the reactor was heated to target temperature (e.g., 100° C.) and shaken at 800 rpm for a certain period of time (e.g., 60 min). After the reaction was completed, the shaking was stopped and the reactor was cooled down to room temperature. Samples were prepared for HPLC analysis by sampling from each reactor after diluting the sample with dimethyl sulfoxide (DMSO) and $H_2O$. Reaction products were hydroxymethylfurancarboxylic acid (HMFCA) and 5-methyl-2-furoic acid (MFA) from hydrogenation of FFCA, and tetrahydrofuran dicarboxylic acid (THFDCA) from hydrogenation of FDCA. Yields of HMFCA and MFA were calculated based on the amount of FFCA used, while yield of THFDCA was calculated based on the amount of FDCA used.

All catalysts were commercially available and screened as a powder. If powder was not available, extrudate catalyst was grinded into powder before hydrogenation reactions. Cu Clariant T-4874 was the powder from extrudate Cu catalyst Clariant T-4874 after rinsing stabilizing solution iso-decanol with dioxane. Ni JM HTC 500RP was the powder from extrudate Ni catalyst Johnson Matthey, Inc. HTC 500RP. Catalyst Pd/C JM-10 (A102038-5 Lot #C-9074), Pd/C JM-4 (A405032-5 Lot #C-9191), Ru/C JM-37 (D101023-5 Lot #C-9219), and Ru/C JM-38 (D101038-5 Lot #C-9220) were from Johnson Matthey, Inc. and used as is. Catalysts Ru/C JM-37* and Ru/C JM-38* were further reduced form (350° C. in forming gas for 3 hours) of Ru/C JM-37 (D101023-5 Lot #C-9219) and Ru/C JM-38 (D101038-5 Lot #C-9220) from Johnson Matthey, Inc. The results are shown in Table 1.

TABLE 1

Catalyst Composition and Performance in Hydrogenation of FFCA and FDCA

| Catalyst Name | Catalyst Amount (mg) | FFCA Amount (mg) | FDCA Amount (mg) | Hydrogenation Conditions | HMFCA Yield (%) | MFA Yield (%) | THFDCA Yield (%) |
|---|---|---|---|---|---|---|---|
| Cu Clariant T-4874 | 2 | 0.6 | 0 | 100° C./60 min/500 psiH2 | 85 | 0 | 0 |
| Cu Clariant T-4874 | 2 | 0.6 | 0 | 125° C./60 min/800 psiH2 | 75 | 0 | 0 |
| Cu Clariant T-4874 | 5 | 0.6 | 0 | 100° C./60 min/500 psiH2 | 64 | 0 | 0 |
| Cu Clariant T-4874 | 10 | 0.6 | 0 | 100° C./60 min/500 psiH2 | 37 | 0 | 0 |
| Cu Clariant T-4874 | 10 | 0.6 | 12 | 125° C./60 min/800 psiH2 | 40 | 1 | 0 |
| Cu Clariant T-4874 | 10 | 0.6 | 0 | 125° C./60 min/800 psiH2 | 36 | 0 | 0 |
| Cu Clariant T-4874 | 15 | 0.6 | 12 | 125° C./60 min/800 psiH2 | 59 | 1 | 0 |
| Ni JM HTC 500RP | 2 | 0.6 | 0 | 100° C./60 min/200 psiH2 | 60 | 3 | 0 |
| Ni JM HTC 500RP | 2 | 0.6 | 0 | 100° C./60 min/500 psiH2 | 51 | 3 | 0 |
| Ni JM HTC 500RP | 2 | 0.6 | 12 | 100° C./60 min/500 psiH2 | 38 | 0 | 0 |
| Ni JM HTC 500RP | 2 | 0.6 | 12 | 70° C./120 min/200 psiH2 | 26 | 1 | 0 |
| Ni JM HTC 500RP | 2 | 0.6 | 12 | 70° C./120 min/500 psiH2 | 41 | 0 | 0 |
| Ni JM HTC | 5 | 0.6 | 12 | 100° C./60 min/ | 69 | 0 | 0 |

TABLE 1-continued

Catalyst Composition and Performance in Hydrogenation of FFCA and FDCA

| Catalyst Name | Catalyst Amount (mg) | FFCA Amount (mg) | FDCA Amount (mg) | Hydrogenation Conditions | HMFCA Yield (%) | MFA Yield (%) | THFDCA Yield (%) |
|---|---|---|---|---|---|---|---|
| Ni JM HTC 500RP | 5 | 0.6 | 12 | 100° C./ 60 min/ 200 psiH2 | 92 | 0 | 0 |
| Ni JM HTC 500RP | 5 | 0.6 | 12 | 70° C./ 120 min/ 500 psiH2 | 40 | 0 | 0 |
| Ni JM HTC 500RP | 5 | 0.6 | 12 | 70° C./ 120 min/ 200 psiH2 | 64 | 0 | 0 |
| Ni JM HTC 500RP | 20 | 20 | 20 | 100° C./ 60 min/ 500 psiH2 | 47 | 3 | 0 |
| Ni JM HTC 500RP | 20 | 20 | 20 | 70° C./ 120 min/ 800 psiH2 | 45 | 3 | 0 |
| Ni JM HTC 500RP | 20 | 20 | 0 | 70° C./ 120 min/ 800 psiH2 | 42 | 3 | 0 |
| Pd/C JM-10 | 20 | 20 | 20 | 100° C./ 60 min/ 800 psiH2 | 40 | 6 | 0 |
| Pd/C JM-10 | 20 | 20 | 0 | 100° C./ 60 min/ 800 psiH2 | 39 | 5 | 0 |
| Pd/C JM-10 | 20 | 20 | 0 | 70° C./ 120 min/ 800 psiH2 | 44 | 4 | 0 |
| Pd/C JM-10 | 20 | 20 | 20 | 70° C./ 120 min/ 800 psiH2 | 38 | 9 | 0 |
| Pd/C JM-4 | 20 | 20 | 0 | 100° C./ 60 min/ 800 psiH2 | 28 | 6 | 0 |
| Ru/C JM-37* | 2 | 0.6 | 12 | 100° C./ 60 min/ 200 psiH2 | 38 | 8 | 5 |
| Ru/C JM-37* | 2 | 0.6 | 12 | 50° C./ 240 min/ 50 psiH2 | 85 | 1 | 0 |
| Ru/C JM-37* | 2 | 0.6 | 12 | 70° C./ 120 min/ 200 psiH2 | 92 | 2 | 0 |
| Ru/C JM-37* | 2 | 0.6 | 12 | 70° C./ 120 min/ 500 psiH2 | 33 | 5 | 4 |
| Ru/C JM-37* | 2 | 0.6 | 12 | 70° C./ 120 min/ 50 psiH2 | 89 | 1 | 0 |
| Ru/C JM-37* | 5 | 0.6 | 12 | 50° C./ 240 min/ 50 psiH2 | 79 | 3 | 0 |
| Ru/C JM-37* | 5 | 0.6 | 12 | 70° C./ 120 min/ 200 psiH2 | 33 | 6 | 3 |
| Ru/C JM-37* | 5 | 0.6 | 12 | 70° C./ 120 min/ 50 psiH2 | 76 | 5 | 0 |
| Ru/C JM-38 | 20 | 20 | 20 | 70° C./ 120 min/ 800 psiH2 | 37 | 4 | 0 |
| Ru/C JM-38* | 2 | 0.6 | 12 | 100° C./ 60 min/ 200 psiH2 | 36 | 8 | 7 |
| Ru/C JM-38* | 2 | 0.6 | 12 | 50° C./ 240 min/ 50 psiH2 | 88 | 1 | 0 |
| Ru/C JM-38* | 2 | 0.6 | 12 | 70° C./ 120 min/ 200 psiH2 | 87 | 3 | 0 |
| Ru/C JM-38* | 2 | 0.6 | 12 | 70° C./ 120 min/ 500 psiH2 | 41 | 5 | 4 |
| Ru/C | 2 | 0.6 | 12 | 70° C./ | 89 | 1 | 0 |

TABLE 1-continued

Catalyst Composition and Performance in Hydrogenation of FFCA and FDCA

| Catalyst Name | Catalyst Amount (mg) | FFCA Amount (mg) | FDCA Amount (mg) | Hydrogenation Conditions | HMFCA Yield (%) | MFA Yield (%) | THFDCA Yield (%) |
|---|---|---|---|---|---|---|---|
| JM-38* | | | | 120 min/ 50 psiH2 | | | |
| Ru/C JM-38* | 5 | 0.6 | 12 | 50° C./ 240 min/ 50 psiH2 | 81 | 3 | 0 |
| Ru/C JM-38* | 5 | 0.6 | 12 | 70° C./ 120 min/ 200 psiH2 | 27 | 7 | 5 |
| Ru/C JM-38* | 5 | 0.6 | 12 | 70° C./ 120 min/ 50 psiH2 | 79 | 5 | 0 |

Example 2

20 mg of different powder catalyst were placed into separate reaction vessels along with a solution containing 0.6 M FFCA in 3:2 (wt/wt) dioxane:H$_2$O. The powered catalysts were Cu BASF 0602* (reduced in-house), Cu Clariant T-4874, Cu Clariant T-4874* (reduced in-house), Ni JM HTC 500 RP, Pd/C JM-4, Pd/C JM-6, Pd/C JM-10, Pt/C JM-24, Pt/C JM-27, Ru/C JM-37, Ru/C JM-38 and a control without a catalyst. Catalysts Cu BASF 0602* and Cu Clariant T-4874* were used in a further reduced form (350° C. in forming gas for 3 hours). Each reaction vessel was pressurized with hydrogen at target pressure of 55 bar. Reaction vessels were heated to a target temperature of 70° C. and shaken for 2 hours or, alternatively, reaction vessels were heated to a target temperature of 100° C. and shaken for 1 hour. After the reaction was completed, the shaking was stopped and the reactor was cooled down to room temperature.

HMFCA selectivities and FFCA conversions were calculated. The results are shown in FIG. 1.

Figure 2:
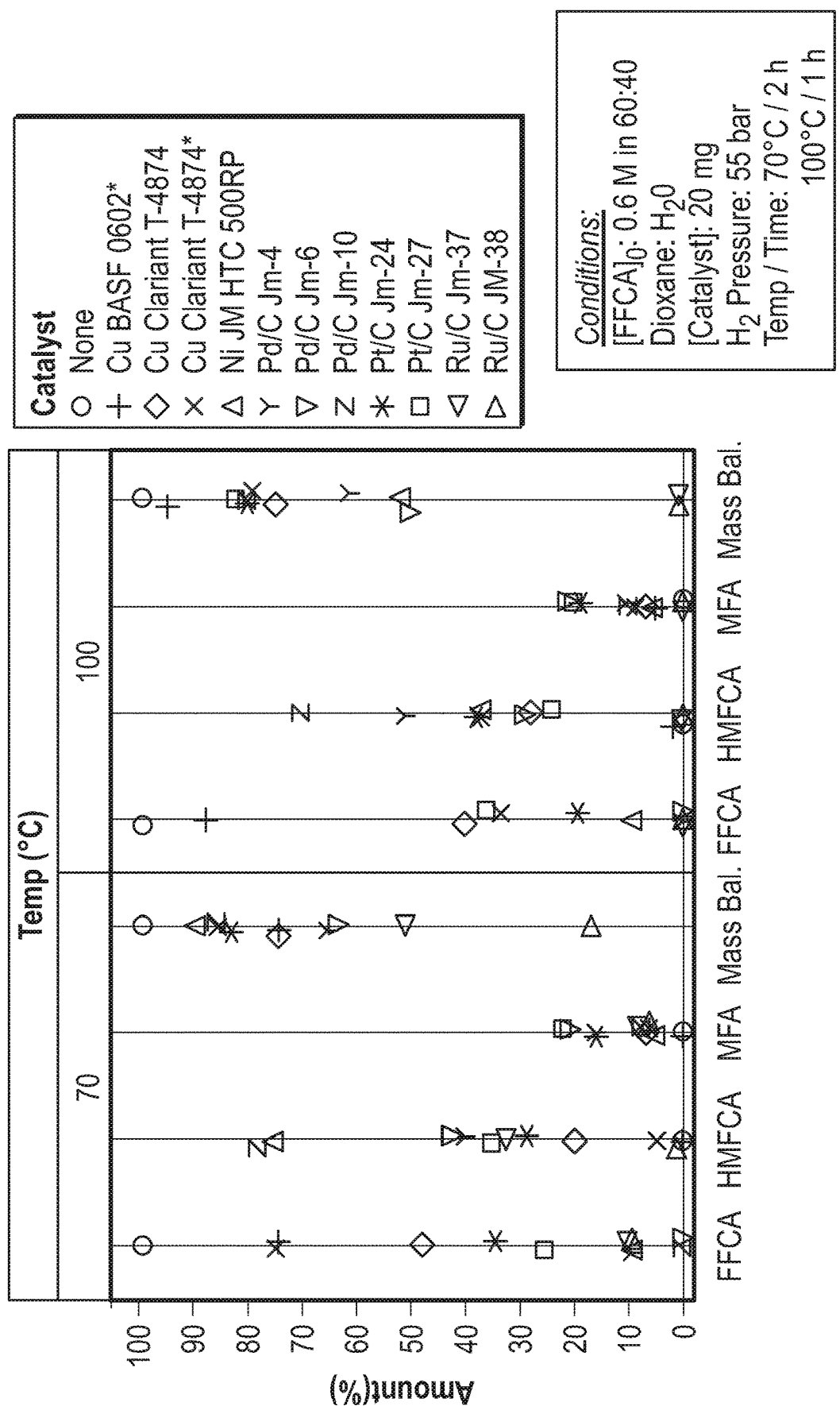
FIG. 2 depicts the reduction of FFCA to HMFCA and MFA using several catalysts, different temperatures and different reaction times.

Yields of HMFCA and MFA, remaining FFCA amounts, and mass balances were calculated. The results are shown in FIG. 2.

Example 3

Figure 3:
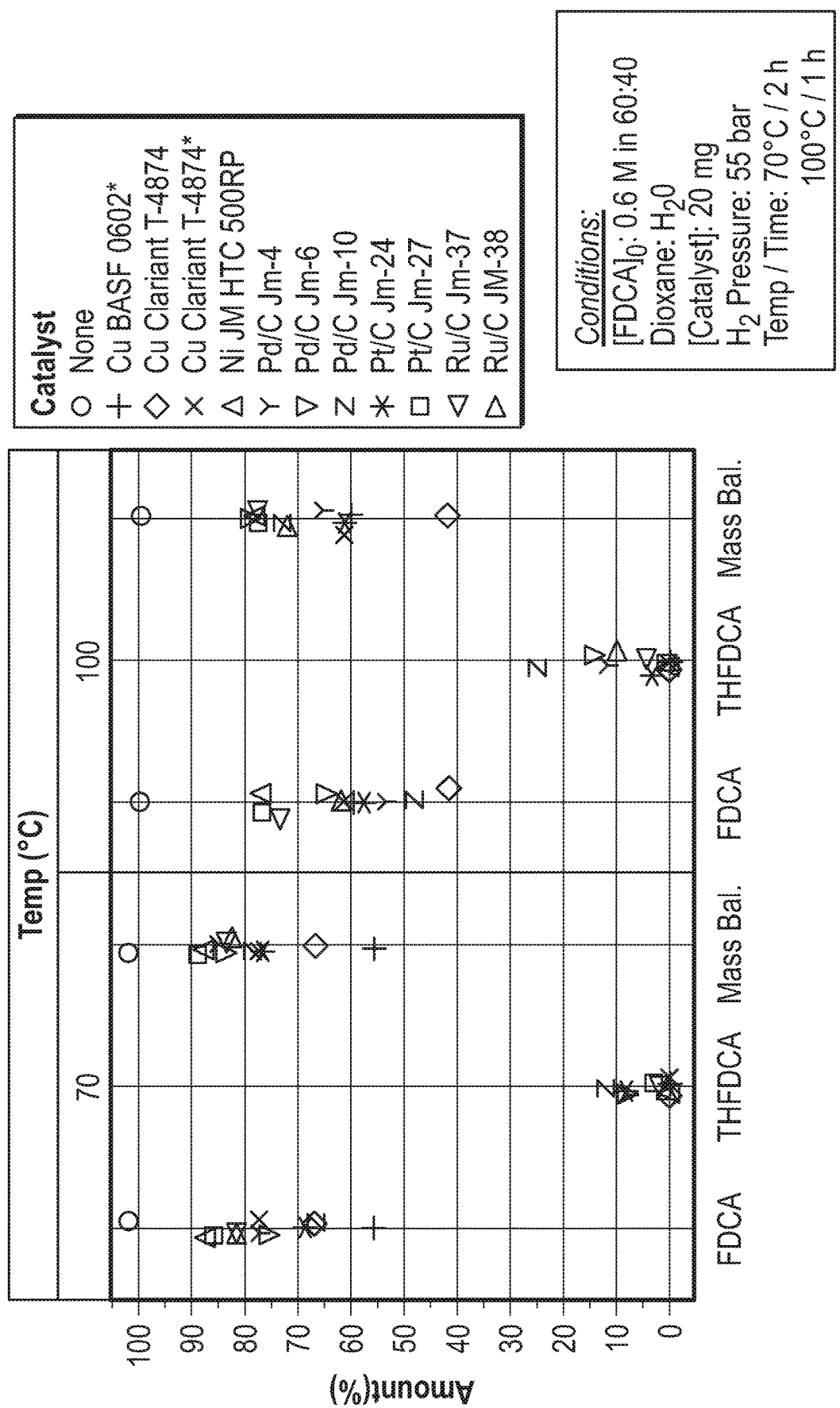
FIG. 3 depicts the reduction of FDCA to THFDCA using several catalysts, different temperatures and different reaction times.

20 mg of different powder catalysts were placed into separate reaction vessels along with a solution containing 0.6 M FDCA in 3:2 (wt/wt) dioxane:H$_2$O. The powered catalysts were Cu BASF 0602* (reduced in-house), Cu Clariant T-4874, Cu Clariant T-4874* (reduced in-house), Ni JM HTC 500 RP, Pd/C JM-4, Pd/C JM-6, Pd/C JM-10, Pt/C JM-24, Pt/C JM-27, Ru/C JM-37, Ru/C JM-38 and a control without a catalyst. Catalysts Cu BASF 0602* and Cu Clariant T-4874* were used in a further reduced form (350° C. in forming gas for 3 hours). Each reaction vessel was pressurized with hydrogen at target pressure of 55 bar. Reaction vessels were heated to a target temperature of 70° C. and shaken for 2 hours or, alternatively, reaction vessels were heated to a target temperature of 100° C. and shaken for 1 hour. After the reaction was completed, the shaking was stopped and the reactor was cooled down to room temperature. Yields of THFDCA and remaining FFCA amounts, and mass balances were calculated. The results are shown in FIG. 3.

Example 4

20 mg of different powder catalysts were placed into separate reaction vessels along with a solution containing 0.6 M FDCA and 0.6 M FFCA in a 3:2 (wt/wt) dioxane:H$_2$O. The powered catalysts were Cu BASF 0602* (reduced in-house), Cu Clariant T-4874, Cu Clariant T-4874* (reduced in-house), Ni JM HTC 500 RP, Pd/C JM-4, Pd/C JM-6, Pd/C JM-10, Pt/C JM-24, Pt/C JM-27, Ru/C JM-37, Ru/C JM-38 and a control without a catalyst. Catalysts Cu BASF 0602* and Cu Clariant T-4874* were used in a further reduced form (350° C. in forming gas for 3 hours). Each reaction vessel was pressurized with hydrogen at target pressure of 55 bar. Reaction vessels were heated to a target temperature of 70° C. and shaken for 2 hours or, alternatively, reaction vessels were heated to a target temperature of 100° C. and shaken for 1 hour. After the reaction was completed, the shaking was stopped and the reactor was cooled down to room temperature.

Figure 4:
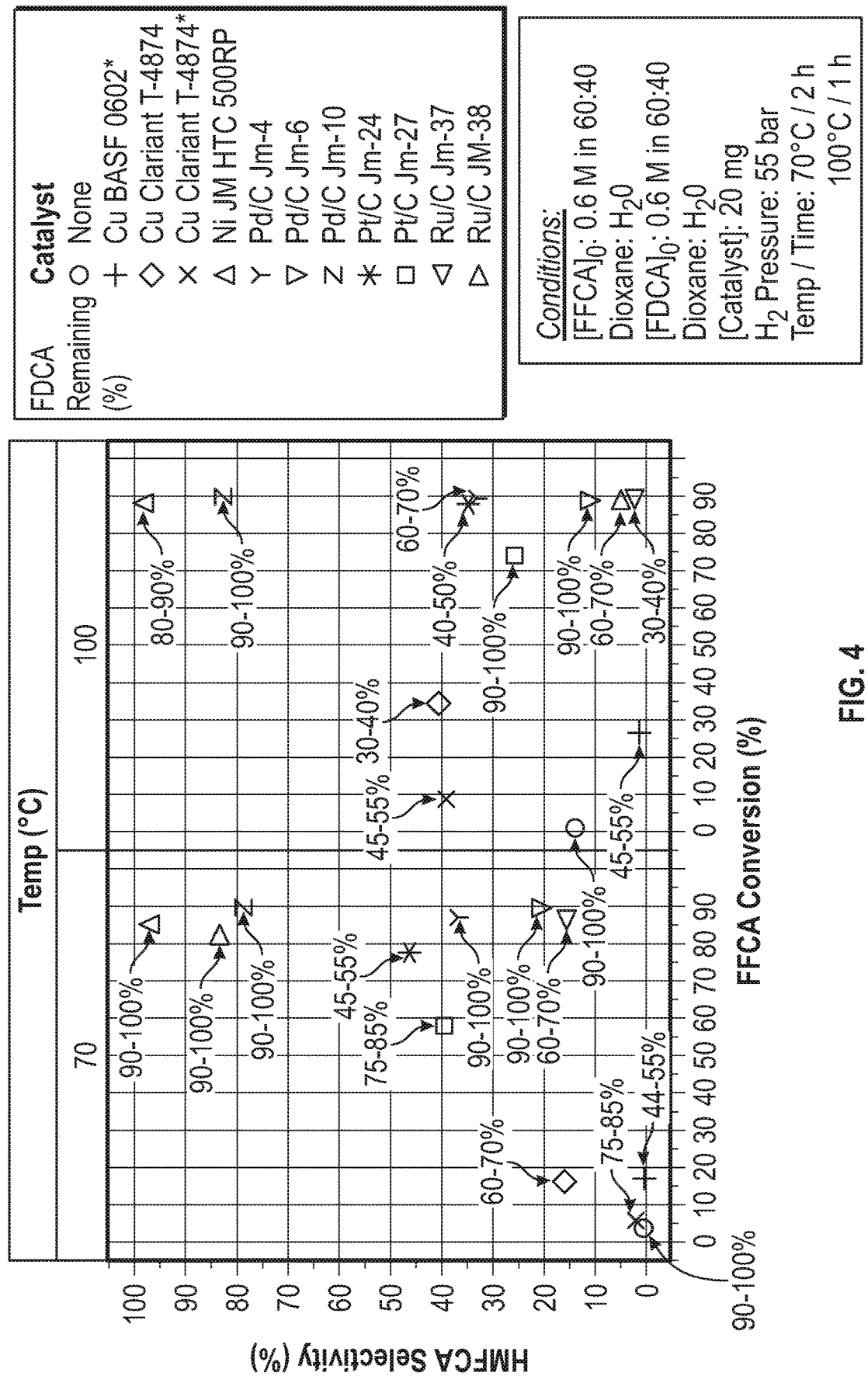
FIG. 4 depicts the selectivity of the reduction of a mixture of FDCA and FFCA to HMFCA using several catalysts, different temperatures and different reaction times, wherein percentages of FDCA remaining are noted for each reduction shown.

HMFCA selectivities and FFCA conversions were calculated. The results are shown in FIG. 4.

Figure 5:
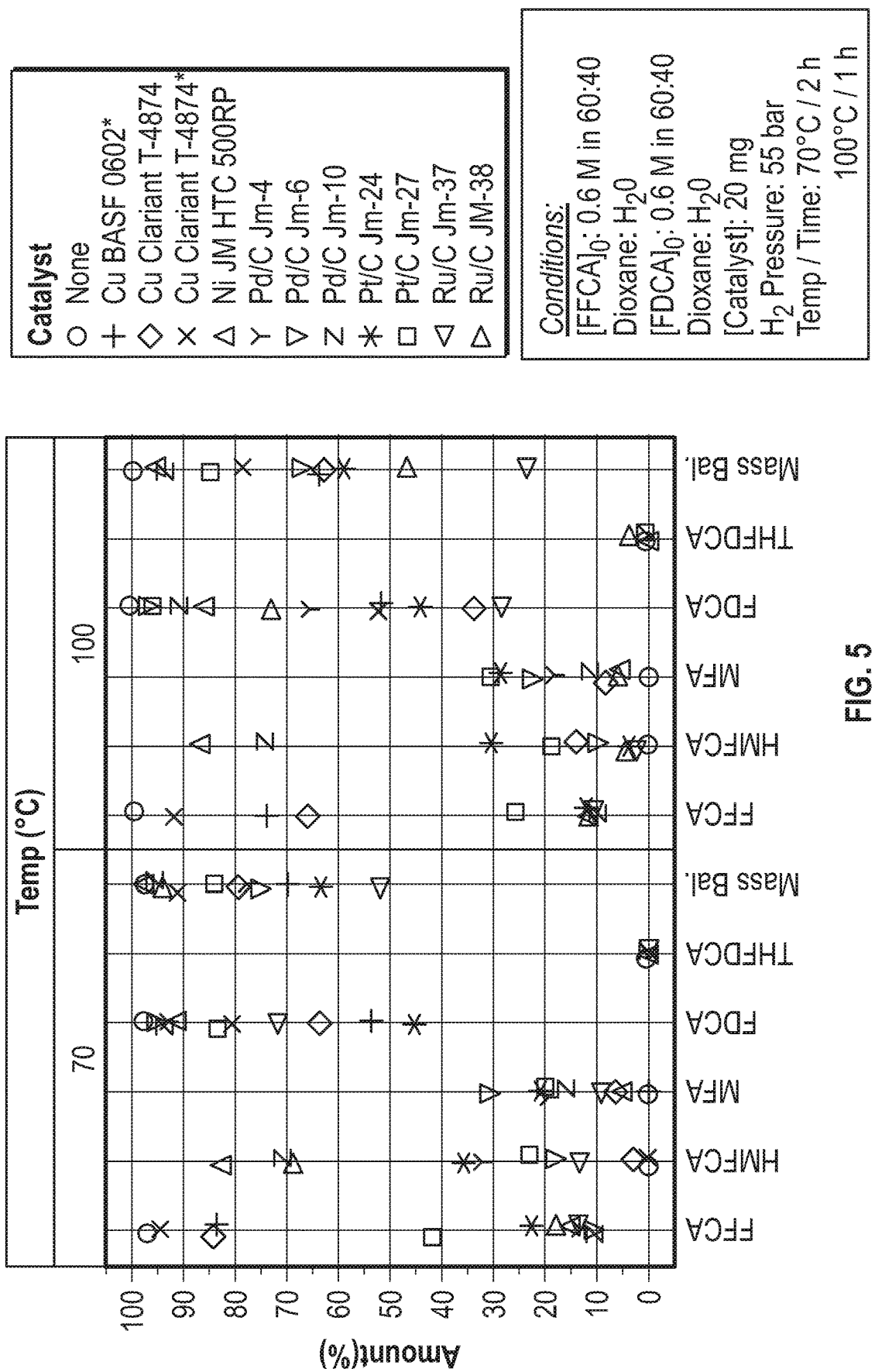
FIG. 5 depicts the reduction of a mixture of FDCA and FFCA to HMFCA, MFA and THFDCA using several catalysts, different temperatures and different reaction times.

Yields of HMFCA, MFA and THFDCA, remaining FFCA and FDCA amounts, and mass balances were calculated. The results are shown in FIG. 5.

Example 5

2 mg and 5 mg of each Ni, Ru, and Pd powdered catalysts were placed into separate reaction vessels along with a solution containing 0.02 M FFCA and 0.38 M FDCA in 3:2 (wt/wt) dioxane:H$_2$O. The Ni, Ru, and Pd powdered catalysts were, Ni JM HTC 500 RP, Pd/C JM-3, Pd/C JM-4, Pd/C JM-5, Ru/C JM-37*, Ru/C JM-38* and controls without a catalyst. Catalysts Ru/C JM-37* and Ru/C JM-38* were used in a further reduced form (350° C. in forming gas for 3 hours). Separately, 2 mg, 5 mg, 10 mg, and 15 mg of Cu Clariant T-4874 were placed into separate reaction vessels along with a solution containing 0.02 M FDCA and 0.38 M FFCA in 3:2 (wt/wt) dioxane:H$_2$O.

The Ni, Ru, and Pd powdered catalyst reactions were each separately tested with 14 and 35 bar of hydrogen. The Ni, Ru, and Pd powdered catalyst reactions were heated to a target temperature of 70° C. and shaken for 2 hours or, alternatively, heated to a target temperature of 100° C. and shaken for 1 hour.

The Cu powdered catalyst reactions were each separately tested with 35 and 55 bar of hydrogen. The Cu powdered reactions were heated to a target temperature of 100° C. and shaken for 1 hour or, alternatively, heated to a target temperature of 125° C. and shaken for 1 hour.

After each reaction was completed, the shaking was stopped and the reactor was cooled down to room temperature. HMFCA selectivities were calculated as follows:

$$\text{Selectivity} = \frac{(HMFCA + FDCA - MFA - THFDCA)}{2} \times \frac{(FFCA\_MB + FDCA\_MB)}{200}$$

Figure 6:
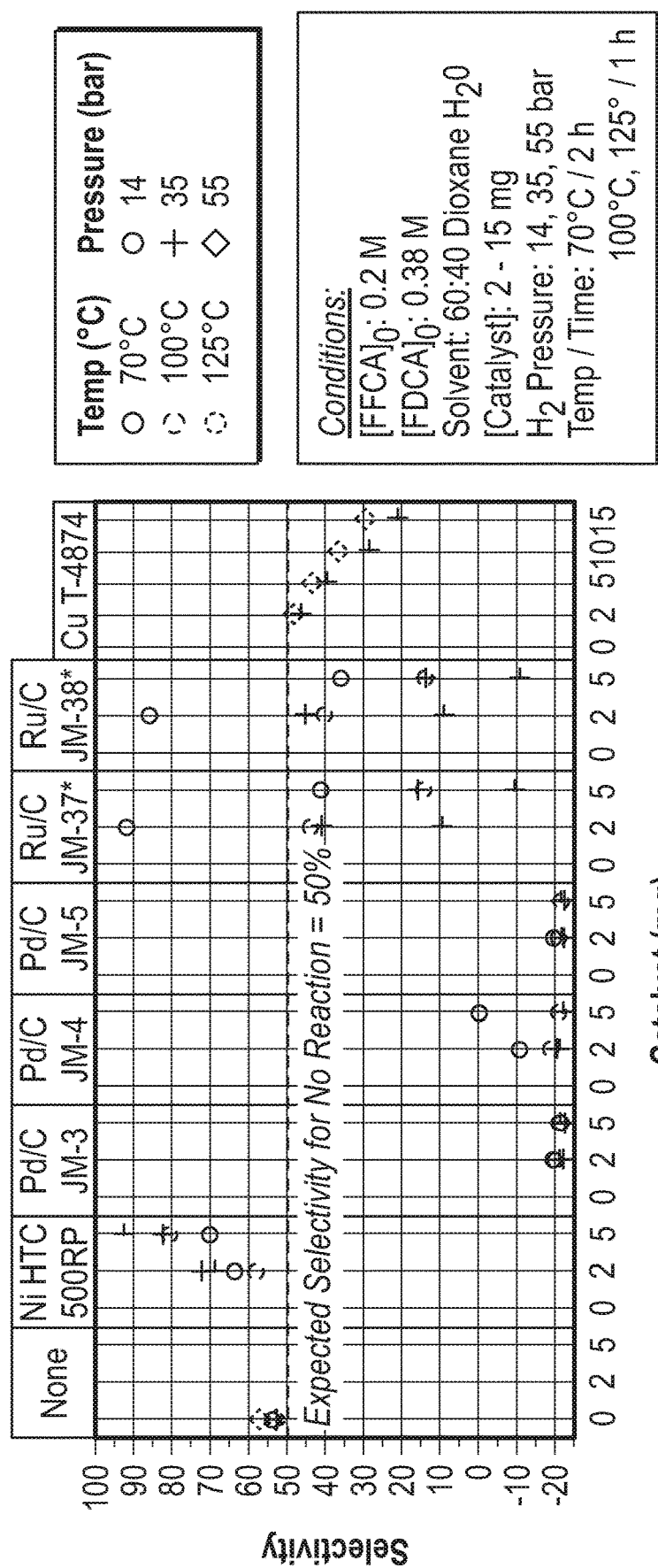
FIG. 6 depicts the selectivity of the reduction of a mixture of FDCA and FFCA using several catalysts, several catalyst amounts, different temperatures and different reaction times and several pressures.

The results are shown in FIG. 6.

Figure 7:
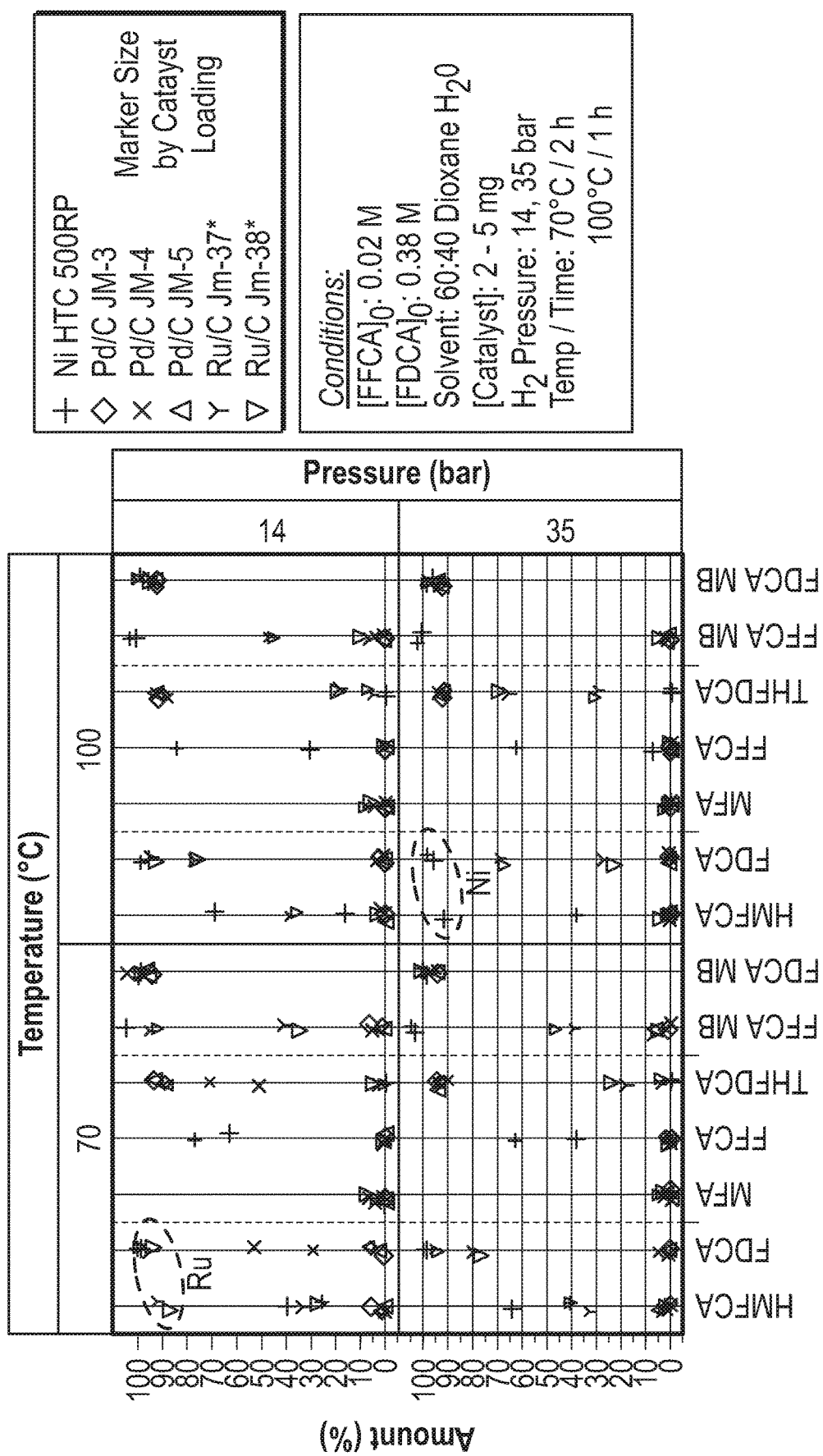
FIG. 7 depicts the distribution of products and mass balances from the reduction of a mixture of FDCA and FFCA to HMFCA, MFA and THFDCA using several catalysts, different catalyst amounts, different temperatures, different reaction times and different pressures.

Yields of HMFCA, MFA and THFDCA, remaining FFCA and FDCA amounts, and mass balances of FFCA and FDCA were calculated for the Ni, Pd, and Ru catalysts. The results are shown in FIG. 7. In FIG. 7, the smaller marker size indicates a reaction vessel in which the powder catalyst was loaded at 2 mg, and the larger marker size indicates a reaction vessel in which the powder catalyst was loaded at 5 mg.

Figure 8:
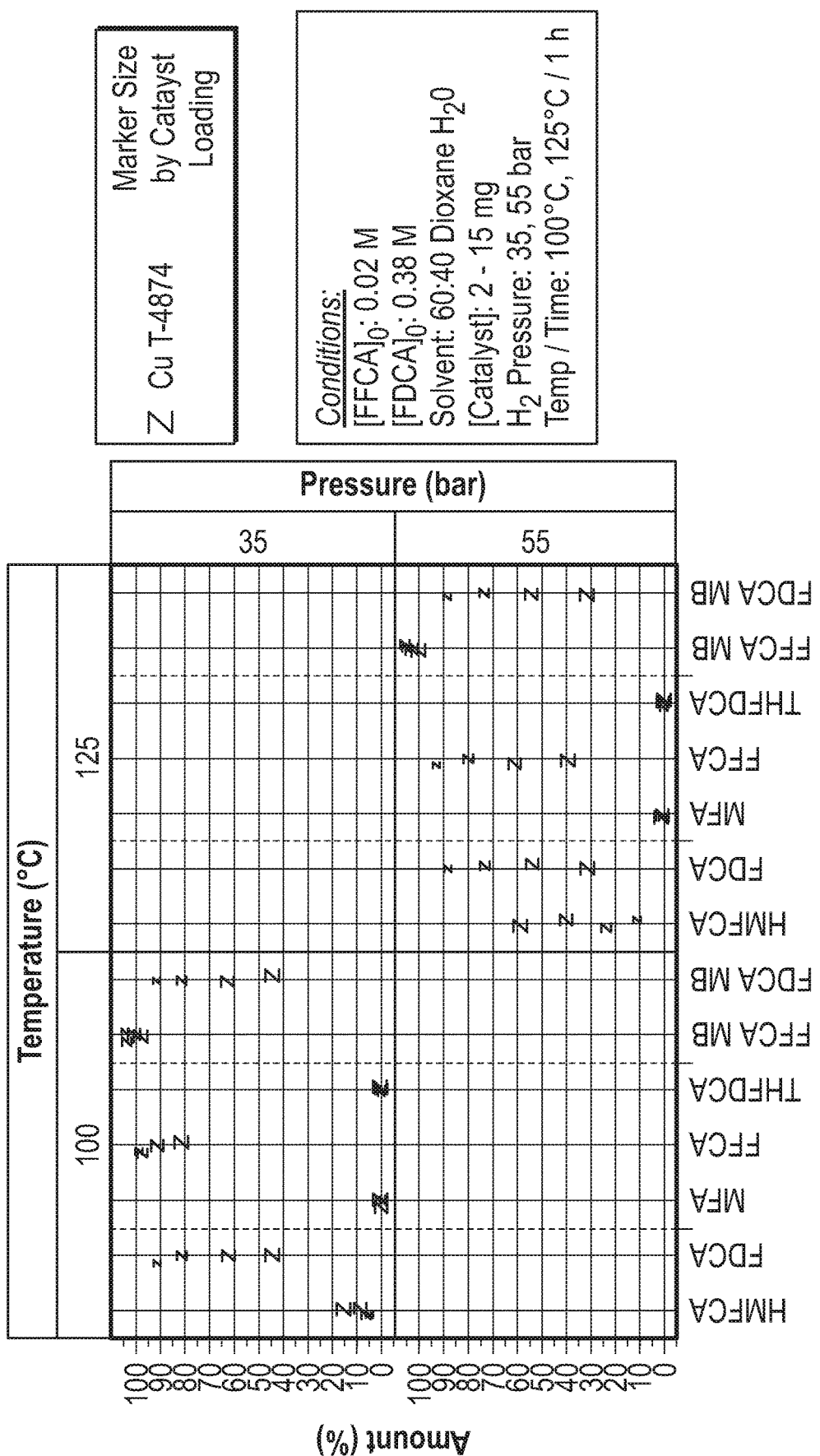
FIG. 8 depicts the distribution of products and mass balances from the reduction of a mixture of FDCA and FFCA to HMFCA, MFA and THFDCA using Cu T-4874 as a catalyst, different catalyst amounts, different temperatures and different pressures.

Yields of HMFCA, MFA and THFDCA, remaining FFCA and FDCA amounts, and mass balances of FFCA and FDCA were calculated for the Cu catalyst. The results are shown in FIG. 8. In FIG. 8, the smallest marker size indicates a reaction vessel in which the Cu powder catalyst was loaded at 2 mg, the second smallest marker size indicates a reaction vessel in which the Cu powder catalyst was loaded at 5 mg, the third smallest marker size indicates a reaction vessel in which the Cu powder catalyst was loaded at 10 mg, and the largest marker size indicates a reaction vessel in which the Cu powder catalyst was loaded at 15 mg.

Example 6

5 mg of different powder catalysts were each placed into separate reaction vessels along with 0.25 ml of a solution containing 0.020 M FFCA and 0.38 M FDCA in 3:2 (wt/wt) dioxane:$H_2O$. The powdered catalysts were Cu T-4874, Pd/C JM-10, and Ru/C JM-37*. Ru/C JM-37* was used in a further reduced form (350° C. in forming gas for 3 hours). Each reaction vessel was pressurized with hydrogen at target pressure of 50 psi. Reaction vessels were shaken for 4 hours at room temperature. After the reaction was completed, the shaking was stopped to check absorption onto the catalyst. Mass balances of FFCA and FDCA were calculated. The results are shown in Table 2.

TABLE 2

| Catalyst Name | Substrate solution | FFCA Mass Balance (%) | FDCA Mass Balance (%) |
|---|---|---|---|
| 5 mg Cu T-4874 | 0.25 ml 0.020M FFCA + 0.38M FDCA | 87 | 66 |
| 5 mg Pd/C JM-10 | 0.25 ml 0.020M FFCA + 0.38M FDCA | 81 | 86 |
| 5 mg Ru/C JM-37* | 0.25 ml 0.020M FFCA + 0.38M FDCA | 83 | 88 |

Example 7

Figure 9:
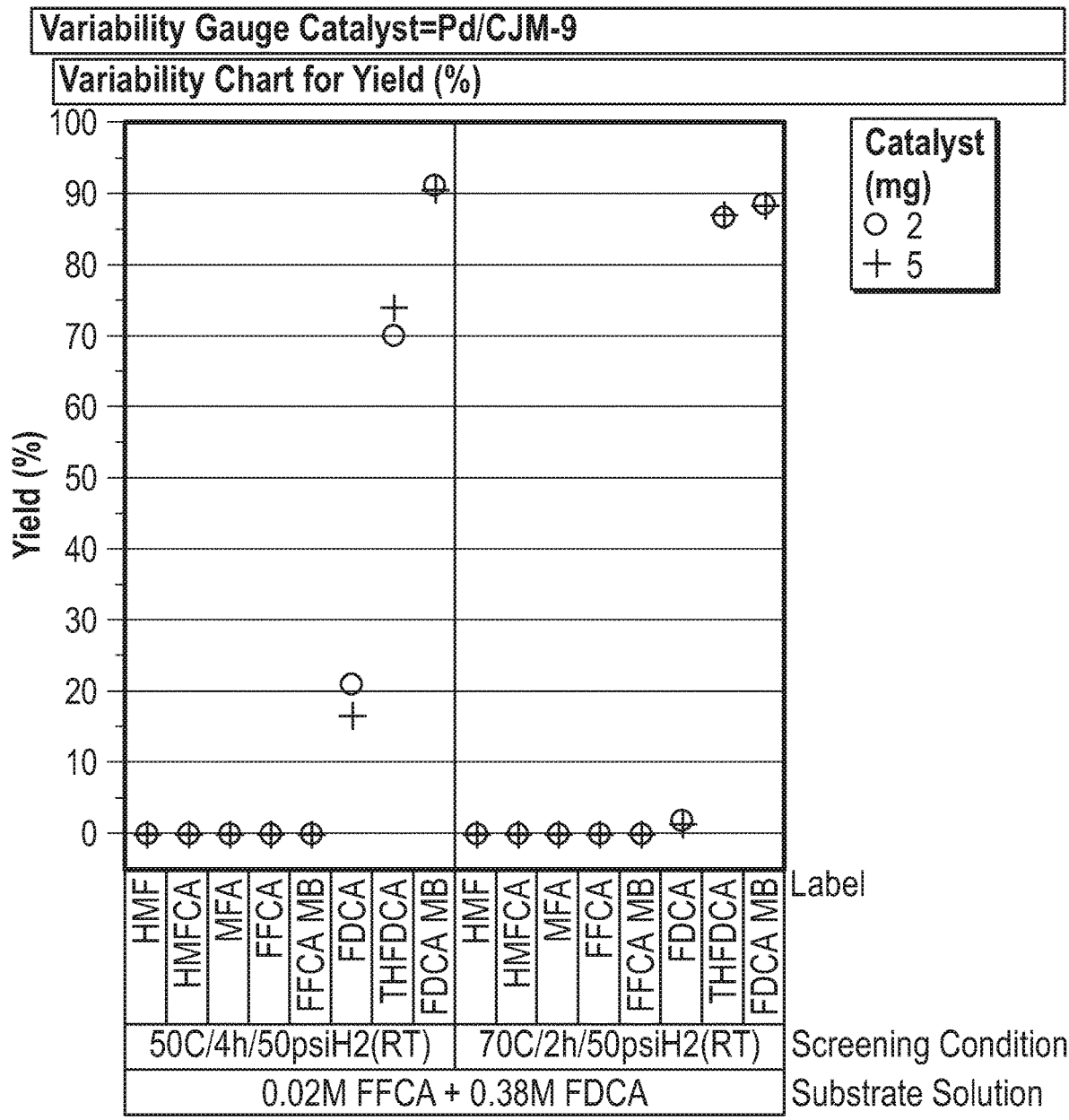
FIG. 9 depicts the distribution of products and mass balances for the reduction of a mixture of FDCA and FFCA to HMFCA, MFA and THFDCA using Pd/C JM-9 as a catalyst, different catalyst amounts, different reaction times and different temperatures.

2 mg or 5 mg of a Pd/C JM-9 powder catalyst was placed into reaction vessels along with 0.25 ml of a solution prepared in a 3:2 (wt/wt) dioxane:$H_2O$ mixture and containing 0.020 M FFCA (0.60 mg) and 0.38 M FDCA (12.0 mg). Reaction vessels were pressurized with hydrogen at target pressure of 50 psi. Reaction vessels were heated to a target temperature of 50° C. and shaken for 4 hours or, alternatively, reaction vessels were heated to a target temperature of 70° C. and shaken for 2 hours. After the reaction was completed, the shaking was stopped and the reactor was cooled down to room temperature. Yields of HMF, HMFCA, MFA and THFDCA, remaining FFCA and FDCA amounts, and mass balances of FFCA and FDCA were calculated. The results are shown in FIG. 9.

Example 8

Figure 10:
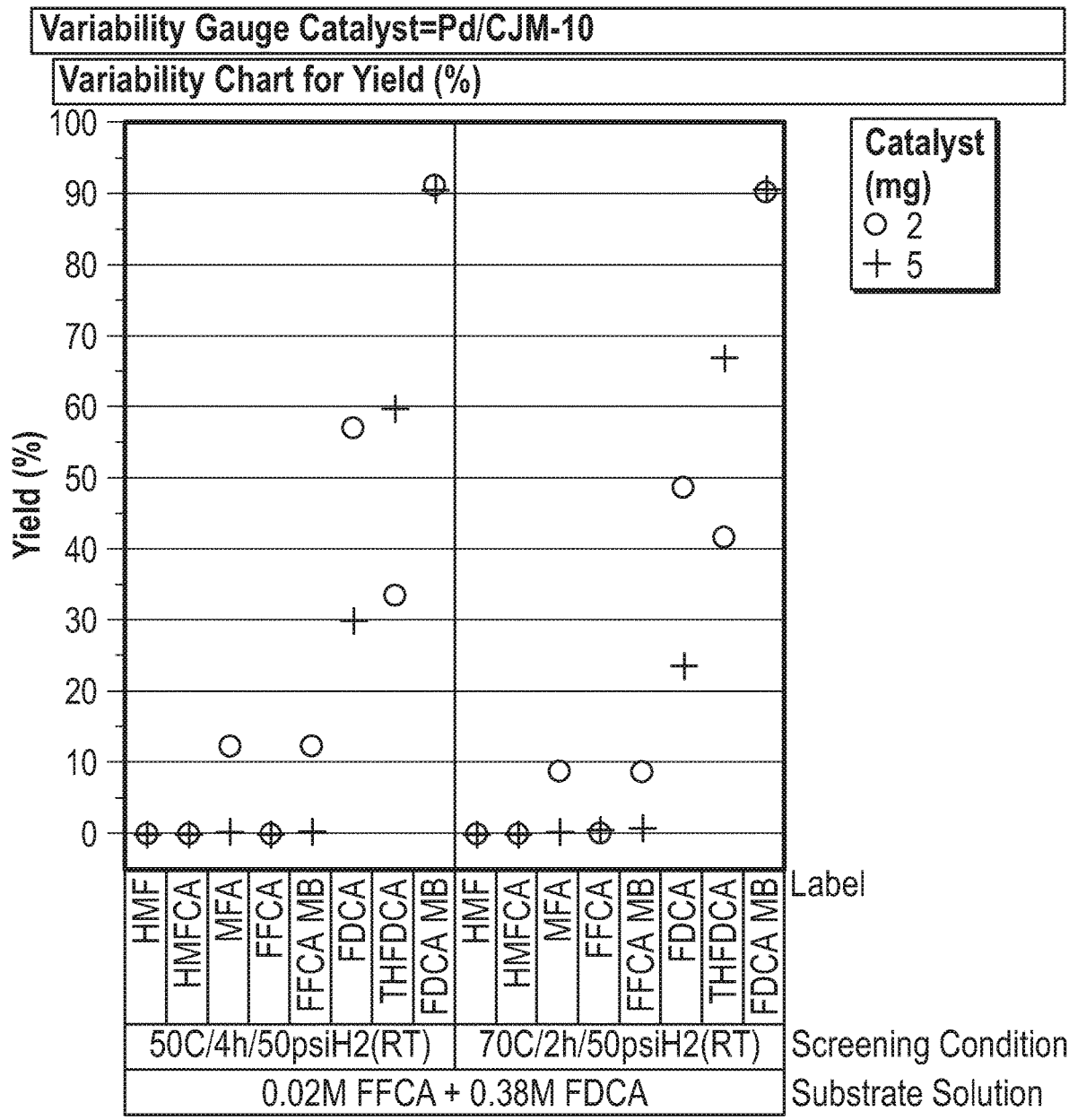
FIG. 10 depicts the distribution of products and mass balances for the reduction of a mixture of FDCA and FFCA to HMFCA, MFA and THFDCA using Pd/C JM-10 as a catalyst, different catalyst amounts, different reaction times and different temperatures.

2 mg or 5 mg of a Pd/C JM-10 powder catalyst was placed into reaction vessels along with 0.25 ml of a solution prepared in a 3:2 (wt/wt) dioxane:$H_2O$ mixture and containing 0.020 M FFCA (0.60 mg) and 0.38 M FDCA (12.0 mg). Reaction vessels were pressurized with hydrogen at target pressure of 50 psi. Reaction vessels were heated to a target temperature of 50° C. and shaken for 4 hours or, alternatively, reaction vessels were heated to a target temperature of 70° C. and shaken for 2 hours. After the reaction was completed, the shaking was stopped and the reactor was cooled down to room temperature. Yields of HMF, HMFCA, MFA and THFDCA, remaining FFCA and FDCA amounts, and mass balances of FFCA and FDCA were calculated. The results are shown in FIG. 10.

Example 9

Figure 11:
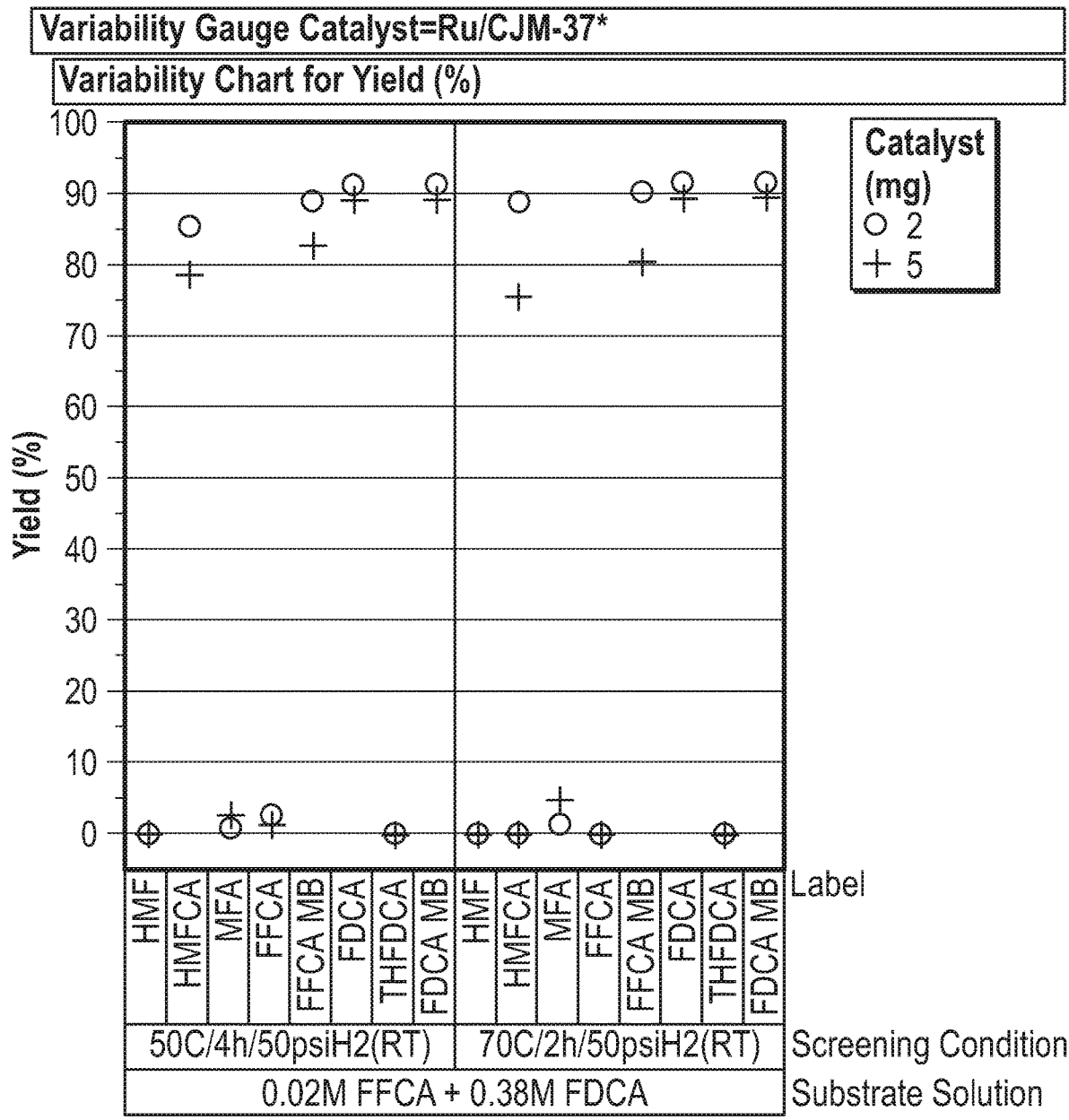
FIG. 11 depicts the distribution of products and mass balances for the reduction of a mixture of FDCA and FFCA to HMFCA, MFA and THFDCA using Ru/C JM-37* as a catalyst, different catalyst amounts, different reaction times and different temperatures.

2 mg or 5 mg of a Ru/C JM-37* powder catalyst was placed into reaction vessels along with 0.25 ml of a solution prepared in a 3:2 (wt/wt) dioxane:$H_2O$ mixture and containing 0.020 M FFCA (0.60 mg) and 0.38 M FDCA (12.0 mg). Ru/C JM-37* was used in a further reduced form (350° C. in forming gas for 3 hours). Reaction vessels were pressurized with hydrogen at target pressure of 50 psi. Reaction vessels were heated to a target temperature of 50° C. and shaken for 4 hours or, alternatively, reaction vessels were heated to a target temperature of 70° C. and shaken for 2 hours. After the reaction was completed, the shaking was stopped and the reactor was cooled down to room temperature. Yields of HMF, HMFCA, MFA and THFDCA, remaining FFCA and FDCA amounts, and mass balances of FFCA and FDCA were calculated. The results are shown in FIG. 11.

Example 10

Figure 12:
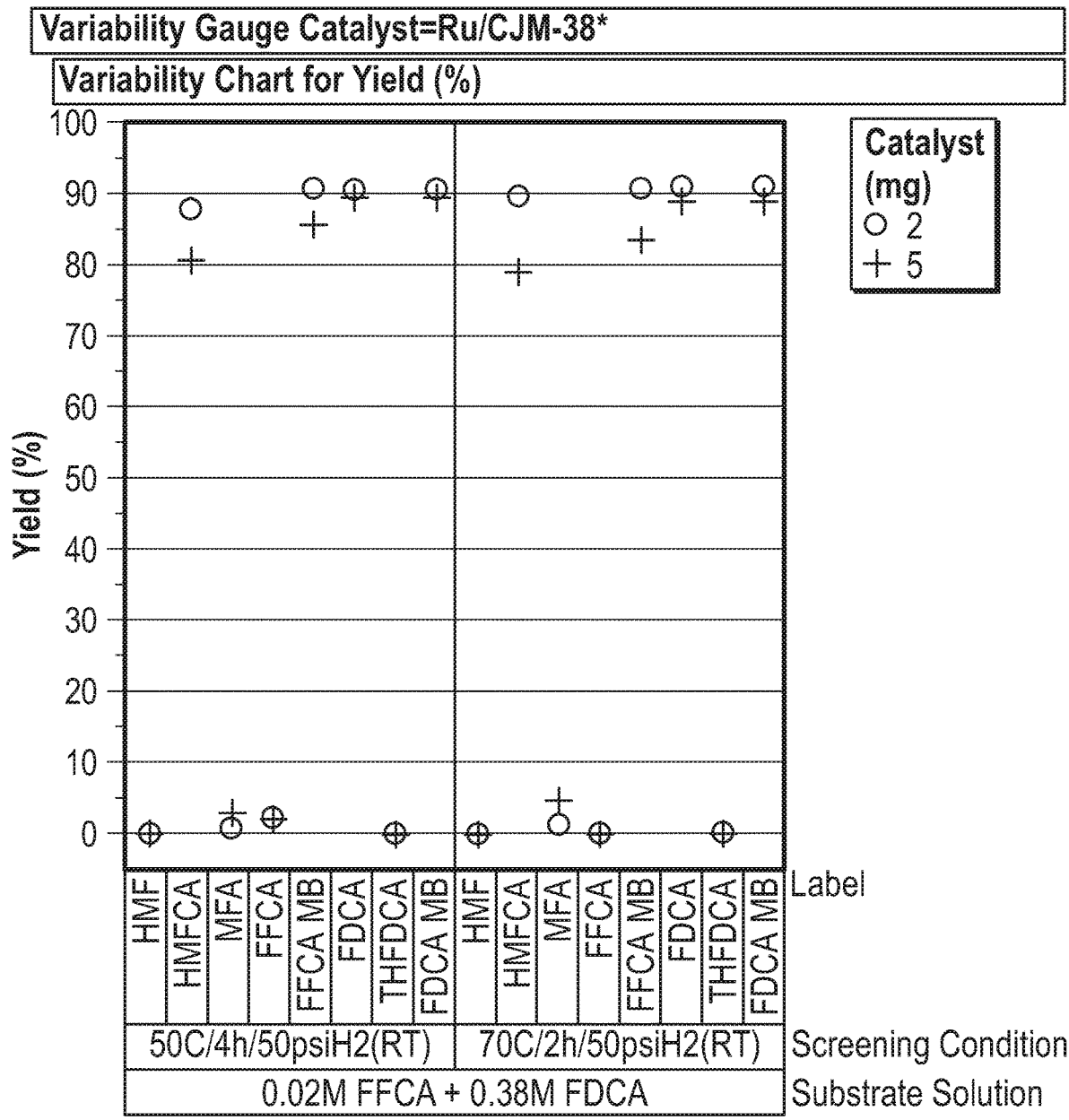
FIG. 12 depicts the distribution of products and mass balances for the reduction of a mixture of FDCA and FFCA to HMFCA, MFA and THFDCA using Ru/C JM-38* as a catalyst, different catalyst amounts, different reaction times and different temperatures.
Figure 13:
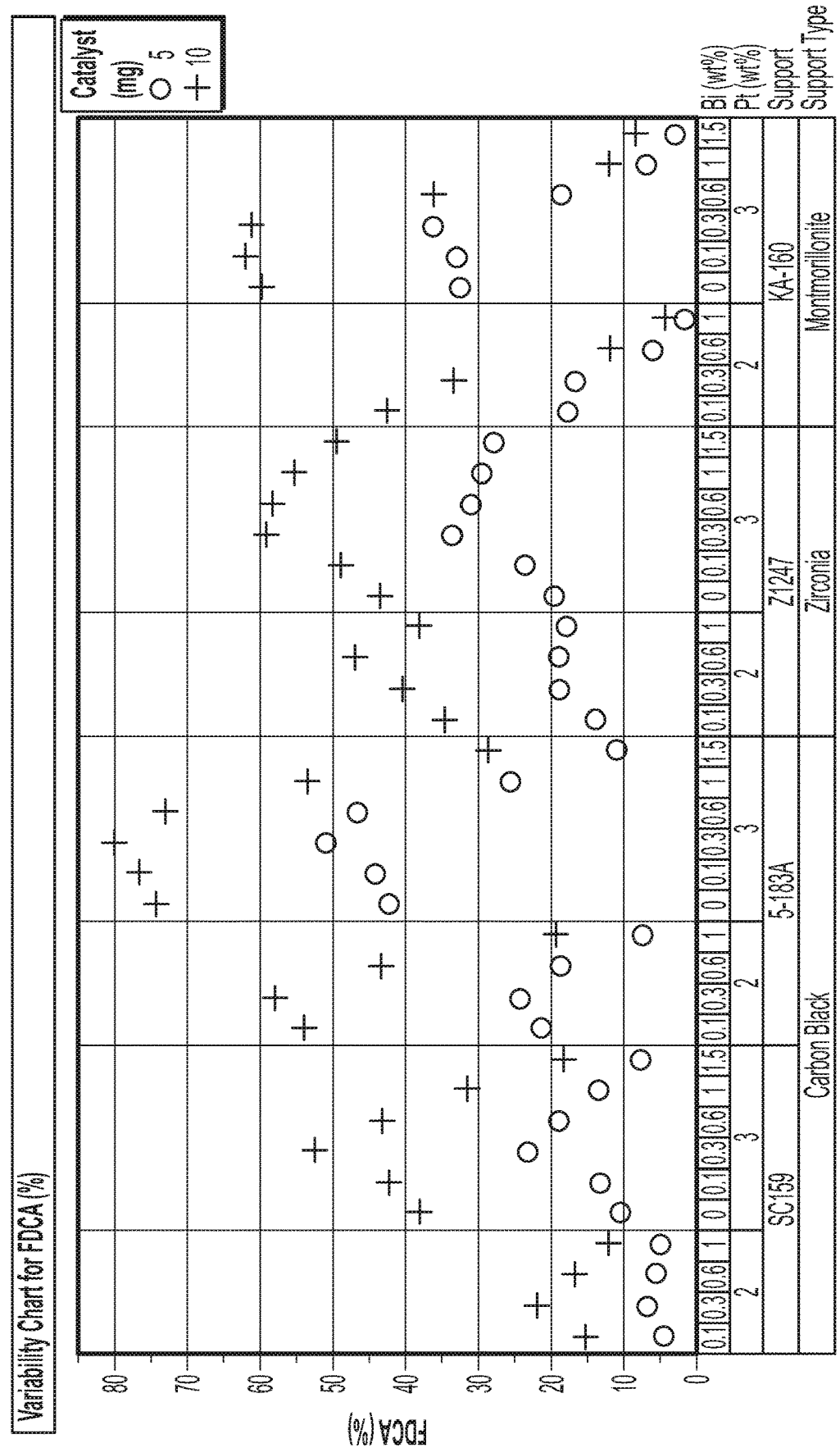
FIGS. 13-20 depict the distribution of products, mass balances and space time yields (STY) for the oxidation of a HMF substrate utilizing various ratios of Bi/Pt on carbon black, zirconia, and montmorillonite supports as catalysts, different catalyst amounts, different Pt amounts, and different Bi amounts.
Figure 14:
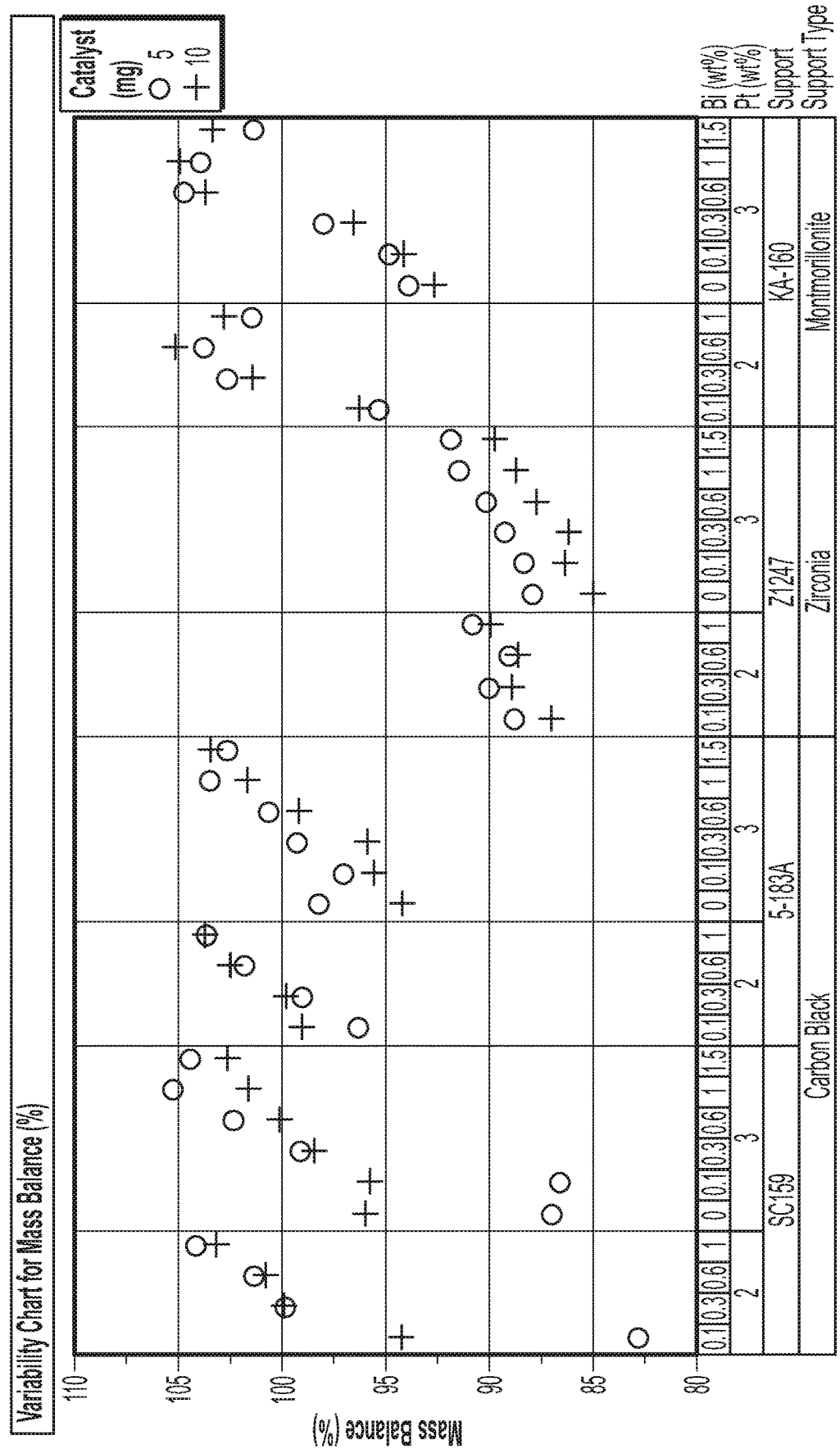
Figure 15:
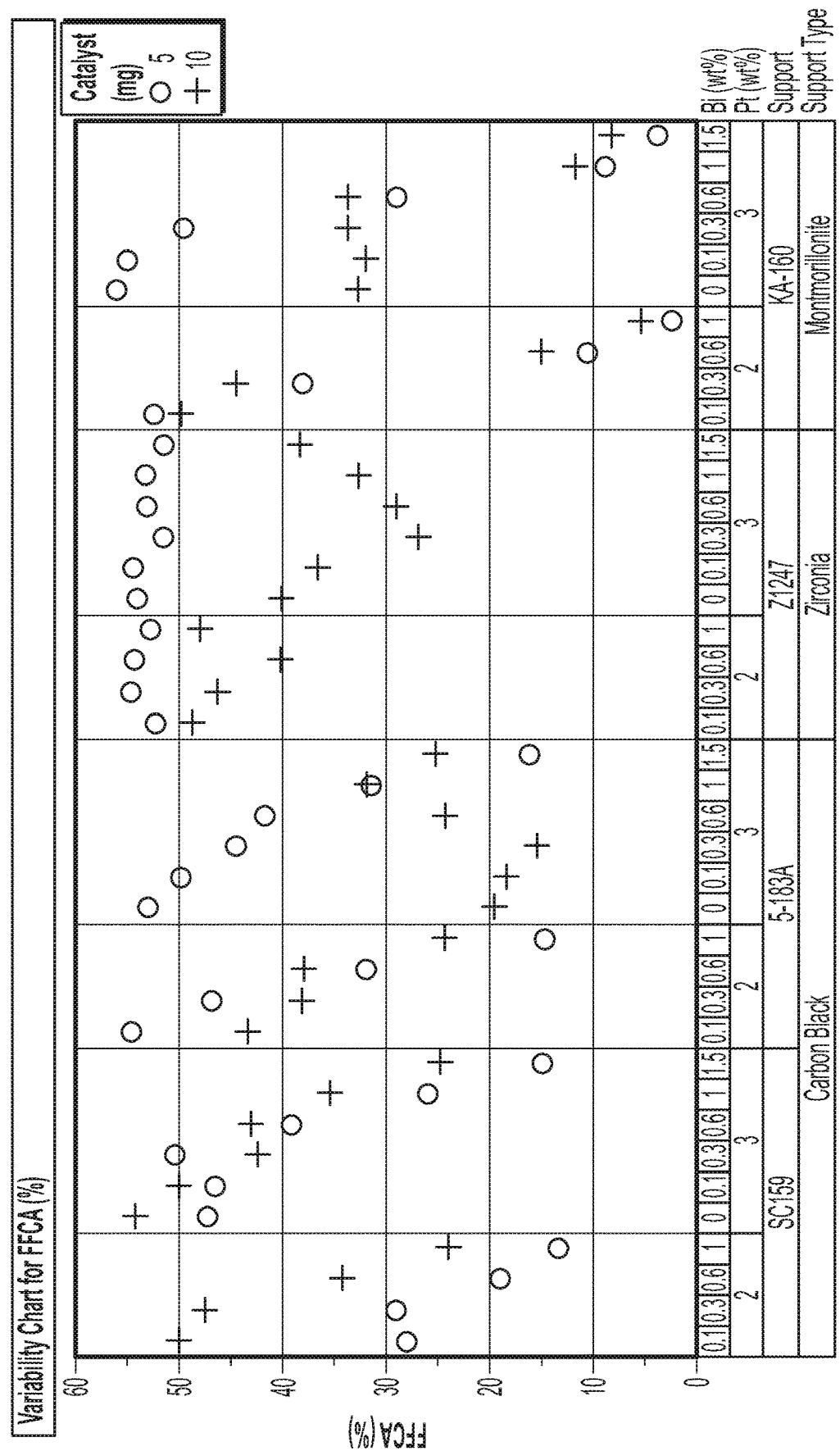
Figure 16:
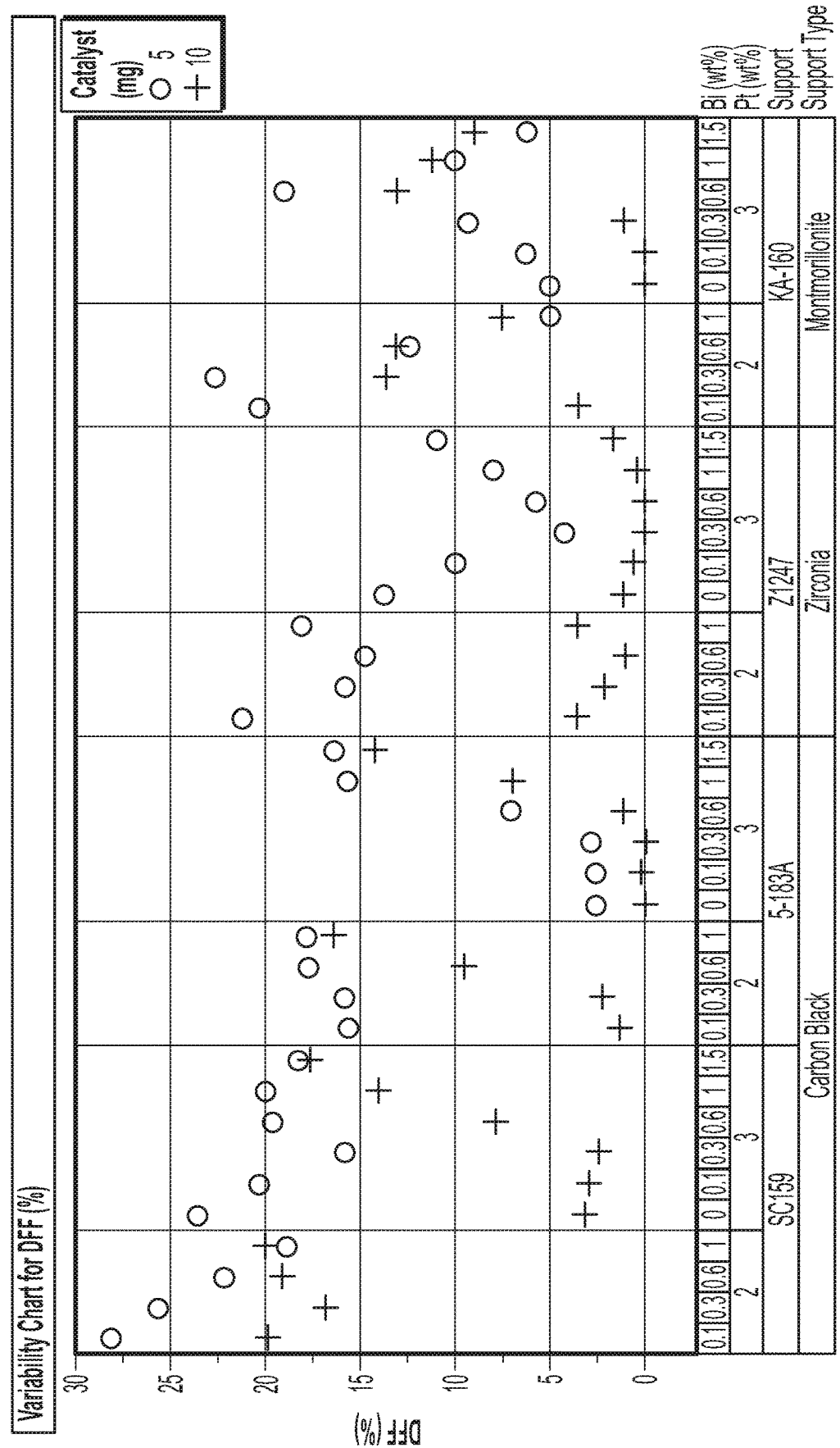
Figure 17:
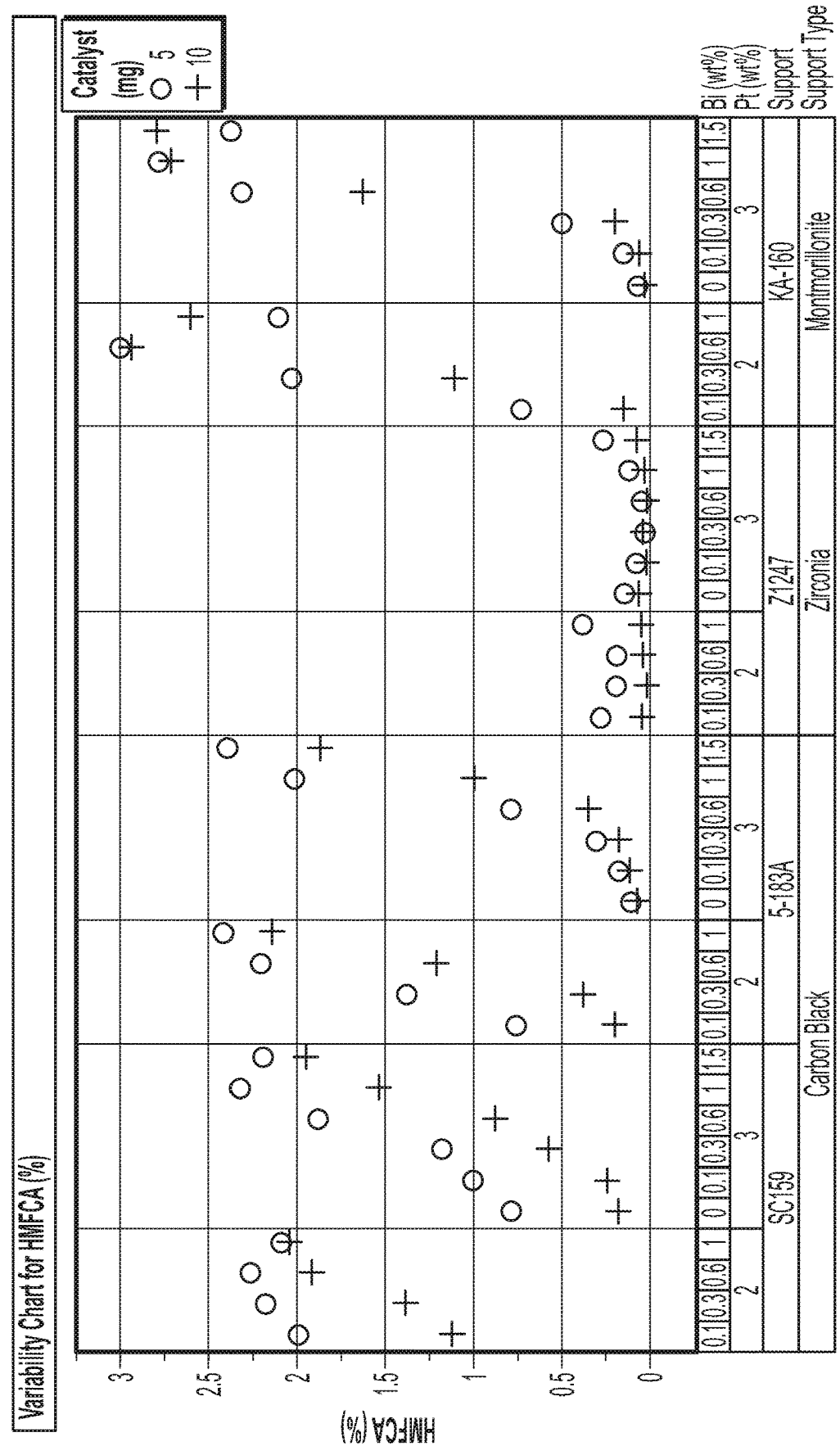
Figure 18:
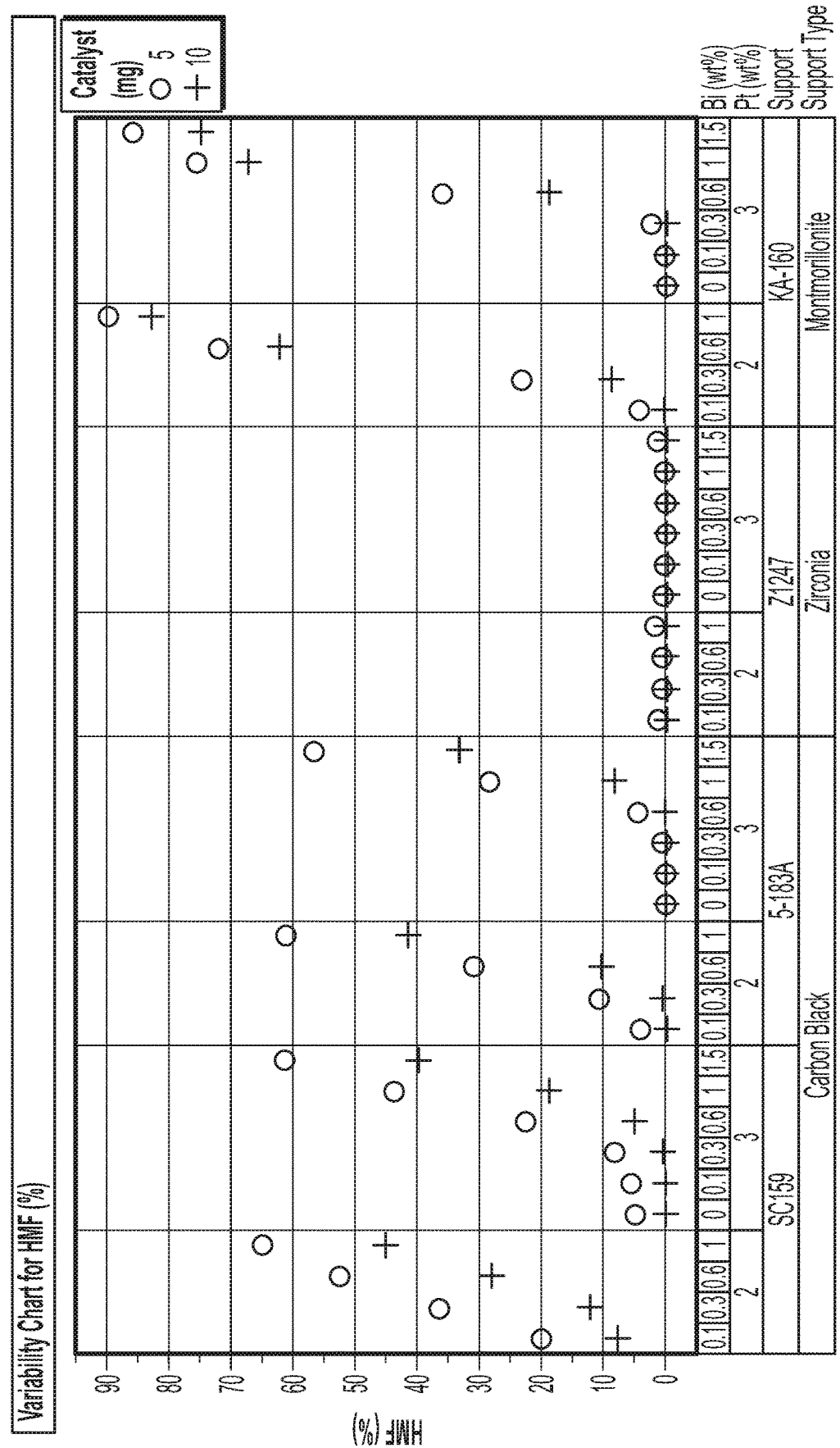
Figure 19:
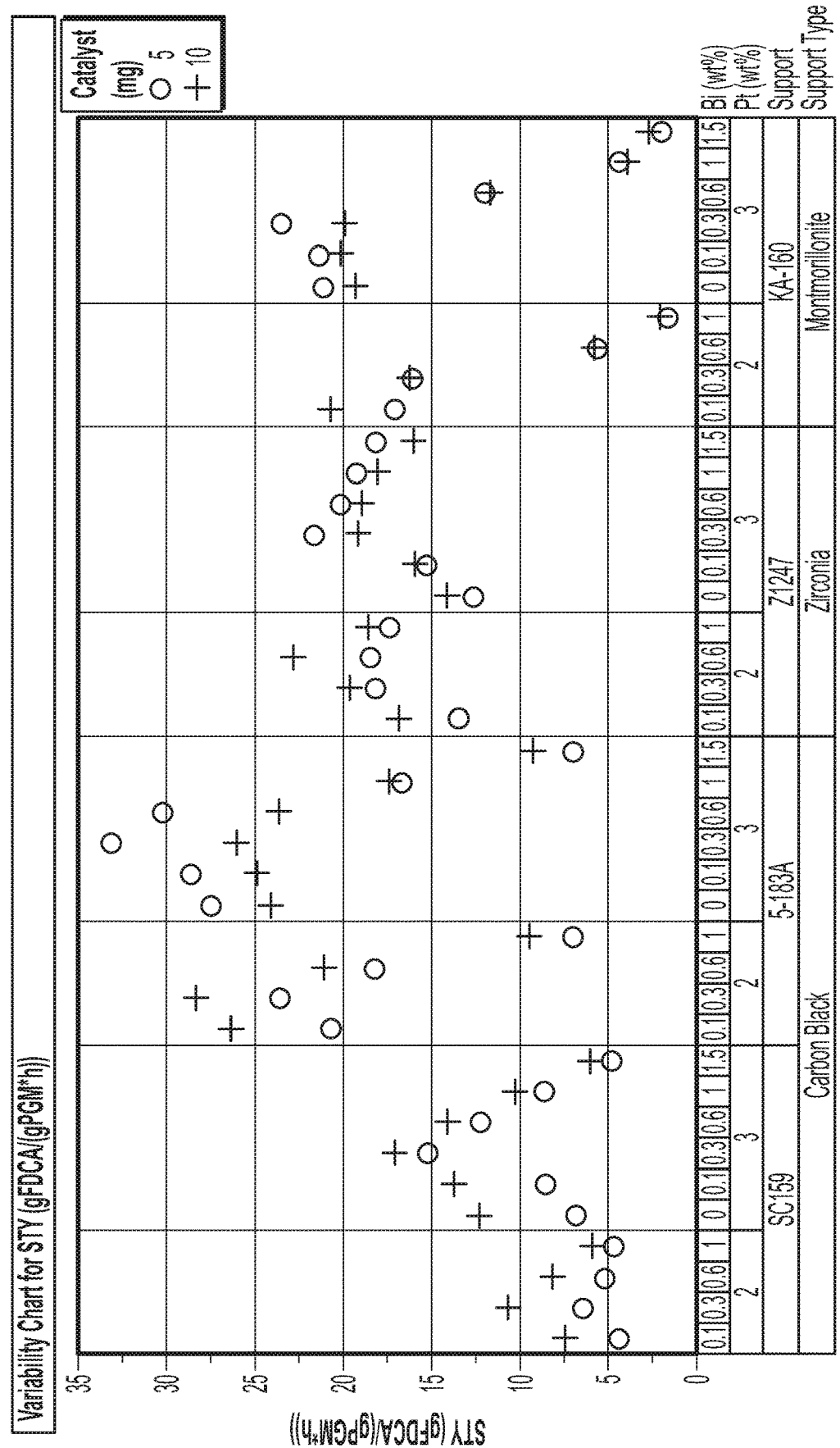
Figure 20:
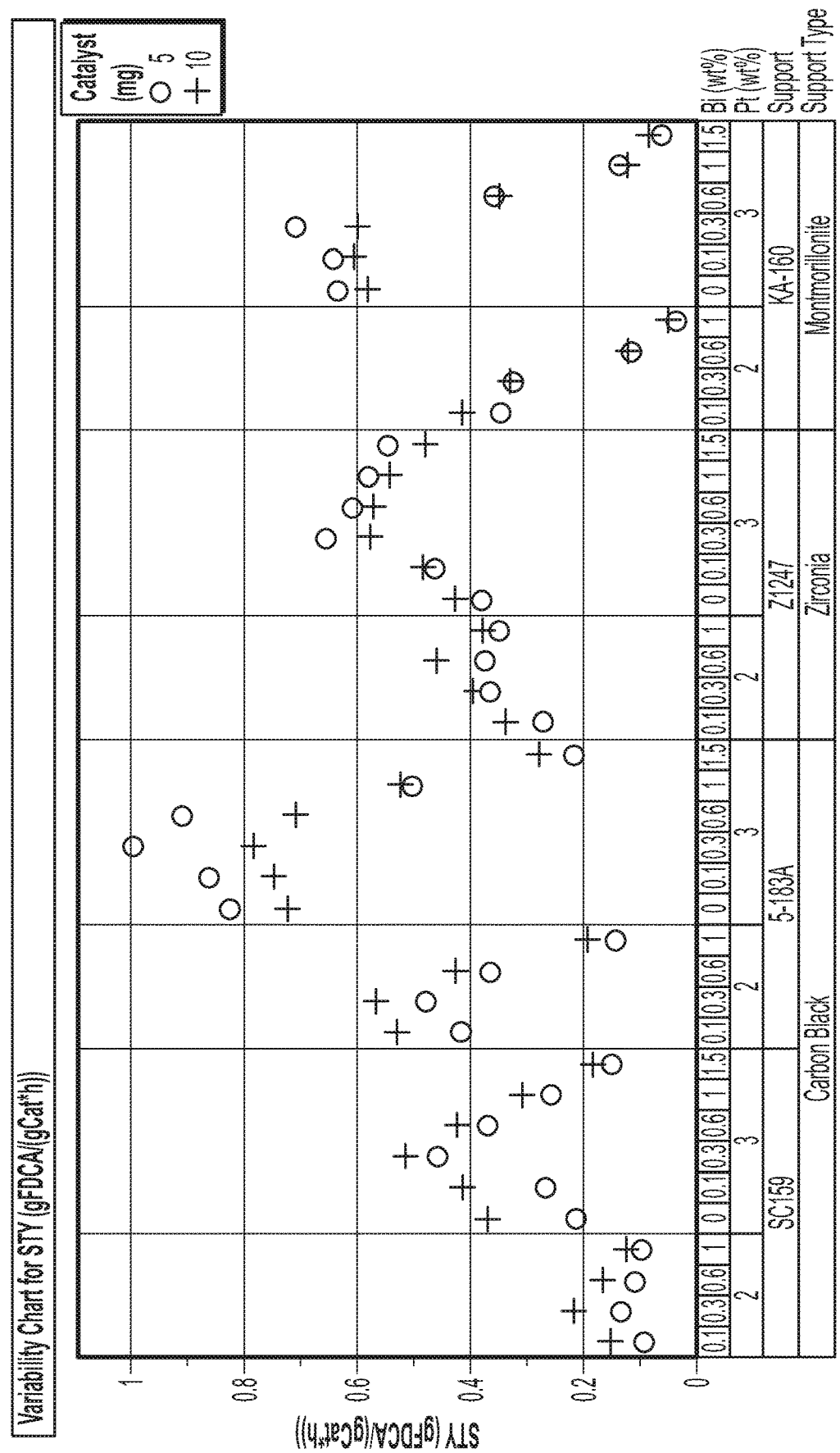
Figure 21:
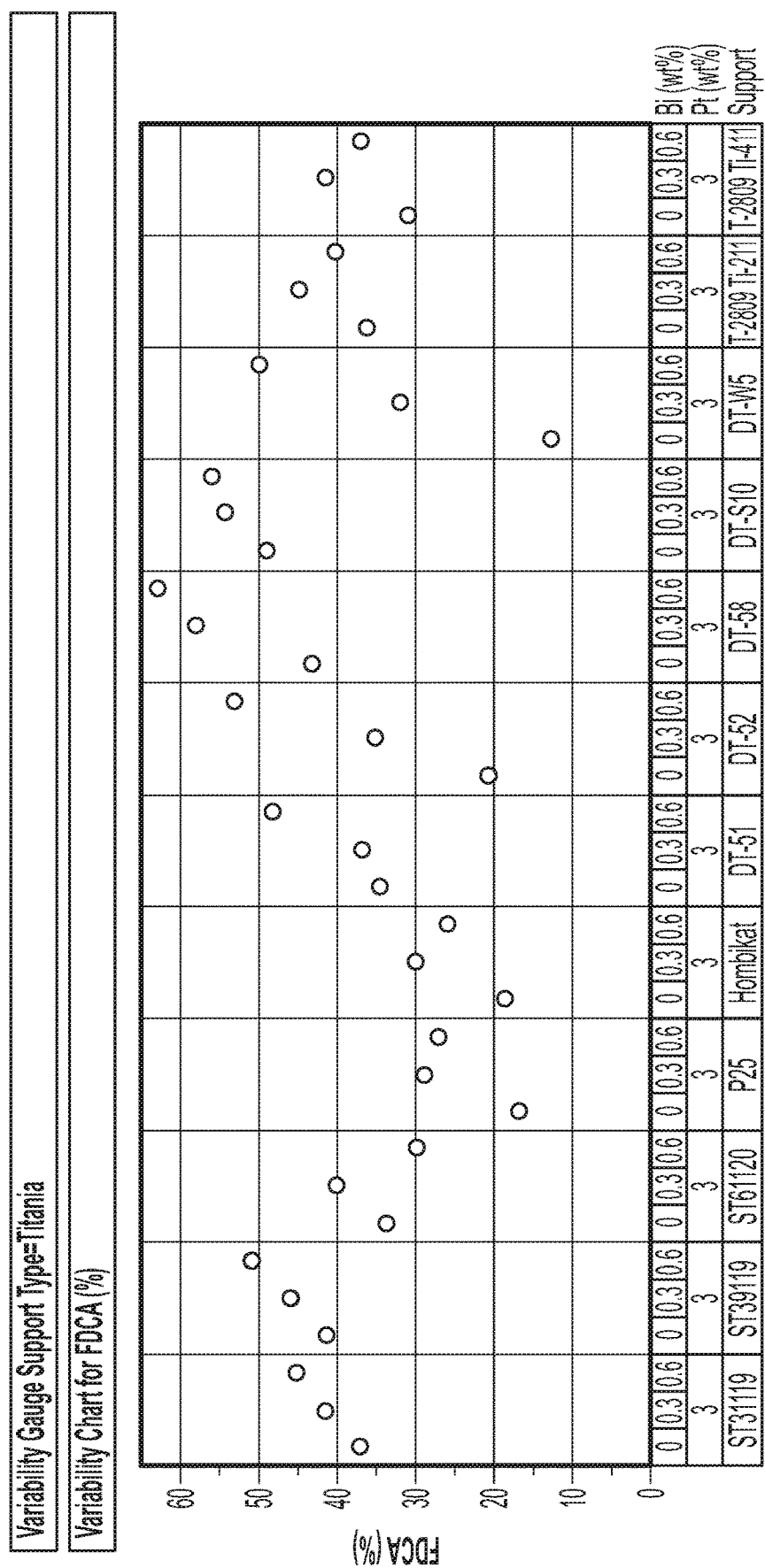
FIGS. 21-28 depict the distribution of products, mass balances and space time yields (STY) for the oxidation of a HMF substrate utilizing various ratios of Bi/Pt titania supports as catalysts, different Pt amounts, and different Bi amounts.
Figure 22:
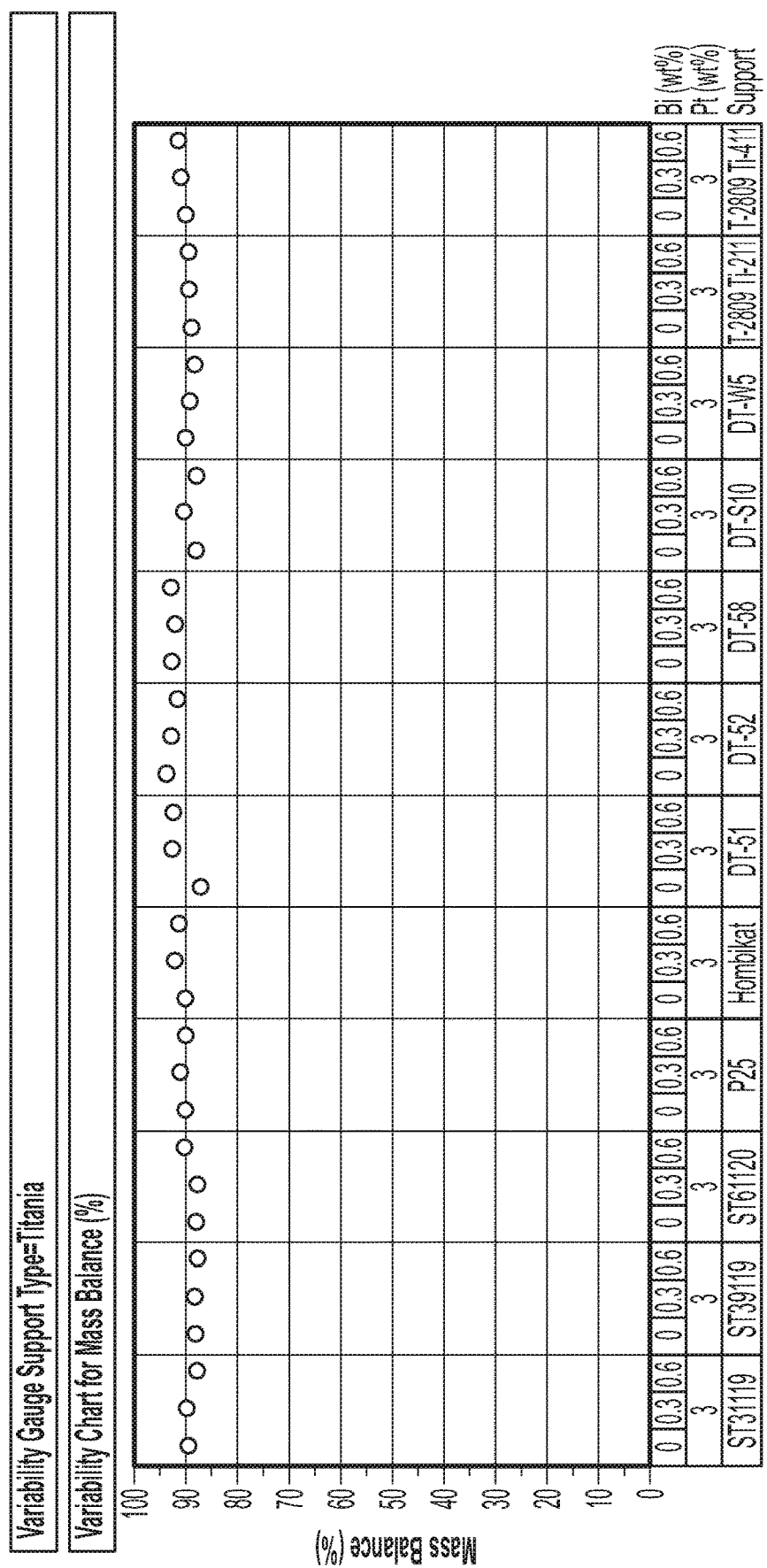
Figure 23:
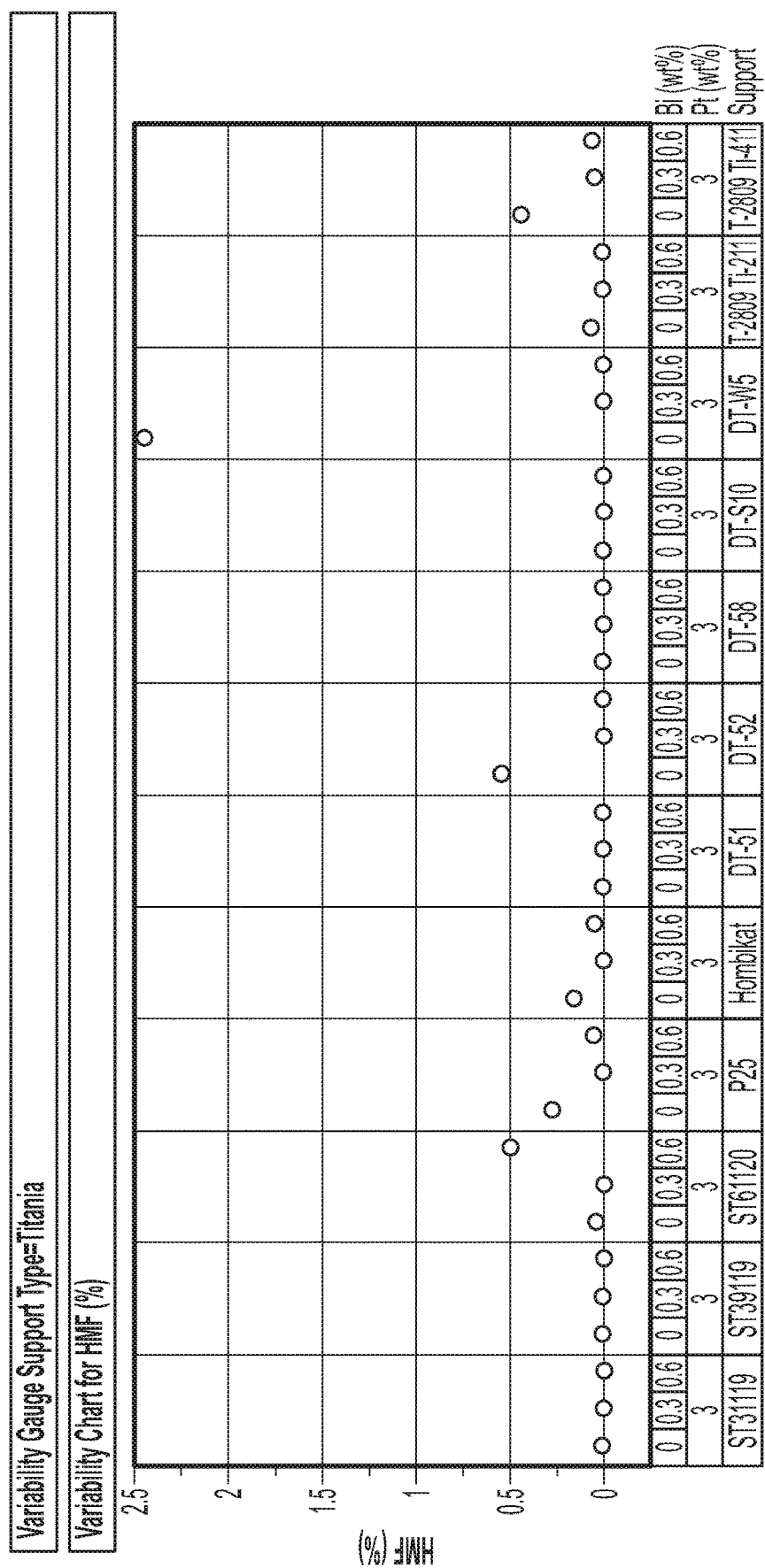
Figure 24:
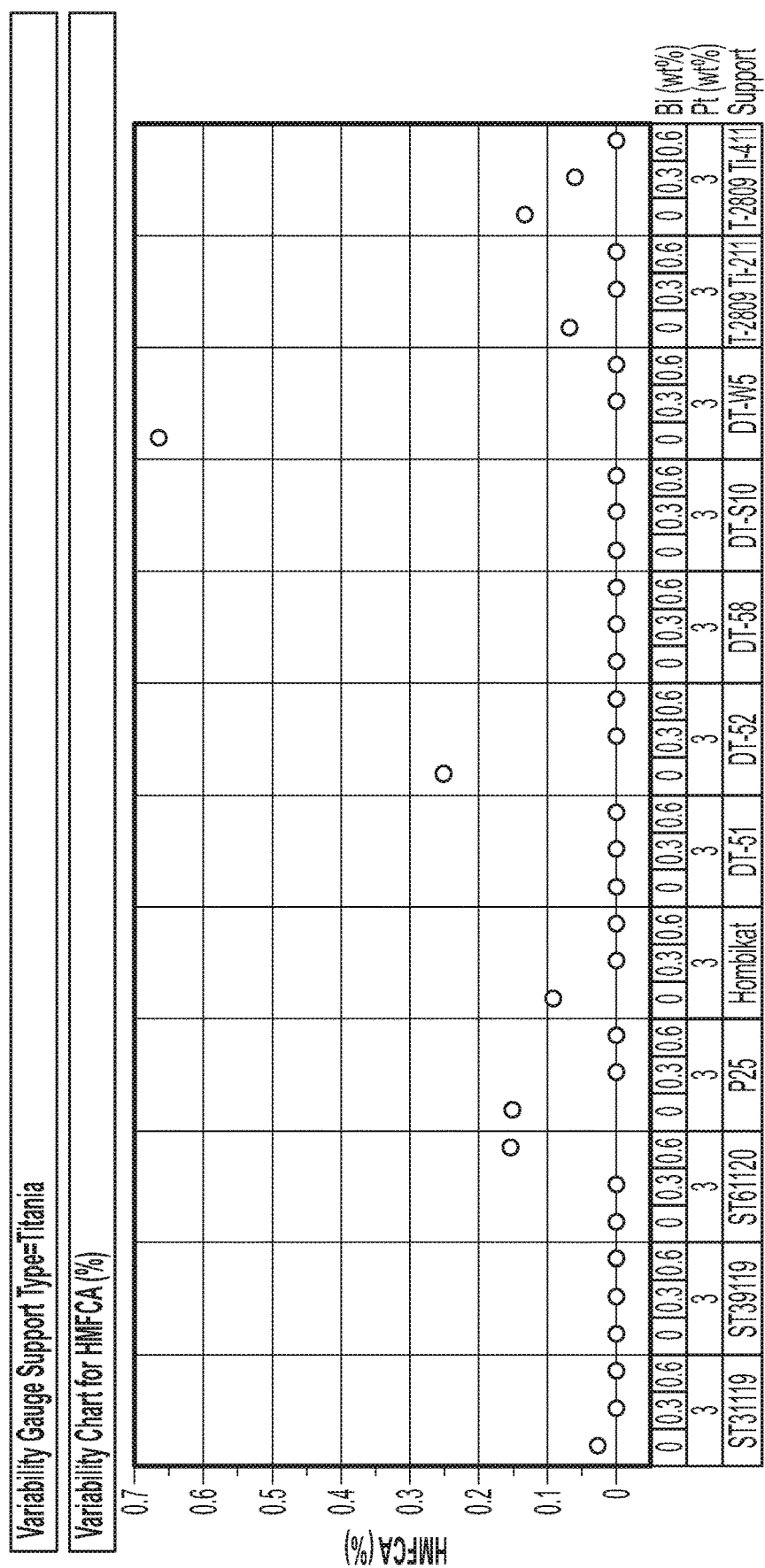
Figure 25:
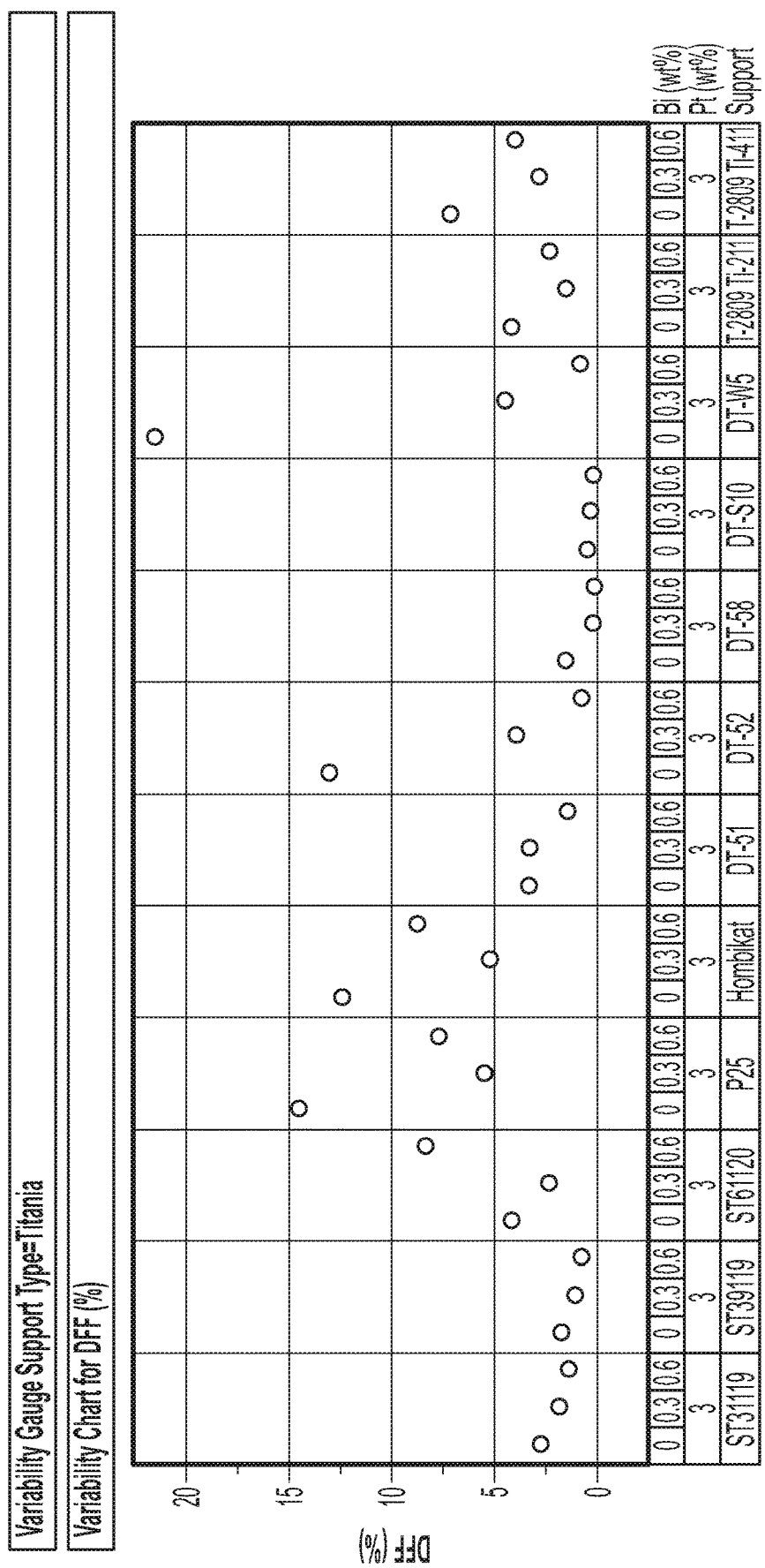
Figure 26:
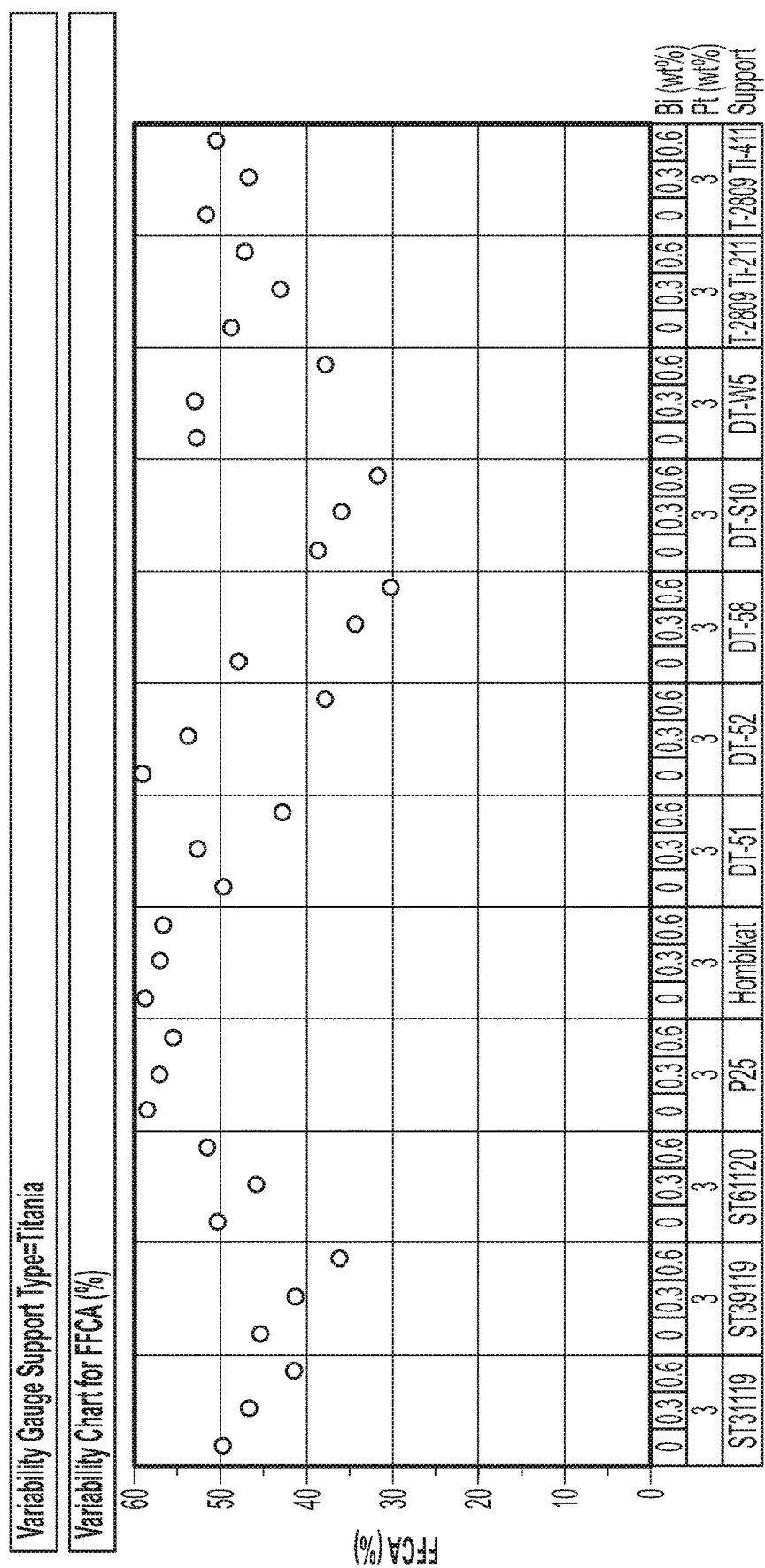
Figure 27:
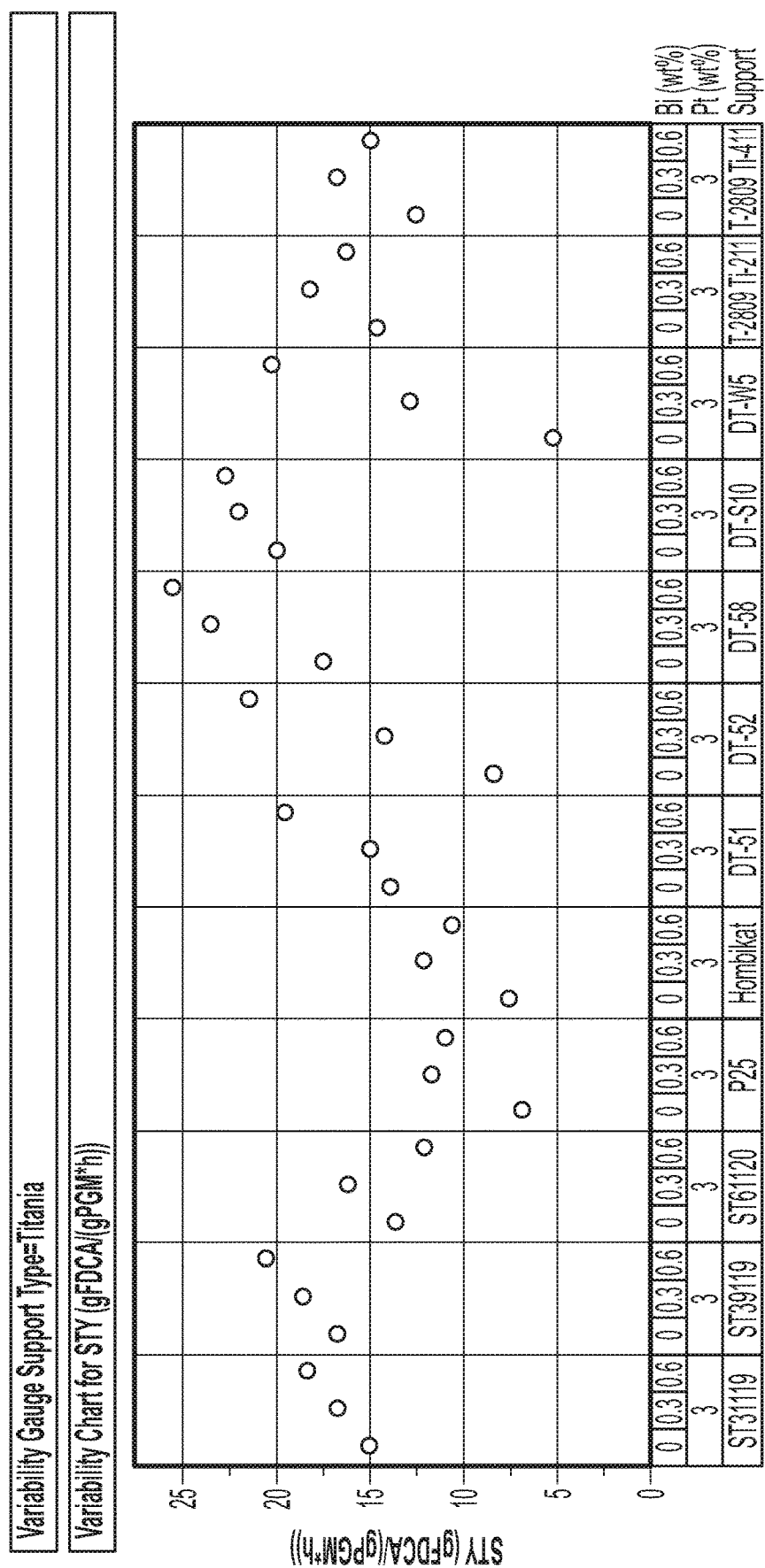
Figure 28:
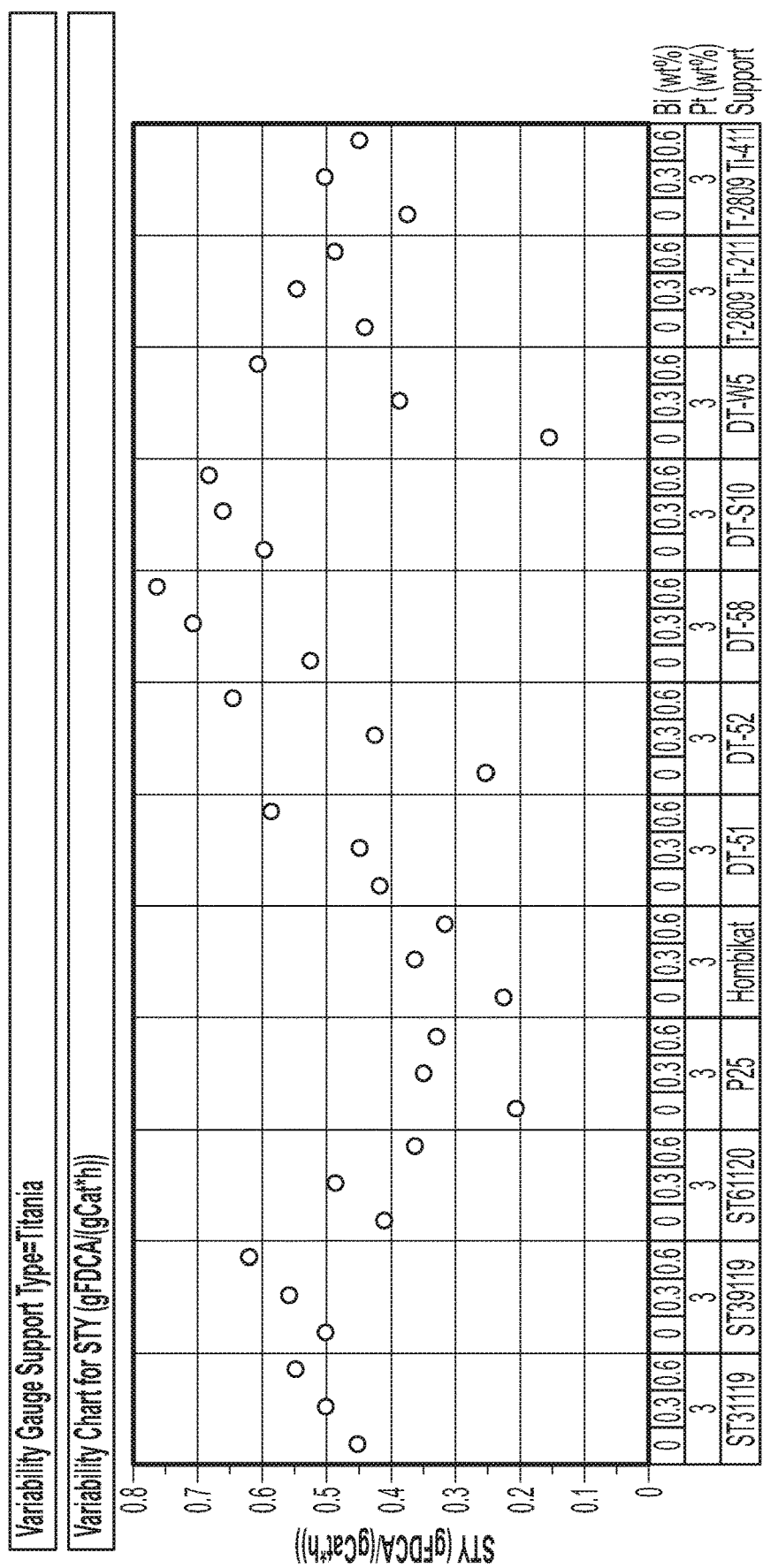
Figure 29:
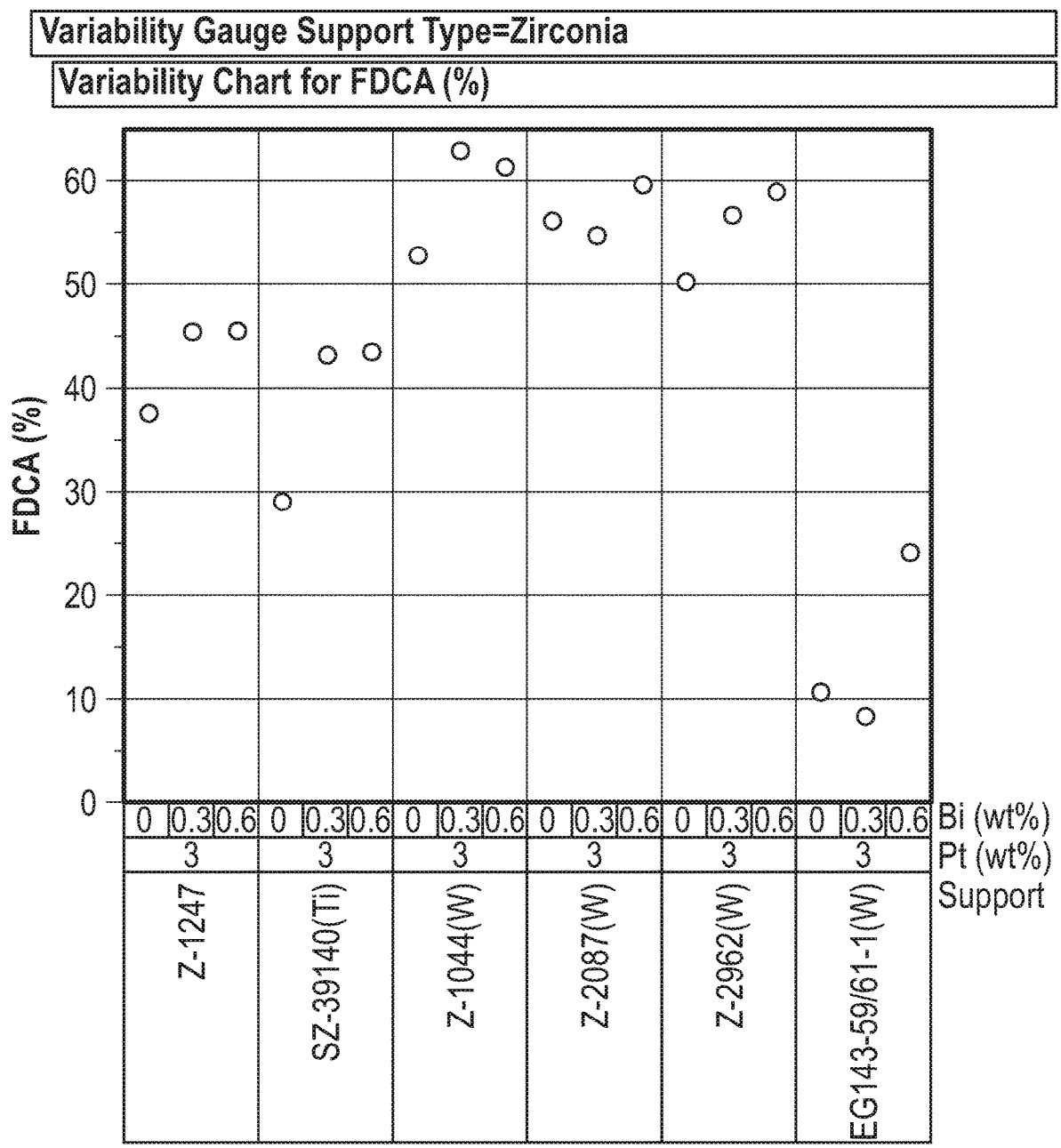
FIGS. 29-36 depict the distribution of products, mass balances and space time yields (STY) for the oxidation of a HMF substrate utilizing Pt and Bi/Pt catalysts on various zirconia supports as catalysts, different Pt amounts, and different Bi amounts.
Figure 30:
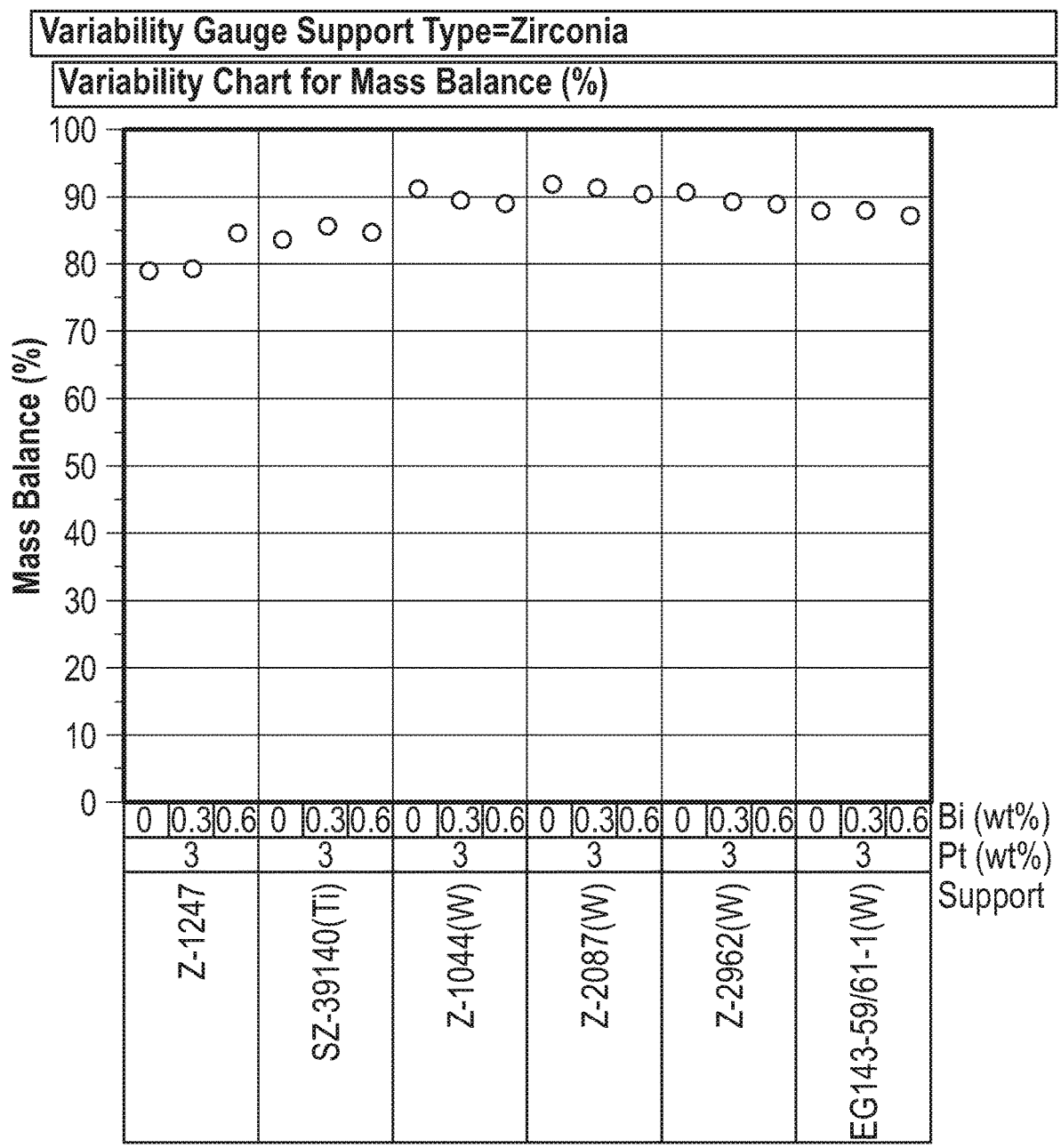
Figure 31:
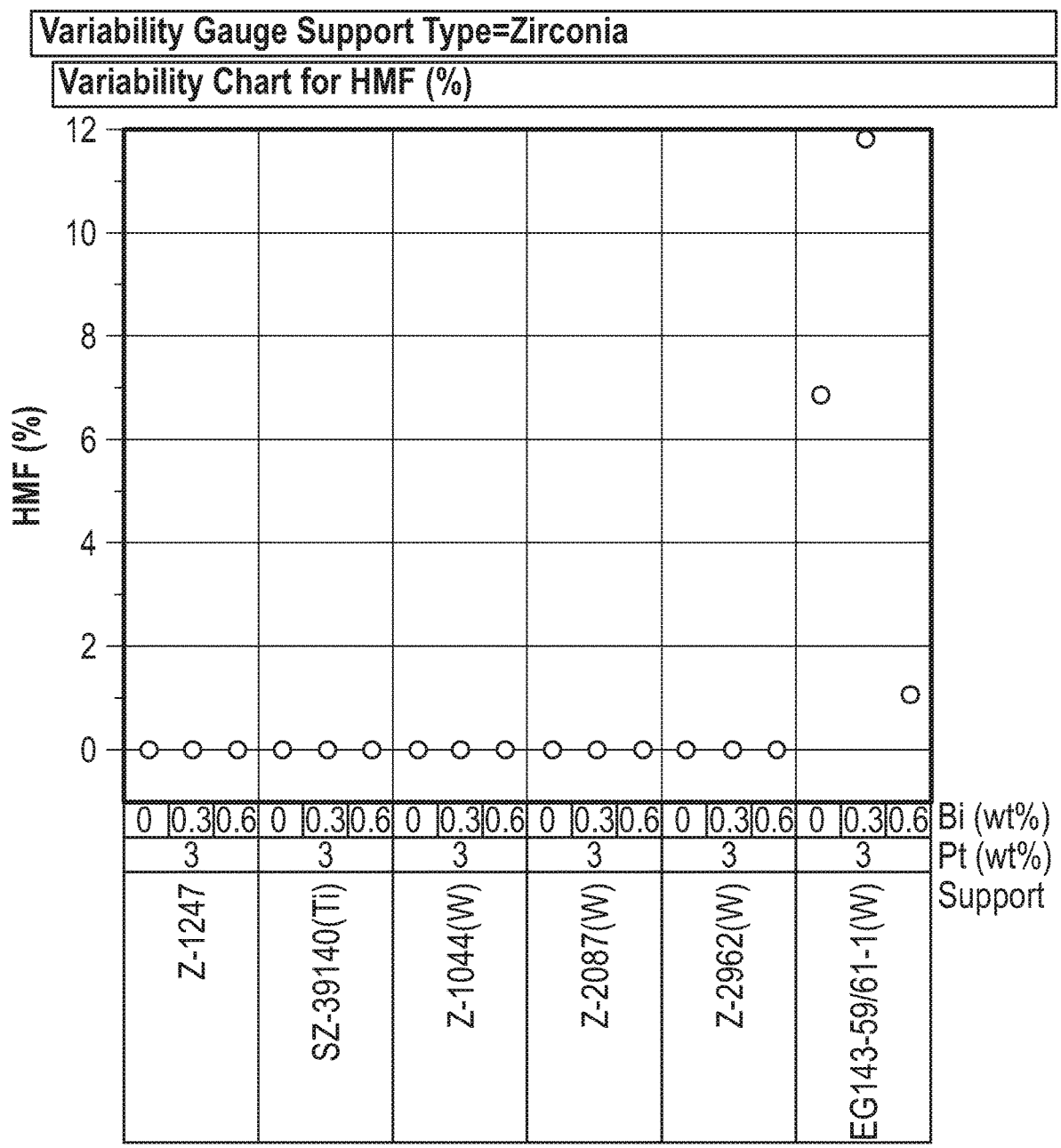
Figure 32:
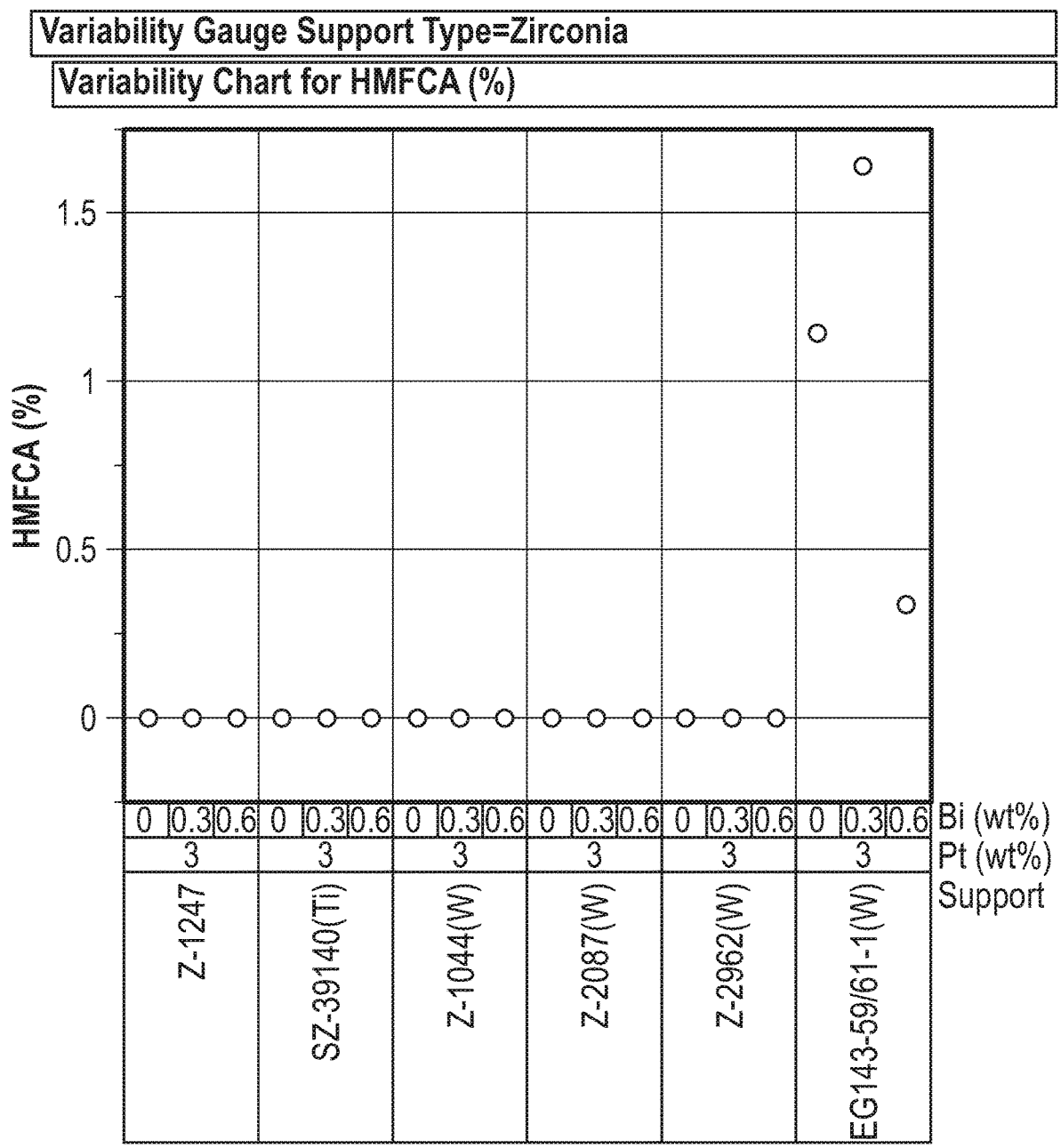
Figure 33:
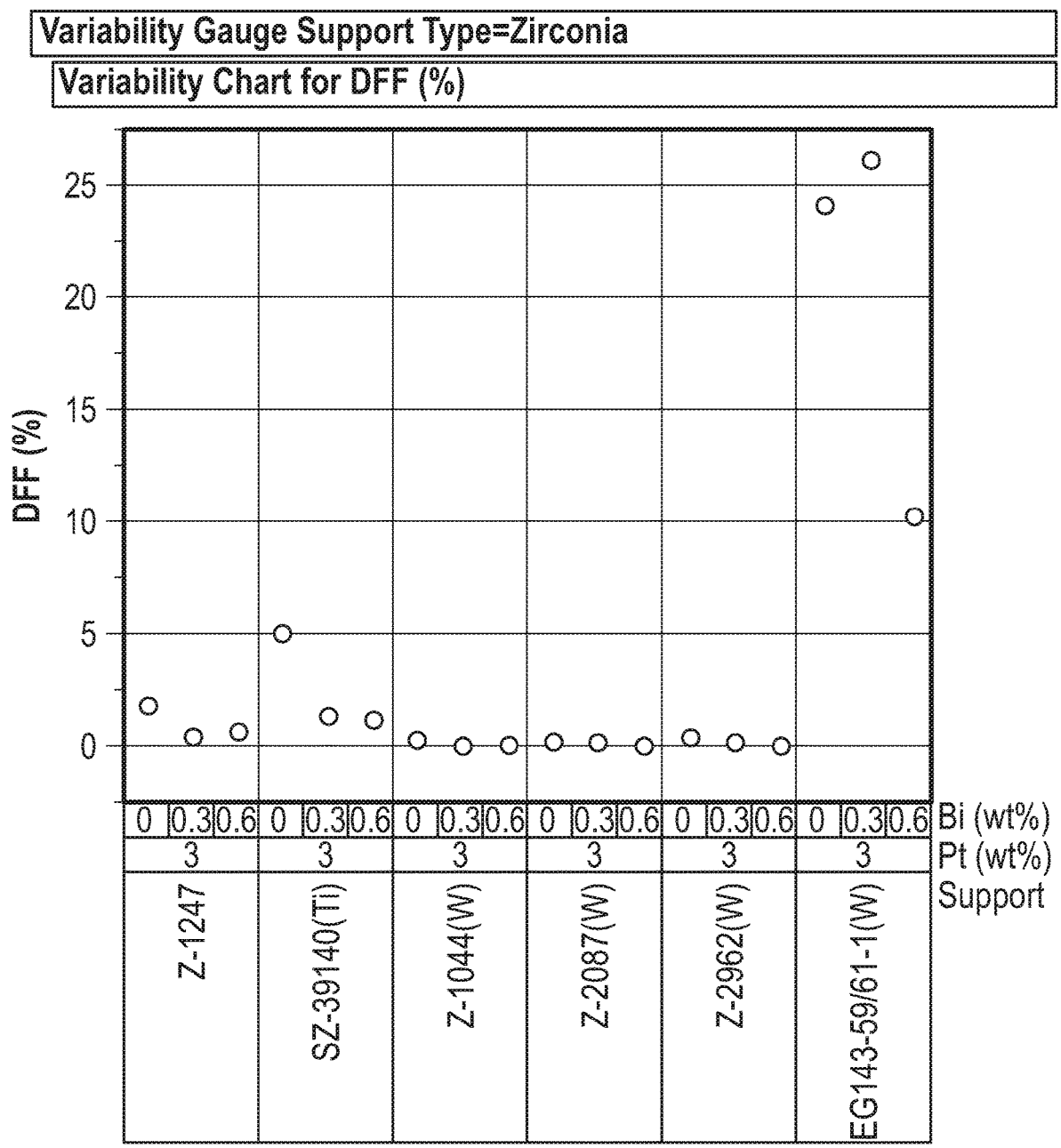
Figure 34:
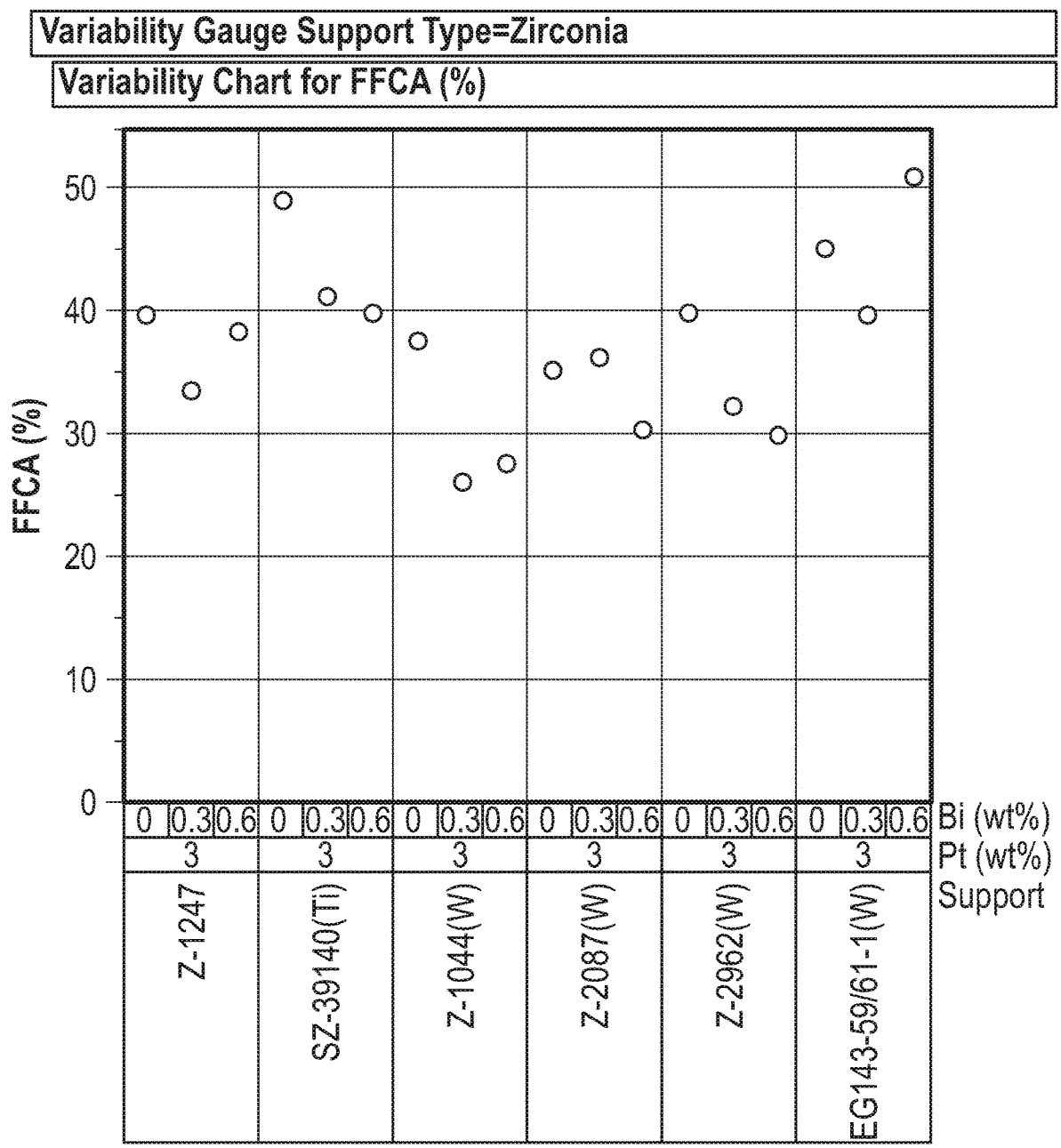
Figure 35:
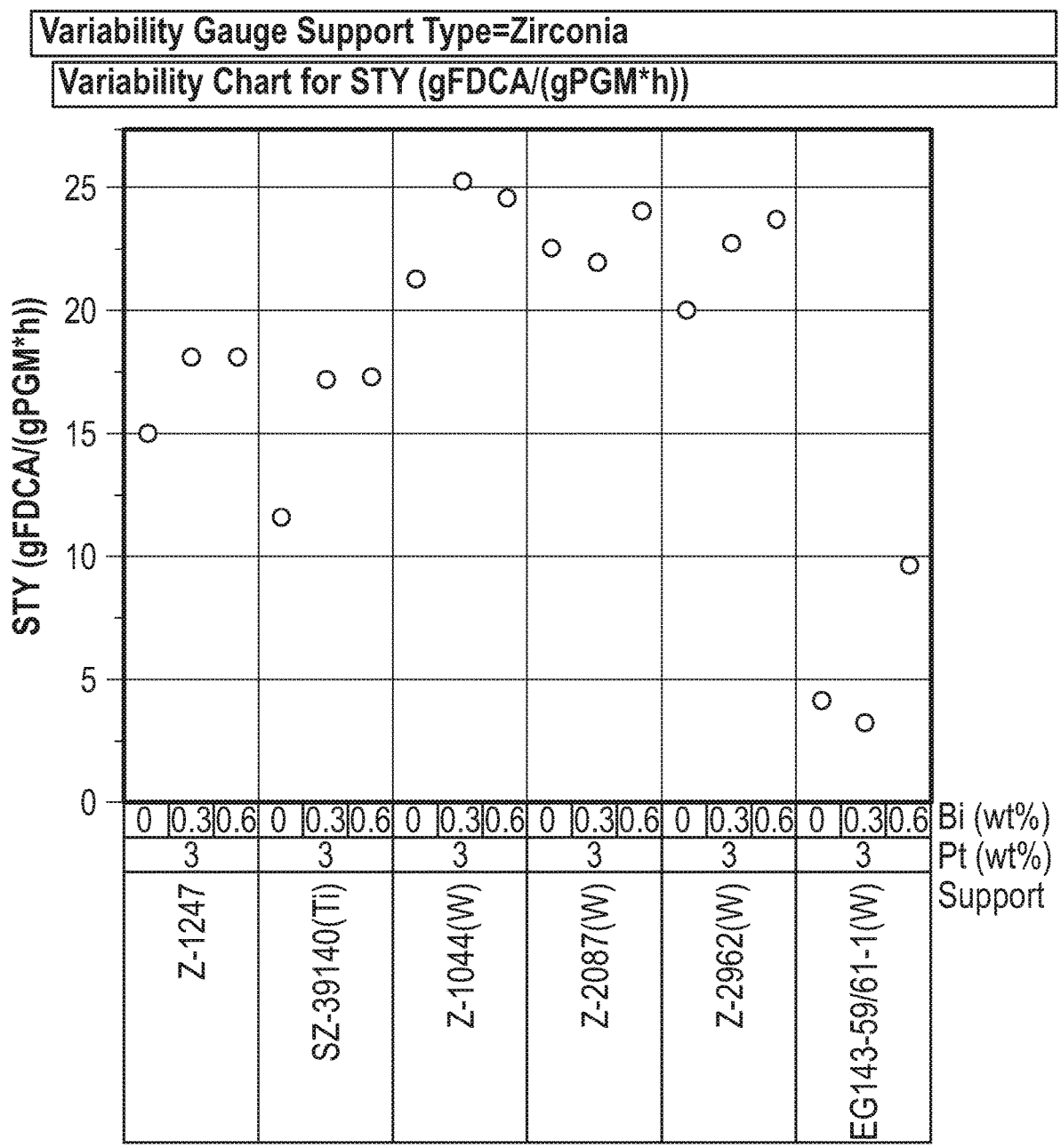
Figure 36:
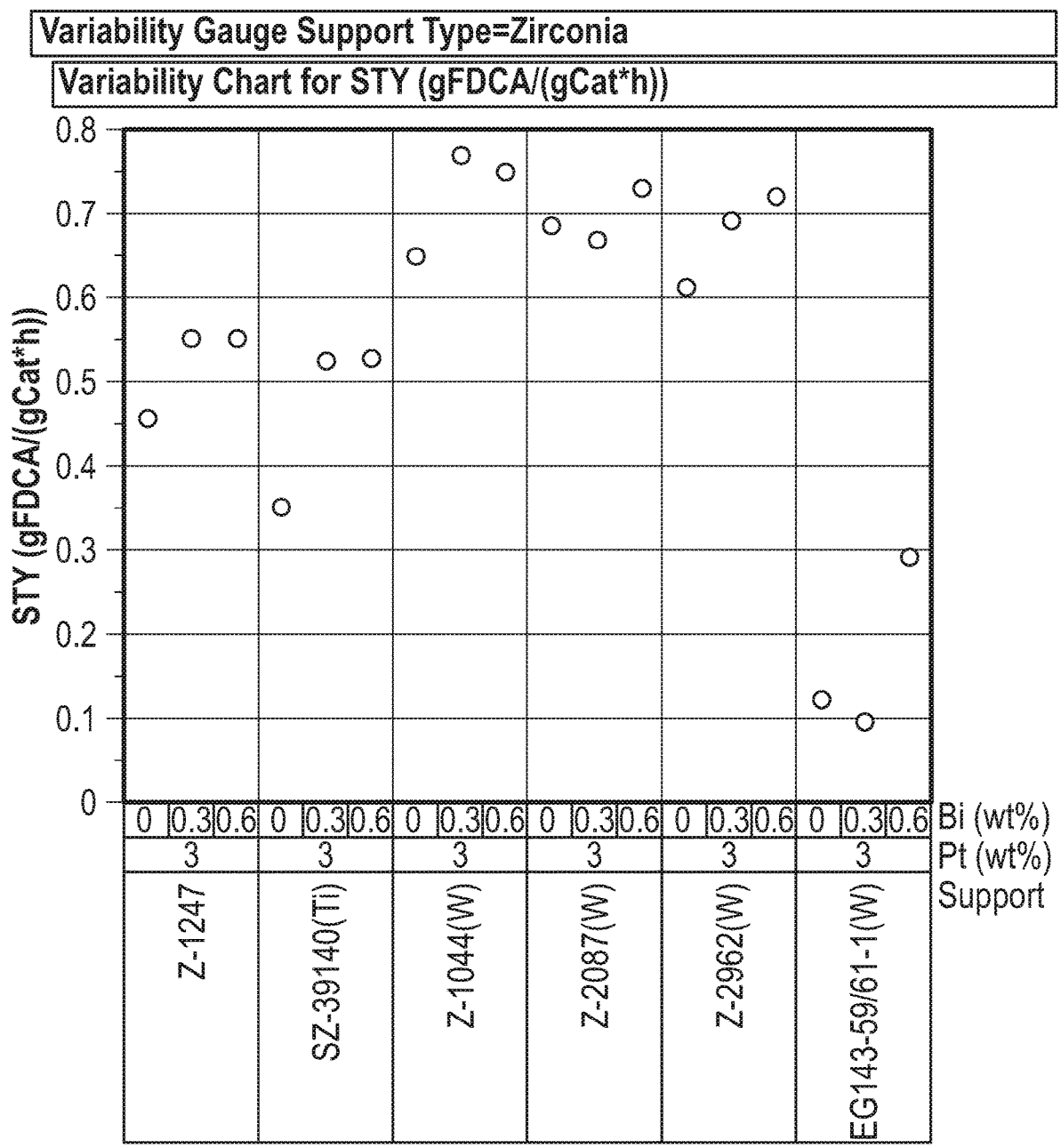
Figure 37:
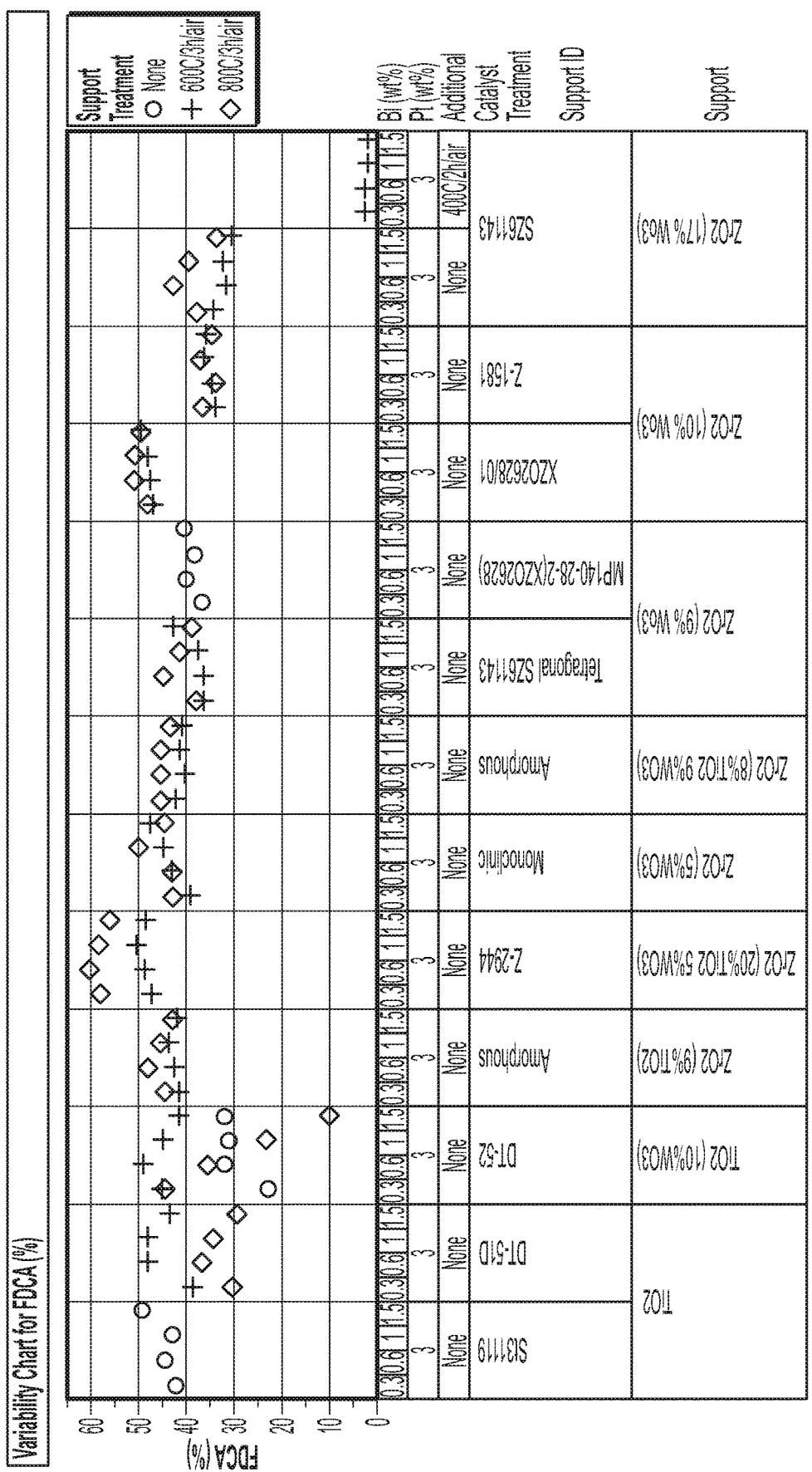
FIGS. 37-44 depict the distribution of products, mass balances and space time yields (STY) for the oxidation of a HMF substrate utilizing Pt and Bi/Pt catalysts on various tungstated titania and zirconia supports as catalysts, different Pt amounts, different Bi amounts, and different support treatments.
Figure 38:
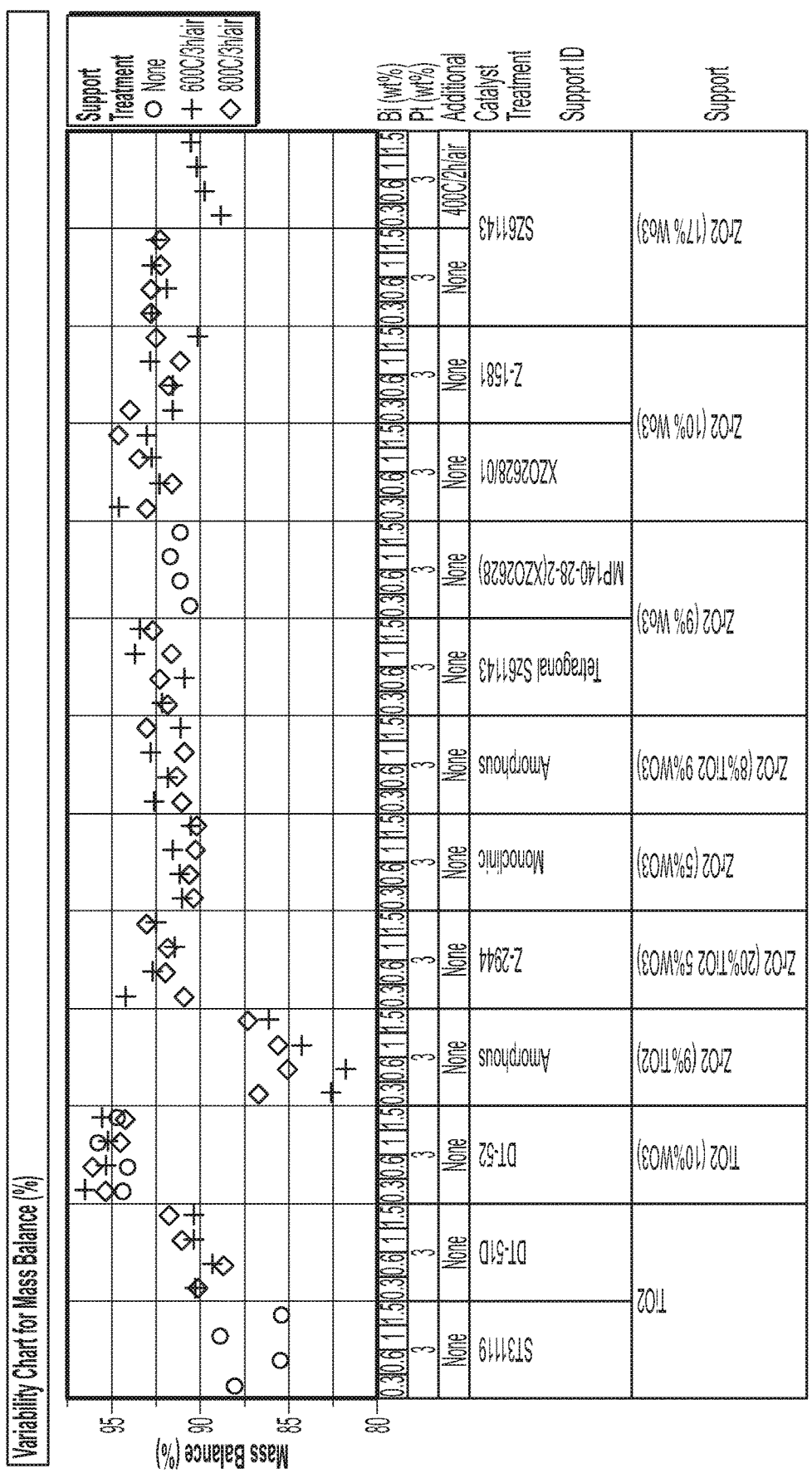
Figure 39:
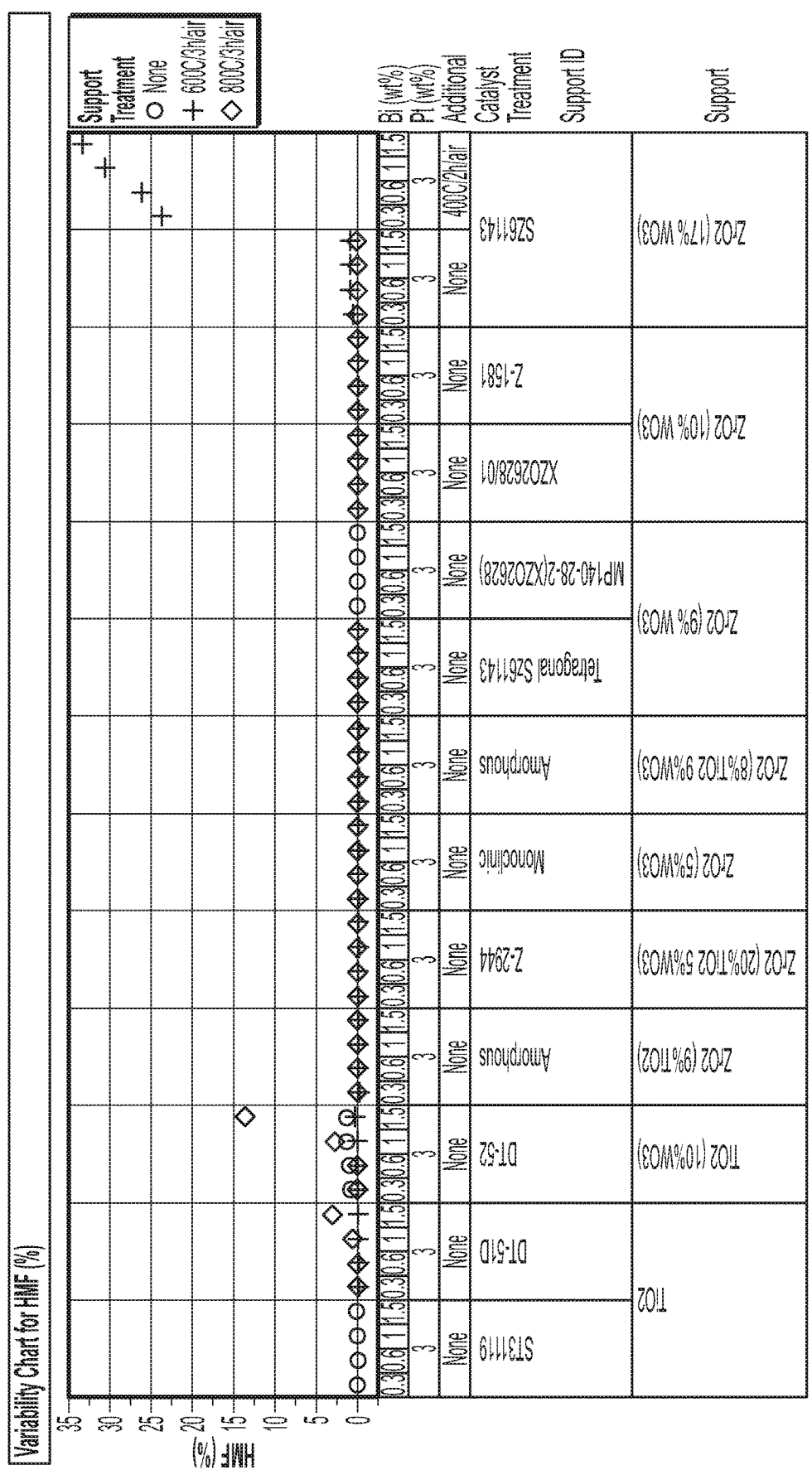
Figure 40:
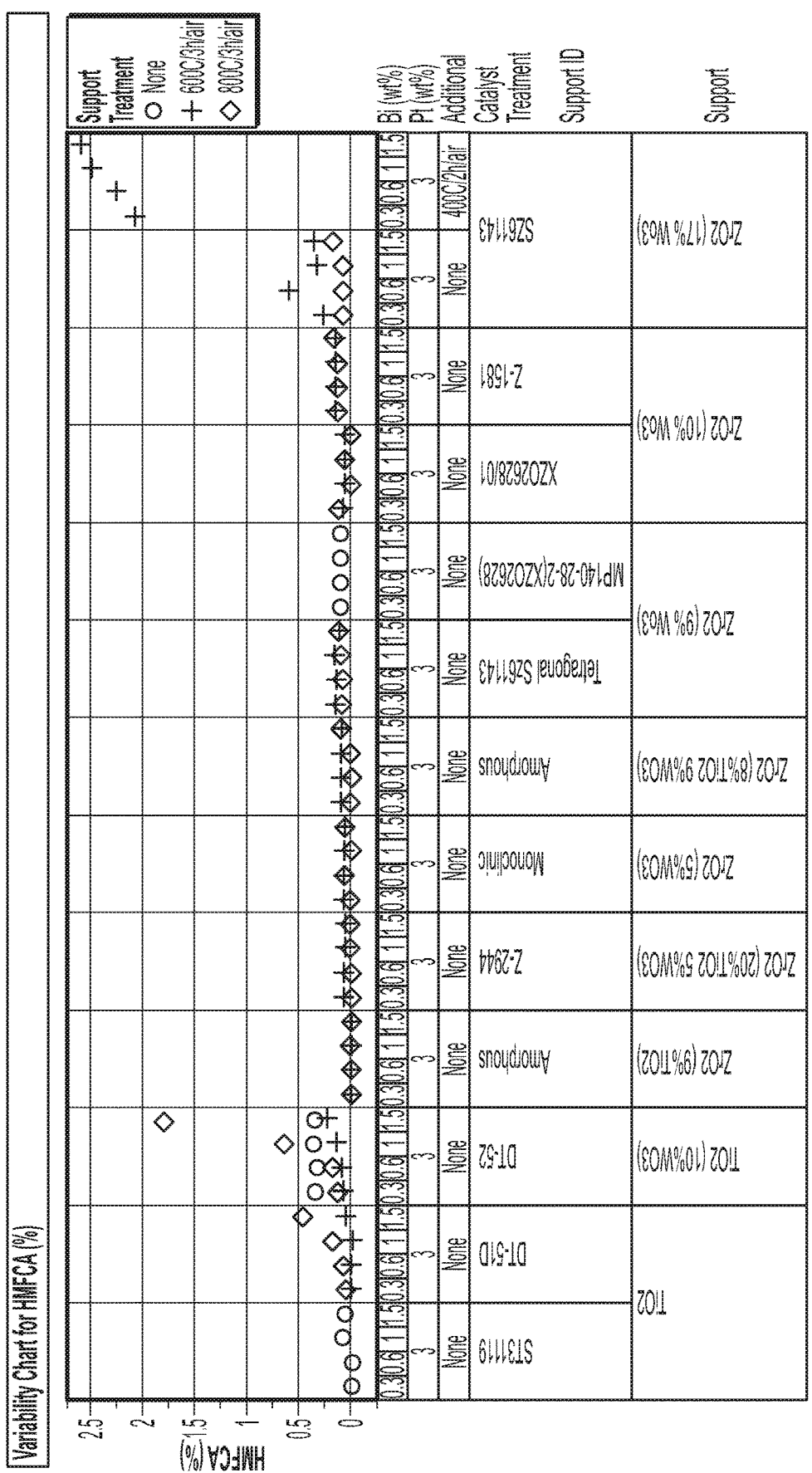
Figure 41:
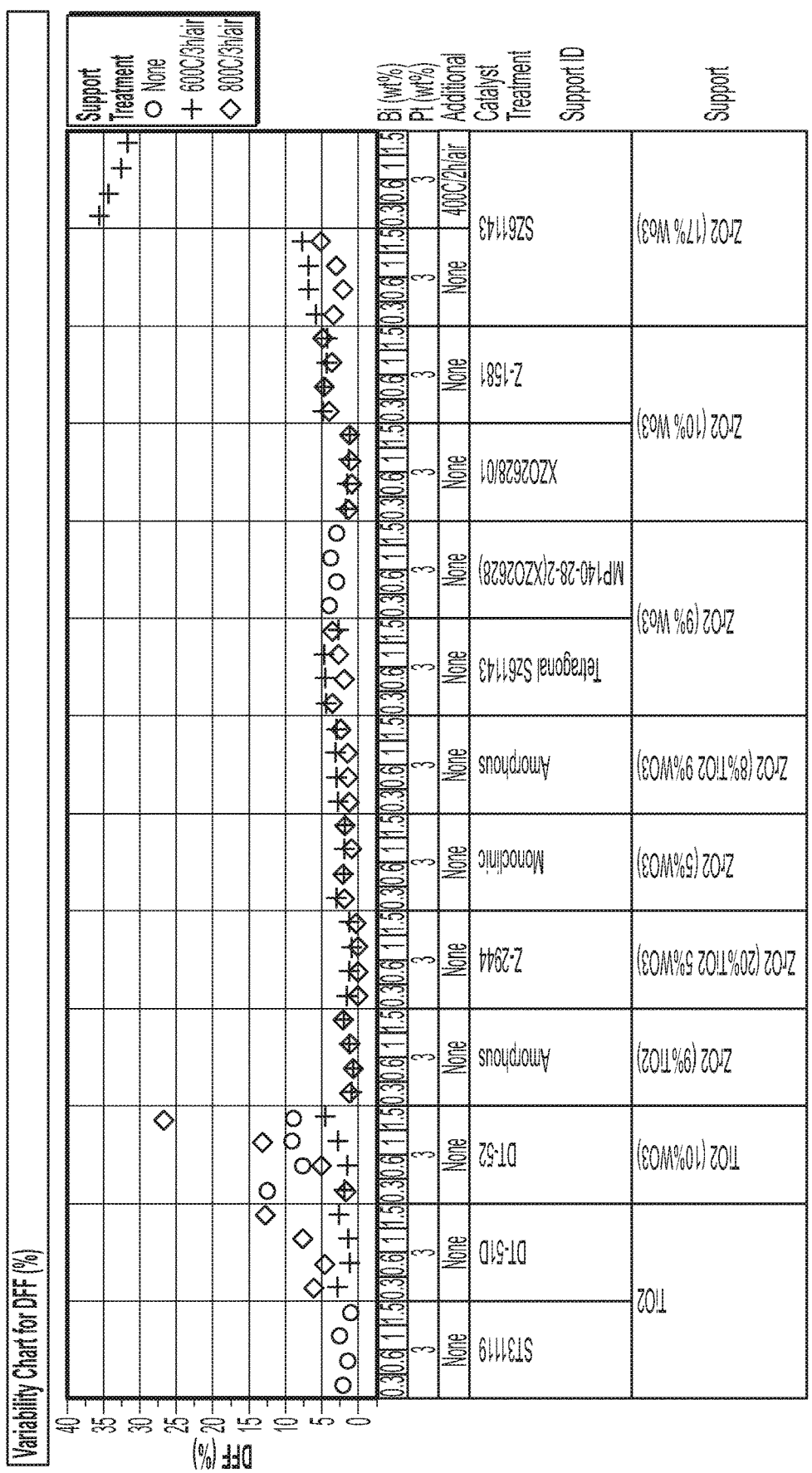
Figure 42:
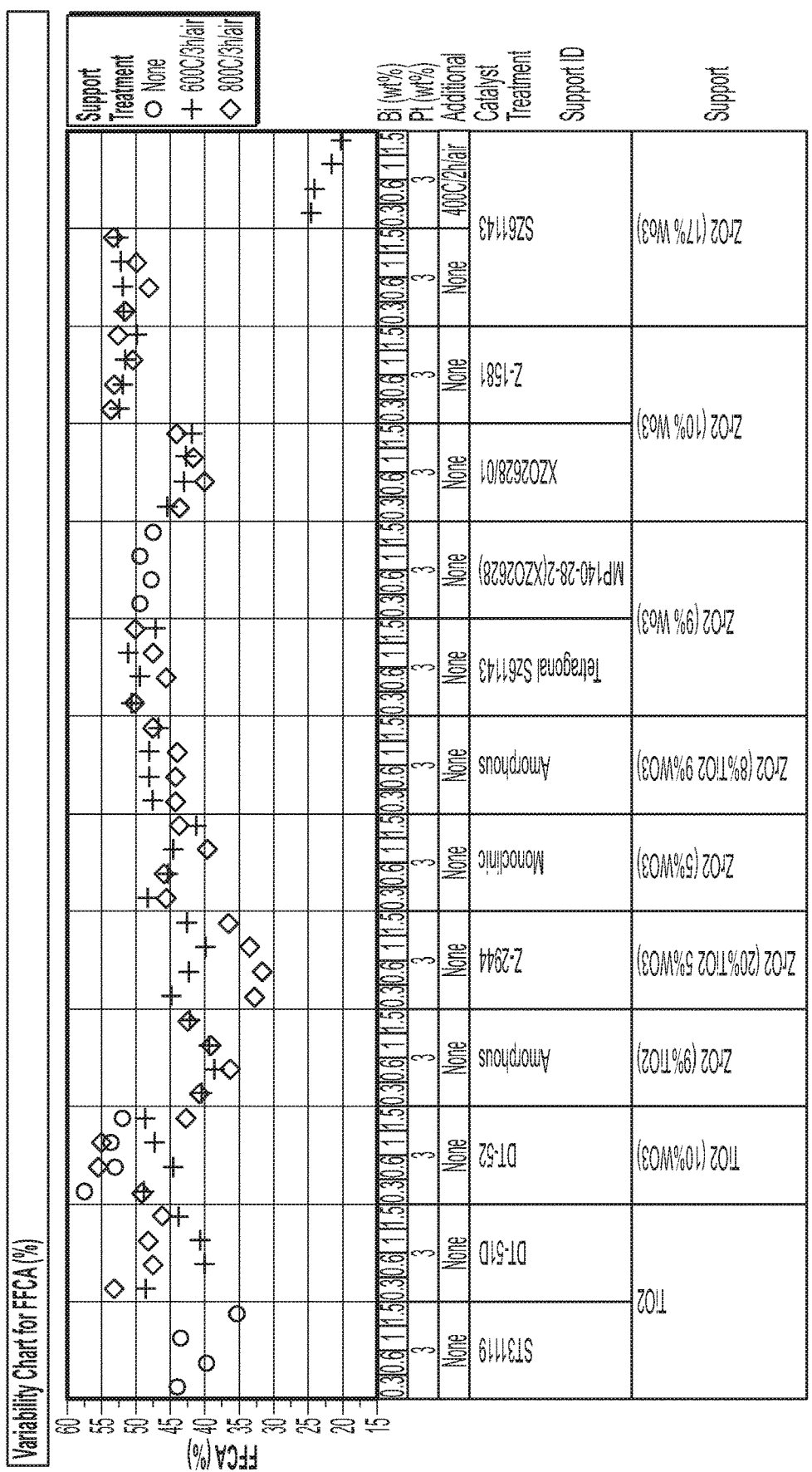
Figure 43:
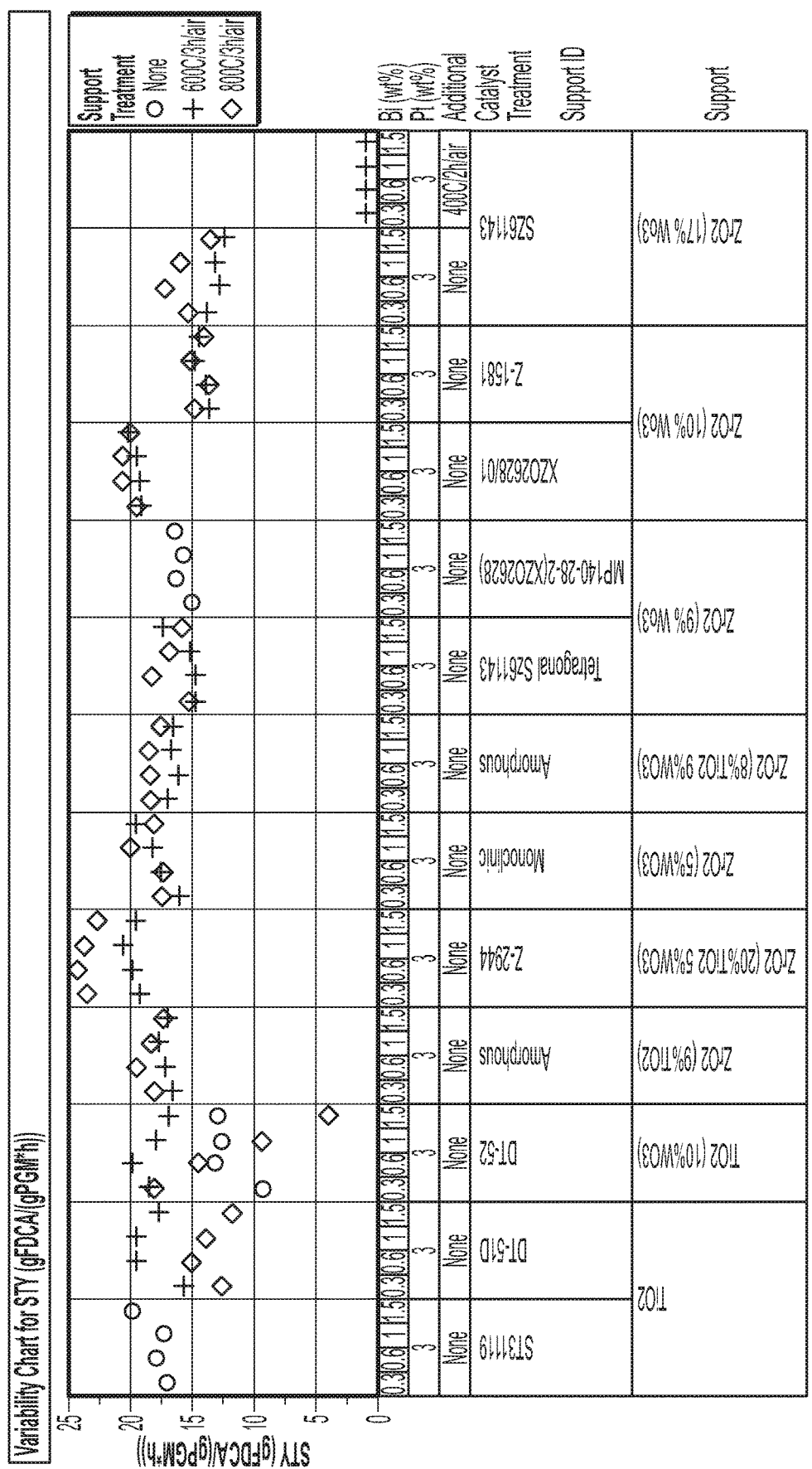
Figure 44:
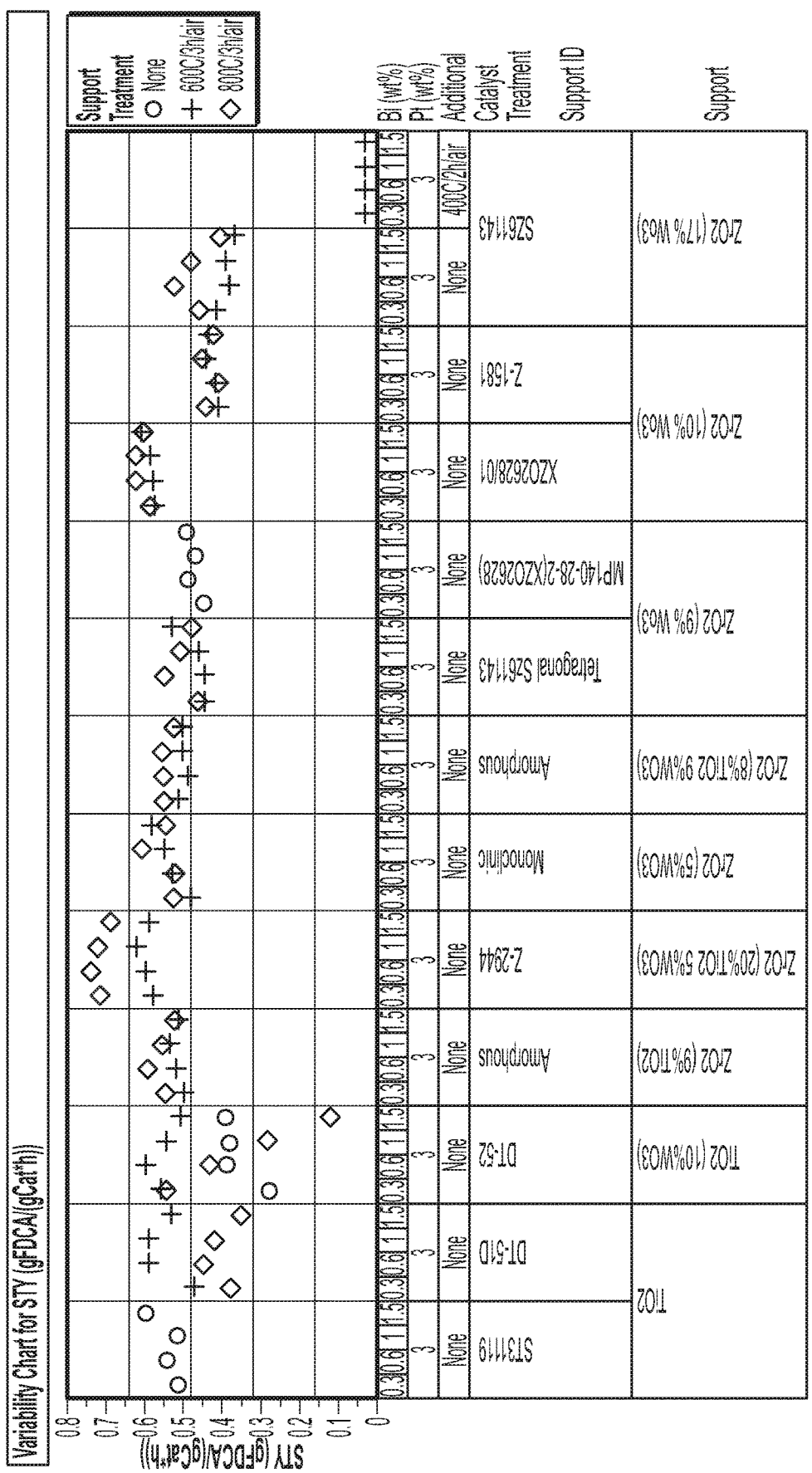

2 mg or 5 mg of a Ru/C JM-38* powder catalyst was placed into reaction vessels along with 0.25 ml of a solution prepared in a 3:2 (wt/wt) dioxane:$H_2O$ mixture and containing 0.020 M FFCA (0.60 mg) and 0.38 M FDCA (12.0 mg). Ru/C JM-38* was used in a further reduced form (350° C. in forming gas for 3 hours). Reaction vessels were pressurized with hydrogen at target pressure of 50 psi. Reaction vessels were heated to a target temperature of 50° C. and shaken for 4 hours or, alternatively, reaction vessels were heated to a target temperature of 70° C. and shaken for 2 hours. After the reaction was completed, the shaking was stopped and the reactor was cooled down to room temperature. Yields of HMF, HMFCA, MFA and THFDCA, remaining FFCA and FDCA amounts, and mass balances of FFCA and FDCA were calculated. The results are shown in FIG. 12.

V. Crystallization Examples

The purity (in weight %) of FDCA (and remaining HMFCA and FFCA) in the crystallized solids and mother liquors were determined using HPLC analysis with UV detection ($\lambda$=254 nm) and the absorbance of FDCA, HMFCA and FFCA at 254 nm was correlated against calibration curves for FDCA, HMFCA and FFCA.

Example 11

FDCA (4.0 g) and HMFCA (0.21 g, FDCA:HMFCA 95:5 wt:wt) were suspended in 1,4-dioxane:water (40.4 g, 80:20 wt:wt). The stirred suspension was heated in an oil-bath to 110-115° C. in a sealed reaction vial until all solids were dissolved. The heat was then turned off and the mixture was allowed to slowly cool to room temperature over 2 h. The crystal suspension was stirred for an additional hour at room temperature. The crystals were filtered off and the mother liquor was collected. The crystals were dried overnight under vacuum to give FDCA (2.53 g, 63% yield, 99.42% purity) as white crystals. HMFCA 0.58 wt % according to HPLC analysis.

The mother liquor was evaporated under reduced pressure and the remaining solids were dried overnight under vacuum to give FDCA:HMFCA (1.48 g, 88.6:11.4 wt:wt) as a pale yellow solid.

Total mass recovery: 4.01 g (95.2%).

Example 12

FDCA (2.47 g, FDCA:HMFCA 99.42:0.58 wt:wt) from EXAMPLE 11 was suspended in 1,4-dioxane:water (22.3 g, 80:20 wt:wt). The stirred suspension was heated in an oil-bath to 120° C. in a sealed reaction vial until all solids were dissolved. The heat was then turned off and the mixture was allowed to slowly cool to room temperature over 2 h. The crystal suspension was stirred for an additional 2 hour at room temperature. The crystals were filtered off and the mother liquor was collected. The crystals were re-slurried in demineralized water (10 mL) and filtered off. The crystals were collected and dried overnight under vacuum giving FDCA (1.60 g, 65% yield, >99.95% purity) as white crystals. HMFCA amounts were below detectable levels according to HPLC analysis.

The mother liquor was evaporated under reduced pressure and the remaining solids were dried overnight under vacuum to give FDCA:HMFCA (0.71 g, 98.5:1.5 wt:wt) as a slightly off-white solid.

Total mass recovery: 2.31 g (93.5%).

Example 13

FDCA (4.0 g) and HMFCA (0.21 g, FDCA:HMFCA 95:5 wt:wt) were suspended in 1,4-dioxane:water (40.4 g, 60:40 wt:wt). The stirred suspension was heated in an oil-bath to 110-115° C. in a sealed reaction vial until all solids were dissolved. The heat was then turned off and the mixture was allowed to slowly cool to room temperature over 2 h. The crystal suspension was stirred for an additional hour at room temperature. The crystals were filtered off and the mother liquor was collected. The crystals were dried overnight under vacuum giving FDCA (3.10 g, 78% yield, 99.56% purity) as white crystals. HMFCA 0.44 wt % according to HPLC analysis.

The mother liquor was evaporated under reduced pressure and the remaining solids were dried overnight under vacuum to give FDCA:HMFCA (0.98 g, 82.2:17.8 wt:wt) as a pale yellow solid.

Total mass recovery: 4.08 g (96.9%).

Example 14

FDCA (3.05 g, FDCA:HMFCA 99.56:0.44 wt:wt) from EXAMPLE 13 was suspended in 1,4-dioxane:water (27.4 g, 60:40 wt:wt). The stirred suspension was heated in an oil-bath to 120° C. in a sealed reaction vial until all solids were dissolved. The heat was then turned off and the mixture was allowed to slowly cool to room temperature over 2 h. The crystal suspension was stirred for an additional 2 hour at room temperature. The crystals were filtered off and the mother liquor was collected. The crystals were re-slurried in demineralized water (10 mL) and filtered off. The crystals were collected and dried overnight under vacuum to give FDCA (2.37 g, 78% yield, >99.95% purity) as white crystals. HMFCA amounts were below detectable levels according to HPLC analysis.

The mother liquor was evaporated under reduced pressure and the remaining solids were dried overnight under vacuum to give FDCA:HMFCA (0.50 g, 98.0:2.0 wt:wt) as a slightly off-white solid.

Total mass recovery, 2.87 g (94.1%).

Example 15

FDCA (3.06 g), HMFCA (0.148 g) and FFCA (12.9 mg, FDCA:HMFCA:FFCA 95:4.6:0.4 wt:wt:wt) were suspended in 1,4-dioxane:water (29.0 g, 60:40 wt:wt). The stirred suspension was heated in an oil-bath to 120° C. in a sealed reaction vial until all solids were dissolved. The heat was then turned off and the mixture was allowed to slowly cool to room temperature over 2 h. The crystal suspension was stirred for an additional hour at room temperature. The crystals were filtered off and the mother liquor was collected. The crystals were dried overnight under vacuum to give FDCA (2.42 g, 79% yield, 99.35% purity) as white crystals. HMFCA 0.34 wt % and FFCA 0.31 wt % according to HPLC analysis.

The mother liquor was evaporated under reduced pressure and the remaining solids were dried overnight under vacuum to give FDCA:HMFCA:FFCA (0.64 g, 81.5:17.8:0.7: wt:wt:wt) as a pale yellow solid.

Total mass recovery, 3.06 g (94.8%).

Example 16

FDCA (2.27 g, FDCA:HMFCA:FFCA 99.35:0.34:0.31 wt:wt:wt) from EXAMPLE 15 was suspended in 1,4-dioxane:water (20.5 g, 60:40 wt:wt). The stirred suspension was heated in an oil-bath to 120° C. in a sealed reaction vial until all solids were dissolved. The heat was then turned off and the mixture was allowed to slowly cool to room temperature over 2 h. The crystal suspension was stirred for an additional 2 hour at room temperature. The crystals were filtered off and the mother liquor was collected. The crystals were dried overnight under vacuum giving FDCA (1.78 g, 78% yield, 99.75% purity) as white crystals. HMFCA 0.08 wt % and FFCA 0.17 wt % according to HPLC analysis.

The mother liquor was evaporated under reduced pressure and the remaining solids were dried overnight under vacuum to give FDCA:HMFCA:FFCA (0.38 g, 97.6:1.6:0.8 wt:wt:wt) as a slightly off-white solid.

Total mass recovery, 2.16 g (95.2%).

Example 17

FDCA (1.70 g, FDCA:HMFCA:FFCA 99.75:0.08:0.17 wt:wt:wt) from EXAMPLE 16 was suspended in 1,4-dioxane:water (15.3 g, 60:40 wt:wt). The stirred suspension was heated in an oil-bath to 120° C. in a sealed reaction vial until all solids were dissolved. The heat was then turned off and the mixture was allowed to slowly cool to room temperature over 2 h. The crystal suspension was stirred for an additional hour at room temperature. The crystals were filtered off and the mother liquor was collected. The crystals were re-slurried in demineralized water (10 mL) and filtered off. The crystals were collected and dried overnight under vacuum giving FDCA (1.29 g, 76% yield, 99.91% purity) as white crystals. FFCA 0.09 wt % and HMFCA below detectable levels according to HPLC.

The mother liquor was evaporated under reduced pressure and the remaining solids were dried overnight under vacuum to give FDCA:HMFCA:FFCA (0.27 g, 99.4:0.1:0.5 wt:wt:wt) as a white solid.

Total mass recovery, 1.56 g (91.8%).

VI. Heterogeneous Oxidation Catalyst Examples

Example 18

Preparation of Pt/Bi on Various Solid Supports

A metal precursor solution was first prepared by mixing $Bi(NO_3)_3 \cdot 5H_2O$ (43 wt % Bi) and a solution of $Pt(NO_3)_x$ (14.5 wt % Pt) in de-ionized water to obtain the various Pt—Bi ratios shown in Table 3. For example, to prepare the metal precursor solution used to form the catalyst in Example No. 1 of Table 3, 0.35 g of the $Bi(NO_3)_3 \cdot 5H_2O$ was mixed with 2.05 mL of the $Pt(NO_3)_x$ solution in 3.0 mL of de-ionized water. This solution was used to impregnate a $ZrO_2$ (Saint Gobain, BET specific surface area 40 m$^2$/g, particle size 75-150 μm), $ZrO_2$—$TiO_2$ (40 wt % $TiO_2$, Saint Gobain SZ 39140, BET specific surface area 80 m$^2$/g, particle size 75-150 μm), $TiO_2$ (Saint Gobain ST 31119, BET specific surface area 40 m$^2$/g, particle size 75-150 μm), or Silicon Carbide (SiCat, BET specific surface area 25 m$^2$/g, particle size 150-250 μm) support. After impregnation, the material was dried at 120° C. for 3 hours, then reduced under a flow of forming gas (5% $H_2$ in $N_2$) at 350° C. for 3 hours.

Example 19

Preparation of Pt/Te on Various Solid Supports

A metal precursor solution was first prepared by mixing $Te(OH)_6$ (55.6 wt % Te) and a solution of $Pt(NO_3)_x$ (14.5 wt % Pt) in de-ionized water to obtain the various Pt—Te ratios shown in Table 3. This solution was used to impregnate a $ZrO_2$ (Saint Gobain, BET specific surface area 40 m$^2$/g, particle size 75-150 μm), $ZrO_2$—$TiO_2$ (40 wt % $TiO_2$, Saint Gobain SZ 39140, BET specific surface area 80 m$^2$/g, particle size 75-150 μm), $TiO_2$ (Saint Gobain ST 31119, BET specific surface area 40 m$^2$/g, particle size 75-150 μm), or Silicon Carbide (SiCat, BET specific surface area 25 m$^2$/g, particle size 150-250 μm) support. After impregnation, the material was dried at 120° C. for 3 hours, then reduced under a flow of forming gas (5% $H_2$ in $N_2$) at 350° C. for 3 hours.

Example 20

Preparation of Pt/Sn on Various Solid Supports

A metal precursor solution was first prepared by mixing a solution of Sn(oxalate)/hydrogen peroxide/citric acid (10.2 wt % Sn) and $PtONO_3$ (62.5 wt % Pt) in de-ionized water to obtain the various Pt—Sn ratios shown in Table 3. This solution was used to impregnate a $ZrO_2$ (Saint Gobain, BET specific surface area 40 m$^2$/g, particle size 75-150 nm), $ZrO_2$—$TiO_2$ (Saint Gobain 40 wt % $TiO_2$, SZ 39140, BET specific surface area 80 m$^2$/g, particle size 75-150 μm), $TiO_2$ (Saint Gobain ST 31119, BET specific surface area 40 m$^2$/g, particle size 75-150 μm), or Silicon Carbide (SiCat, BET specific surface area 25 m$^2$/g, particle size 150-250 μm) support. After impregnation, the material was dried at 120° C. for 3 hours, then reduced under a flow of forming gas (5% $H_2$ in $N_2$) at 350° C. for 3 hours.

Example 21

Catalyst Performance Assay and Production of FDCA Pathway Products

Catalyst testing was conducted within 1 mL glass vials housed in a 96-well insert situated in a high pressure high throughput reactor. See Diamond, G. M., Murphy, V., Boussie, T. R., in *Modern Applications of High Throughput R&D in Heterogeneous Catalysis*, (eds, Hagemeyer, A. and Volpe, A. Jr. Bentham Science Publishers 2014, Chapter 8, 299-309); see also U.S. Pat. No. 8,669,397, both of which are herein expressly incorporated by reference in their entireties. 10 mg of each powder catalyst was placed into a reactor along with 0.25 mL of a solution prepared in a 3:2 (wt/wt) dioxane:$H_2O$ mixture containing 0.5 M 5-hydroxymethylfurfural (HMF) (6.0 wt %). The 1 mL reaction vials within the insert were each covered with a Teflon sheet, a silicon mat and a steel gas diffusion plate each containing pin-holes to enable gas entry. The insert was placed within a pressure vessel which was leak tested under nitrogen pressure. The atmosphere within the reactor was then replaced by oxygen at a target pressure of 200 psig and the reactor was heated to a target temperature of 120° C., and then shaken at 800 rpm for 120 min. After the reaction was completed, the shaking was stopped and the reactor was cooled down to room temperature. Samples were prepared for HPLC analysis by sampling from each reactor after diluting the sample with dimethyl sulfoxide (DMSO) and $H_2O$. Reaction products were 5-hydroxymethylfurancarboxylic acid (HMFCA), 2,5-furandicarboxaldehyde (DFF), 5-formylfuran-3-carboxylic acid (FFCA) and 2,5-furandicarboxylic acid (FDCA). Each of the above products as well as remaining HMF were quantified through a calibration curve for each analyte by plotting the relative concentration against the relative detector response for calibration standards, and performing a fit to a parabolic expression. The mass balance (MB) is the sum of remaining HMF (not shown in Table 3), FFCA, and FDCA pathway products. The results are shown in Table 3.

TABLE 3

Catalyst Composition and Performance in Oxidation of HMF

| Experiment No. | Support | Pt (wt %) | Promoter (wt %) | HMFCA Yield (%) | DFF Yield (%) | FFCA Yield (%) | FDCA Yield (%) | MB Yield (%) |
| --- | --- | --- | --- | --- | --- | --- | --- | --- |
| 1 | ZrO$_2$ | 3 | Bi (1.0) | 0 | 0.1 | 34.3 | 54.1 | 88.5 |
| 2 | ZrO$_2$ | 3 | Te (0.3) | 0 | 0 | 33.1 | 52.6 | 85.7 |

TABLE 3-continued

Catalyst Composition and Performance in Oxidation of HMF

| Experiment No. | Support | Pt (wt %) | Promoter (wt %) | HMFCA Yield (%) | DFF Yield (%) | FFCA Yield (%) | FDCA Yield (%) | MB Yield (%) |
|---|---|---|---|---|---|---|---|---|
| 3 | ZrO$_2$ | 3 | Te (1.0) | 0 | 0 | 16.0 | 66.3 | 82.3 |
| 4 | ZrO$_2$ | 3 | Sn (0.3) | 0.1 | 0 | 31.1 | 53.2 | 84.4 |
| 5 | ZrO$_2$ | 3 | Sn (0.6) | 0.1 | 0 | 27.7 | 57.7 | 85.5 |
| 6 | ZrO$_2$—TiO$_2$ | 3 | Bi (0.3) | 0 | 1.3 | 41.2 | 42.9 | 85.4 |
| 7 | ZrO$_2$—TiO$_2$ | 3 | Bi (0.6) | 0 | 1.2 | 39.8 | 43.1 | 84.1 |
| 8 | ZrO$_2$—TiO$_2$ | 3 | Te (0.3) | 0 | 0.4 | 35.6 | 48.3 | 84.4 |
| 9 | ZrO$_2$—TiO$_2$ | 3 | Te (1.0) | 0 | 0 | 19.3 | 62.9 | 82.2 |
| 10 | ZrO$_2$—TiO$_2$ | 3 | Sn (0.3) | 0.1 | 0.4 | 36.0 | 46.4 | 82.7 |
| 11 | ZrO$_2$—TiO$_2$ | 3 | Sn (0.6) | 0.1 | 0.3 | 35.5 | 47.3 | 83.2 |
| 12 | TiO$_2$ | 3 | Bi (0.3) | 0 | 0.4 | 39.2 | 52.8 | 92.5 |
| 13 | TiO$_2$ | 3 | Bi (1.0) | 0 | 0.1 | 31.7 | 59.7 | 91.6 |
| 14 | TiO$_2$ | 3 | Te (0.3) | 0 | 0 | 27.6 | 58.1 | 85.7 |
| 15 | TiO$_2$ | 3 | Te (1.0) | 0 | 0 | 10.4 | 73.8 | 84.2 |
| 16 | TiO$_2$ | 3 | Sn (0.3) | 0.1 | 0 | 27.8 | 57.7 | 85.6 |
| 17 | TiO$_2$ | 3 | Sn (0.6) | 0.1 | 0 | 20.2 | 65.4 | 85.7 |
| 18 | SiC | 3 | Bi (1.0) | 2.5 | 7.9 | 4.5 | 3.0 | 92.6 |
| 19 | SiC | 3 | Te (0.3) | 0 | 0 | 20.0 | 70.4 | 90.5 |
| 20 | SiC | 3 | Te (0.6) | 0 | 0 | 8.3 | 76.3 | 84.7 |
| 21 | SiC | 3 | Sn (0.3) | 0.1 | 0 | 33.7 | 56.2 | 90.0 |
| 22 | SiC | 3 | Sn (1.0) | 0.1 | 0 | 19.1 | 68.3 | 87.5 |

Example 22

Performance of Various Bi/Pt Ratios Solid Supports

HMF to FDCA oxidations utilizing various ratios of Bi/Pt on carbon black, zirconia, and montmorillonite supports were performed. Four supports were used: Sid Richardson SC159 (carbon black), Orion Asperse 5-183A (carbon black), zirconia Z1247, and montmorillonite KA-160. All supports were crushed and sieved from their corresponding extrudates to about 75-150 μm. Single fixed co-impregnation of the solid support was performed with PtONO$_3$+Bi(NO$_3$)$_3$ in 2.0M HNO$_3$ followed by drying and a forming gas reduction at 350° C. for 3 h. Single fixed co-impregnation was performed with 3 wt. % Pt and 0 wt. %, 0.1 wt. %, 0.3 wt. %, 0.6 wt. %, 1 wt. % and 1.5 wt. % Bi corresponding to Bi/Pt ratios of 0.033, 0.1, 0.2, 0.33 and 0.5 (control excluded), or performed with 2 wt. % Pt and 0.1 wt. %, 0.3 wt. %, 0.6 wt. % and 1 wt. % Bi corresponding to Bi/Pt ratios of 0.05, 0.15, 0.3 and 0.5. 5 or 10 mg of catalyst were used in reactions with 0.25 mL of a substrate of 6.0 wt. % (0.50M) HMF in 60 wt. % dioxane/40 wt. % H$_2$O. The reaction was carried out in a reactor with 200 psi O$_2$ (RT) at 125° C. for 2 h and 800 rpm. The results are shown in FIGS. 13-20.

Example 23

Performance of Bi/Pt on Various Titania Supports

HMF to FDCA oxidations utilizing Pt and Bi/Pt catalysts on various titania supports were performed. 12 Powder titania supports were used: Saint-Gobain NorPro ST61120, ST31119 and ST39119 (wherein ST31119 and ST39119 are the same Titania support but with different shape); Süd-Chemie T-2809 Ti-211 and T-2809 Ti-411; Cristal Global ACTiV DT-S10, DT-51, DT-52, DT-58, DT-W5 (in the form of ultrafine powders); and Hombikat, Degussa P25 (in the form of an ultrafine powder). Three metal and/or promoter loadings were produced: 3.0 wt. % Pt, 0.30 wt. % Bi+3.0 wt. % Pt, and 0.60 wt. % Bi+3.0 wt. % Pt. Single fixed co-impregnation of the solid support was performed with PtONO$_3$ for the 3.0 wt. % Pt loading, Bi(NO$_3$)$_3$+PtONO$_3$ for the 0.30 wt. % Bi+3.0 wt. % Pt loading, and Bi(NO$_3$)$_3$+PtONO$_3$ in 1.0M HNO$_3$ for the 0.60 wt. % Bi+3.0 wt. % Pt loading, followed by drying at 120° C. for 2 h and a forming gas reduction at 350° C. for 3 h. 8.0 mg of catalyst was used in reactions with 0.25 mL of a substrate of 6.0 wt. % (0.50M) HMF in 60 wt. % dioxane/40 wt. % H$_2$O. The reaction was carried out at 200 psi O$_2$ (RT) at 125° C. for 2 h at 800 rpm. The results are shown in FIGS. 21-28.

Example 24

Performance of Bi/Pt on Various Zirconia Supports

HMF to FDCA oxidations utilizing Pt and Bi/Pt catalysts on various zirconia supports were performed. Six powder zirconia supports were used: Saint-Gobain NorPro SZ-1247 and SZ-39140(Ti); Daiichi Kigenso Kagaku Kogyo Z-2962 (W), Z-2087(W) and Z-1044(W); and an in-house prepared EG143-59/61-1 (W) (Morgan Parr & Elif Gurbuz). Three metal and/or promoter loadings were produced: 3.0 wt. % Pt, 0.30 wt. % Bi+3.0 wt. % Pt, and 0.60 wt. % Bi+3.0 wt. % Pt. Single fixed co-impregnation of the solid support was performed with PtONO$_3$ for the 3.0 wt. % Pt loading, Bi(NO$_3$)$_3$+PtONO$_3$ for the 0.30 wt. % Bi+3.0 wt. % Pt loading, and Bi(NO$_3$)$_3$+PtONO$_3$ in 1.0M HNO$_3$ for the 0.60 wt. % Bi+3.0 wt. % Pt loading, followed by drying at 120° C. for 2 h and a forming gas reduction at 350° C. for 3 h. 8.0 mg of catalyst was used in reactions with 0.25 mL of a substrate of 6.0 wt. % (0.50M) HMF in 60 wt. % dioxane/40 wt. % H$_2$O. The reaction was carried out at 200 psi O$_2$ (RT) at 125° C. for 2 h at 800 rpm. The results are shown in FIGS. 29-36.

Example 25

Performance of Bi/Pt on Tungstated Titania and Zirconia Supports with High Bi Loadings HMF to FDCA oxidations utilizing Pt and Bi/Pt catalysts on various tungstated titania and zirconia supports were performed. Titania supports used are: Saint-Gobain NorPro ST31119, Crystal ActiV DT-51D, and Crystal ActiV DT-52 with 10 wt. % $WO_3$. Zirconia supports used are: Saint-Gobain NorPro 61143 with 17 wt. % $WO_3$, Tetragonal like 61143 with 9 wt. % $WO_3$, Monoclinic with 5 wt. % $WO_3$, $Zr(OH)_4$ with 8 wt. % TiO and 29 wt. % $WO_3$ and $Zr(OH)_4$ with 9 wt. % $TiO_2$; DKKK Z-1581 with 10 wt. % $WO_3$, Z-2944 with 20 wt. % TiO and 25 wt. % $WO_3$; MEL Cat $Zr(OH)_4$ XZ02628/01 with 10 wt. % $WO_3$; and in-house prepared MP140-28-2 with 9 wt. % $WO_3$ from XZ02628/01 with 10% binder of Nyacol $ZrO_2$(AC) & Zusoplast WE-8 (Morgan Parr). 3 wt. % Pt was loaded with 0.30 wt. % Bi, 0.60 wt. % Bi, 1.0 wt. % Bi, or 1.5 wt. % Bi. Supports were treated at 600° C. for 3 h in air or at 800° C. for 3 h in air. Single fixed co-impregnation of the solid support was performed with $Bi(NO_3)_3$+$PtONO_3$ in 1.0M $HNO_3$, followed by drying at 120° C. for 2 h and a 350° C./3 h forming gas reduction. An additional 400° C. for 2 h in air calcination was performed after forming gas reduction of catalysts was used on the catalyst formed of $BiPt/ZrO_2$ (17 wt. % $WO_3$) SZ61143. Without being bound to theory, an additional 400° C. for 2 h in air calcination may oxidize some reduced WIn support to back into $WO_3$. 8.0 mg of catalyst was used in reactions with 0.25 mL of a substrate of 6.0 wt. % (0.50M) HMF in 60 wt. % dioxane/40 wt. % $H_2O$. The reaction was carried out at 200 psi $O_2$ (RT) at 125° C. for 2 h at 800 rpm. The results are shown in FIGS. 37-44.

Example 26

Fixed Bed Reaction with Pt on Zirconia Support

Figure 45:
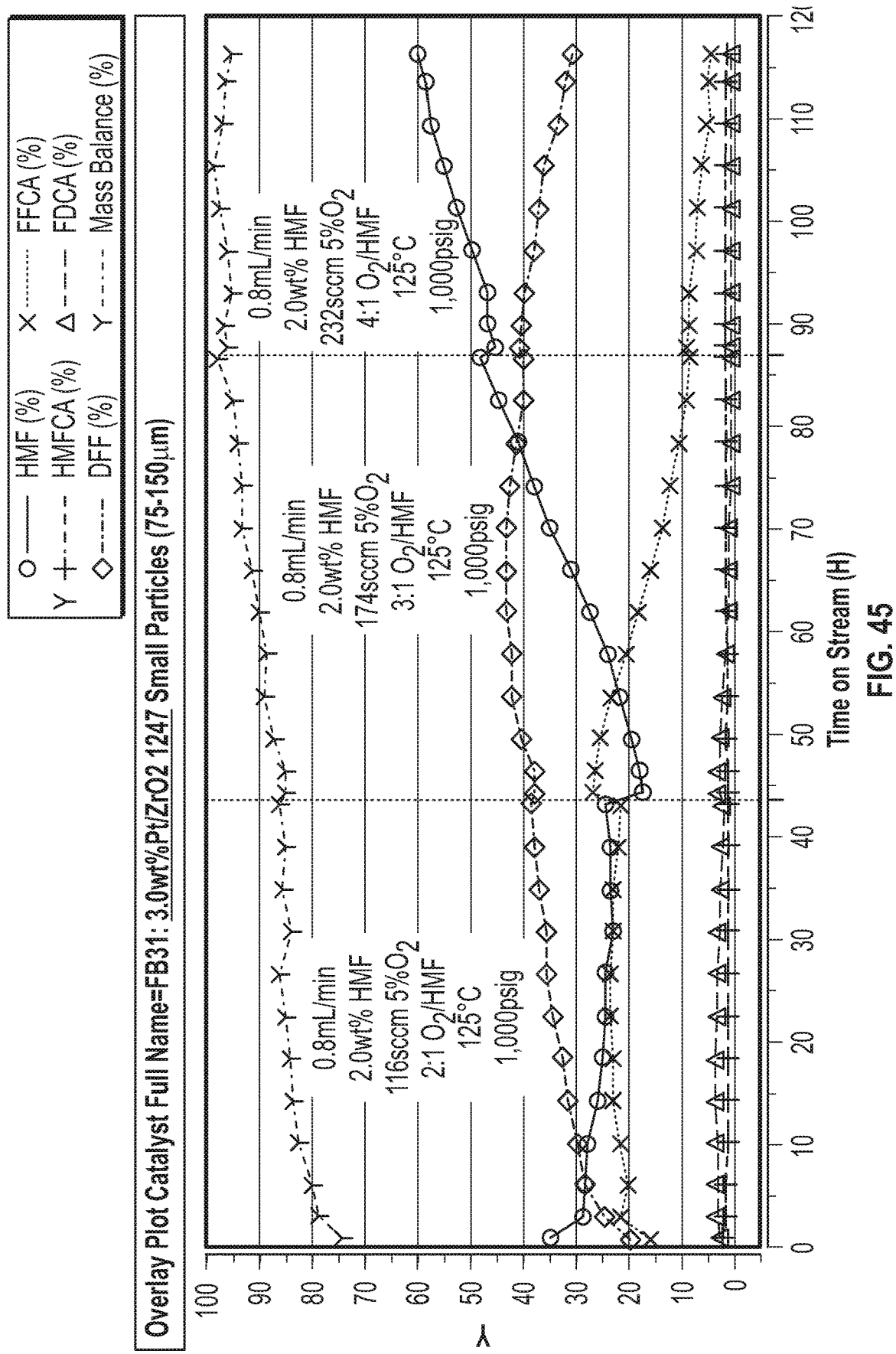
FIGS. 45-47 depict the distribution of products and metal leaching for the fixed bed oxidation of a HMF substrate utilizing Pt catalysts on zirconia supports with varying reaction conditions.
Figure 46:
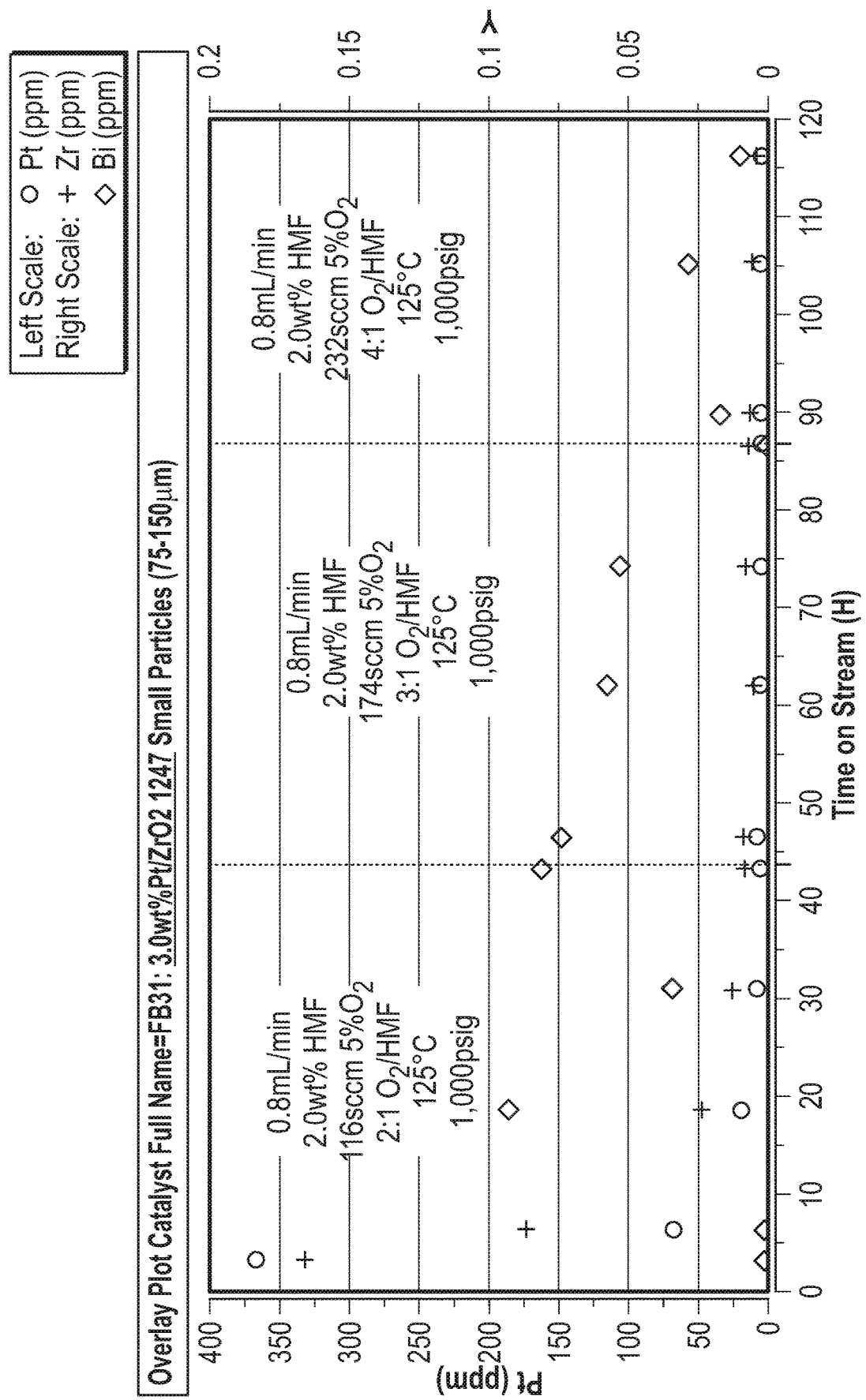
Figure 47:
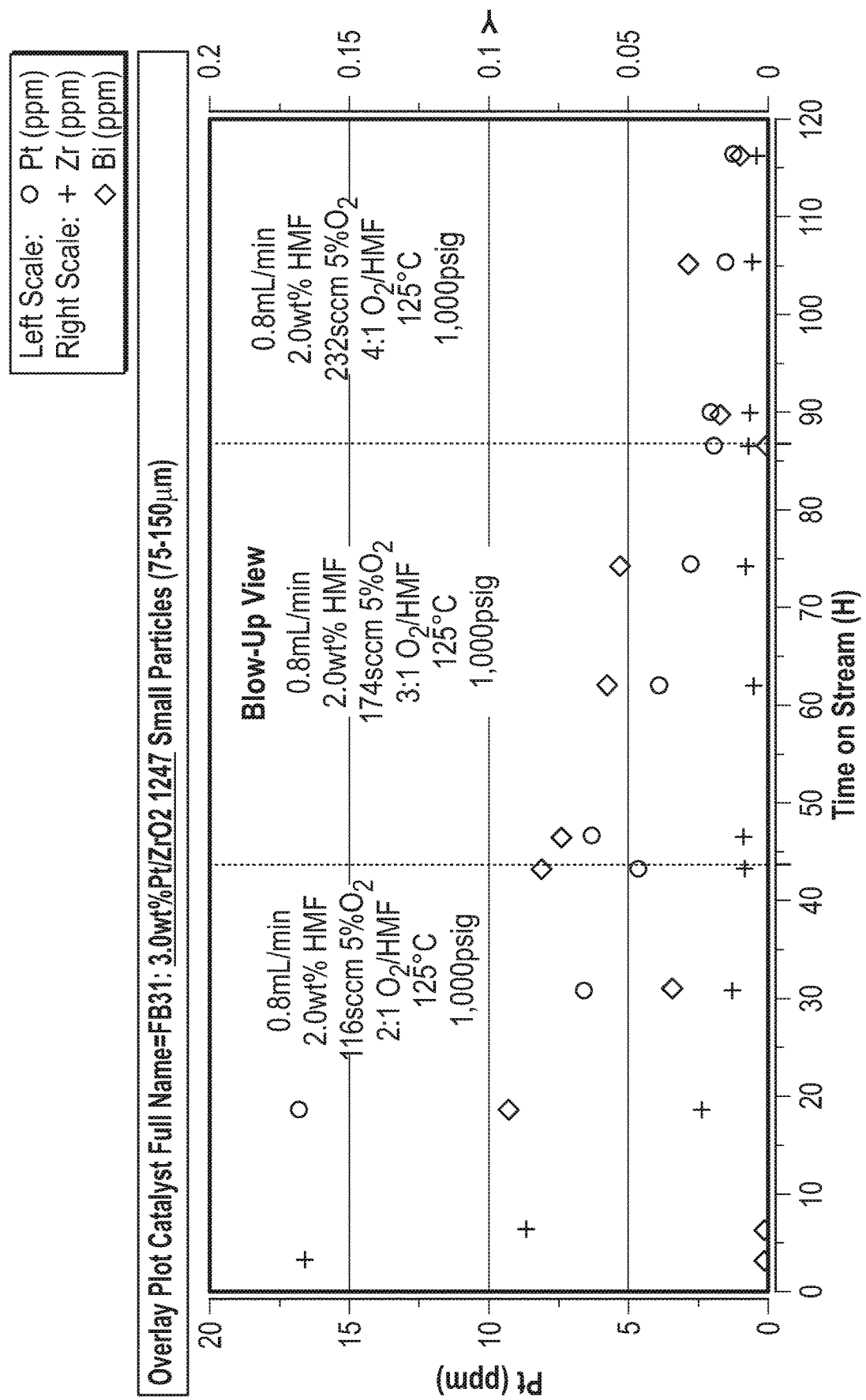

HMF to FDCA fixed bed oxidation reactions utilizing Pt catalysts on zirconia supports were performed in a ¼ inch reactor. The catalyst comprises 4.2 g of 3.0 wt. % $Pt/ZrO_2$ 1247 (75-150 μm) on a 23 cm bed length in a ¼ inch OD SS tubing. The catalyst was prepared from single fixed impregnation using $PtONO_3$ followed by a forming gas reduction at 350° C. for 3 h. $ZrO_2$ 1247 support is fragile and catalyst synthesis results in 35% loss of material in the desired range of support size. The reaction was carried out in a reactor with 125° C. and 1000 psig at an initially rate of 0.80 mL/min with 116 sccm 5% $O_2$/95% $N_2$ (2:1 $O_2$/HMF molar ratio), 174 sccm 5% $O_2$/95% $N_2$ (3:1 $O_2$/HMF molar ratio), the 232 sccm 5% $O_2$/95% $N_2$ (4:1 $O_2$/HMF molar ratio). A substrate of 2.0 wt % (0.17M) HMF in 60 wt. % dioxane/40 wt. % $H_2O$. Only the bottom half of the reactor was heated due to the short catalyst bed length of the $ZrO_2$ support. The catalyst showed low activity and extremely high initial Pt leaching. The results are shown in FIGS. 45-47.

Example 27

Fixed Bed Reaction with Bi/Pt on Zirconia Support

Figure 48:
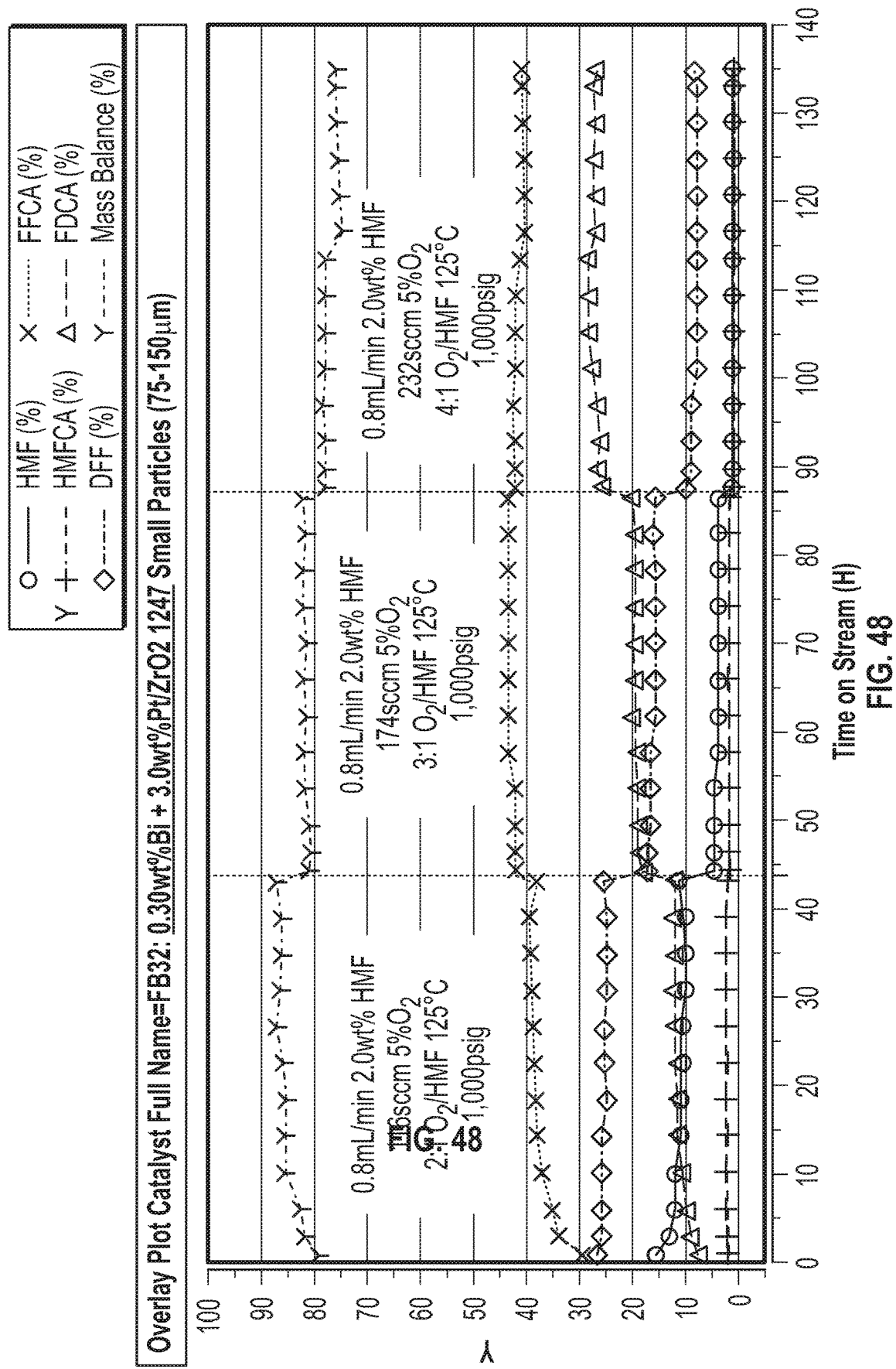
FIGS. 48-50 depict the distribution of products, space time yields (STY) and metal leaching for the fixed bed oxidation of a HMF substrate utilizing Bi/Pt catalysts on zirconia supports with varying reaction conditions.
Figure 49:
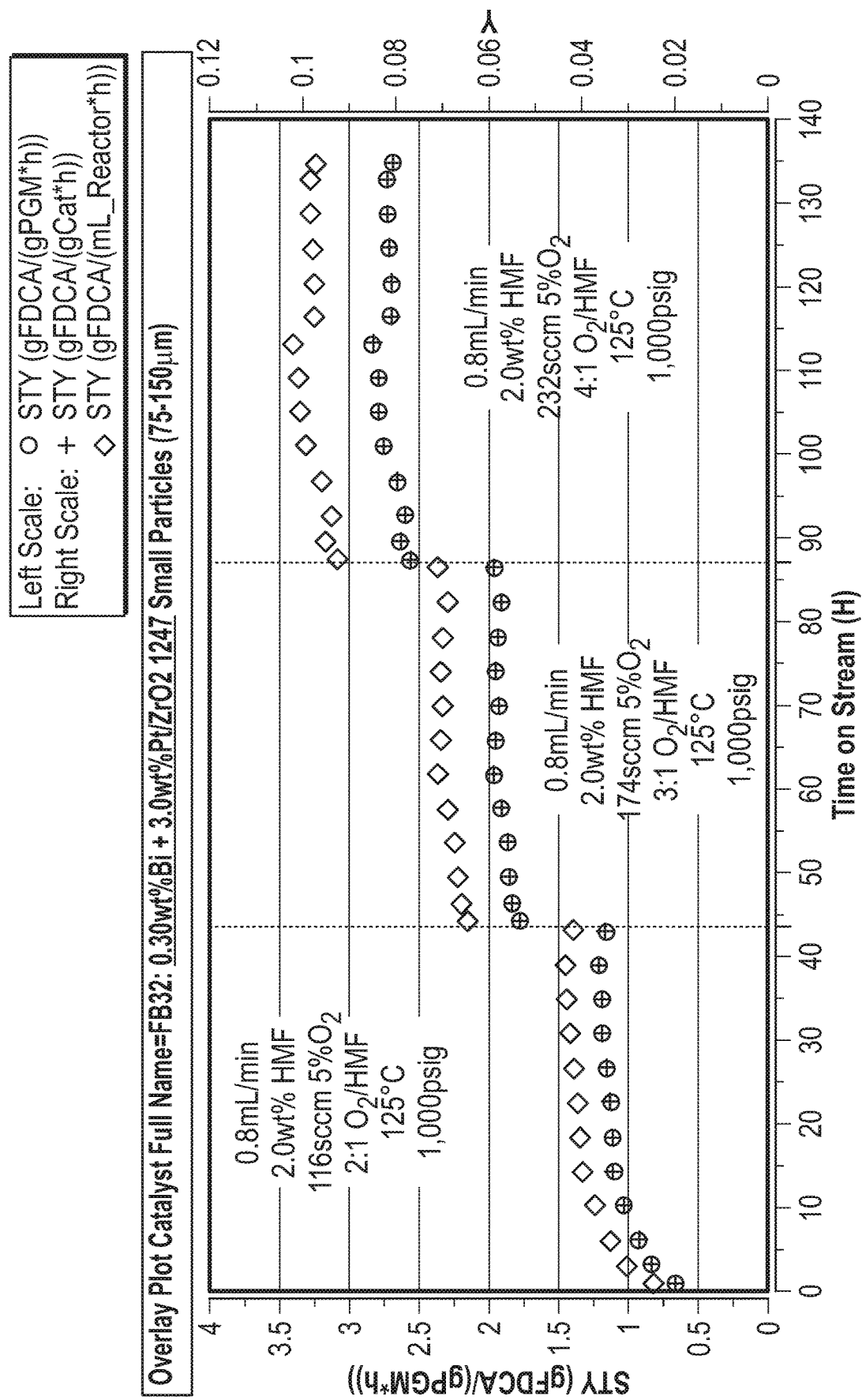
Figure 50:
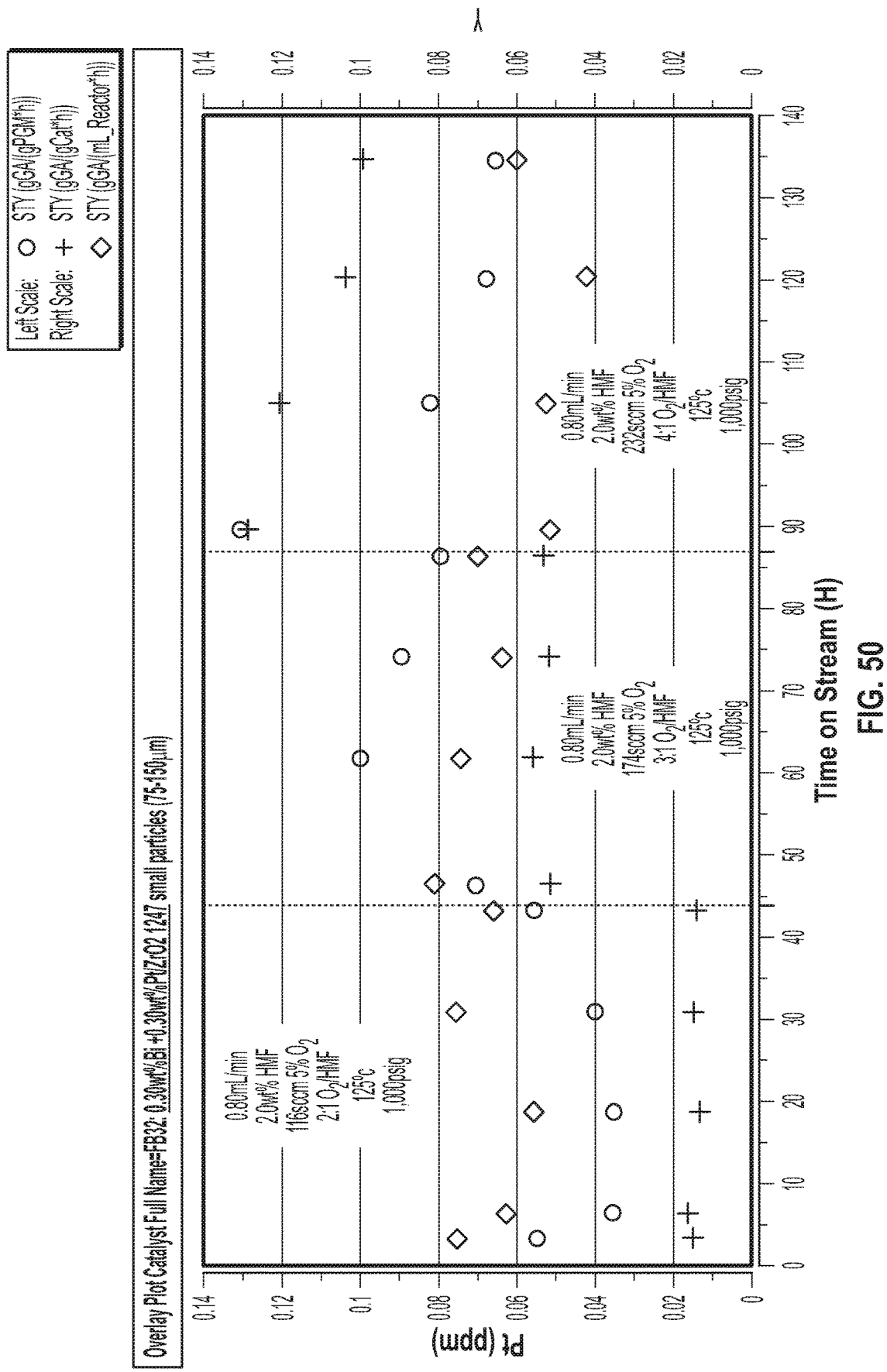
Figure 51:
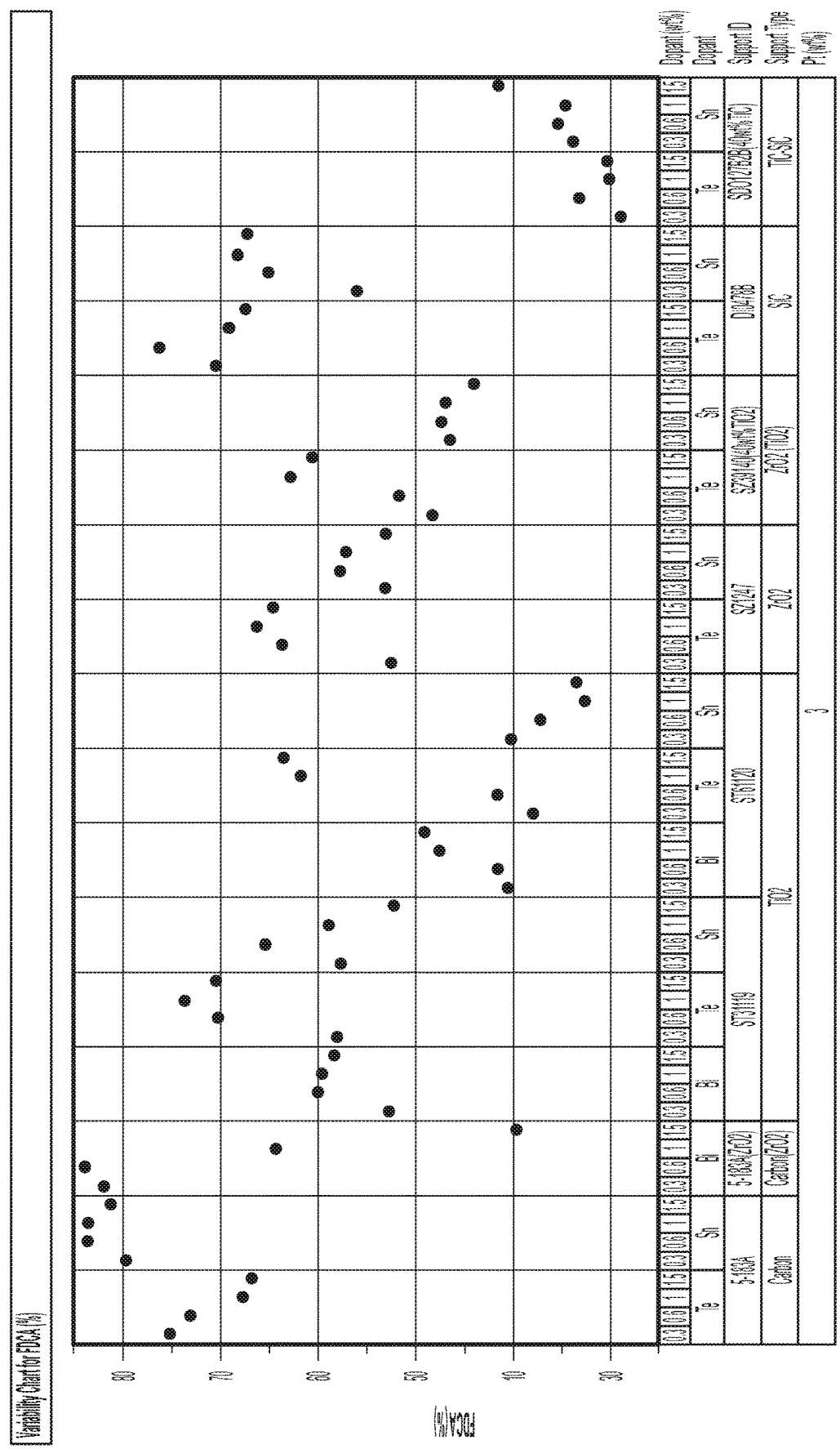
FIGS. 51-55 depict the distribution of products and mass balances for the oxidation of a HMF substrate utilizing Pt/Bi, Pt/Te and Pt/Sn catalysts on various carbon, carbon/$ZrO_2$, $TiO_2$, $ZrO_2$, $ZrO_2/TiO_2$, SiC, and TiC—SiC supports as catalysts, different Pt amounts, and different Bi amounts.
Figure 52:
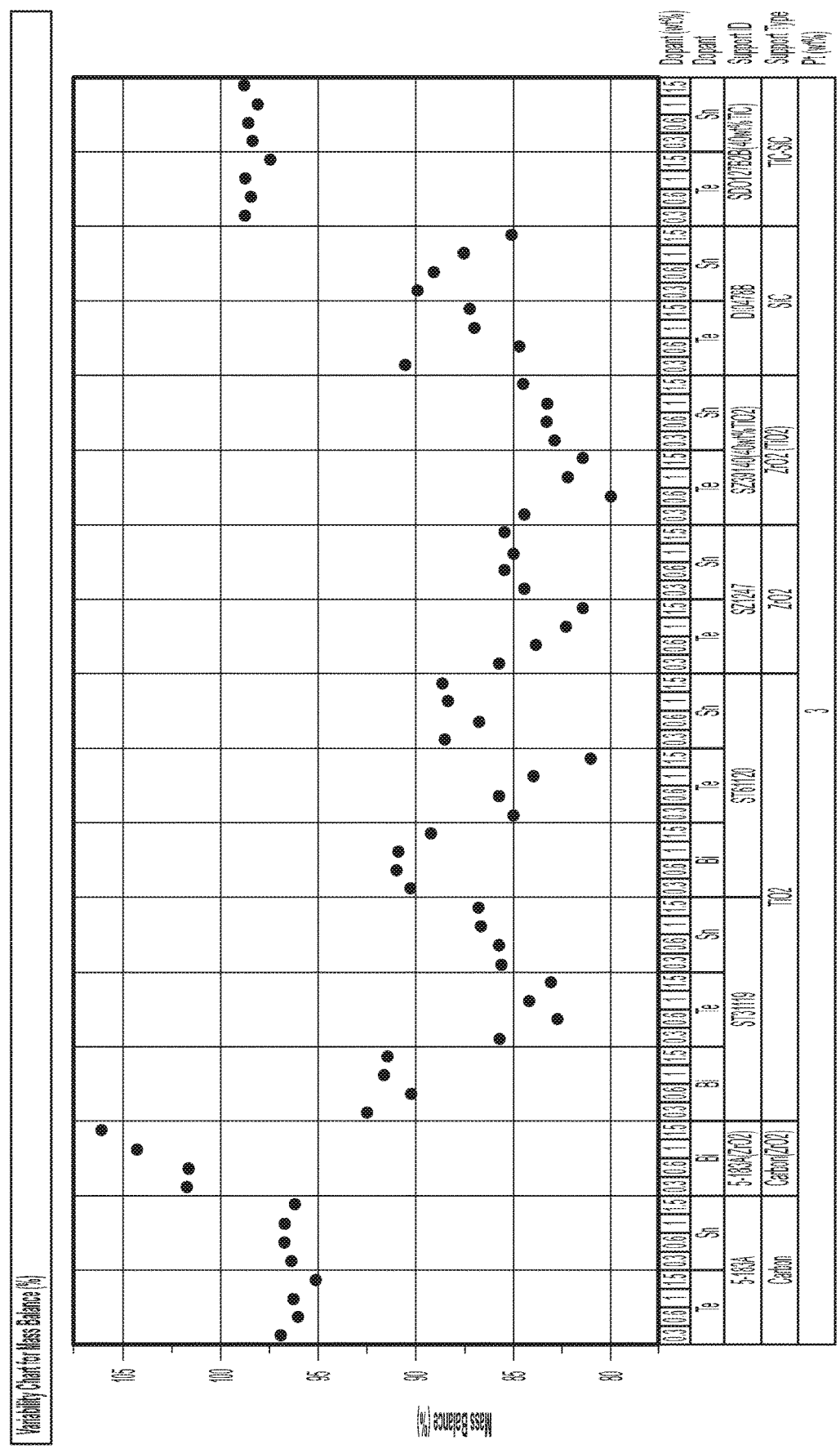
Figure 53:
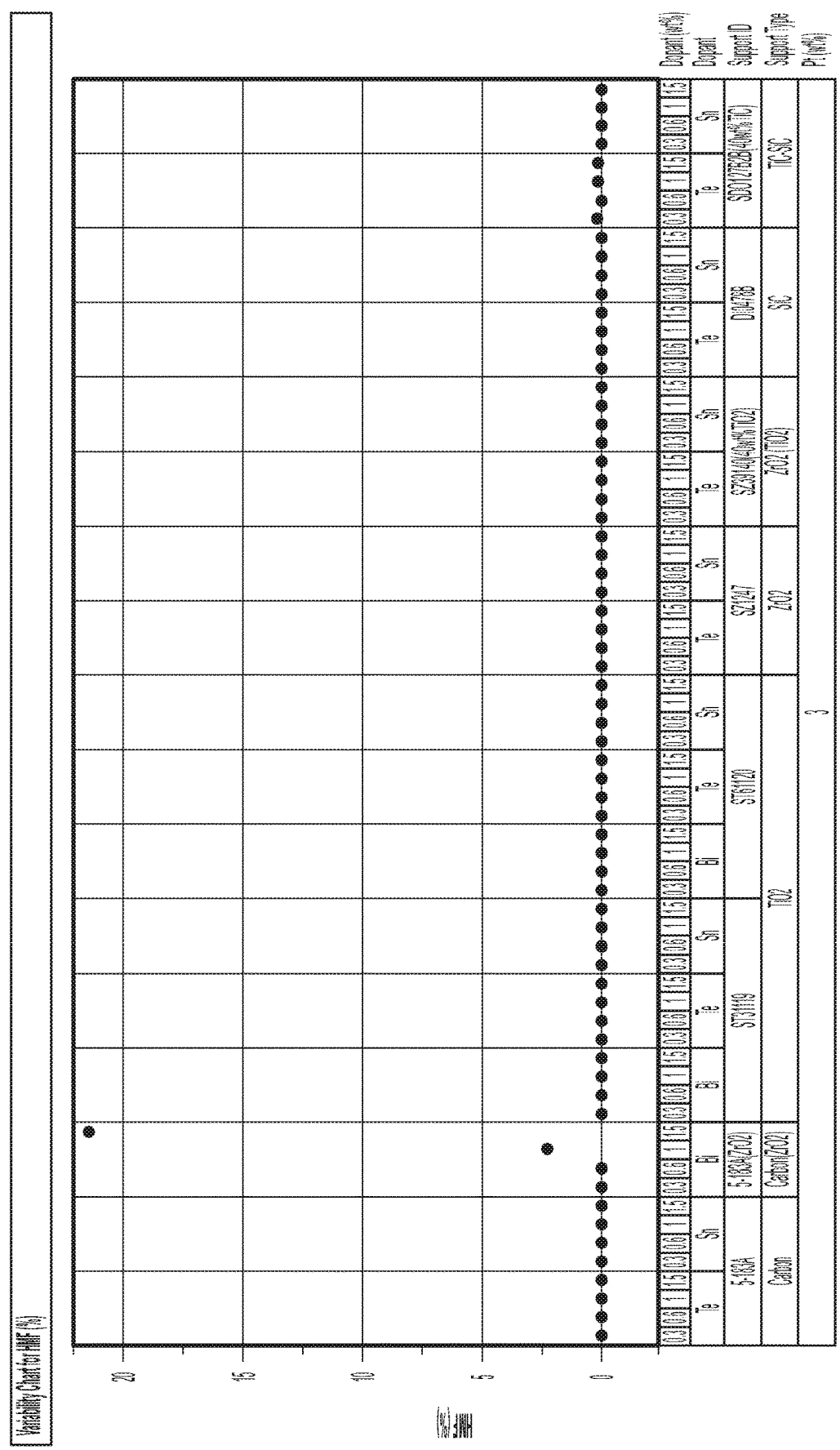
Figure 54:
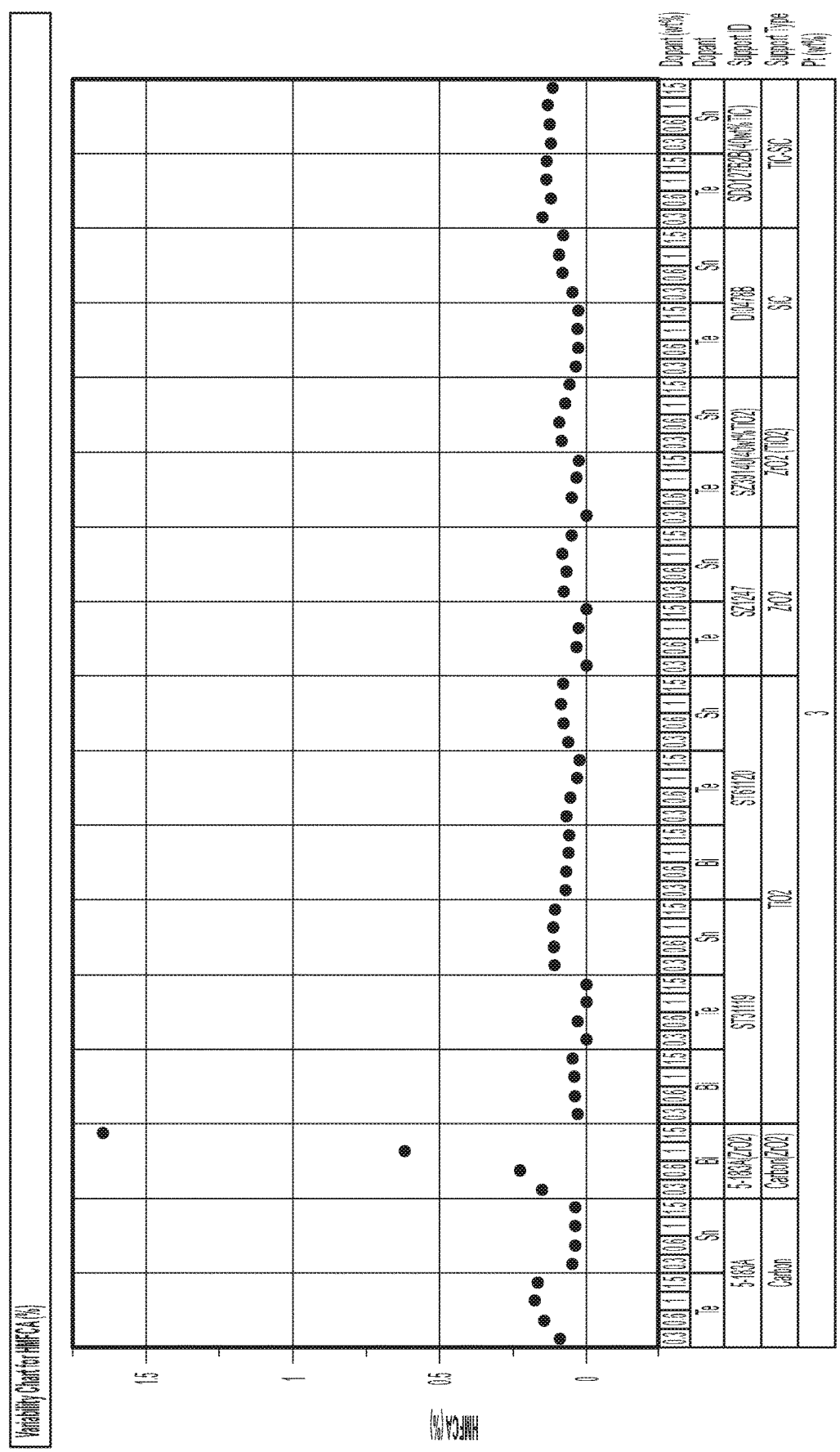
Figure 55:
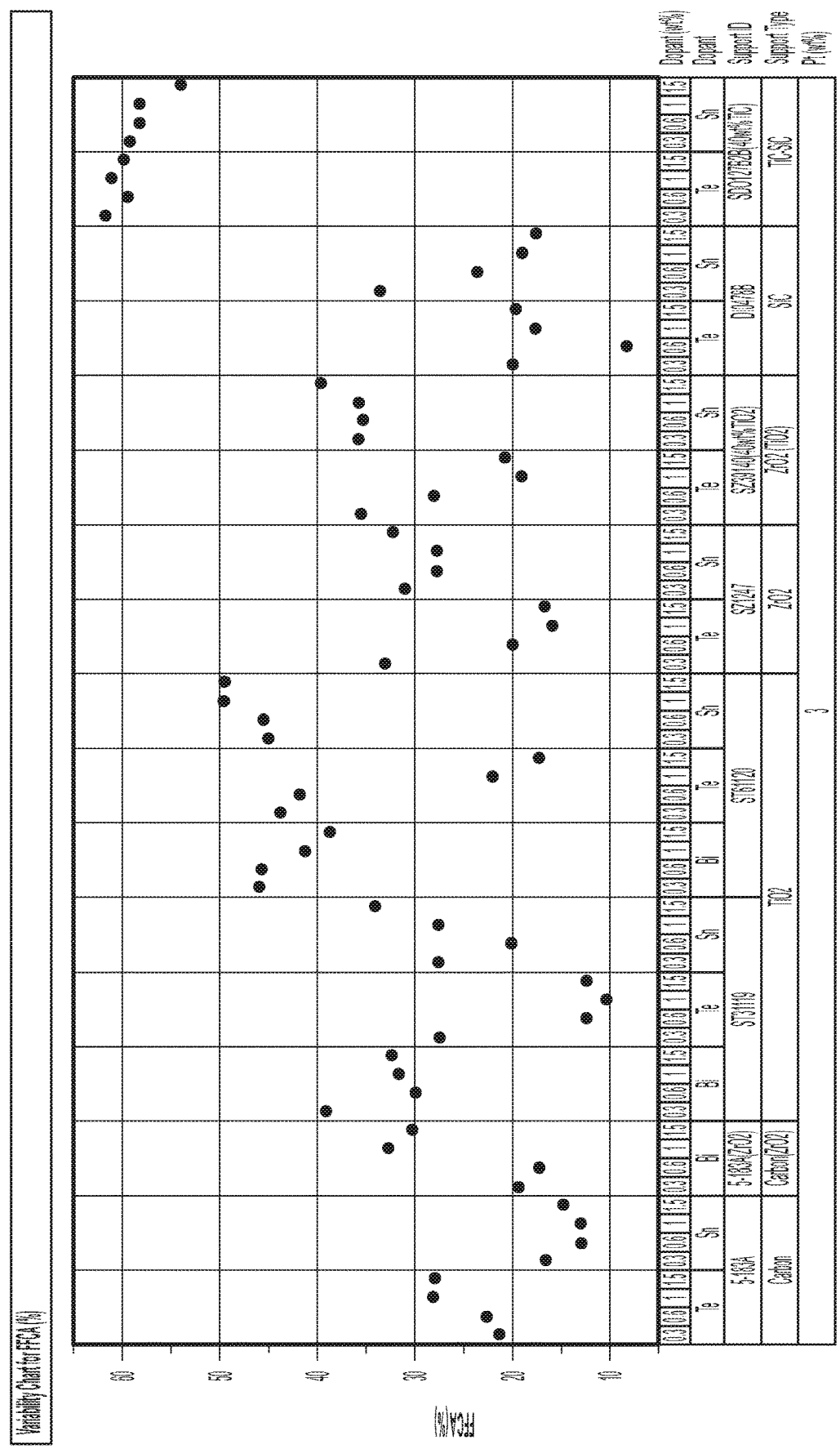

HMF to FDCA fixed bed oxidation reactions utilizing Bi/Pt catalysts on zirconia supports were performed in a ¼ inch reactor. The catalyst comprises 4.2 g of 0.30 wt. % Bi+3.0 wt. % $Pt/ZrO_2$ 1247 (75-150 μm) on a 23 cm bed length in a ¼ inch OD SS tubing. The catalyst was prepared from single fixed co-impregnation using $Bi(NO3)_3$+$PtONO_3$ followed by a forming gas reduction at 350° C. for 3 h. $ZrO_2$ 1247 support is fragile and catalyst synthesis results in 35% loss of material in the desired range of support size. The reaction was carried out in a reactor with 125° C. and 1000 psig at an initially rate of 0.80 mL/min with 116 sccm 5% $O_2$/95% $N_2$ (2:1 $O_2$/HMF molar ratio), 174 sccm 5% $O_2$/95% $N_2$ (3:1 $O_2$/HMF molar ratio), the 232 sccm 5% $O_2$/95% $N_2$ (4:1 $O_2$/HMF molar ratio). A substrate of 2.0 wt % (0.17M) HMF in 60 wt. % dioxane/40 wt. % $H_2O$. Only the bottom half of the reactor was heated due to the short catalyst bed length of the $ZrO_2$ support. The catalyst showed higher activity than Example 26 catalyst, very low Pt leaching, very low Bi leaching, and very low Zr leaching. The results are shown in FIGS. 48-50.

Example 28

Performance of Pt/Bi, Pt/Te and Pt/Sn on Various Solid Supports

HMF to FDCA oxidations utilizing Pt/Bi, Pt/Te and Pt/Sn catalysts on various carbon, carbon/$ZrO_2$, $TiO_2$, $ZrO_2$, $ZrO_2$/$TiO_2$, SiC, and TiC—SiC supports were performed. Pt/Bi catalysts comprise 3 wt. % Pt loaded with 0.30 wt. % Bi, 0.60 wt. % Bi, 1.0 wt. % Bi, or 1.5 wt. % Bi. The Pt/Bi catalysts were prepared on the following supports: in-house prepared carbon 5-183A with 40 wt. % $ZrO_2$ (powder); and Saint-Gobain NorPro $TiO_2$ ST31119 (<75 μm) and ST61120 (<75 μm). Pt/Te and Pt/Sn catalysts comprise 3.0 wt. % Pt loaded with 0.30 wt. % Te or Sn, 0.60 wt. % Te or Sn, 1.0 wt. % Te or Sn, or 1.5 wt. % Te or Sn. The Pt/Te and Pt/Sn catalysts were prepared on the following supports: carbon 5-183A (<75 μm); Saint-Gobain NorPro $TiO_2$ ST31119 (<75 μm), ST61120 (<75 μm); Saint-Gobain NorPro $ZrO_2$ SZ1247 (<75 μm), $ZrO_2$ with 40 wt. % $TiO_2$ SZ39140 (<75 μm); and SiCat SiC DI0478B (150-250 μm), TiC—SiC 40/60 SD0127B2B (powder). Catalyst were synthesized with single fixed co-impregnation of $Pt(NO_3)_x$ with $Bi(NO_3)_3$, $Te(OH)_6$, or Sn(oxalate)/$H_2O_2$/citric acid, followed by forming gas reduction at 350° C. for 3 h. 10.0 mg of powder or small particle catalyst was used in reactions with 0.25 mL of a substrate of 6.0 wt % (0.50M) HMF in 60 wt. % dioxane/40 wt. % $H_2O$. The reaction was carried out at 200 psi $O_2$ (RT) at 125° C. for 2 h at 800 rpm. The results are shown in FIGS. 51-55.

Example 29

Fixed Bed Reaction with Bi/Pt on Zirconia Support

Figure 56:
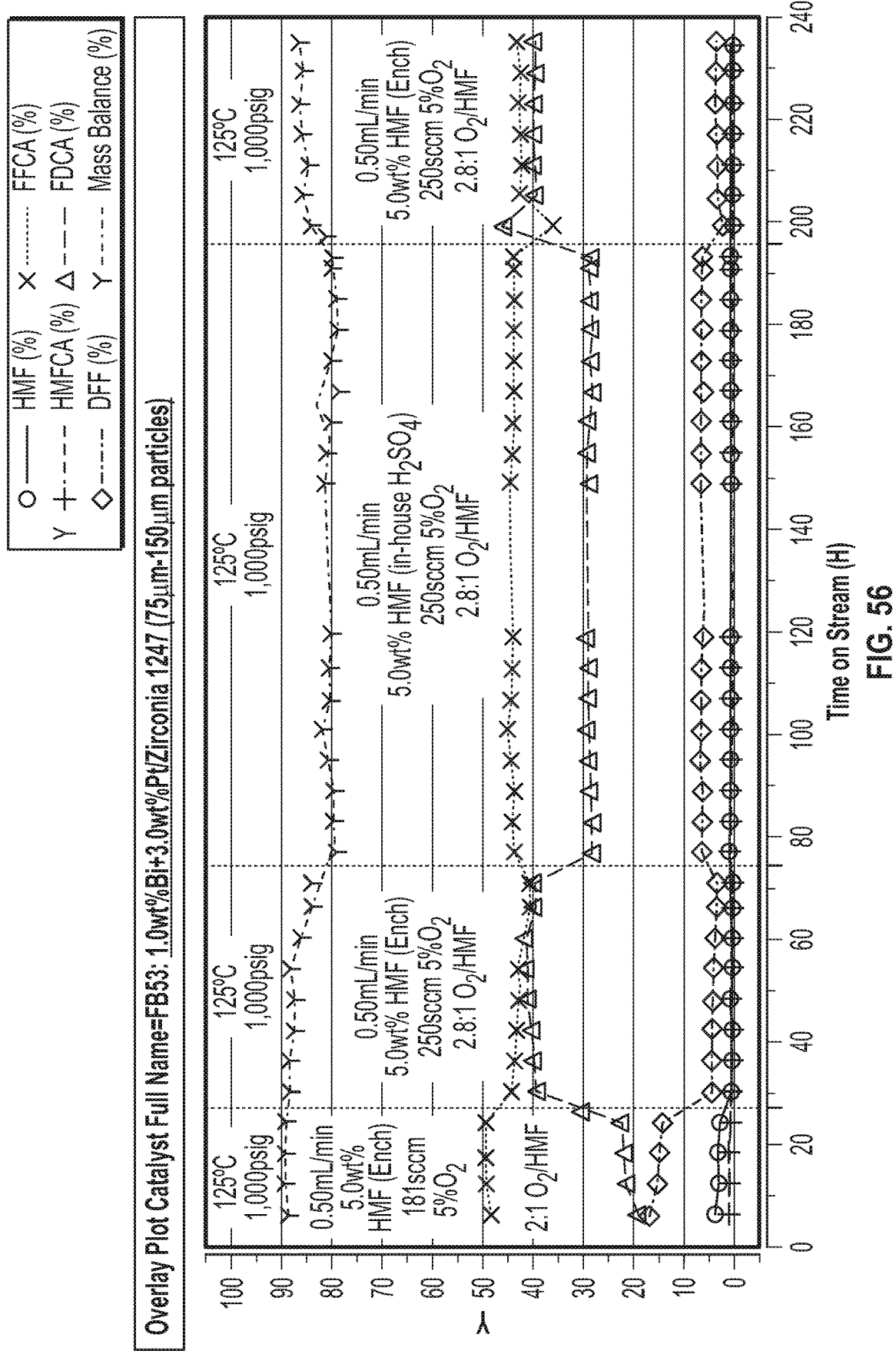
FIGS. 56-58 depict the distribution of products, space time yields (STY) and metal leaching for the fixed bed oxidation of a HMF substrate utilizing small particle Bi/Pt catalysts on zirconia supports with varying reaction conditions.
Figure 57:
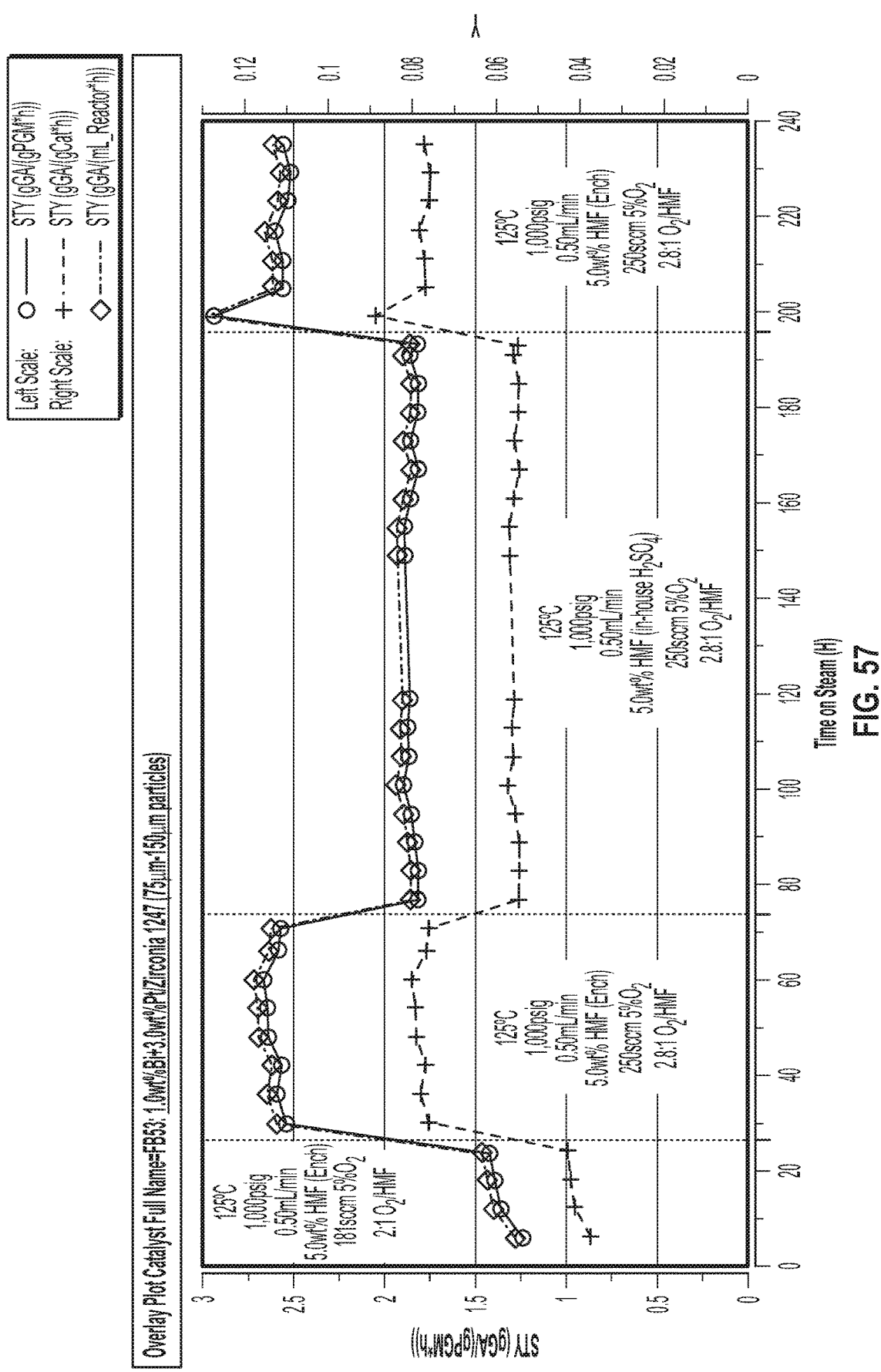
Figure 58:
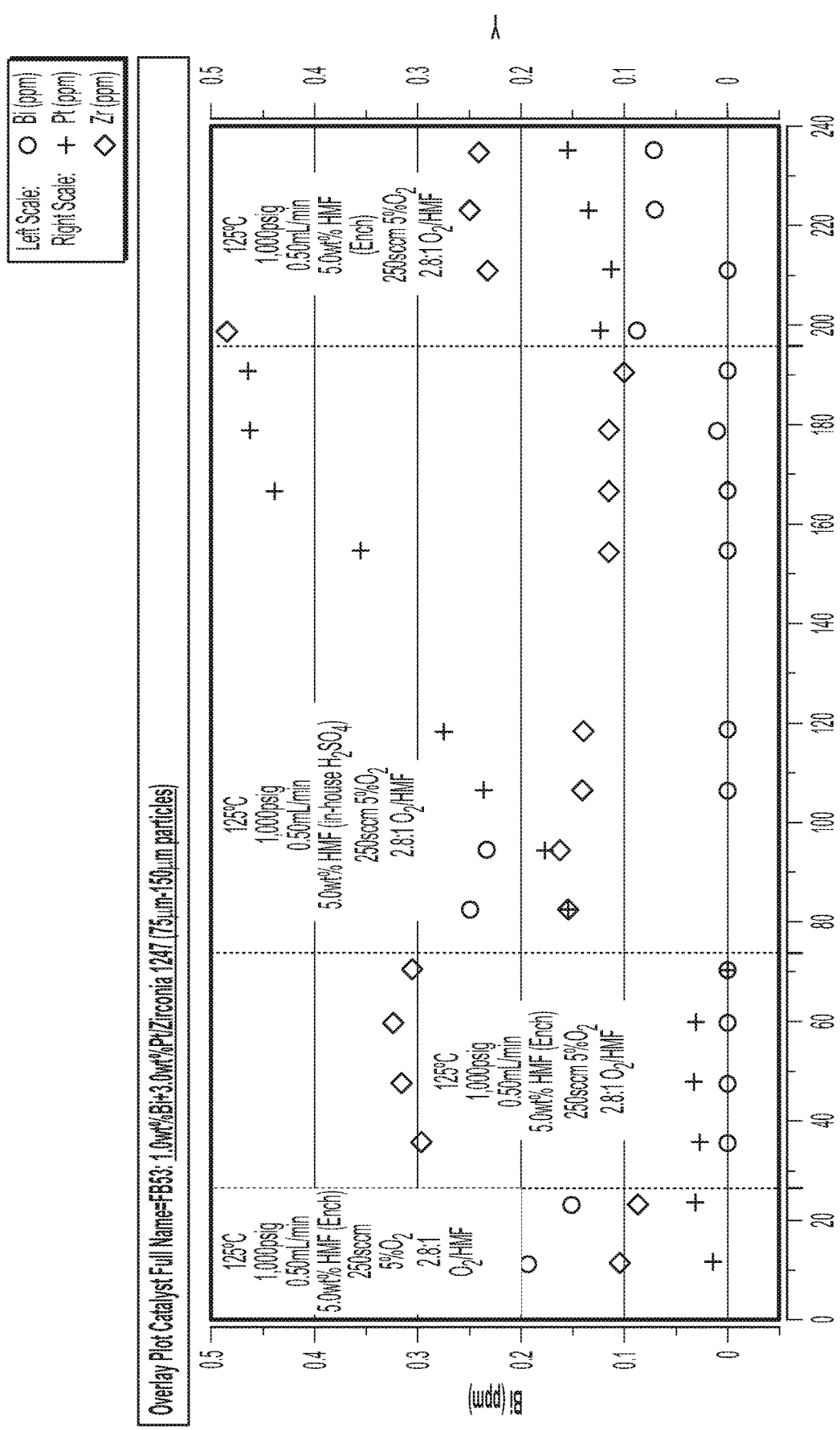

HMF to FDCA fixed bed oxidation reactions utilizing small particle Bi/Pt catalysts on zirconia supports were performed in a ¼ inch MCR. The catalyst comprises 1.0 wt. % Bi+3.0 wt. % Pt/zirconia 1247 (75-150 μm) (Pablo XRF measured 0.92 wt. % Bi+2.82 wt. % Pt). The catalyst was prepared from single fixed co-impregnation using $Bi(NO_3)_3$+$Pt(NO_3)_x$ followed by a forming gas reduction at 120° C. for 2 h in air and 350° C. for 3 h in air. The reaction began with commercial HMF (Ench Industry), switched to $H_2SO_4$ based in-house HMF, and then switched back to commercial HMF (Ench Industry). The reaction was carried out in a reactor with 125° C. and 1000 psig at 0.50 mL/min with 181 sccm 5% $O_2$/95% $N_2$ (2:1 $O_2$/HMF molar ratio), then 250 sccm 5% $O_2$/95% $N_2$ (2.8:1 $O_2$/HMF molar ratio). The catalyst comprises 45 cm of 10.1 g 1.0 wt. % Bi+3.0 wt. % Pt/Zirconia 1247 (75-150 μm). A substrate of 5.0% HMF (EnchIndustry) in 60 wt. % dioxane/40 wt. % $H_2O$. With commercial HMF, both Bi and Pt leaching is very low after initial spike. $H_2SO_4$ based in-house HMF gives more initial Bi and Pt leaching, but lower Zr leaching than commercial HMF (EnchIndustry). The results are shown in FIGS. 56-58.

Example 30

Fixed Bed Reaction with Bi/Pt on Zirconia/Titania Support

Figure 59:
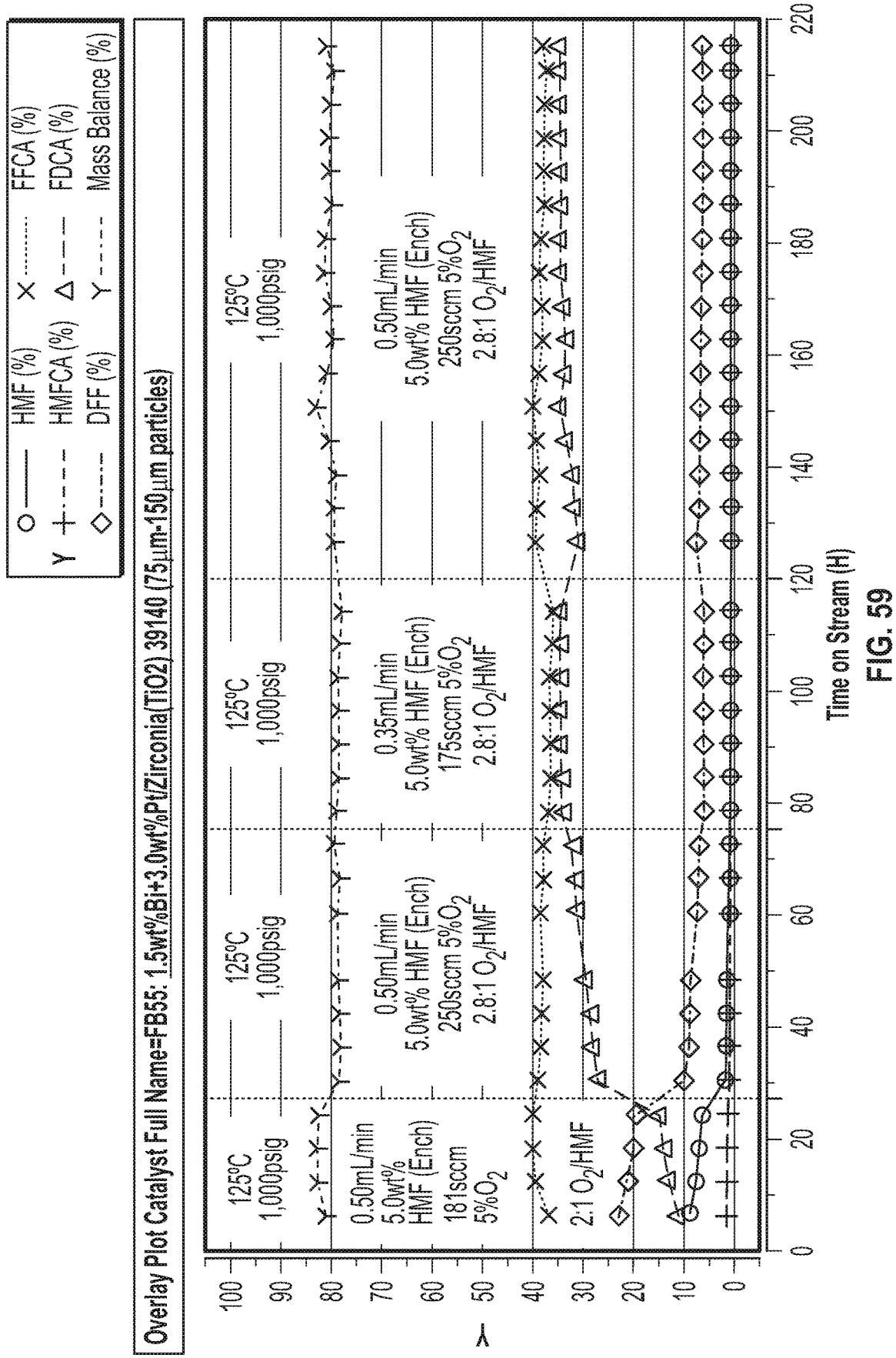
FIGS. 59-60 depict the distribution of products and space time yields (STY) for the fixed bed oxidation of a HMF substrate utilizing small particle Bi/Pt catalysts on zirconia/titania supports with varying reaction conditions.
Figure 60:
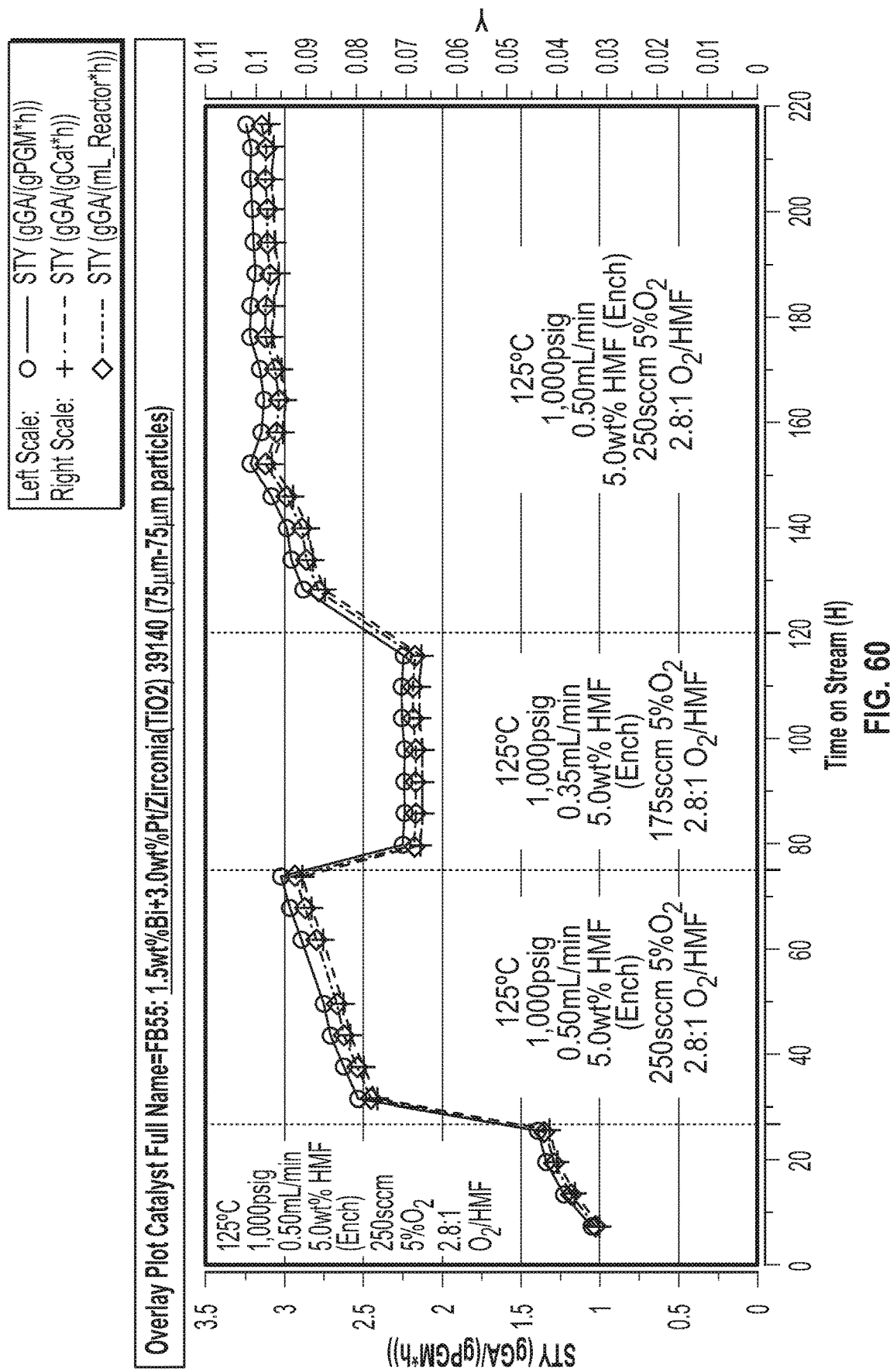
Figure 61:
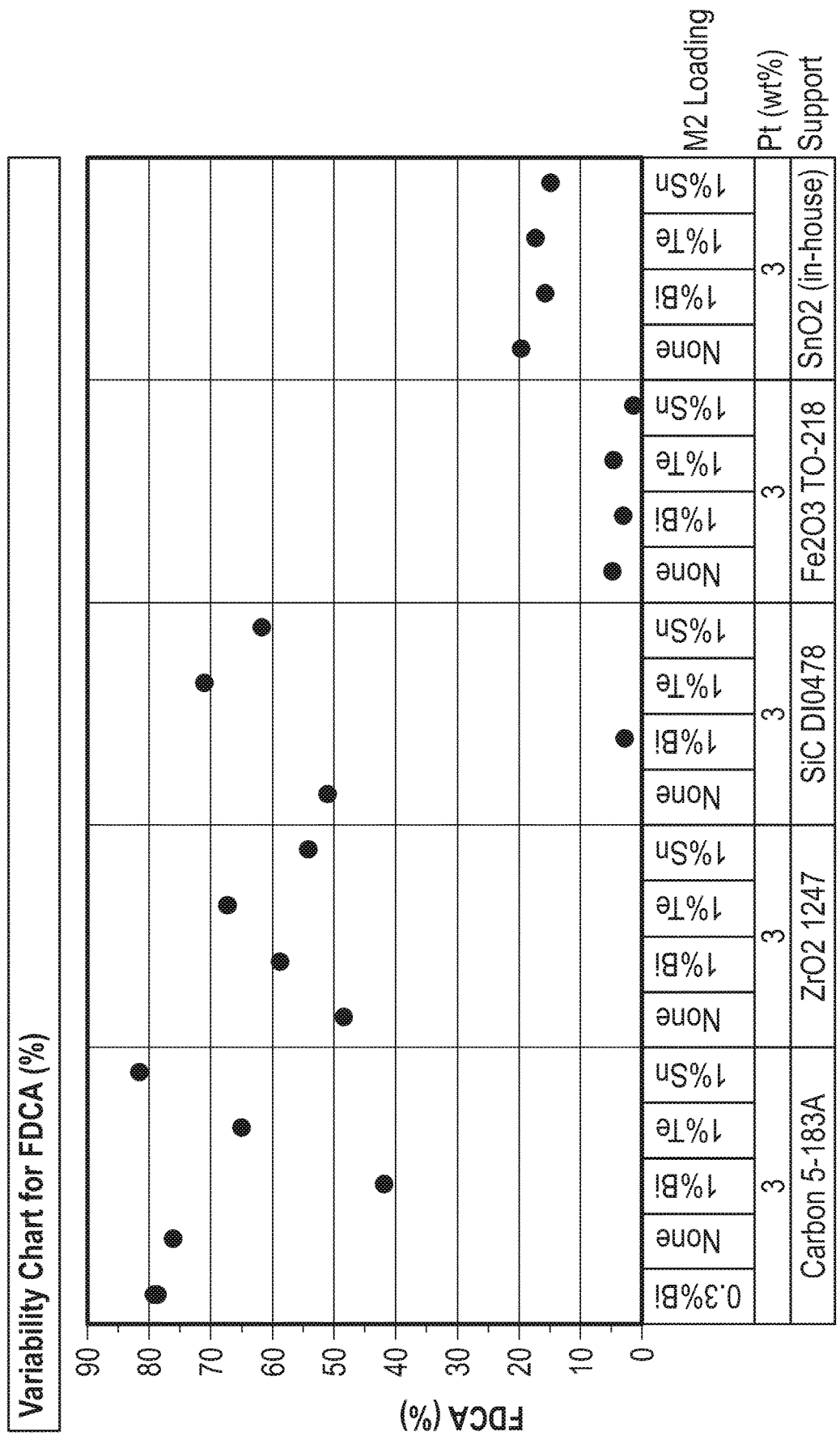
FIGS. 61-68 depict the distribution of products, mass balances and space time yields (STY) for the oxidation of a HMF substrate utilizing Pt, Pt/Bi, Pt/Te and Pt/Sn catalysts on various supports.
Figure 62:
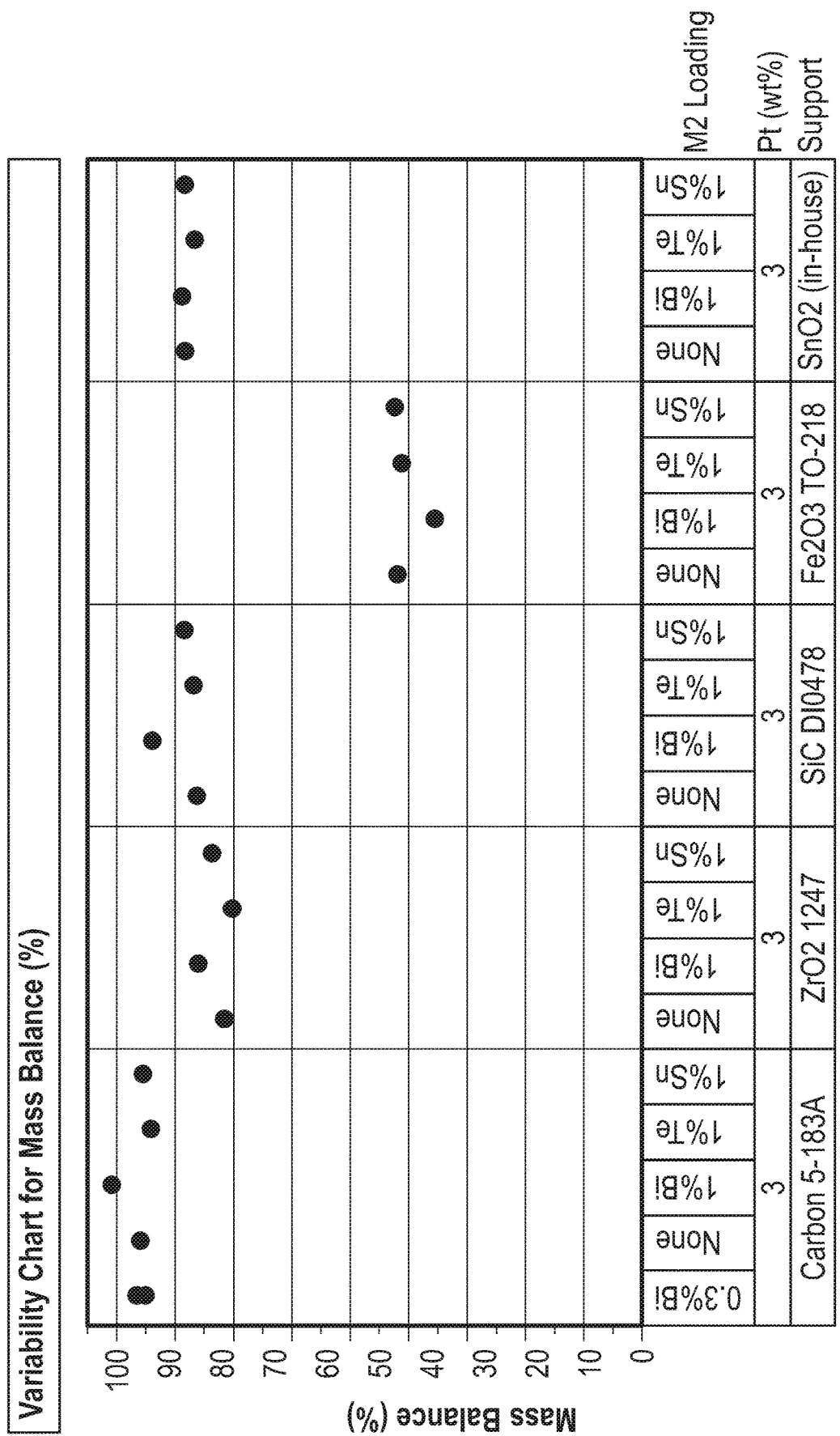
Figure 63:
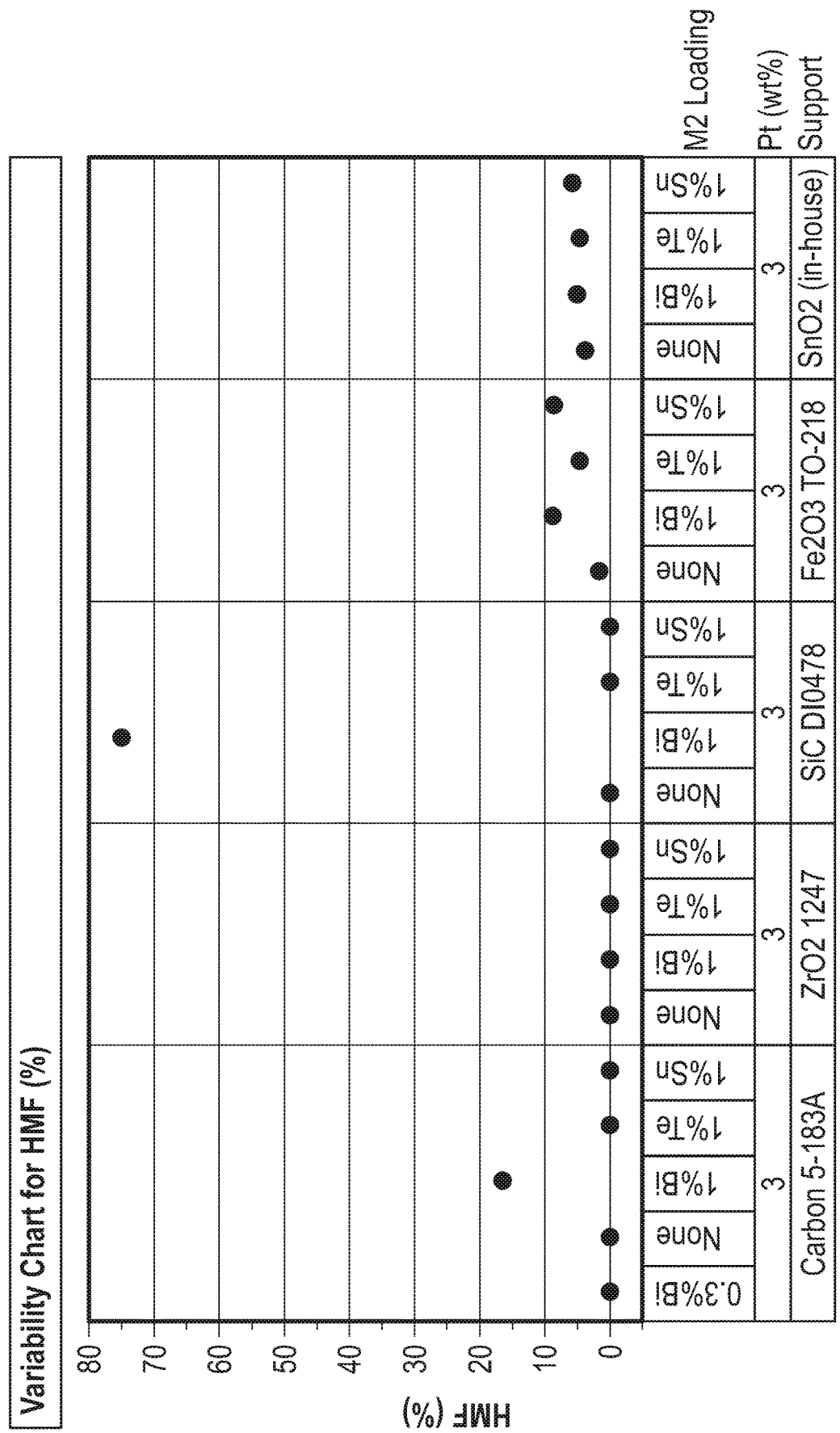
Figure 64:
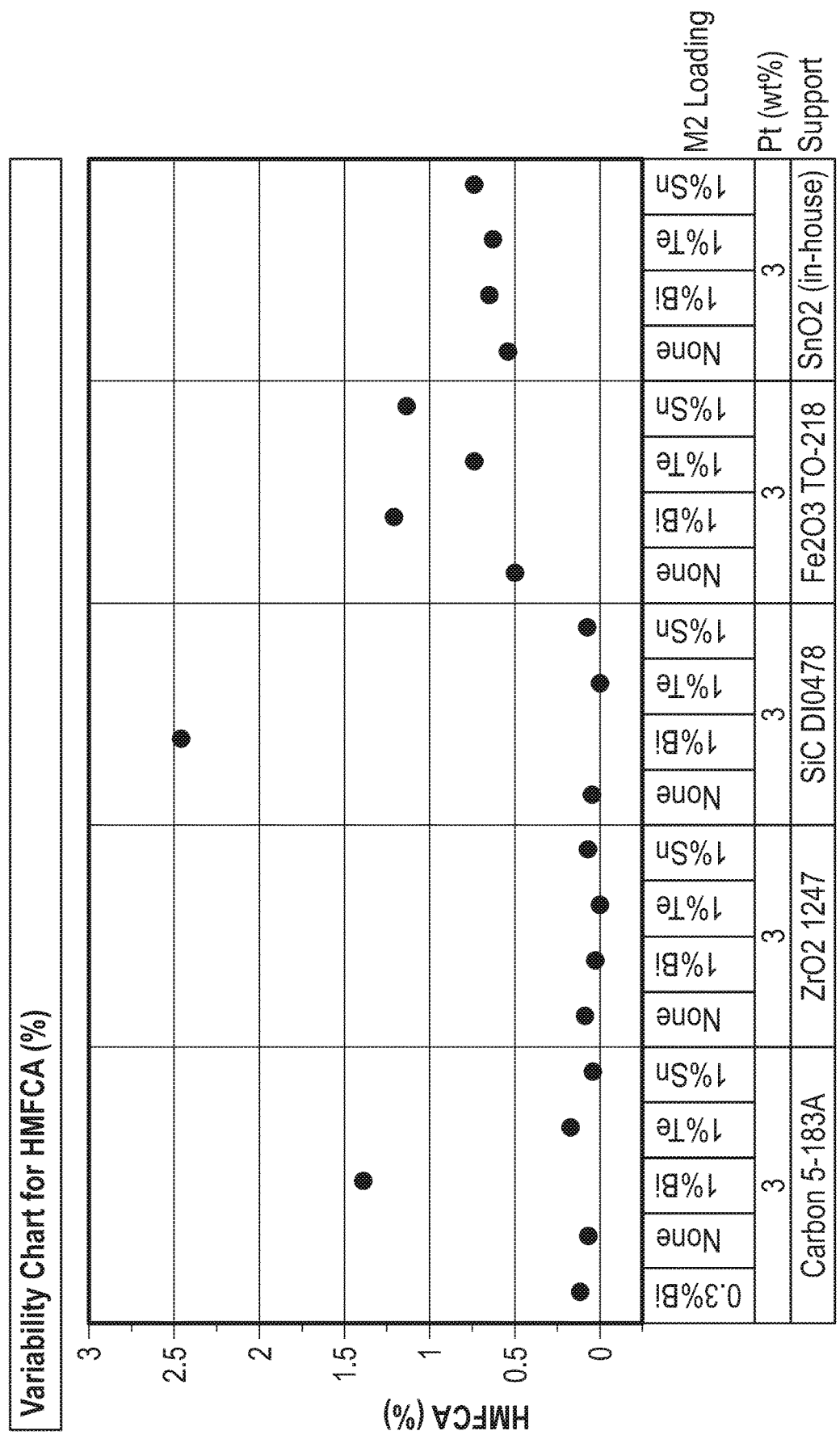
Figure 65:
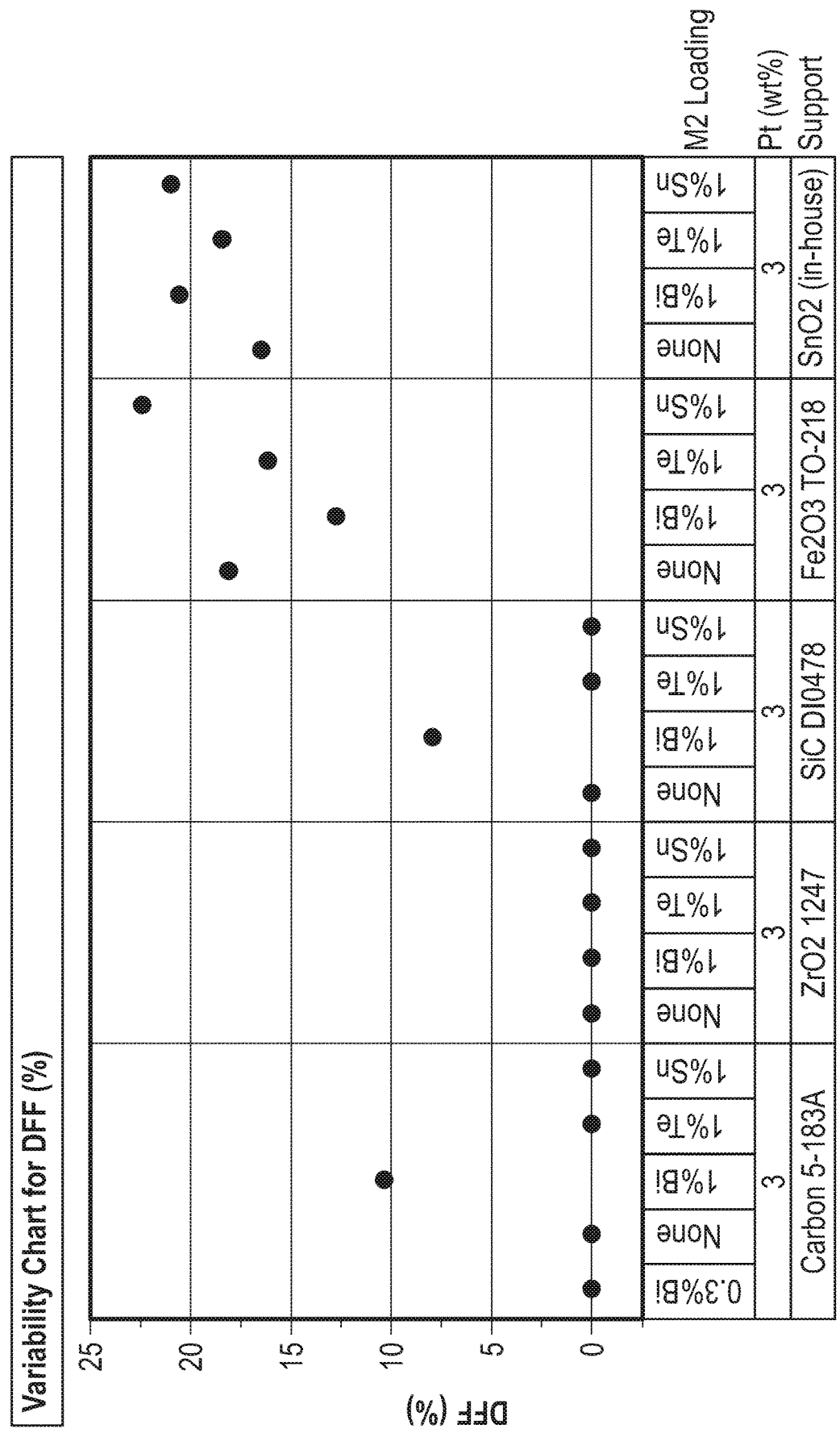
Figure 66:
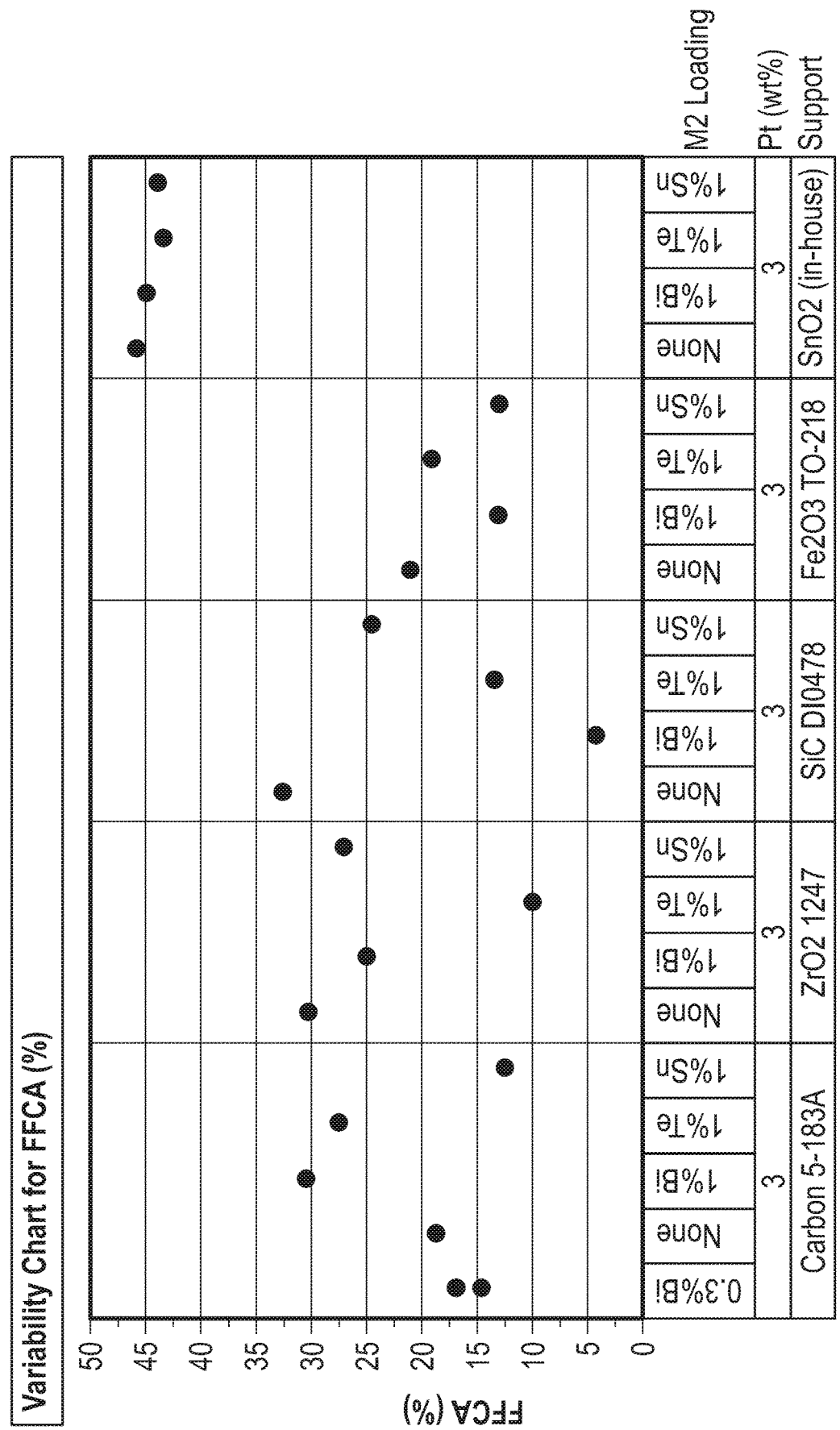
Figure 67:
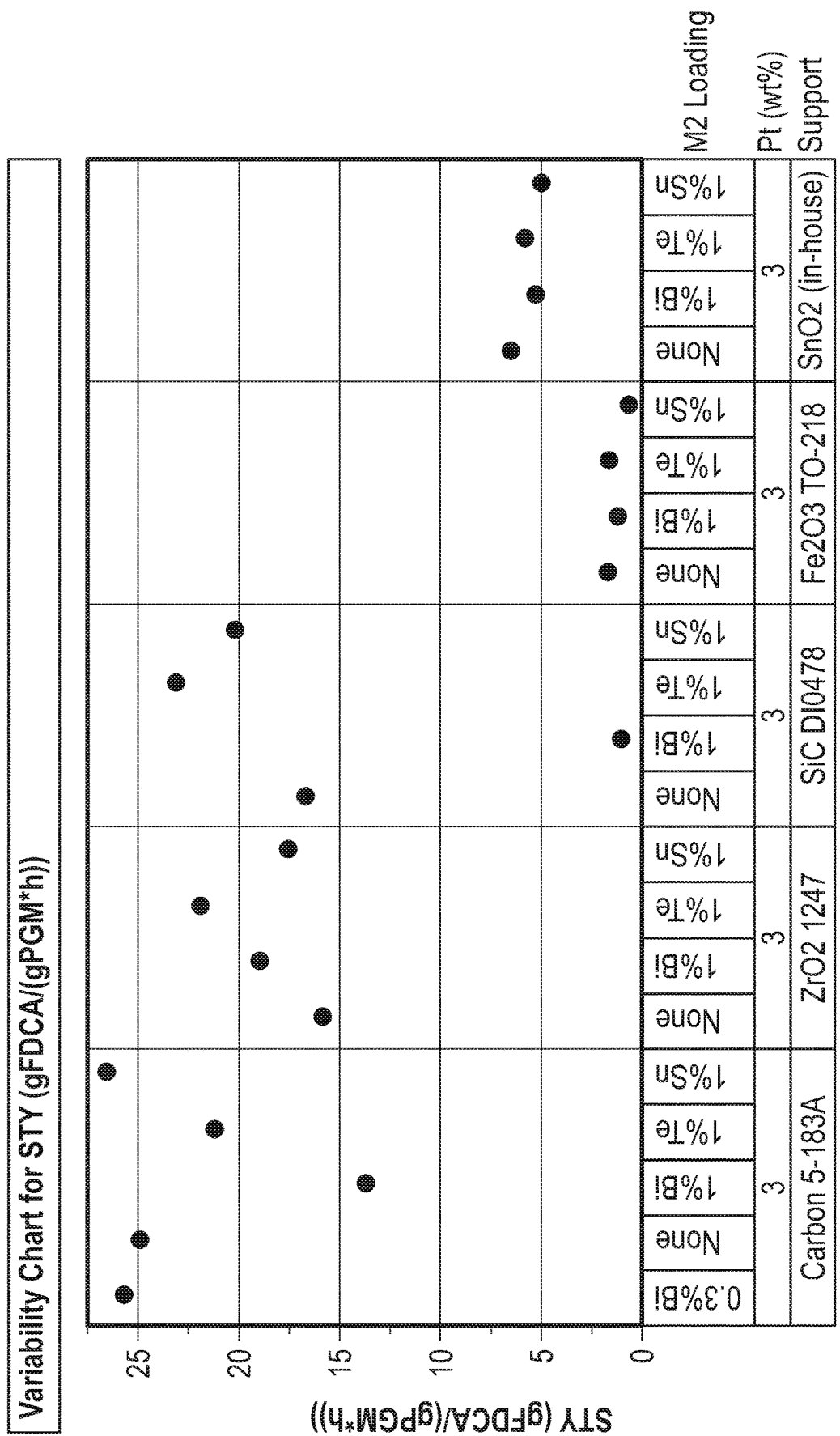
Figure 68:
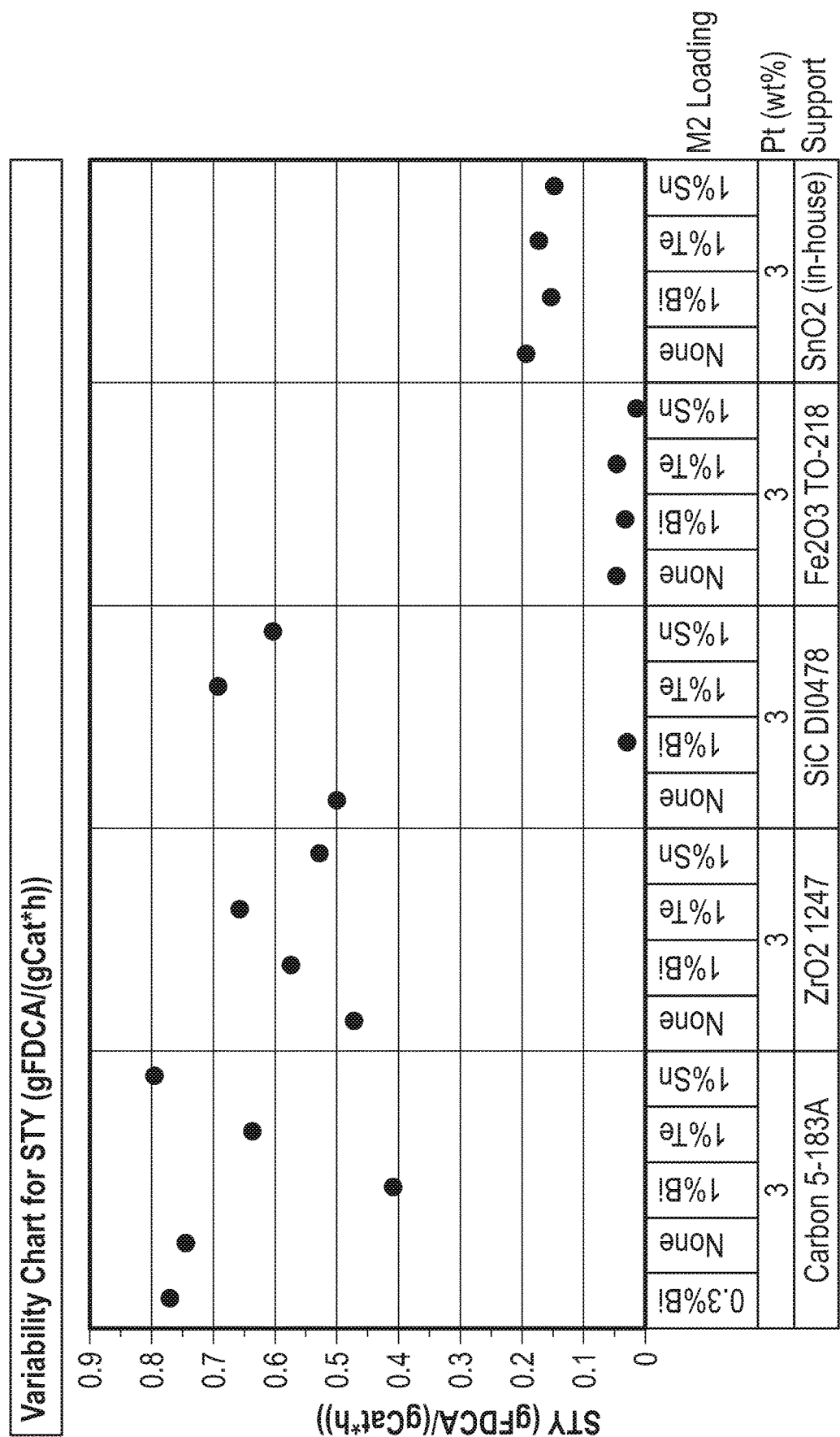

HMF to FDCA fixed bed oxidation reactions utilizing small particle Bi/Pt catalysts on zirconia/titania supports were performed in a ¼ inch MCR. The catalyst comprises 1.5 wt. % Bi+3.0 wt. % Pt/zirconia with 40 wt. % $TiO_2$ 39140 (75-150 µm). The catalyst was prepared from single fixed co-impregnation using $Bi(NO_3)_3$+$Pt(NO_3)_x$ followed by a forming gas reduction at 120° C. for 2 h in air and 350° C. for 3 h in air. The catalyst packing density is about 2 times of that of carbon catalysts, and ⅔ of that of zirconia catalysts. The reaction was carried out with commercial HMF (Ench Industry) and in a reactor with 125° C. and 1000 psig at 0.50 mL/min with 181 sccm 5% $O_2$/95% $N_2$ (2:1 $O_2$/HMF molar ratio), at 0.50 mL/min with 250 sccm 5% $O_2$/95% $N_2$ (2.8:1 $O_2$/HMF molar ratio), at 0.35 mL/min with 175 sccm 5% $O_2$/95% $N_2$ (2.8:1 $O_2$/HMF molar ratio), then at 0.50 mL/min with 250 sccm 5% $O_2$/95% $N_2$ (2.8:1 $O_2$/HMF molar ratio). The catalyst comprises 46 cm of 7.1 g 1.5 wt. % Bi+3.0 wt. % Pt/zirconia with 40 wt. % $TiO_2$ 39140 (75-150 µm). A substrate of 5.0 wt. % HMF (Ench Industry) in 60 wt. % dioxane/40 wt. % $H_2O$. Metals in effluents were measured by Inductively coupled plasma mass spectrometry (ICP-MS) with average 0.02 ppm Pt, 0.21 ppm Zr, and Bi and Ti were not detected. No detectable leaching of Bi, Pt and Ti were detected, and very low leaching of Zr was detected. The results are shown in FIGS. 59-60.

Example 31

Performance of Pt, Pt/Bi, Pt/Te and Pt/Sn on Various Solid Supports

HMF to FDCA oxidations utilizing Pt, Pt/Bi, Pt/Te and Pt/Sn on various solid supports. Catalysts were prepared on the following supports: Carbon 5-183A (<75 µm), Zirconia 1247 (<75 µm), SiC (SiCat DI0478B, 150-250 µm); $Fe_2O_3$ (Bayoxide E Iron Red, TO-218, powder), $SnO_2$ (in-house prepared from K2SnO3+HNO3, powder). Four platinum group metal (PGM) loadings were used: 3.0 wt. % Pt, or 3.0 wt. % Pt doped with 1.0 wt. % Bi, 1.0 wt. % Te or 1.0 wt. % Sn. Catalyst were synthesized by Alfred and M2 loadings using $Pt(NO_3)_x$, $Bi(NO_3)_3$+$Pt(NO_3)_x$, $Te(OH)_6$+$Pt(NO_3)_x$, Sn(oxalate)/$H_2O_2$ then $Pt(NO_3)_x$. 10.0 mg of powder or small particle catalyst was used in reactions with 0.25 mL of a substrate of 6.0 wt % (0.50M) HMF in 60 wt. % dioxane/40 wt. % $H_2O$. The reaction was carried out at 200 psi $O_2$ (RT) at 125° C. for 2 h at 800 rpm. The results are shown in FIGS. 61-68.

Unless defined otherwise, all technical and scientific terms used herein have the same meaning as is commonly understood by one of ordinary skill in the art. All patents, applications, published applications and other publications referenced herein are expressly incorporated by reference in their entireties unless stated otherwise. In the event that there are a plurality of definitions for a term herein, those in this section prevail unless stated otherwise.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components.

While preferred embodiments of the disclosure have been illustrated and described, it will be appreciated that various changes can be made therein without departing from the spirit and scope of the disclosure. Therefore it should be clearly understood that the forms disclosed herein are illustrative only and are not intended to limit the scope of the present disclosure.

What is claimed is:

1. A process for producing a purified 2,5-furandicarboxylic acid (FDCA) pathway product comprising:
   contacting an FDCA pathway product comprising FDCA and 5-formylfurancarboxylic acid (FFCA) with hydrogen in the presence of a heterogeneous reduction catalyst and a solvent under conditions, which form a reaction mixture for reducing the FFCA to hydroxymethylfurancarboxylic acid (HMFCA), and producing a purified FDCA pathway product;
   wherein the purified FDCA pathway product comprises FDCA, HMFCA, less than 10% molar impurities of FFCA, less than 10% molar impurities of 5-methyl-2-furoic acid (MFA), and less than 10% molar impurities of tetrahydrofuran-2,5-dicarboxylic acid (THFDCA);
   wherein the solvent is a multi-component solvent comprising water and a water-miscible aprotic organic solvent; and
   wherein the heterogeneous reduction catalyst comprises a solid support and a metal selected from the group consisting of Cu, Ni, Co, Pd, Pt, Ru, Ag, Au, Rh, Os, Ir, and any combination thereof.

2. The process of claim 1, wherein the purified FDCA pathway product comprises greater than 90% of FDCA by molar purity.

3. The process of claim 1, wherein the purified FDCA pathway product comprises less than 5% of FFCA by molar purity.

4. The process of claim 1, wherein the purified FDCA pathway product comprises less than 5% of MFA by molar purity.

5. The process of claim 1, wherein the purified FDCA pathway product comprises less than 0.9% of THFDCA by molar purity.

6. The process of claim 1, wherein the yield of HMFCA reduced from FFCA is greater than 25%.

7. The process of claim 1, wherein the solid support is selected from the group consisting of carbon, zirconium dioxide, titanium dioxide, silicon carbide, silicon dioxide, $Al_2O_3$, and any combination thereof.

8. The process of claim 1, wherein the heterogeneous reduction catalyst further comprises a promoter.

9. The process of claim 8, wherein the promoter is selected from the group consisting of Ti, Zr, Cr, Mo, W, Mn, Ru, Cu, Zn, Sb, Bi, Sn, Au, Ag, Pb, Te, and any combination thereof.

10. The process of claim 1, wherein the solid support has a surface area of less than 200 $m^2$/g.

11. The process of claim 1, wherein the water-miscible aprotic organic solvent is selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone.

12. The process of claim 11, wherein the glyme is selected from the group consisting of a monoglyme (1,2-dimethoxyethane), ethyl glyme, diglyme (diethylene glycol dimethyl ether), ethyl diglyme, triglyme, butyl diglyme, tetraglyme, and a polyglyme.

13. The process of claim 1, wherein the water and the water-miscible aprotic organic solvent are present in a ratio of from or any number in between 1:6 to 6:1 v/v water:water-miscible organic solvent.

14. The process of claim 1, wherein the heterogeneous reduction catalyst and FFCA are present in the FDCA pathway product in a weight % ratio range of 1:0.001 to 1:1 of heterogeneous reduction catalyst:FFCA.

15. The process of claim 1, further comprising:
producing the FDCA pathway product by:
(a) contacting an oxidation feedstock comprising a furanic oxidation substrate and an oxidation solvent with oxygen in the presence of a heterogeneous oxidation catalyst under conditions sufficient to form a reaction mixture for oxidizing the furanic oxidation substrate to an FDCA pathway product, and producing the FDCA pathway product;
wherein the FDCA pathway product comprises FDCA and FFCA;
wherein no base is added to the reaction mixture during (first) contacting step (a);
wherein the heterogeneous oxidation catalyst comprises a solid support and a noble metal; and
wherein the solvent recited in claim 1 and the oxidation solvent are substantially the same.

16. The process of claim 15, wherein the furanic oxidation substrate is selected from the group consisting of 5-(hydroxymethyl)furfural (HMF), diformylfuran (DFF), hydroxymethylfurancarboxylic acid (HMFCA), and formylfurancarboxylic acid (FFCA).

17. The process of claim 15, wherein the oxidation feedstock comprises the furanic oxidation substrate at a concentration of at least 5% by weight.

18. The process of claim 17, wherein the furanic oxidation substrate is present in the oxidation feedstock at a concentration of at least 10% by weight.

19. The process of claim 15, further comprising a second oxidation step, wherein the second oxidation step comprises:

(b) contacting a second oxidation feedstock comprising a second furanic oxidation substrate and a second oxidation solvent with oxygen in the presence of a second heterogeneous oxidation catalyst under conditions sufficient to form a second reaction mixture for oxidizing the second furanic oxidation substrate to produce a second FDCA pathway product, and producing the second FDCA pathway product;
wherein the second FDCA pathway product comprises FDCA and FFCA;
wherein (first) contacting step (a) produces a first FDCA pathway product that is an FDCA pathway intermediate compound, either alone or together with FDCA;
wherein the second furanic oxidation substrate is the first FDCA pathway product;
wherein no base is added to the second reaction mixture during (second) contacting step (b); and
wherein the second heterogeneous oxidation catalyst comprises a second solid support and a second noble metal.

20. The process of claim 1, further comprising:
crystallizing the purified FDCA product to produce FDCA having a molar purity of greater than 99%.

21. A mixture comprising:
a purified 2,5-furandicarboxylic acid (FDCA) pathway product comprising FDCA, HMFCA, less than 10% molar impurities of FFCA, less than 10% molar impurities of 5-methyl-2-furoic acid (MFA), and less than 10% molar impurities of tetrahydrofuran-2,5-dicarboxylic acid (THFDCA);
a heterogeneous reduction catalyst comprising a solid support and a metal selected from the group consisting of Cu, Ni, Pd, Pt, Ru, Ag, Au, Rh, Os, Ir, and any combination thereof; and
a multi-component solvent comprising water and a water-miscible aprotic organic solvent.

22. The mixture of claim 21, further comprising hydrogen.

23. The mixture of claim 21, wherein the purified FDCA pathway product comprises less than 10% molar impurities of 2,5-diformylfuran (DFF).

24. The mixture of claim 21, wherein the FFCA and FDCA are at least partially dissolved in the multi-component solvent.

* * * * *